United States Patent
Mallett et al.

(10) Patent No.: US 8,204,620 B2
(45) Date of Patent: Jun. 19, 2012

(54) METHOD FOR COMBINED DISPOSAL AND DISPENSING OF MEDICAL ITEMS

(75) Inventors: Scott R. Mallett, Coto De Caza, CA (US); Randall C. Danta, Tustin, CA (US); James R. Benson, Huntington Beach, CA (US); Alan D. Corey, Newport Beach, CA (US); Alan A. Davidner, Claremont, CA (US); Peter Regla, Placentia, CA (US)

(73) Assignee: Vesta Medical, LLC, San Diego, CA (US)

( * ) Notice: Subject to any disclaimer, the term of this patent is extended or adjusted under 35 U.S.C. 154(b) by 389 days.

(21) Appl. No.: 12/026,463

(22) Filed: Feb. 5, 2008

(65) Prior Publication Data
US 2008/0195247 A1   Aug. 14, 2008

Related U.S. Application Data

(63) Continuation of application No. 12/025,712, filed on Feb. 4, 2008, and a continuation-in-part of application No. 11/777,243, filed on Jul. 12, 2007, now Pat. No. 7,487,100, which is a continuation of application No. 11/347,823, filed on Feb. 3, 2006, now Pat. No. 7,275,645, which is a continuation-in-part of application No. 10/945,223, filed on Sep. 20, 2004, now Pat. No. 7,119,689, and a continuation-in-part of application No. 11/347,823, filed on Feb. 3, 2006.

(60) Provisional application No. 60/888,266, filed on Feb. 5, 2007, provisional application No. 60/888,269, filed on Feb. 5, 2007, provisional application No. 60/504,170, filed on Sep. 19, 2003, provisional application No. 60/589,118, filed on Jul. 19, 2004, provisional application No. 60/649,819, filed on Feb. 3, 2005, provisional application No. 60/679,187, filed on May 9, 2005, provisional application No. 60/712,256, filed on Aug. 29, 2005, provisional application No. 60/742,212, filed on Dec. 2, 2005.

(51) Int. Cl.
*G06F 17/00* (2006.01)
(52) U.S. Cl. ......... 700/236; 700/240; 700/242; 700/244
(58) Field of Classification Search ....................... None
See application file for complete search history.

(56) References Cited

U.S. PATENT DOCUMENTS 3,176,840 A   4/1965   Bickel
(Continued)

FOREIGN PATENT DOCUMENTS
EP         387389 A1    9/1990
(Continued)

OTHER PUBLICATIONS

Quinn, Paul. "How the Waste was Won." Supply & Chain System (Dec. 1997): 4 pp. Online. Internet. Oct. 26, 2004.

(Continued)

*Primary Examiner* — Timothy Waggoner

(57) ABSTRACT

A system and method related to dispensing and disposing medical items is provided. The dispensing portion is generally configured to dispense medical items stored within compartments based on dispensing instructions. The disposal portion is generally configured to sort waste items into a plurality of containers according to applicable rules and regulations governing the handling and/or disposal of such items. In some embodiments, a system comprises sorting stations each of which houses a number of disposable containers. Each station can identify an item of waste, determine the most appropriate container for the item, and facilitate disposal of the item in the appropriate container.

30 Claims, 85 Drawing Sheets

U.S. PATENT DOCUMENTS

| | | |
|---|---|---|
| 4,043,562 A | 8/1977 | Shillington |
| 4,114,965 A | 9/1978 | Dye et al. |
| 4,164,320 A | 8/1979 | Irazoqui et al. |
| 4,181,948 A | 1/1980 | Jackson et al. |
| 4,230,031 A | 10/1980 | Pedroso et al. |
| 4,248,389 A | 2/1981 | Thompson et al. |
| 4,257,272 A | 3/1981 | Sloman |
| 4,365,634 A | 12/1982 | Bare et al. |
| 4,393,584 A | 7/1983 | Bare et al. |
| 4,452,358 A | 6/1984 | Simpson |
| 4,454,944 A | 6/1984 | Shillington et al. |
| 4,502,606 A | 3/1985 | Shillington et al. |
| 4,522,211 A | 6/1985 | Bare et al. |
| 4,554,077 A | 11/1985 | Brown et al. |
| 4,579,053 A | 4/1986 | Beesley et al. |
| 4,600,112 A | 7/1986 | Shillington et al. |
| 4,605,124 A | 8/1986 | Sandel et al. |
| 4,667,821 A | 5/1987 | Shillington |
| 4,670,634 A | 6/1987 | Bridges et al. |
| 4,674,676 A | 6/1987 | Sandel et al. |
| 4,677,909 A | 7/1987 | Beesley et al. |
| 4,700,363 A | 10/1987 | Tomlinson et al. |
| 4,702,385 A | 10/1987 | Shillington et al. |
| D292,777 S | 11/1987 | Shillington et al. |
| 4,717,042 A | 1/1988 | McLaughlin |
| 4,736,860 A | 4/1988 | Bemis |
| 4,750,437 A | 6/1988 | Rouse |
| 4,773,027 A | 9/1988 | Neumann |
| 4,779,728 A | 10/1988 | Hanifl et al. |
| 4,785,969 A | 11/1988 | McLaughlin |
| D298,864 S | 12/1988 | Jefferson |
| 4,802,423 A | 2/1989 | Pennington |
| 4,804,090 A | 2/1989 | Schuh et al. |
| 4,809,850 A | 3/1989 | Laible et al. |
| 4,821,120 A | 4/1989 | Tomlinson |
| 4,839,806 A | 6/1989 | Goldfischer et al. |
| 4,842,138 A | 6/1989 | Sandel et al. |
| 4,844,252 A | 7/1989 | Barron et al. |
| 4,847,764 A | 7/1989 | Halvorson |
| 4,852,794 A | 8/1989 | Bennett et al. |
| 4,853,208 A | 8/1989 | Reimers et al. |
| 4,853,521 A | 8/1989 | Claeys et al. |
| 4,857,713 A | 8/1989 | Brown |
| 4,857,716 A | 8/1989 | Gombrich et al. |
| 4,860,317 A | 8/1989 | Tomlinson |
| 4,886,164 A | 12/1989 | Stein et al. |
| 4,919,086 A | 4/1990 | Shillington |
| 4,925,048 A | 5/1990 | Noack |
| 4,940,157 A | 7/1990 | Inagaki |
| 4,950,105 A | 8/1990 | Meess et al. |
| 4,953,745 A | 9/1990 | Rowlett, Jr. |
| 4,972,950 A | 11/1990 | Shillington |
| D313,670 S | 1/1991 | Barron et al. |
| 4,984,686 A | 1/1991 | Shillington |
| 5,005,532 A | 4/1991 | Shillington |
| 5,005,793 A | 4/1991 | Shillington |
| 5,014,875 A | 5/1991 | McLaughlin et al. |
| 5,022,548 A | 6/1991 | Stakis |
| 5,024,326 A | 6/1991 | Sandel et al. |
| 5,024,327 A | 6/1991 | Shillington |
| D318,159 S | 7/1991 | Noack |
| 5,035,858 A | 7/1991 | Held et al. |
| 5,036,866 A | 8/1991 | Eldrige, Jr. et al. |
| 5,046,614 A | 9/1991 | Torres et al. |
| 5,048,766 A | 9/1991 | Gaylor et al. |
| 5,051,565 A | 9/1991 | Wolfram |
| 5,058,764 A | 10/1991 | Gaba |
| 5,064,124 A | 11/1991 | Chang |
| 5,072,832 A | 12/1991 | Valentine et al. |
| 5,076,429 A | 12/1991 | Patrick et al. |
| 5,080,251 A | 1/1992 | Noack |
| 5,085,338 A | 2/1992 | Inagaki |
| 5,092,480 A | 3/1992 | Waterston |
| 5,097,950 A | 3/1992 | Weiss et al. |
| 5,100,005 A | 3/1992 | Noble et al. |
| 5,103,997 A | 4/1992 | Shillington et al. |
| 5,104,047 A | 4/1992 | Simmons |
| 5,106,594 A | 4/1992 | Held et al. |
| 5,107,990 A | 4/1992 | Wicherski et al. |
| 5,124,125 A | 6/1992 | Brent |
| 5,125,995 A | 6/1992 | D'Haese et al. |
| 5,145,063 A | 9/1992 | Lee |
| 5,152,751 A | 10/1992 | Kozlowski |
| 5,154,345 A | 10/1992 | Shillington |
| 5,163,375 A | 11/1992 | Withers et al. |
| 5,164,897 A | 11/1992 | Clark et al. |
| 5,167,193 A | 12/1992 | Withers et al. |
| D332,680 S | 1/1993 | Ramirez |
| 5,178,322 A | 1/1993 | Shillington |
| 5,178,752 A | 1/1993 | McKinnon |
| 5,184,720 A | 2/1993 | Packer et al. |
| D334,449 S | 3/1993 | Gaba et al. |
| 5,195,635 A | 3/1993 | Cornwell |
| D334,973 S | 4/1993 | Valentine et al. |
| 5,213,758 A | 5/1993 | Kawashima et al. |
| 5,226,065 A | 7/1993 | Held et al. |
| 5,230,496 A | 7/1993 | Shillington et al. |
| 5,231,938 A | 8/1993 | Gore |
| 5,236,135 A | 8/1993 | Wilson et al. |
| 5,240,108 A | 8/1993 | Tonna |
| 5,249,680 A | 10/1993 | Shillington |
| 5,251,757 A | 10/1993 | Relyea et al. |
| 5,256,861 A | 10/1993 | Anthony |
| 5,257,577 A | 11/1993 | Clark |
| 5,265,724 A | 11/1993 | Dondlinger |
| RE34,477 E | 12/1993 | Cornwell |
| 5,271,892 A | 12/1993 | Hanson et al. |
| 5,272,318 A | 12/1993 | Gorman |
| 5,276,253 A | 1/1994 | Circeo, Jr. et al. |
| 5,277,869 A | 1/1994 | Glazer et al. |
| 5,281,391 A | 1/1994 | Hanson et al. |
| 5,286,262 A | 2/1994 | Herweck et al. |
| 5,289,787 A | 3/1994 | Eshleman |
| 5,295,582 A | 3/1994 | Dan |
| 5,299,493 A | 4/1994 | Durbin et al. |
| 5,303,642 A | 4/1994 | Durbin et al. |
| 5,312,429 A | 5/1994 | Noack |
| 5,314,243 A | 5/1994 | McDonald et al. |
| 5,322,603 A | 6/1994 | Kameda et al. |
| 5,323,716 A | 6/1994 | Eshleman |
| 5,323,994 A | 6/1994 | Shillington et al. |
| D349,058 S | 7/1994 | Farce |
| 5,330,448 A | 7/1994 | Chu |
| 5,338,144 A | 8/1994 | Eshleman |
| 5,339,955 A | 8/1994 | Horan et al. |
| 5,346,297 A | 9/1994 | Colson, Jr. et al. |
| 5,348,235 A | 9/1994 | Pappas |
| 5,350,562 A | 9/1994 | Anthony |
| D351,906 S | 10/1994 | Marsh |
| 5,353,719 A | 10/1994 | Eshleman et al. |
| 5,354,000 A | 10/1994 | Wright et al. |
| 5,361,709 A | 11/1994 | Eshleman |
| 5,363,958 A | 11/1994 | Horan |
| 5,372,725 A | 12/1994 | Halff et al. |
| 5,377,839 A | 1/1995 | Relyea et al. |
| 5,384,092 A | 1/1995 | Sawhill et al. |
| 5,385,105 A | 1/1995 | Withers, Jr. et al. |
| 5,388,535 A | 2/1995 | Eshleman |
| 5,389,084 A | 2/1995 | Horan et al. |
| 5,392,951 A | 2/1995 | Gardner et al. |
| 5,395,008 A | 3/1995 | Bemis et al. |
| 5,395,338 A | 3/1995 | Gaba |
| 5,397,068 A | 3/1995 | Solomons et al. |
| 5,397,535 A | 3/1995 | Kaneko |
| 5,401,444 A | 3/1995 | Spinello |
| 5,402,887 A | 4/1995 | Shillington |
| 5,405,048 A | 4/1995 | Rogers et al. |
| D358,326 S | 5/1995 | Tomasello |
| D358,327 S | 5/1995 | Tomasello |
| 5,413,243 A | 5/1995 | Bemis et al. |
| 5,415,180 A | 5/1995 | Horan |
| 5,415,315 A | 5/1995 | Ramirez |
| 5,417,659 A | 5/1995 | Gaba |
| 5,419,435 A | 5/1995 | Perzan et al. |
| 5,421,672 A | 6/1995 | Ankeny et al. |
| 5,423,450 A | 6/1995 | Shillington et al. |
| 5,423,492 A | 6/1995 | Willis |

| | | | | | | |
|---|---|---|---|---|---|---|
| 5,425,458 A | 6/1995 | Gilcreest et al. | | 5,735,406 A | 4/1998 | Keffeler |
| 5,427,238 A | 6/1995 | Weiss | | 5,735,639 A | 4/1998 | Payne et al. |
| 5,427,737 A | 6/1995 | Glazer et al. | | 5,745,366 A | 4/1998 | Higham et al. |
| 5,431,299 A | 7/1995 | Brewer et al. | | 5,752,234 A | 5/1998 | Withers |
| 5,433,412 A | 7/1995 | Watt et al. | | 5,755,698 A | 5/1998 | Kagan et al. |
| 5,441,622 A | 8/1995 | Langford | | 5,762,235 A | 6/1998 | Coughlin |
| 5,445,294 A | 8/1995 | Gardner et al. | | 5,772,059 A | 6/1998 | McCord |
| H1477 H | 9/1995 | Payne | | 5,785,591 A | 7/1998 | Payne |
| 5,449,068 A | 9/1995 | Gharibian | | 5,794,789 A | 8/1998 | Payson et al. |
| 5,460,294 A | 10/1995 | Williams | | 5,797,515 A | 8/1998 | Liff et al. |
| 5,465,461 A | 11/1995 | Sandel | | 5,805,456 A | 9/1998 | Higham et al. |
| 5,465,841 A | 11/1995 | Wilson et al. | | 5,829,588 A | 11/1998 | Bloomfield |
| 5,469,600 A | 11/1995 | Sandel | | 5,830,419 A | 11/1998 | Held et al. |
| 5,470,022 A | 11/1995 | Wright et al. | | 5,833,683 A | 11/1998 | Fuller et al. |
| 5,471,705 A | 12/1995 | Dao | | 5,833,922 A | 11/1998 | Held et al. |
| 5,472,167 A | 12/1995 | Shillington et al. | | 5,836,989 A | 11/1998 | Shelton |
| 5,474,181 A | 12/1995 | Shillington et al. | | 5,837,171 A | 11/1998 | Danzik et al. |
| 5,476,634 A | 12/1995 | Bridges et al. | | 5,842,652 A | 12/1998 | Warsing et al. |
| 5,480,062 A | 1/1996 | Rogers et al. | | 5,842,976 A | 12/1998 | Williamson |
| 5,493,757 A | 2/1996 | Horan et al. | | 5,845,255 A | 12/1998 | Mayaud |
| 5,494,186 A | 2/1996 | Marsh | | 5,845,264 A | 12/1998 | Nellhaus |
| 5,495,941 A | 3/1996 | Leonard | | 5,848,593 A | 12/1998 | McGrady et al. |
| 5,507,408 A | 4/1996 | Mosior et al. | | 5,848,692 A | 12/1998 | Thorne et al. |
| 5,508,004 A | 4/1996 | Held et al. | | 5,852,590 A | 12/1998 | De La Huerga |
| 5,508,912 A | 4/1996 | Schneiderman | | 5,857,993 A | 1/1999 | Atanasoska et al. |
| 5,511,908 A | 4/1996 | Van Valkenburgh et al. | | 5,862,530 A | 1/1999 | Shillington |
| 5,514,338 A | 5/1996 | Simon et al. | | 5,883,806 A | 3/1999 | Meador et al. |
| 5,519,931 A | 5/1996 | Reich | | 5,905,653 A | 5/1999 | Higham et al. |
| 5,520,282 A | 5/1996 | Williams, Jr. | | 5,912,818 A | 6/1999 | McGrady et al. |
| 5,520,450 A | 5/1996 | Colson, Jr. et al. | | 5,914,047 A | 6/1999 | Griffiths |
| 5,523,052 A | 6/1996 | Bridges et al. | | 5,916,202 A | 6/1999 | Haswell |
| 5,527,329 A | 6/1996 | Gharibian | | 5,923,001 A | 7/1999 | Morris et al. |
| 5,533,974 A | 7/1996 | Gaba | | 5,927,540 A | 7/1999 | Godlewski |
| 5,536,898 A | 7/1996 | Conner et al. | | 5,933,809 A | 8/1999 | Hunt et al. |
| 5,536,945 A | 7/1996 | Reich | | 5,940,306 A | 8/1999 | Gardner et al. |
| 5,538,132 A | 7/1996 | Propp et al. | | 5,941,385 A | 8/1999 | Barton |
| 5,568,871 A | 10/1996 | Shantzis | | 5,947,285 A | 9/1999 | Gaba et al. |
| 5,570,783 A | 11/1996 | Thorne et al. | | 5,947,950 A | 9/1999 | Shillington et al. |
| 5,573,113 A | 11/1996 | Shillington et al. | | 5,950,632 A | 9/1999 | Reber et al. |
| 5,573,529 A | 11/1996 | Haak et al. | | 5,958,241 A | 9/1999 | DeBenedetto et al. |
| D376,647 S | 12/1996 | Marsh et al. | | 5,961,036 A * | 10/1999 | Michael et al. ............... 700/231 |
| 5,582,793 A | 12/1996 | Glazer et al. | | 5,965,858 A | 10/1999 | Suzuki et al. |
| 5,584,302 A | 12/1996 | Sillaway et al. | | 5,979,941 A | 11/1999 | Mosher, Jr. et al. |
| 5,587,572 A | 12/1996 | Kirby | | 5,991,728 A | 11/1999 | DeBusk et al. |
| 5,605,245 A | 2/1997 | Bemis et al. | | 5,993,046 A | 11/1999 | McGrady et al. |
| 5,609,820 A | 3/1997 | Bridges et al. | | 6,003,006 A | 12/1999 | Colella et al. |
| 5,611,270 A | 3/1997 | Harrington | | 6,010,444 A | 1/2000 | Honeycutt et al. |
| 5,616,136 A | 4/1997 | Shillington et al. | | 6,011,999 A | 1/2000 | Holmes |
| D379,405 S | 5/1997 | Shillington | | 6,019,242 A | 2/2000 | Wysocki et al. |
| 5,626,240 A | 5/1997 | Friedrichs et al. | | 6,021,392 A | 2/2000 | Lester et al. |
| 5,628,412 A | 5/1997 | Hulls | | 6,021,920 A | 2/2000 | Aldape |
| 5,630,506 A | 5/1997 | Thorne et al. | | 6,024,216 A | 2/2000 | Shillington et al. |
| 5,637,101 A | 6/1997 | Shillington | | 6,027,490 A | 2/2000 | Radford et al. |
| 5,639,031 A | 6/1997 | Wright et al. | | 6,032,155 A | 2/2000 | De La Huerga |
| 5,641,423 A | 6/1997 | Bridges et al. | | 6,039,467 A | 3/2000 | Holmes |
| 5,647,502 A | 7/1997 | Marsh | | 6,055,507 A | 4/2000 | Cunningham |
| 5,661,405 A | 8/1997 | Simon et al. | | RE36,693 E | 5/2000 | Reich |
| 5,661,978 A | 9/1997 | Holmes et al. | | 6,062,001 A | 5/2000 | Kunik |
| 5,664,112 A | 9/1997 | Sturgeon et al. | | 6,065,819 A | 5/2000 | Holmes |
| 5,665,070 A | 9/1997 | McPhee | | 6,066,243 A | 5/2000 | Anderson et al. |
| 5,667,069 A | 9/1997 | Williams, Jr. | | 6,068,156 A | 5/2000 | Liff et al. |
| 5,669,102 A | 9/1997 | Sandel | | 6,073,834 A | 6/2000 | Michael et al. |
| 5,672,883 A | 9/1997 | Reich | | 6,085,092 A | 7/2000 | Schmidt et al. |
| 5,676,255 A | 10/1997 | Flowers | | 6,097,995 A | 8/2000 | Tipton et al. |
| 5,678,568 A | 10/1997 | Uchikubo et al. | | 6,100,804 A | 8/2000 | Brady et al. |
| 5,688,399 A | 11/1997 | Halff et al. | | 6,109,774 A | 8/2000 | Holmes et al. |
| 5,690,248 A | 11/1997 | Hulls | | 6,110,848 A | 8/2000 | Bouchette |
| 5,693,028 A | 12/1997 | Shillington | | 6,112,502 A * | 9/2000 | Frederick et al. ............. 700/237 |
| RE35,715 E | 1/1998 | Circeo, Jr. et al. | | 6,116,461 A | 9/2000 | Broadfield et al. |
| 5,709,842 A | 1/1998 | Held et al. | | 6,119,869 A | 9/2000 | Geiman |
| 5,712,990 A | 1/1998 | Henderson | | 6,138,558 A | 10/2000 | Harrington |
| 5,713,485 A | 2/1998 | Liff et al. | | 6,139,495 A | 10/2000 | De La Huerga |
| 5,713,487 A | 2/1998 | Coughlin | | 6,151,536 A | 11/2000 | Arnold et al. |
| 5,716,114 A | 2/1998 | Holmes et al. | | 6,170,230 B1 | 1/2001 | Chudy et al. |
| 5,718,168 A | 2/1998 | Harrington | | 6,170,746 B1 | 1/2001 | Brook et al. |
| D391,726 S | 3/1998 | Williams et al. | | 6,170,929 B1 * | 1/2001 | Wilson et al. ................. 700/243 |
| 5,725,993 A | 3/1998 | Bringley et al. | | 6,204,056 B1 | 3/2001 | Barnes et al. |
| 5,726,884 A | 3/1998 | Sturgeon et al. | | 6,206,282 B1 | 3/2001 | Hayes, Sr. et al. |
| 5,732,401 A | 3/1998 | Conway | | 6,219,587 B1 | 4/2001 | Ahlin et al. |

| Patent | Type | Date | Inventor |
|---|---|---|---|
| 6,226,214 | B1 | 5/2001 | Choi |
| 6,226,617 | B1 | 5/2001 | Suzuki et al. |
| H1960 | H | 6/2001 | Conrad et al. |
| 6,247,592 | B1 | 6/2001 | Racicot et al. |
| 6,250,465 | B1 | 6/2001 | Daniels et al. |
| 6,253,916 | B1 | 7/2001 | Bickel |
| 6,255,951 | B1 | 7/2001 | De La Huerga |
| 6,283,322 | B1 | 9/2001 | Liff et al. |
| 6,294,999 | B1 | 9/2001 | Yarin et al. |
| 6,302,461 | B1 | 10/2001 | Debras et al. |
| D451,195 | S | 11/2001 | Daniels et al. |
| 6,315,113 | B1 | 11/2001 | Britton et al. |
| 6,317,719 | B1 | 11/2001 | Schrier et al. |
| 6,317,900 | B1 | 11/2001 | Braxton |
| 6,338,007 | B1 | 1/2002 | Broadfield et al. |
| 6,339,732 | B1 * | 1/2002 | Phoon et al. ............ 700/237 |
| 6,341,287 | B1 | 1/2002 | Sziklai et al. |
| 6,344,638 | B1 | 2/2002 | Tomasello |
| 6,360,186 | B1 | 3/2002 | Durbin |
| 6,361,263 | B1 | 3/2002 | Dewey et al. |
| 6,366,206 | B1 | 4/2002 | Ishikawa et al. |
| 6,367,377 | B1 | 4/2002 | Gawley et al. |
| 6,370,841 | B1 | 4/2002 | Chudy et al. |
| 6,386,386 | B1 | 5/2002 | George |
| 6,397,115 | B1 | 5/2002 | Basden |
| 6,408,261 | B1 | 6/2002 | Durbin |
| 6,425,487 | B1 | 7/2002 | Emmott et al. |
| 6,450,356 | B1 | 9/2002 | Alexander et al. |
| 6,453,270 | B1 | 9/2002 | Durbin |
| 6,471,089 | B2 | 10/2002 | Liff et al. |
| 6,474,472 | B1 | 11/2002 | Shaw |
| 6,488,675 | B1 | 12/2002 | Radford et al. |
| 6,499,270 | B2 | 12/2002 | Peroni et al. |
| 6,527,758 | B2 | 3/2003 | Ko |
| 6,529,446 | B1 | 3/2003 | De La Huerga |
| 6,532,399 | B2 | 3/2003 | Mase |
| 6,542,902 | B2 | 4/2003 | Dulong et al. |
| 6,558,077 | B1 | 5/2003 | Colson |
| 6,561,085 | B1 | 5/2003 | Durbin et al. |
| 6,574,166 | B2 | 6/2003 | Niemiec |
| 6,576,918 | B1 | 6/2003 | Fu et al. |
| 6,581,204 | B2 | 6/2003 | DeBusk et al. |
| 6,581,798 | B2 | 6/2003 | Liff et al. |
| 6,585,114 | B2 | 7/2003 | Kennedy et al. |
| 6,601,772 | B1 | 8/2003 | Rubin et al. |
| 6,609,047 | B1 | 8/2003 | Lipps |
| D479,744 | S | 9/2003 | Mallett et al. |
| 6,625,952 | B1 | 9/2003 | Chudy et al. |
| 6,633,795 | B1 | 10/2003 | Suzuki et al. |
| 6,640,159 | B2 | 10/2003 | Holmes et al. |
| 6,650,964 | B2 | 11/2003 | Spano, Jr. et al. |
| 6,663,004 | B2 | 12/2003 | Wagner et al. |
| 6,671,563 | B1 | 12/2003 | Engelson et al. |
| 6,671,579 | B2 | 12/2003 | Spano, Jr. et al. |
| 6,682,289 | B1 | 1/2004 | Credle, Jr. |
| 6,687,656 | B2 | 2/2004 | Durbin et al. |
| 6,699,701 | B1 | 3/2004 | Sulakvelidze |
| 6,701,345 | B1 | 3/2004 | Carley et al. |
| 6,712,561 | B1 | 3/2004 | Valerino, Sr. et al. |
| 6,727,294 | B2 | 4/2004 | Kanayama et al. |
| 6,730,059 | B2 | 5/2004 | Caizza et al. |
| 6,738,732 | B2 | 5/2004 | Durbin et al. |
| 6,748,400 | B2 | 6/2004 | Quick |
| 6,753,454 | B1 | 6/2004 | Smith et al. |
| 6,759,959 | B2 | 7/2004 | Wildman |
| 6,760,643 | B2 | 7/2004 | Lipps |
| 6,774,277 | B2 | 8/2004 | Fisher |
| 6,776,304 | B2 | 8/2004 | Liff et al. |
| 6,779,816 | B2 | 8/2004 | Williams |
| 6,785,589 | B2 | 8/2004 | Eggenberger et al. |
| 6,788,997 | B1 | 9/2004 | Frederick |
| 6,790,198 | B1 | 9/2004 | White et al. |
| 6,799,725 | B1 | 10/2004 | Hess et al. |
| 6,814,254 | B2 | 11/2004 | Liff et al. |
| 6,814,255 | B2 | 11/2004 | Liff et al. |
| 6,823,714 | B2 | 11/2004 | Megerle |
| 6,830,180 | B2 | 12/2004 | Walsh |
| 6,830,197 | B2 | 12/2004 | Rubin et al. |
| 6,842,736 | B1 | 1/2005 | Brzozowski |
| 6,847,861 | B2 | 1/2005 | Lunak et al. |
| 6,861,954 | B2 | 3/2005 | Levin |
| 6,935,560 | B2 | 8/2005 | Andreasson et al. |
| 6,961,000 | B2 | 11/2005 | Chung |
| 6,965,310 | B1 | 11/2005 | Hoben et al. |
| 6,975,922 | B2 | 12/2005 | Duncan et al. |
| 6,985,870 | B2 | 1/2006 | Martucci et al. |
| 6,996,455 | B2 | 2/2006 | Eggenberger et al. |
| 7,006,893 | B2 | 2/2006 | Hart et al. |
| 7,010,389 | B2 | 3/2006 | Lunak et al. |
| 7,019,650 | B2 | 3/2006 | Volpi et al. |
| 7,035,856 | B1 | 4/2006 | Morimoto |
| 7,040,504 | B2 | 5/2006 | Broadfield et al. |
| 7,052,097 | B2 | 5/2006 | Meek, Jr. et al. |
| 7,061,831 | B2 | 6/2006 | De La Huerga |
| 7,072,737 | B2 | 7/2006 | Lunak et al. |
| 7,072,738 | B2 | 7/2006 | Bonney et al. |
| 7,072,840 | B1 | 7/2006 | Mayaud |
| 7,072,855 | B1 | 7/2006 | Godlewski et al. |
| 7,080,751 | B2 | 7/2006 | Grazziotin |
| 7,080,755 | B2 | 7/2006 | Handfield et al. |
| 7,080,777 | B2 | 7/2006 | Wagner et al. |
| 7,086,592 | B2 | 8/2006 | Wagner et al. |
| 7,096,161 | B2 * | 8/2006 | Smith et al. ............ 700/9 |
| 7,098,793 | B2 | 8/2006 | Chung |
| 7,100,792 | B2 | 9/2006 | Hunter et al. |
| 7,103,419 | B2 | 9/2006 | Engleson et al. |
| 7,114,314 | B2 | 10/2006 | Stravitz |
| 7,114,629 | B2 | 10/2006 | Panek, Jr. |
| 7,119,688 | B2 | 10/2006 | Wildman |
| 7,119,689 | B2 | 10/2006 | Mallett et al. |
| 7,123,150 | B2 | 10/2006 | Mallett et al. |
| 7,123,989 | B2 | 10/2006 | Pinney et al. |
| 7,126,480 | B2 | 10/2006 | Mallett et al. |
| 7,138,918 | B2 | 11/2006 | Mallett et al. |
| 7,140,542 | B2 | 11/2006 | Andreasson et al. |
| 7,144,550 | B2 | 12/2006 | Devine et al. |
| 7,146,247 | B2 | 12/2006 | Kirsch et al. |
| 7,146,785 | B2 | 12/2006 | Stravitz |
| 7,151,982 | B2 | 12/2006 | Liff et al. |
| 7,156,226 | B1 | 1/2007 | Van Sickle |
| 7,158,030 | B2 | 1/2007 | Chung |
| 7,165,721 | B2 | 1/2007 | Wagner et al. |
| 7,175,081 | B2 | 2/2007 | Andreasson et al. |
| 7,177,721 | B2 | 2/2007 | Kirsch et al. |
| 7,203,571 | B2 | 4/2007 | Kirsch et al. |
| 7,216,802 | B1 | 5/2007 | De La Huerga |
| 7,218,231 | B2 | 5/2007 | Higham |
| 7,222,749 | B2 | 5/2007 | Holdway et al. |
| 7,232,066 | B2 | 6/2007 | Andreasson et al. |
| 7,246,706 | B1 | 7/2007 | Shakes et al. |
| 7,249,688 | B2 | 7/2007 | Hunter et al. |
| 7,265,662 | B2 | 9/2007 | Belanger |
| 7,275,645 | B2 | 10/2007 | Mallett et al. |
| 7,281,655 | B2 | 10/2007 | Wagner et al. |
| 7,296,688 | B2 | 11/2007 | Mallett et al. |
| 7,303,080 | B2 | 12/2007 | Mallett et al. |
| 7,303,081 | B2 | 12/2007 | Mallett et al. |
| 7,303,082 | B2 | 12/2007 | Mallett et al. |
| 7,303,124 | B2 | 12/2007 | Wagner et al. |
| 7,311,207 | B2 | 12/2007 | Mallett et al. |
| 7,318,529 | B2 | 1/2008 | Mallett et al. |
| 7,328,842 | B2 | 2/2008 | Wagner et al. |
| 7,341,147 | B2 | 3/2008 | Mallett et al. |
| 7,344,063 | B2 | 3/2008 | Wagner et al. |
| 7,366,640 | B2 | 4/2008 | Smith et al. |
| 7,383,195 | B2 | 6/2008 | Mallett et al. |
| RE40,453 | E | 8/2008 | Lasher et al. |
| 7,415,375 | B2 | 8/2008 | Shakman et al. |
| 7,454,358 | B2 | 11/2008 | Mallett et al. |
| 7,481,160 | B1 | 1/2009 | Simon et al. |
| 7,483,837 | B2 | 1/2009 | Mallett et al. |
| 7,487,100 | B2 | 2/2009 | Mallett et al. |
| 7,500,430 | B2 | 3/2009 | Claflin et al. |
| 7,501,951 | B2 | 3/2009 | Maruca et al. |
| 7,533,028 | B2 | 5/2009 | Mallett et al. |
| 7,533,029 | B2 | 5/2009 | Mallett et al. |
| 7,562,025 | B2 | 7/2009 | Mallett et al. |
| 7,565,299 | B2 | 7/2009 | Mallett et al. |

| | | |
|---|---|---|
| 7,617,113 B2 | 11/2009 | Mallett et al. |
| 7,620,559 B2 | 11/2009 | Mallett et al. |
| 7,660,724 B2 | 2/2010 | Mallett et al. |
| 7,664,656 B2 | 2/2010 | Mallett et al. |
| 7,677,395 B2 | 3/2010 | Bennett et al. |
| 7,681,792 B2 | 3/2010 | Wagner et al. |
| 7,708,188 B2 | 5/2010 | Stravitz et al. |
| 7,784,635 B2 | 8/2010 | Luburic |
| 7,886,973 B2 | 2/2011 | Wagner et al. |
| 2001/0026359 A1 | 10/2001 | Raymond |
| 2002/0026330 A1 | 2/2002 | Klein |
| 2002/0027140 A1 | 3/2002 | George |
| 2002/0030000 A1 | 3/2002 | Van Peperzeel et al. |
| 2002/0035750 A1 | 3/2002 | Braxton |
| 2002/0143434 A1 | 10/2002 | Greeven et al. |
| 2002/0173875 A1* | 11/2002 | Wallace et al. ............... 700/242 |
| 2003/0004965 A1 | 1/2003 | Farmer et al. |
| 2003/0131011 A1 | 7/2003 | Haunschild et al. |
| 2003/0139640 A1 | 7/2003 | Whittacre et al. |
| 2003/0140828 A1 | 7/2003 | Liu |
| 2003/0160698 A1 | 8/2003 | Andreasson et al. |
| 2004/0104271 A1 | 6/2004 | Martucci et al. |
| 2004/0112960 A1 | 6/2004 | Wagner et al. |
| 2004/0163981 A1 | 8/2004 | Rigling |
| 2004/0191224 A1 | 9/2004 | Sulakvelidze et al. |
| 2004/0195308 A1 | 10/2004 | Wagner et al. |
| 2004/0195309 A1 | 10/2004 | Wagner et al. |
| 2004/0199401 A1 | 10/2004 | Wagner et al. |
| 2004/0199545 A1 | 10/2004 | Wagner et al. |
| 2004/0205343 A1 | 10/2004 | Forth et al. |
| 2004/0208853 A1 | 10/2004 | Sulakvelidze et al. |
| 2004/0235970 A1 | 11/2004 | Smith et al. |
| 2004/0243444 A1 | 12/2004 | Steusloff et al. |
| 2005/0062238 A1 | 3/2005 | Broadfield et al. |
| 2005/0065640 A1 | 3/2005 | Mallett et al. |
| 2005/0080520 A1 | 4/2005 | Kline et al. |
| 2005/0080651 A1 | 4/2005 | Morrison et al. |
| 2005/0110640 A1 | 5/2005 | Chung |
| 2005/0119909 A1 | 6/2005 | Mallett et al. |
| 2005/0119915 A1 | 6/2005 | Mallett et al. |
| 2005/0209825 A1 | 9/2005 | Ogawa |
| 2005/0215961 A1 | 9/2005 | Romano et al. |
| 2005/0228682 A1 | 10/2005 | Firestone, III |
| 2006/0036407 A1 | 2/2006 | Smith et al. |
| 2006/0070933 A1 | 4/2006 | Bennett |
| 2006/0070934 A1 | 4/2006 | Bennett et al. |
| 2006/0100907 A1 | 5/2006 | Holland et al. |
| 2006/0138133 A1 | 6/2006 | Holland |
| 2006/0151497 A1 | 7/2006 | Underwood |
| 2006/0152367 A1 | 7/2006 | Narayanaswamy |
| 2006/0206354 A1 | 9/2006 | Mallett et al. |
| 2006/0218002 A1 | 9/2006 | Mallett et al. |
| 2006/0226167 A1 | 10/2006 | Broadfield et al. |
| 2006/0229551 A1 | 10/2006 | Martinez et al. |
| 2006/0253297 A1 | 11/2006 | Mallett et al. |
| 2006/0255136 A1 | 11/2006 | Wagner et al. |
| 2006/0255137 A1 | 11/2006 | Wagner et al. |
| 2006/0261165 A1 | 11/2006 | Wagner et al. |
| 2007/0135965 A1 | 6/2007 | Nguyen et al. |
| 2007/0159332 A1 | 7/2007 | Koblasz |
| 2007/0250339 A1 | 10/2007 | Mallett et al. |
| 2007/0278140 A1 | 12/2007 | Mallett et al. |
| 2007/0293979 A1 | 12/2007 | Mallett et al. |
| 2008/0015898 A1 | 1/2008 | Mallett et al. |
| 2008/0015899 A1 | 1/2008 | Mallett et al. |
| 2008/0021722 A1 | 1/2008 | Mallett et al. |
| 2008/0021734 A1 | 1/2008 | Mallett et al. |
| 2008/0133264 A1 | 6/2008 | Wagner et al. |
| 2008/0190953 A1 | 8/2008 | Mallett et al. |
| 2008/0203861 A1 | 8/2008 | Wingate |
| 2008/0223928 A1 | 9/2008 | Wagner et al. |
| 2008/0314978 A1 | 12/2008 | Fedorko et al. |
| 2009/0032423 A1 | 2/2009 | Japuntich |
| 2009/0037244 A1 | 2/2009 | Pemberton |
| 2009/0127168 A1 | 5/2009 | Mallett et al. |
| 2009/0139907 A1 | 6/2009 | Hollingsworth et al. |
| 2009/0272677 A1 | 11/2009 | Mallett et al. |
| 2010/0213250 A1 | 8/2010 | Mallett et al. |
| 2010/0219237 A1 | 9/2010 | Mallett et al. |
| 2010/0219238 A1 | 9/2010 | Mallett et al. |
| 2010/0241270 A1 | 9/2010 | Eliuk et al. |

FOREIGN PATENT DOCUMENTS

| | | |
|---|---|---|
| EP | 454122 B1 | 8/1995 |
| EP | 478634 B1 | 8/1995 |
| EP | 522231 B1 | 9/1998 |
| EP | 772558 B1 | 12/1998 |
| EP | 502164 B1 | 4/1999 |
| EP | 697271 B1 | 3/2000 |
| EP | 710125 B1 | 5/2000 |
| EP | 1083939 B1 | 3/2001 |
| GB | 02252316 A | 8/1992 |
| GB | 2330063 | 4/1999 |
| GB | 2449710 | 12/2008 |
| JP | 02-010116 | 1/1990 |
| JP | 09-029224 | 2/1997 |
| JP | 2002-014031 | 1/2002 |
| JP | 2005-334056 | 12/2005 |
| WO | WO 9105572 A1 | 5/1991 |
| WO | WO 9204920 A1 | 4/1992 |
| WO | WO 9306931 A1 | 4/1993 |
| WO | WO 94/08780 | 4/1994 |
| WO | WO 9514496 A1 | 6/1995 |
| WO | WO 9630059 A1 | 10/1996 |
| WO | WO 99/17218 | 4/1999 |
| WO | WO 01/67246 | 9/2001 |
| WO | WO 02/091297 | 11/2002 |
| WO | WO 03/017021 | 2/2003 |
| WO | WO03/071943 | 9/2003 |
| WO | WO 03/076174 | 9/2003 |
| WO | WO 03/078150 | 9/2003 |
| WO | WO 2004/074964 | 9/2004 |
| WO | WO 2005/029286 A2 | 3/2005 |
| WO | WO 2005/036447 | 4/2005 |
| WO | WO 2007/031978 | 3/2007 |
| WO | WO 2007/081823 | 7/2007 |
| WO | WO 2007/149468 | 12/2007 |
| WO | WO 2010/105334 | 9/2010 |

OTHER PUBLICATIONS

Daughton, Christian G. "Cradle-to-Cradle Stewardship of Drugs for Minimizing Their Environmental Disposition While Promoting Human Health. II. Drug Disposal, Waste Reduction, and Future Directions." Environmental Health Perspectives. vol. 111, No. 5, May 2003.

Townsend, Mark. "Stay calm everyone, there's Prozac in the drinking water." The Observer. Aug. 8, 2004.

Daughton, Christian G. "I. PPCPs as Environmental Pollutants. II. Pharmaceuticals and Personal Care Products in the Environment: Overarching Issues and Overview." U.S. Environmental Protection Agency, National Exposure Research Laboratory Environmental Sciences.

Kuspis DA, Krenzelok EP. "What happens to expired medications? A survey of community medication disposal." Vet Hum Toxicl. Feb. 1997; 38(1):48-9.

DOE Environmental Policy and Guidance. Posted Sep. 2000.

Saar S., Thomas, V. "Toward Trash That Thinks." Journal of Industrial Ecology. vol. 6, Issue 2—E-commerce, the Internet, and the Environment. pp. 133-146. © 2003.

Tata A., Beone F. "Hospital Waste Sterilization: A Technical and Economic Comparison Between Radiation and Microwaves Treatments" Radiat. Phys. Chen. vol. 46, No. 4-6, pp. 1153-1157, 1995.

Shafer, Mariana. "Development of a Novel Disinfectant and Mechanical-Chemical Process for Disinfection of Biomedical Waste" Thesis of Master of Science, Graduate Department of Microbiology, University of Toronto, © 1996.

Walker, Richard E. "State of Art Study of Hospital Wastes" Journal of Hazardous Materials, V. 24, Nos. 2-3, Sep. 1990, pp. 301-302.

Cross Jr., Frank L., P.E. "Siting a Medical Waste Treatment Facility" Pollution Engineering, V. 22, No. 9, Sep. 1990, pp. 68-73.

"Stericycle, Inc.: Recycling Potentially Infectious Waste." Healthcare Hazardous Material Management, Jul. 1992, pp. 7-10.

Yasmeen, Farhana et al. "Recycling of Medical Plastic Wastes" Popular Plastic and Packaging, V. 47, No. 4, Apr. 2002, pp. 71-74.

Humber, H. "Recycling Plastics in Medical Wastes" Biomedical Waste Systems, Inc., Davos Recycle '93 International Forum and Exposition, Davos, Switzerland, Mar. 22-26, 1993.

Slavik, N.S. "Infectious Waste Management: Strategies for the Health Care Facility" Compliance Resources, Inc., 1990 Polymers, Laminations & Coatings Conference Proceedings, Boston, MA., Sep. 4-7, 1990, pp. 37-39.

Letter dated Aug. 27, 2004 from Andy D. Kubalak, Regulatory Services Unit, Division of Hazardous Waste Management to Mr. Alan Davidner, President of Vesta Medical.

"New Waste Tracking Software Embraced as Potent Tool." *Medical Waste News*, Mar. 4, 1997, vol. 9, No. 5, pp. 37-38. Business Publishers, Inc.

"Medical Waste: Study: Microwaving Beats Incineration, Autoclaving in Treating Hospital Waste." *Solid Waste Report*, Jul. 23, 1998, vol. 29, No. 30, p. 238.

"NSWMA, SWANA Advise Waste Industry on Coping with Anthrax, Bioterrorism." *Solid Waste Report*, Nov. 23, 2001, vol. 32, No. 46, p. 361-362.

"Regulators Mull Options for 'Orphan Sources' Left at Solid-Waste Facilities." *Solid Waste Report*, Oct. 15, 1998, vol. 29, No. 41, p. 327.

"Risk Factors—Hospitals Emit Cancer-Causing Dioxin When They Burn Waste." *Cancer Weekly Plus*, Mar. 24, 1997, Charles Henderson (Publisher).

Anonymous (ED.) "Proceedings of the 1992 National Waste Processing Conference", 1992, p. 477. ASME New York, NY.

Anonymous, "BFI Concentrates on a Centralized Approach for Handling and Tracking Medical Waste." *Packaging Digest*, Sep. 1998, vol. 35, No. 10, p. 112.

Faure, P., et al. "Hospital and Environment: Waste Disposal." *Ann Pharm Fr*. Nov. 2003, vol. 61, No. 6, pp. 373-377.

Jager et al. "Medical Waste. 1. Microbiologic Studies of Wastes of Various Specialties at a Large and Small Hospital in Comparison to Housekeeping Waste." *Zentralbl Hygiene Umweltmedizin*. Jun. 1989, vol. 188, Nos. 3-4, pp. 346-364.

Jager, et al. "Medical Wastes. 2. Comparative Studies of the Microbial Contamination of Wastes From Medical Practices of Different Disciplines and Household Garbage." *Zentralblatt fur Hygiene Umweltmedizin*. May 1990, vol. 190, Nos. 1-2, pp. 188-206.

Tarling, et al. "The Use of Absorbent Materials for the Disposal of Controlled Drugs." *Anaesthesia* Sep. 1996, vol. 51, No. 9, pp. 836-838.

US 6,019,218, 02/2000, Racicot et al. (withdrawn)

\* cited by examiner

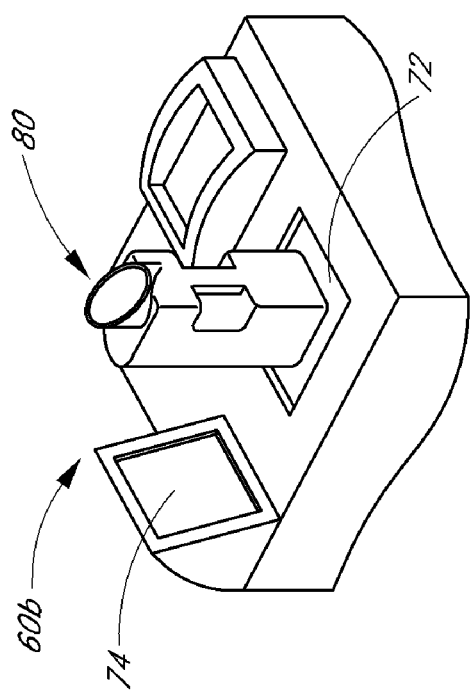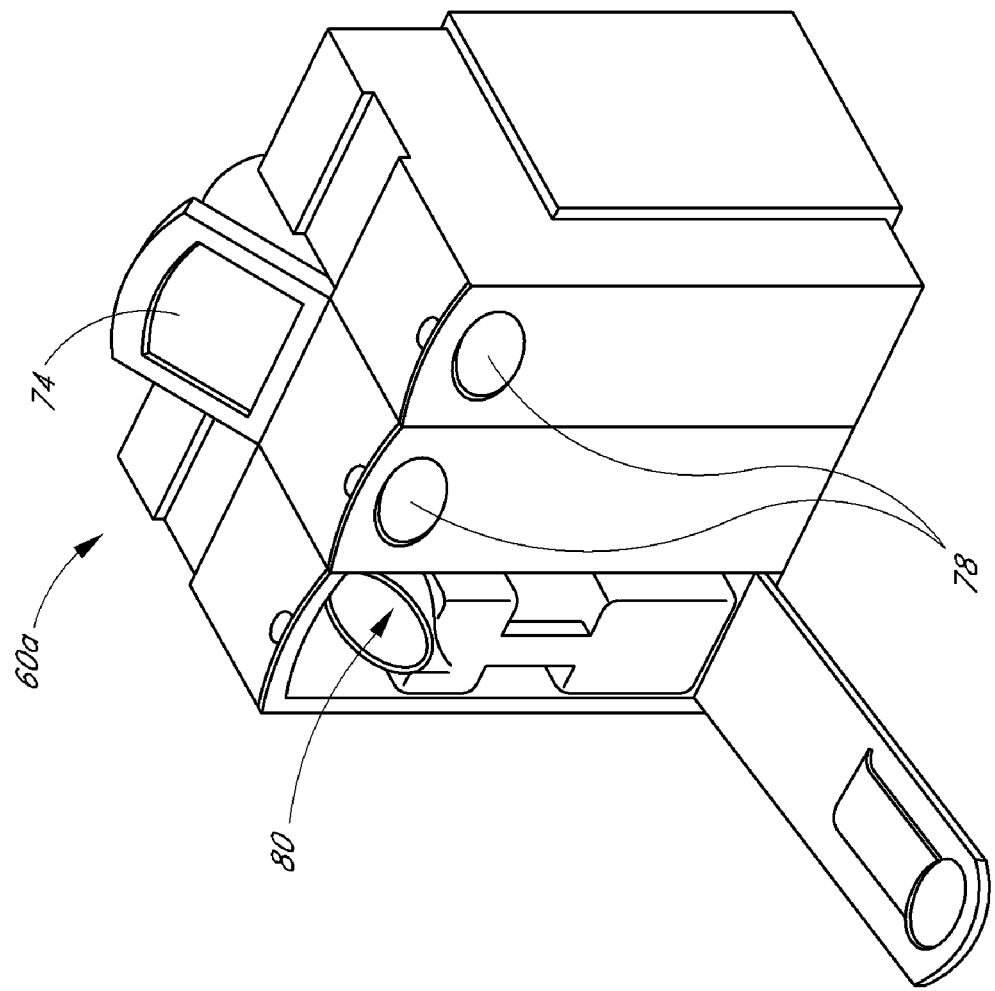

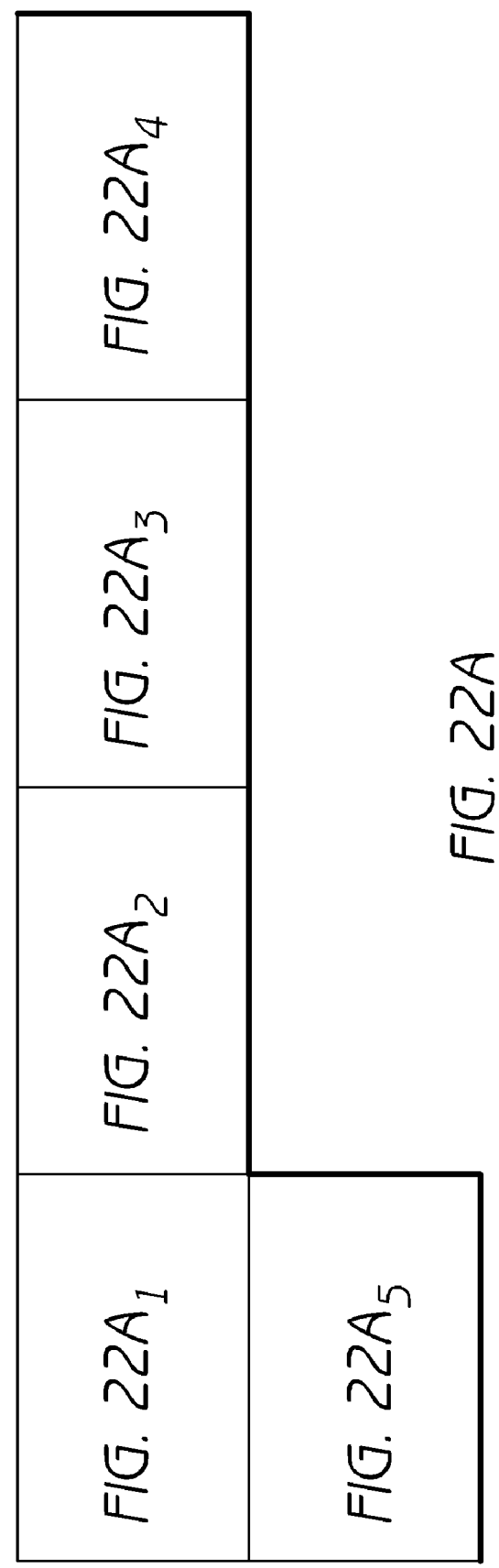

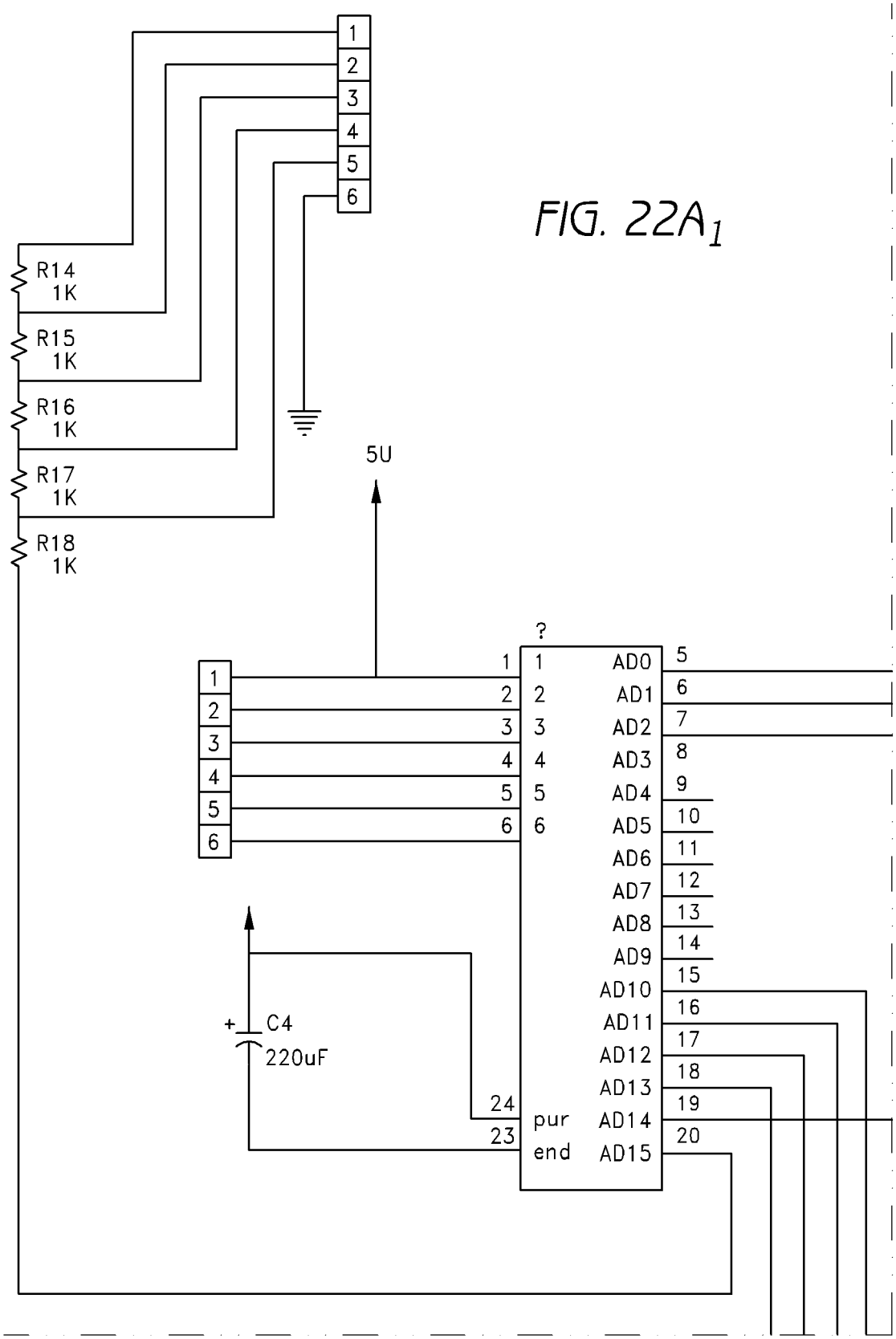
FIG. 22A₁

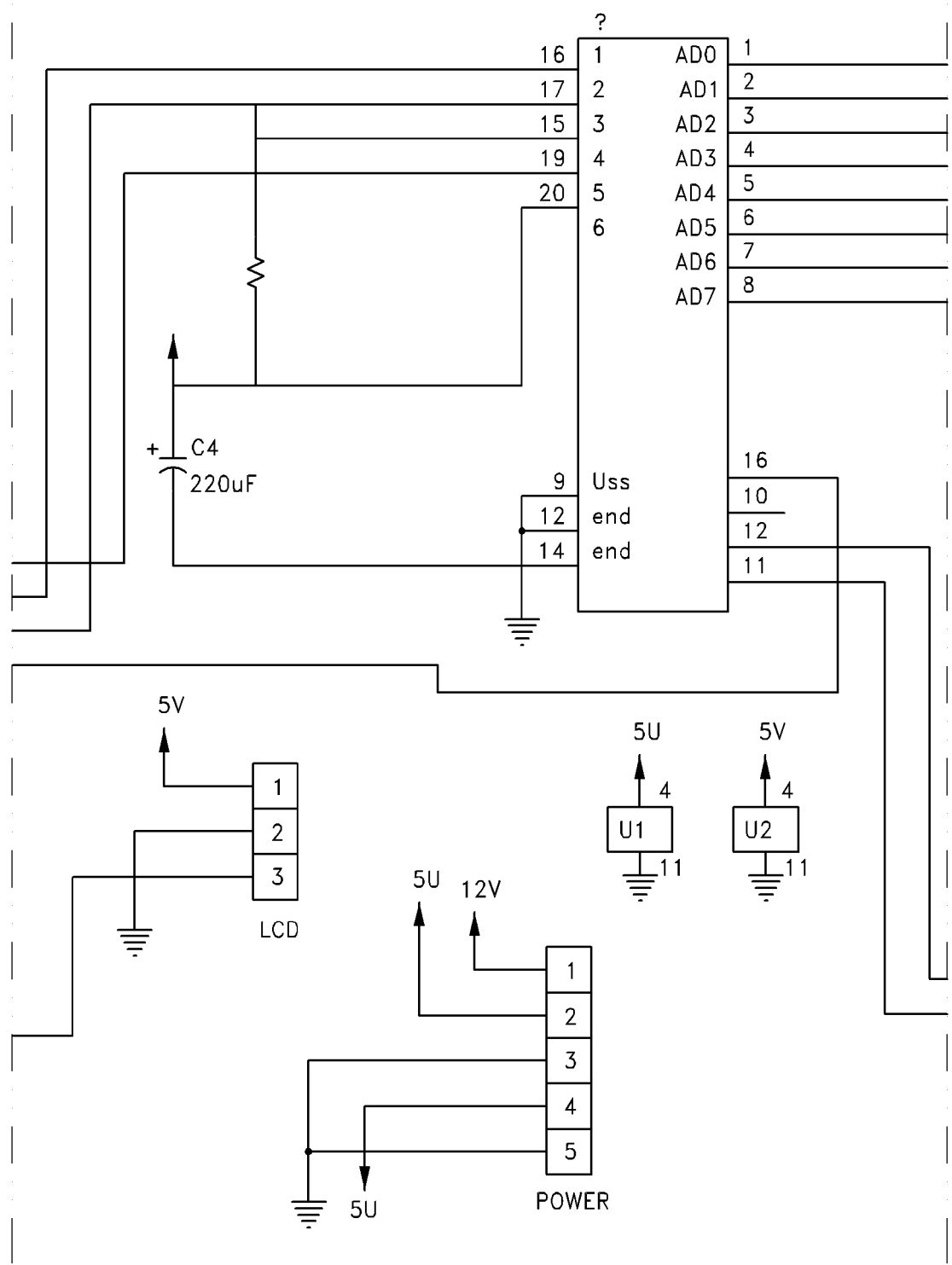
FIG. 22A₂

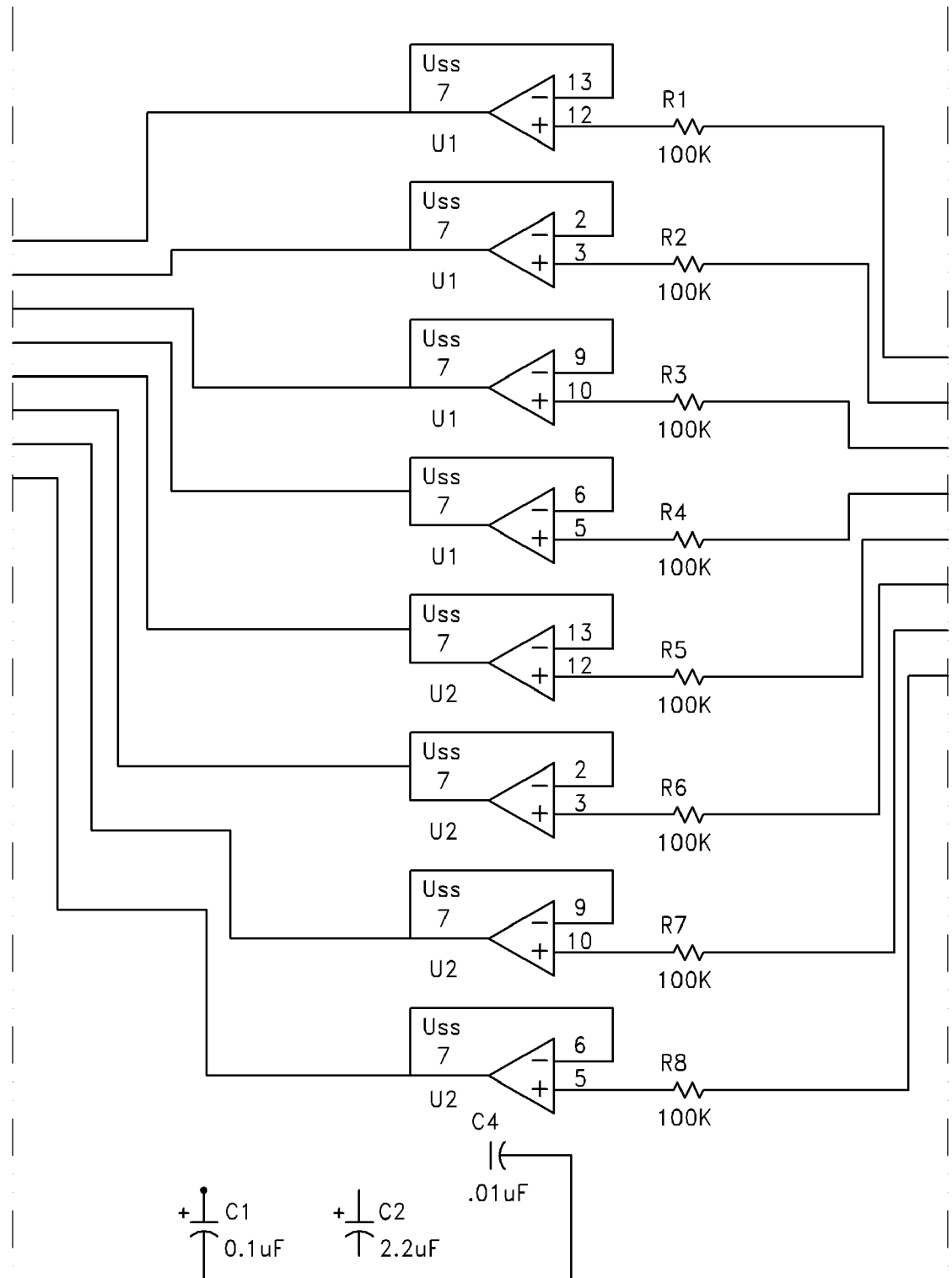
FIG.22A₃

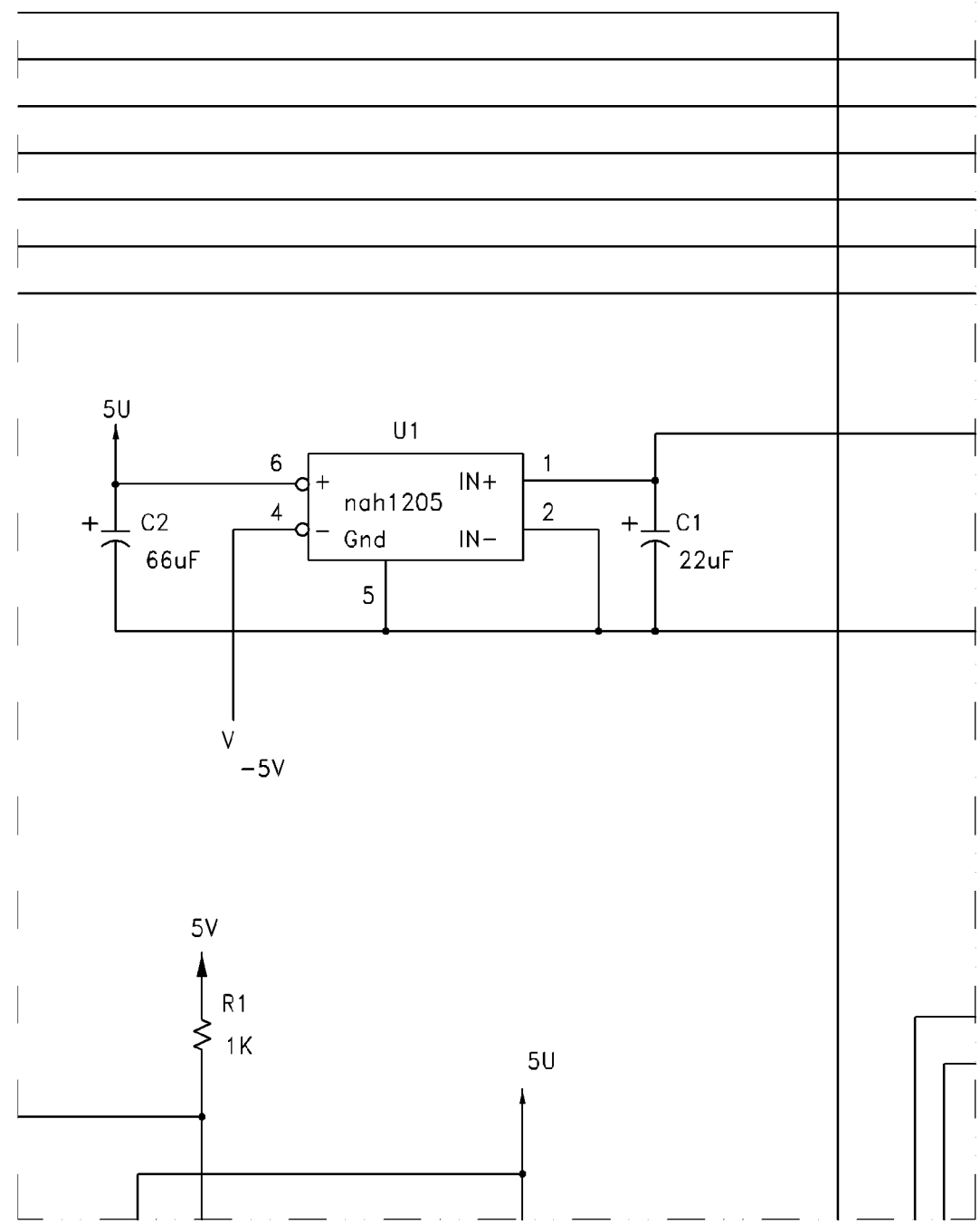
FIG. 22A₄

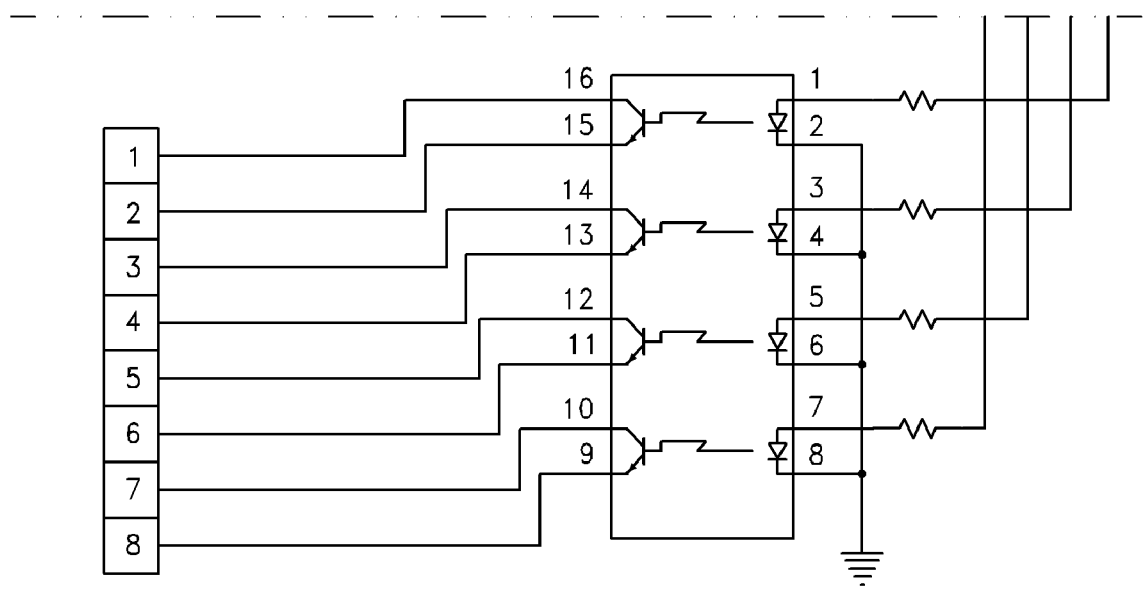
FIG. 22A₅

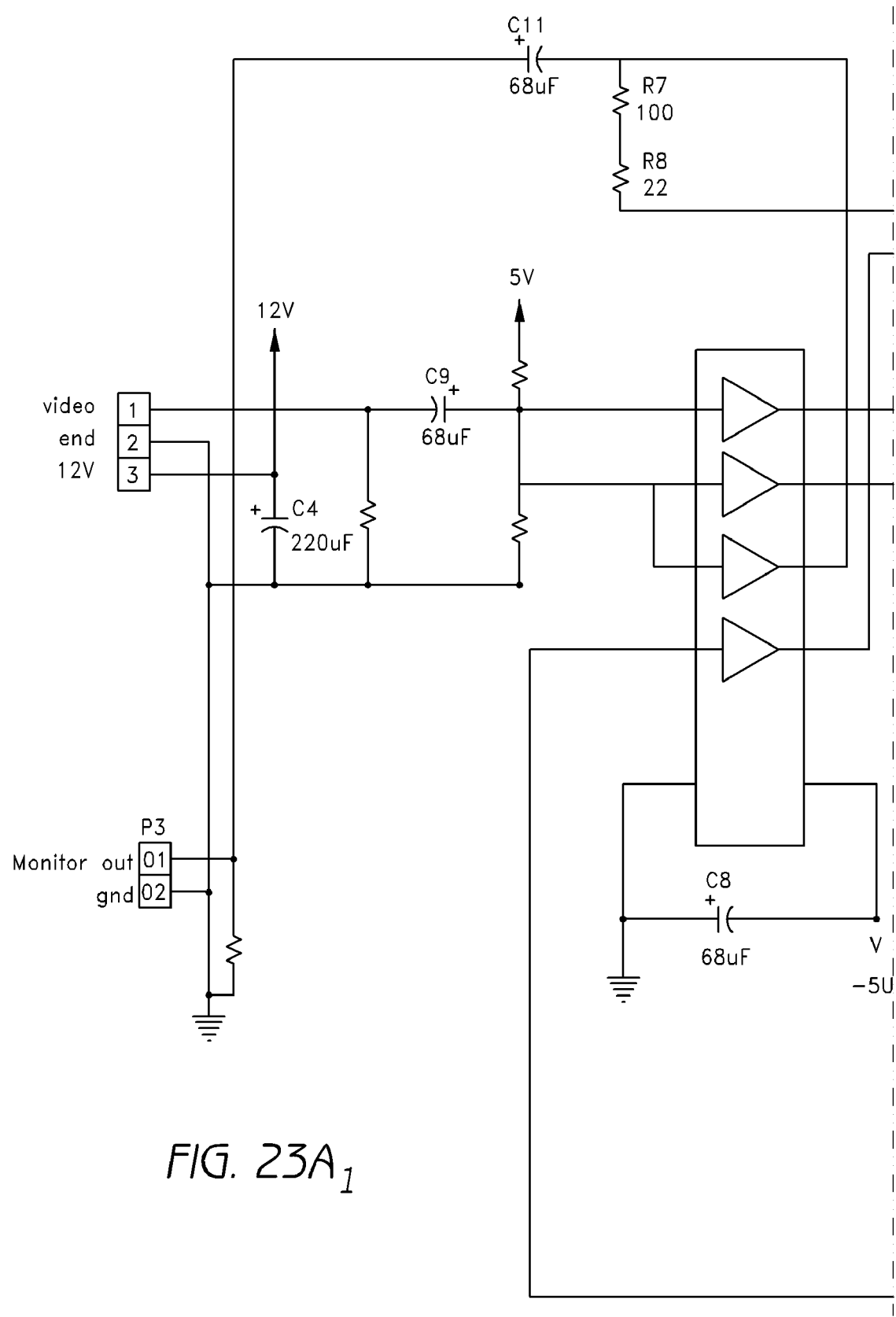
FIG. 23A₁

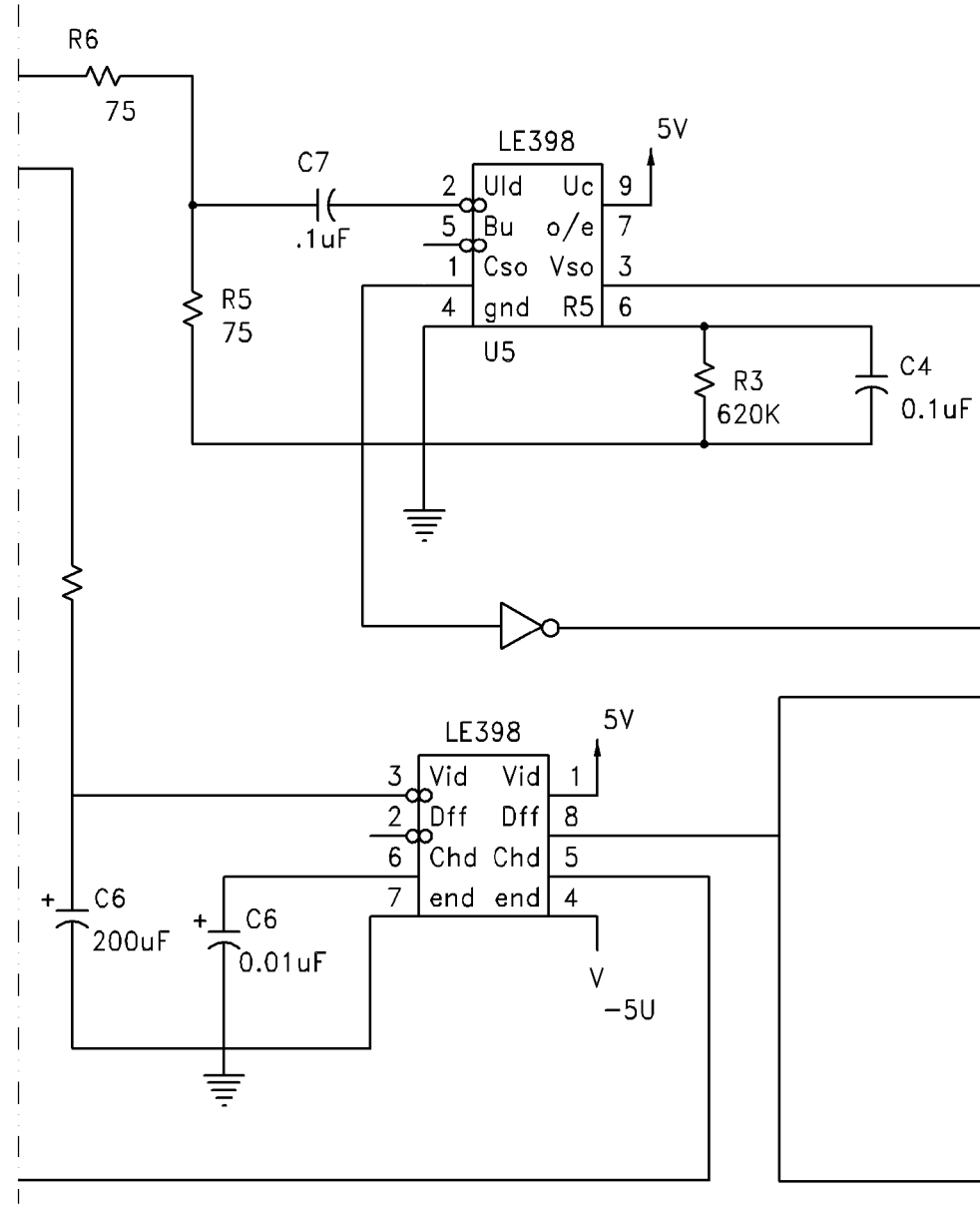
FIG. 23A₂

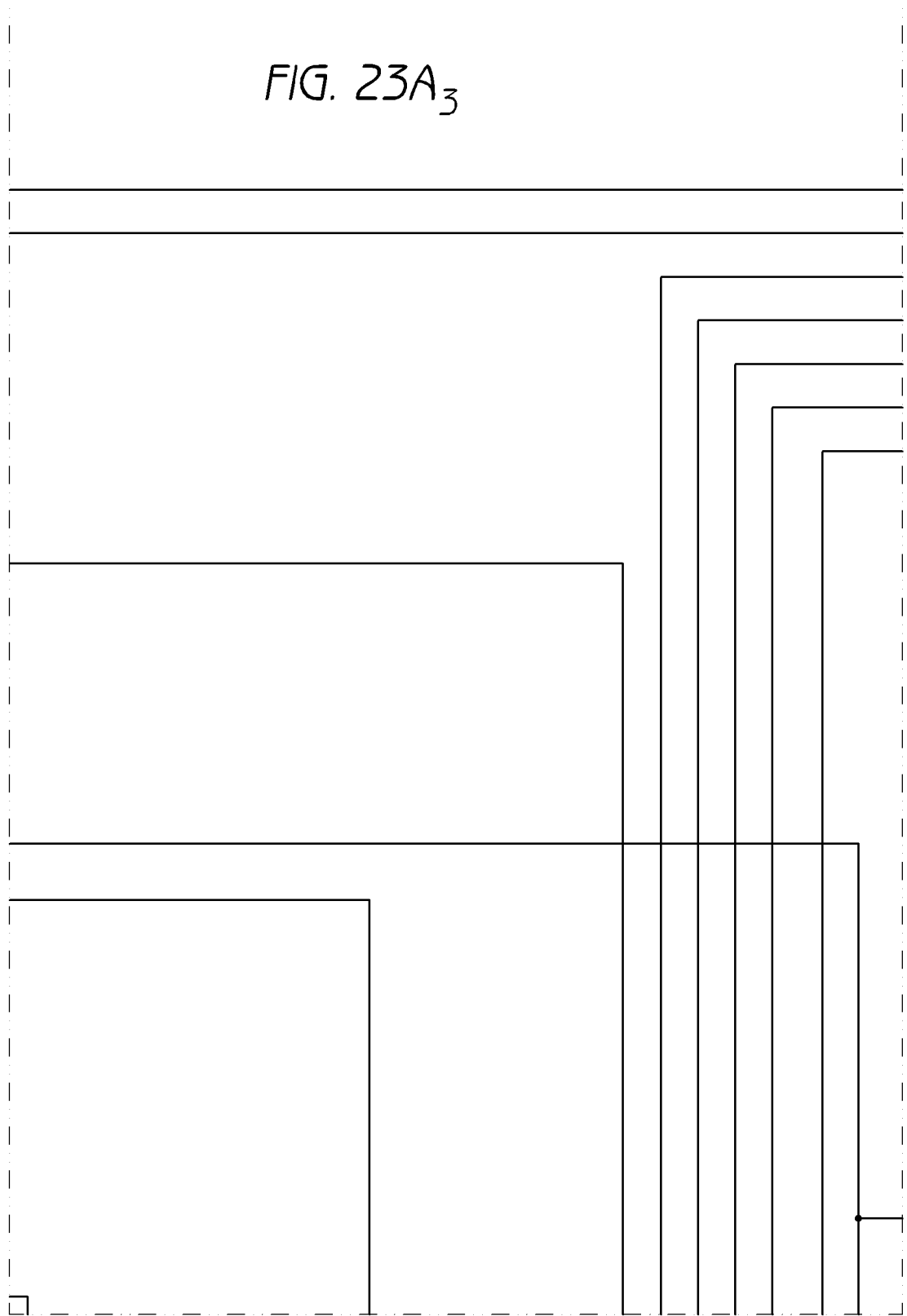
FIG. 23A₃

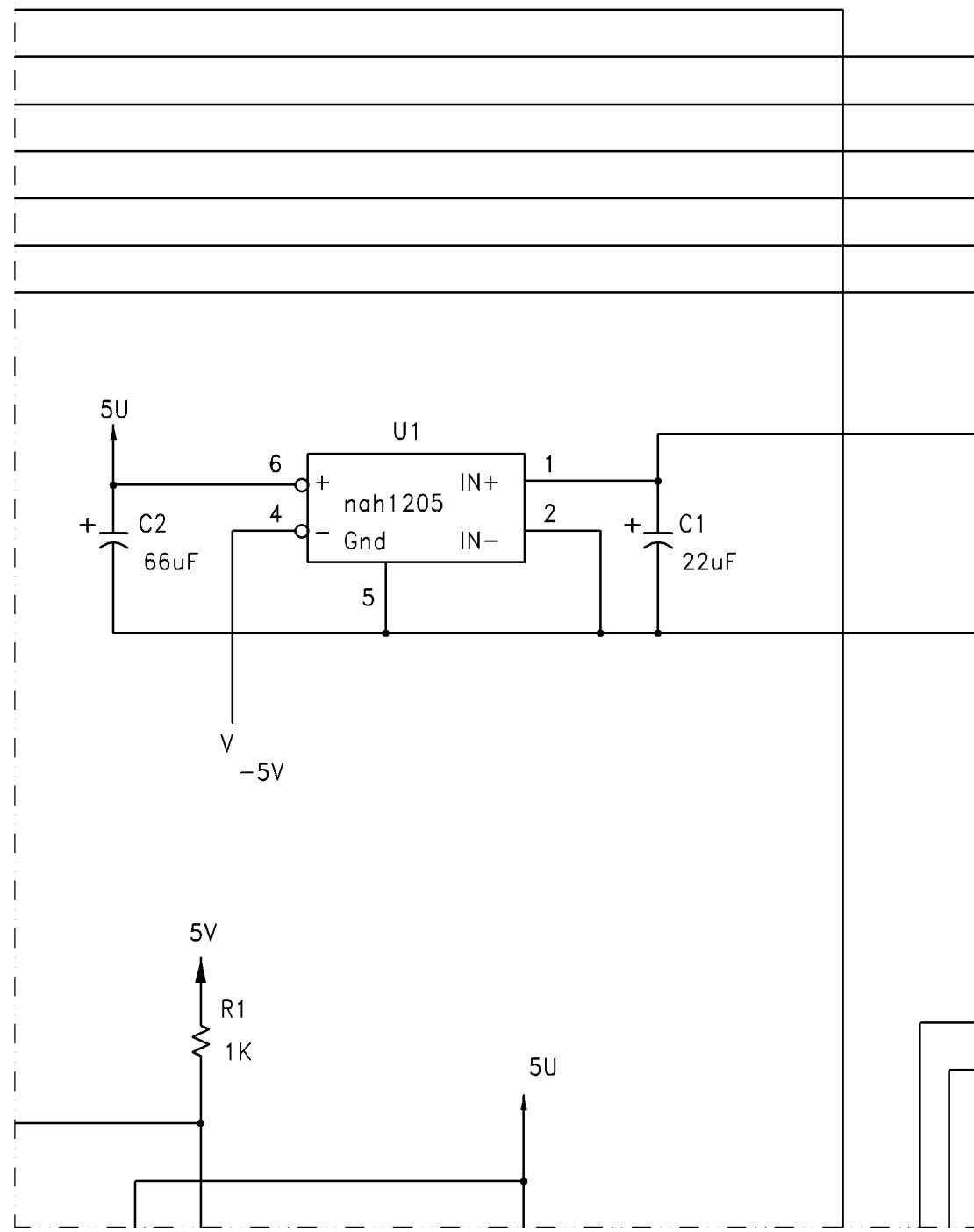
FIG. 23A₄

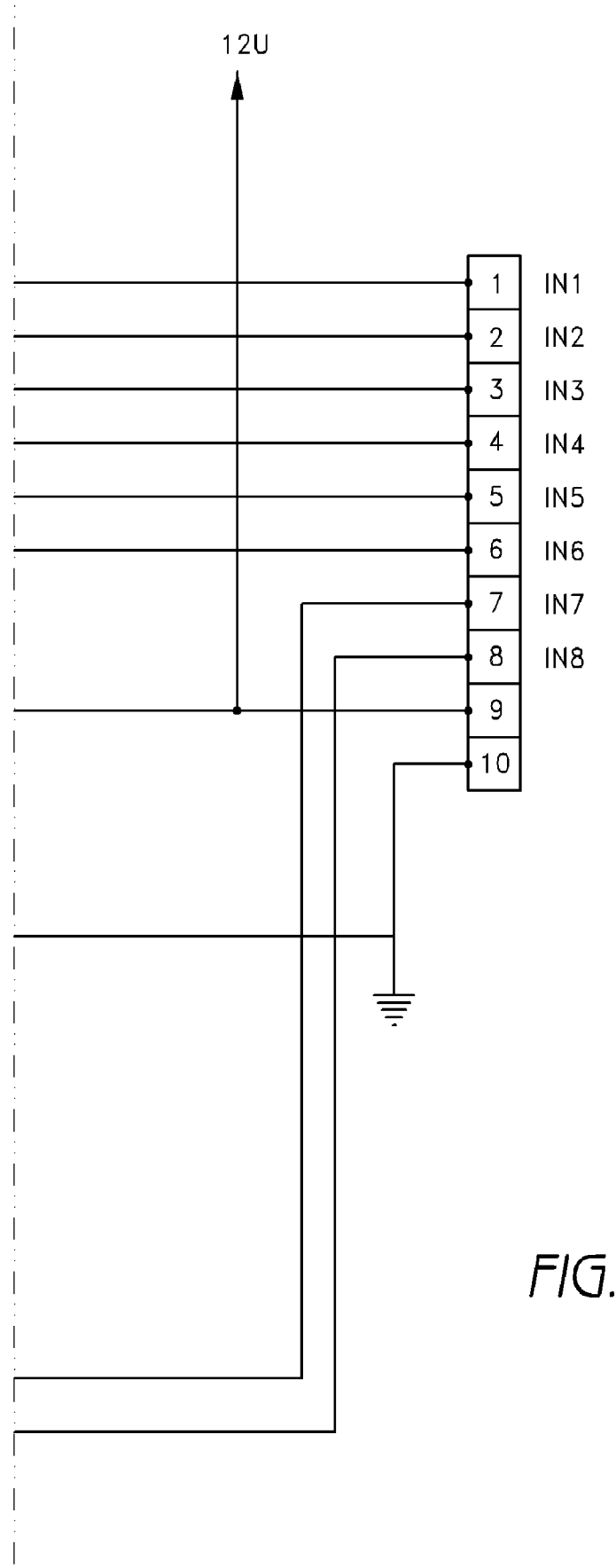
FIG. 23A₅

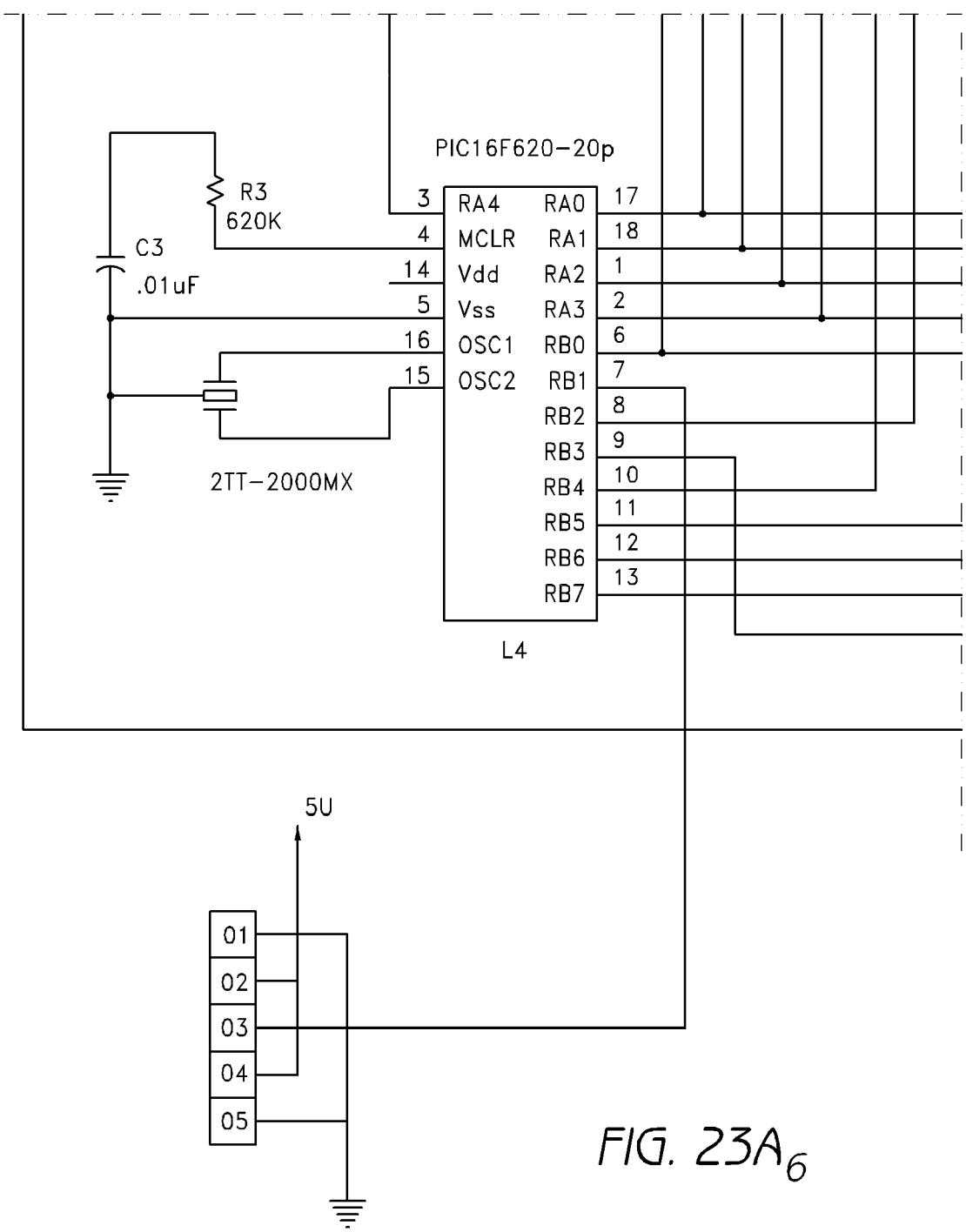
FIG. 23A₆

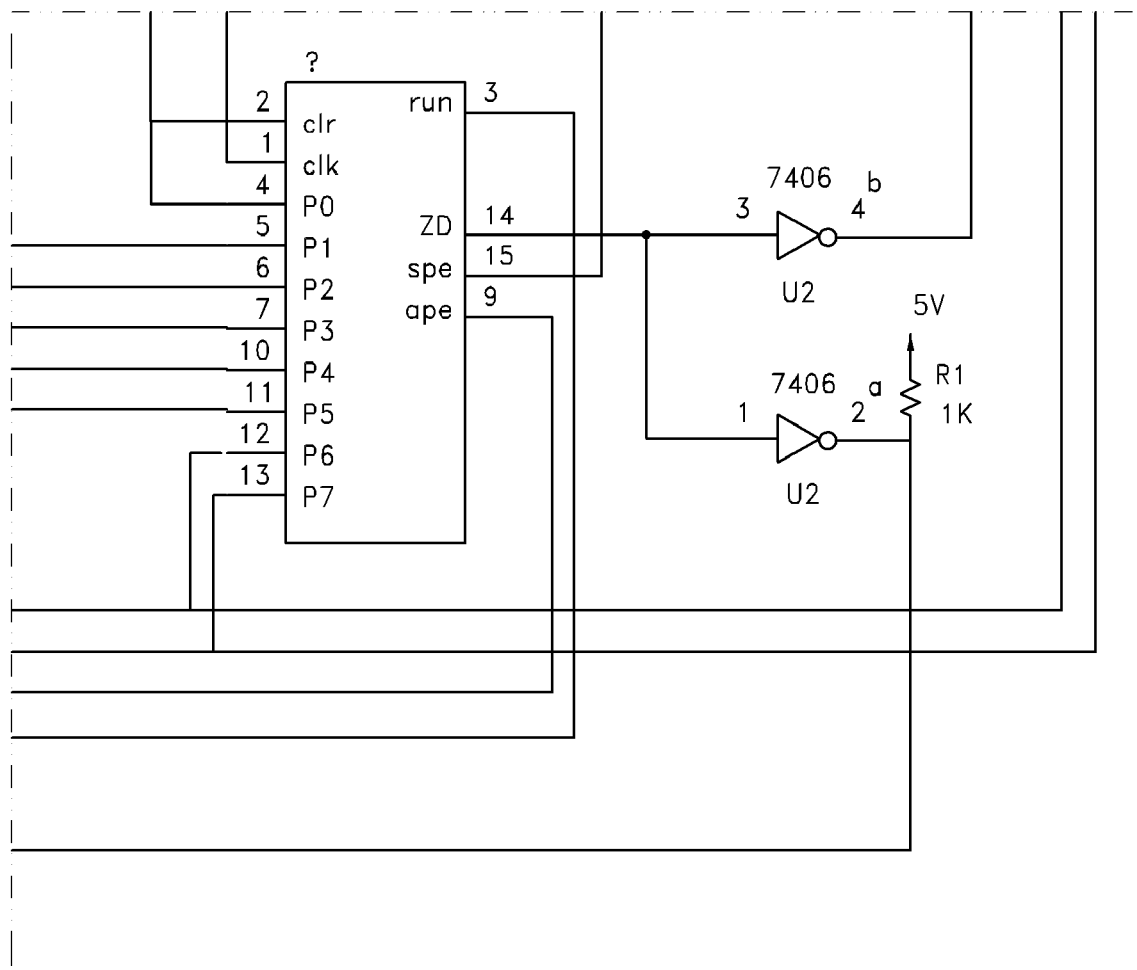
FIG. 23A$_7$

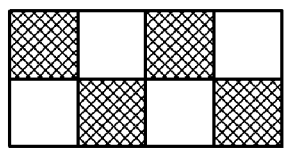
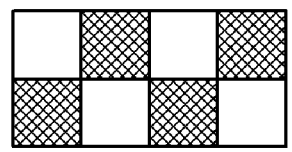
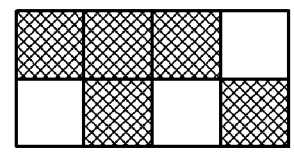
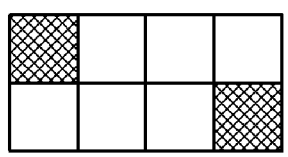
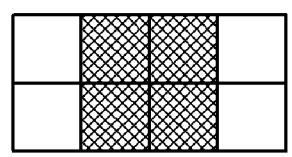
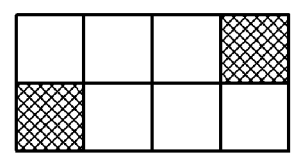
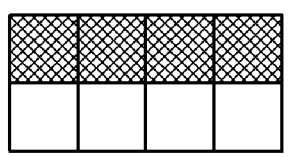
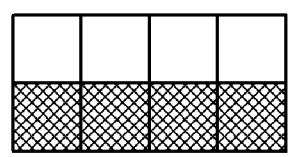
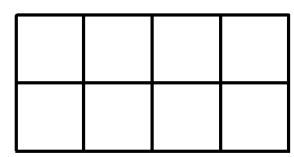
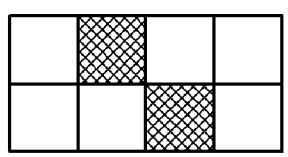
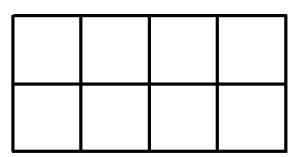
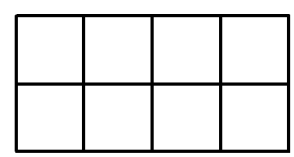
FIG. 26

| Basic Drug Type | Local Site Preference | 1st action Display Message | 1st action Yes Pointer | 1st action No Pointer |
|---|---|---|---|---|
| Ignitable | Eco | Accept – Ignitable Empty? <Y N> | Ask Sharps Question | Open Ignitable |
| Ignitable | Cost | Accept – Ignitable Empty? <Y N> | Ask Sharps Question | Open Ignitable |
| | | 2nd action Display Message | 2nd action Yes Pointer | 2nd action No Pointer |
| Ignitable | Eco | Accept – Ignitable Sharps? <Y N> | Open Red Sharps | Ordinary Solid Waste |
| Ignitable | Cost | Accept – Ignitable Sharps? <Y N> | Open Red Sharps | Ordinary Solid Waste |

FIG. 27

| Basic Drug Type | Local Site Preference | Waste Stream ID | Comment Display Message | Empty Not Sharp Pointer | Empty Sharp Pointer | Not-Empty Not-Sharp Pointer | Not-Empty Sharp Pointer |
|---|---|---|---|---|---|---|---|
| P-Ignitable | Eco | A-EPI | Open-P-Ignitable | O-PUD | O-PUD | O-IGN | O-IGN |
| P-Ignitable | Cost | A-CPI | Open-P-Ignitable | O-PUD | O-PUD | O-IGN | O-IGN |

FIG. 29

METHOD FOR COMBINED DISPOSAL AND DISPENSING OF MEDICAL ITEMS

RELATED APPLICATIONS

This application is a continuation of U.S. patent application Ser. No. 12/025,712, filed Feb. 4, 2008, and claims the benefit of U.S. Provisional Application No. 60/888,266, filed Feb. 5, 2007 and U.S. Provisional Application No. 60/888,269, filed Feb. 5, 2007, and is a continuation-in-part of U.S. patent application Ser. No. 11/777,243, filed Jul. 12, 2007, now U.S. Pat. No. 7,487,100 which is a continuation of U.S. patent application Ser. No. 11/347,823, filed Feb. 3, 2006, now issued as U.S. Pat. No. 7,275,645 which is a continuation-in-part of U.S. patent application Ser. No. 10/945,223, filed Sep. 20, 2004, now issued as U.S. Pat. No. 7,119,689, which claims priority to U.S. Provisional Application No. 60/504,170, filed Sep. 19, 2003 and U.S. Provisional Application No. 60/589,118, filed Jul. 19, 2004; and U.S. patent application Ser. No. 11/347,823, identified above, also claims priority to U.S. Provisional Application No. 60/649,819, filed Feb. 3, 2005, U.S. Provisional Application No. 60/679,187, filed May 9, 2005, U.S. Provisional Application No. 60/712,256, filed Aug. 29, 2005, and U.S. Provisional Application No. 60/742,212, filed Dec. 2, 2005, all herein incorporated by reference.

BACKGROUND

1. Field of the Invention

The invention relates in general to the field of disposal systems and dispensing systems, and in particular to a combination system for sorting medical waste for disposal and for dispensing certain medications and other medically-related items.

2. Description of the Related Art

The Environmental Protection Agency (EPA) enforces the Resource Conservation & Recovery Act (RCRA) which was enacted in 1976 in order to control the disposal of harmful or hazardous waste materials. There are currently over 100,000 drugs commercially available in the United States, of which about 14,000 are considered hazardous by RCRA requirements. A typical medium size hospital utilizes thousands of different drugs in a year of which hundreds are considered hazardous. The EPA is increasingly enforcing hospitals' compliance with the RCRA requirements because it has been shown in several studies that the 72 million pounds of pharmaceutical waste generated each year by hospitals and individuals is contributing to the pollution of groundwater and endocrine system damage in humans and other species. In addition, many organizations including Hospital for a Healthy Environment (H2E) and Joint Council for Accreditation of Healthcare Organizations (JCAHO) are pressing hospitals to be more environmentally friendly. In view of these changes, hospitals are increasing efforts to audit their own compliance with the laws. As a result, these hospitals are becoming more aware of the difficulty of sorting the numerous pharmaceutical waste streams that the EPA, Department of Transportation (DOT), Drug Enforcement Administration (DEA), and some states require.

More than 3.2 million tons of medical waste is generated by hospitals, medical clinics and pharmaceutical manufacturers each year. Half of this waste is considered infectious. Most of the infectious waste was treated in over 2400 incinerators throughout the country, until 1998 when the EPA began to enforce tough environmental emission laws that have reduced the number of incinerators to just over a hundred nationwide. Now much of the infectious waste is treated by alternative technologies such as autoclaves and chemical processors. There is very little choice for hospitals because of the upfront cost and large footprint of the processing equipment. Although many companies have offered different kinds of equipment, the prices vary from a few hundred thousand dollars for smaller units to a few million for large units. Because of the long cycling times to decontaminate the waste, the equipment typically is very large in order to provide acceptable throughput. There are also several companies that provide a service to hospitals by utilizing chemical processors mounted on trucks. They go to a facility and decontaminate the infectious waste, allowing the treated waste to be hauled to a local landfill. There are concerns that this technology may not completely treat the waste in all circumstances and the chemical residue left after processing may remain an ecological issue.

Increasingly, hospitals are required to comply with the recent and projected enforcement of federal and state hazardous pharmaceutical waste regulations. Currently, clinicians must manually sort pharmaceutical waste streams into different colored containers for proper disposal of the separate waste streams. A hospital formulary may contain an average of 4000 different pharmaceuticals. As many as 1,000,000 spent pharmaceuticals are sorted each year in a typical hospital. It is often not clear to a clinician which pharmaceuticals or waste materials are hazardous simply by looking at the container. Such confusion may lead to clinicians throwing hazardous drugs in non-hazardous containers such as sharps containers, infectious waste bags, non-hazardous pharmaceutical containers or simply down the drain. Clinicians are consumed with patient care and patient safety; thus, manually sorting of pharmaceuticals is not a priority.

Further, floorspace in hospitals and other medical facilities has become increasingly limited, especially since such facilities typically attempt to maximize the number of patient or treatment rooms.

SUMMARY OF THE INVENTION

There remains a need for a system for allowing clinicians to more easily sort medical waste items for appropriate disposal. There also remains a need for an automated system of waste disposal that encourages and facilitates hospital compliance with the relevant federal and state regulations. Because individual institutions typically both dispense drugs and dispose of drugs and other medical items, there is also a need for a combined disposal and dispensing apparatus. In several embodiments, this combination device is smaller in size than using both devices together. In other words, the combined device has a "reduced footprint," which is advantageous in many institutions where space is limited. A combined system, as used herein shall include a device that dispenses drugs or medical devices and a device that sorts and/or disposes of said drugs and devices. The two devices can be combined in several ways, including coupled, attached, coordinated, or integrated into a single device. In some embodiments, the two systems are physically separated but combined in the sense that they share a common database and/or a processor. In alternative embodiments, the dispensing system is used without the disposing system, and vice versa.

Several embodiments of the present application describe systems and devices to sort and process infectious and pharmaceutical waste streams, which, in some embodiments, are coupled to a drug dispensing system. A dispensing system that dispenses medical items may dispense, for example, medications, pharmaceuticals, vitamins, biological fluids, syringes, needles, medical apparel, and other medical items.

In one embodiment, the invention comprises a system for dispensing drugs that automates dispensing of medical items. Automation of drug retrieval, access, and replenishment will reduce patent error and increase user compliance various medical regulations. Automated and efficient packaging systems, using for example bar code labeling, RFIDs, coded containers, and/or scanners, will facilitate accurate delivery of medications to patients.

Several embodiments of a medical waste sorting system advantageously provide a labor savings for doctors, nurses and other clinicians by taking the bulk of the decision making associated with sorting medical waste away from the clinician. In one embodiment, a medical waste sorting system is provided, which will help clinicians conveniently comply with the recent and projected enforcement of federal and state hazardous waste laws. In some embodiments, the system can be configured to scan a bar code, RFID tag, or other system for identifying a spent drug. The spent drug can then be classified into an appropriate waste category, and a door can be automatically opened to provide access to a unique waste container for convenient disposal of the drug in compliance with applicable regulations.

In addition to the need for medical and pharmaceutical waste sorting, there exists a need to improve areas of water quality analysis and workplace safety. These areas include sampling water quality throughout the hospital to pinpoint inappropriate dumping of hazardous materials down the drain and improved programs that reduce hospital worker exposure to hazardous materials in the workplace.

In one embodiment, the invention comprises a system and method for sorting waste using one or more restricted access containers. In a preferred embodiment, the system and method comprises a plurality of containers associated with a plurality of waste categories, wherein at least one of the containers is configured to restrict access to the internal portion of the container when the container is open. In one embodiment, the container prevents unauthorized personnel from accessing the waste item once the item has been deposited into the container, thereby restricting access to the internal contents of that container. Restricted access containers can be also be used for dispensing drugs and other medical items. In other words, in some embodiments, only authorized users can gain access to pharmaceuticals and other medical items.

In one embodiment, a system for sorting a plurality of waste items and dispensing a plurality of dispensable items includes a disposal portion and a dispensing portion. In some embodiments, the disposal portion includes a plurality of waste containers, each of which is associated with one or more waste categories. The disposal portion additionally includes a waste item identification device, which is configured to receive identification data for a waste item, and a database, which includes waste item classification information. The disposal control system is configured to compare identification data received by the waste item identification device with information contained in the database. Further, the disposal control system is configured to assign a waste item to at least one waste category. The system is configured to identify at least one of the waste containers based on the waste category. In some embodiments, the dispensing portion includes a plurality of dispensing compartments, each of which is configured to hold at least one dispensable item. The dispensing portion also includes a dispensing data entry device configured to receive a dispensing instruction and a dispensing control system configured to process a dispensing instruction and allow access to an interior of a corresponding dispensing compartment.

In one embodiment, the dispensing portion can employ a robotic function such as a "pick and place mechanism"; essentially an xy or xyz mechanism, that upon a dispensing instruction and a dispensing control system configured to process a dispensing instruction will pick a packaged medication in a magazine. The magazine may include like medications. The picked medications that are specific to a particular patient are automatically deposited into a portable container by the pick and place mechanism or manually to the clinician who engages the dispenser. The footprint of the combo device can be reduced if the dispenser is designed to reach the ceiling or even beyond such as into the headspace between hospital floors. The compartments of medications could be reached by employing a dumb waiter approach for medications that are above or near the ceiling. The pick and place and mechanism would also accomplish the same in some embodiments.

In another embodiment, the database is located on a remote server which is physically separated from the control system. In other embodiments, the disposal control system is further configured to notify a user of the assigned waste category. In yet another embodiment, the disposal control system is configured to provide access to a waste container associated with the assigned waste category. In one embodiment, the disposal control system is configured to provide access to a waste container associated with the assigned waste category by exposing an opening in such waste container.

In one embodiment, the waste item identification device includes a barcode scanner, which is configured to scan waste items. In another embodiment, the disposal portion additionally includes a data entry device, which is configured to receive information regarding a waste item. In some embodiments, the waste data entry device includes a keypad.

In one embodiment, one or more dispensing compartments include a tray, which is configured to slide between a closed and an open position. In other embodiments, the tray includes two or more subcompartments. In some embodiments, at least one dispensing compartment comprises a closure member, which is configured to move between an open and a closed position.

In one embodiment, the dispensing data entry device of the dispensing portion includes a keypad. In other embodiments, the dispensing portion additionally comprises a display. In yet other embodiments, the disposal portion and the dispensing portion comprise a unitary member.

In one embodiment, a combination system includes a disposal portion and a dispensing portion. The disposal portion includes a plurality of waste containers, each of which is associated with at least one of a plurality of waste categories, and a waste item identification device, which is configured to receive identification data for a waste item. In some embodiments, the combination system is configured to identify at least one of the waste containers based on the identification data received by the waste item identification device. In one embodiment, the dispensing portion of the combination system includes a plurality of dispensing compartments, each of which is configured to hold at least one dispensable item, and a data entry device, which is configured to receive a dispensing instruction. The dispensing portion additionally comprises a dispensing control system configured to process a dispensing instruction and allow access to an interior of a corresponding dispensing compartment.

In one embodiment, the combination disposal and dispensing system is further configured to notify a user of the identified waste container. In other embodiments, the combination system is configured to notify a user of the identified waste container by exposing an opening in said waste container. In yet other embodiments, the waste item identification device includes a barcode scanner which is configured to scan the waste item.

In some embodiments, one or more dispensing compartments include a tray which is configured to slide between a closed and an open position. In other embodiments, one or more dispensing compartments comprise a closure member which is configured to move between an open and a closed position.

In one embodiment, the data entry device of the dispensing portion includes a keypad. In another embodiment, the combination disposal and dispensing system is connected to a network. In yet other embodiments, the waste items comprise pharmaceutical waste.

In one embodiment, a device for sorting a plurality of medical waste items and dispensing a plurality of dispensable medical items includes disposal and dispensing portions. In one embodiment, the disposing portion is configured to receive at least one of the medical items (e.g., in at least a partially used, expired or otherwise undesired state) that was dispensed by the dispensing portion. In some embodiments, the disposal portion comprises a plurality of medical waste containers, each of which is associated with at least one of a plurality of waste categories, and a waste item identification device, which is configured to receive identification data for a medical waste item. The disposal portion of the device is configured to identify at least one of the medical waste containers based on the identification data received by the waste item identification device. In other embodiments, the dispensing portion comprises a plurality of dispensing compartments, each of which is configured to hold at least one dispensable medical item. The dispensing portion of the device additionally includes a dispensing data entry device configured to receive a dispensing instruction and a dispensing control system configured to process a dispensing instruction and allow the corresponding dispensing compartment to move to an open position.

In one embodiment, a waste item identification device configured to determine a qualitative parameter of an item of waste, and a database comprising waste item classification information is provided. The system and method may also include a control system programmed to compare the qualitative parameter of the item to information contained in the database, and assign the item to a waste category. The system and method (e.g., the control system in one embodiment) can be further configured to identify at least one of the containers based on the waste category.

In a combined waste dispensing and disposal system, an identification device is provided for identifying the drug or other medical item to be dispensed. For example, in one embodiment, a user will scan a bar code from a patient's wristband or other source. The drug dispensing system will read the code, and display all of the medications that patient has been administered or should be administered. The user then confirms which of the drugs should be dispensed. In another embodiment, a user can manually enter a patient's name and/or other identifying information to obtain the dispensed pharmaceutical.

In one embodiment, the waste disposal system or the combined disposal/dispensing system includes containers comprising one or more lids. In one embodiment, one of the containers comprises a lid. In another embodiment, all of the containers comprise lids. In yet another embodiment, some of the containers comprise lids. In a further embodiment, one lid is used to cover two or more containers. In one embodiment, the system comprises one or more lids, wherein the lid is formed integrally with the container.

In one embodiment, a system and method for sorting waste based on primary and alternate disposal strategies is disclosed. In a preferred embodiment, the system and method comprises a plurality of containers associated with a plurality of waste categories. The system and method may also comprise a waste item identification device configured to determine a qualitative parameter of a waste item. In one embodiment, the system also comprises a database comprising waste item classification information. The system and method may also comprise a control system programmed to compare the qualitative parameter of the waste item to information contained in the database, assign the waste item to a waste category, determine the preferred container in which the waste item should be placed based on the assigned waste category, determine if said preferred container is capable of accepting the waste item and direct a user to perform an alternative disposal action if the preferred container is not capable of accepting the waste item.

In one embodiment, the user is directed to dispose of the waste item in an alternative waste container. In a further embodiment, the user is directed to dispose of the waste item in a waste container located in another room. In yet another embodiment, the user is directed to dispose of the waste item in a waste container located on another floor. In one embodiment, the user is directed to dispose of the waste item in a bulk container. In a further embodiment, the user does not have access to the internal contents of the containers.

The use of primary and alternate strategies described herein may also be extended to the dispensing of drugs and other medical items. For example, the system may be configured to query the user whether or not a generic drug may be substituted as an alternative to the requested brand name drug. Alternatively, the user may activate a setting that automatically dispenses the generic version of a drug, unless the brand name is specifically requested. In other embodiments, comparable drugs or other medical items that are more environmentally friendly or more compliant with the institution's disposal system may be automatically substituted for the requested drug.

In one embodiment, a system and method for sorting waste using a manual input system is disclosed. The manual system or method may also be used for the combined drug dispensing/disposal combination. In one embodiment, the system and method comprises a plurality of container compartments, with each container compartment configured to receive a removable container. The system may also comprise a plurality of removable containers, wherein each removable container comprises an opening and a movable lid. In another embodiment, the removable containers are configured to be placed within the container compartments, wherein each of the removable containers is associated with at least one of a plurality of waste categories. In one embodiment, the movable lid is movable to an open position and/or a covered position. The system may comprise a manual input system for entering additional information regarding the waste item. The system and method may also comprise a waste item identification device configured to read a barcode on an item of waste. The system and method may further comprise a database comprising waste item classification information derived from rules and regulations affecting the disposal of the waste item. In yet another embodiment, a control system configured to compare information obtained from the barcode to information contained in the database is provided. The control system may further configured to assign the item to at least one waste category, to identify at least one of the removable containers based on the waste category, to allow the movable lid of the identified removable container to move to the open position and/or to lock the movable lid in the covered position when the control system determines that the removable container is full.

In some embodiments, the waste identification device comprises a handheld device. In some embodiments, the waste identification device may comprise a wireless handheld device that is operable to open the appropriate container for disposal of the waste item. In yet other embodiments, the waste identification device comprises a wireless handheld device that is operable to signal the appropriate container for disposal of the waste item.

In one embodiment of the invention, a system for sorting a plurality of waste items is disclosed. In one embodiment, the system comprises a plurality of containers, with each container associated with at least one waste category. In a preferred embodiment, a handheld waste item identification device is configured to determine a qualitative parameter of an item of waste. In one embodiment, a database comprising waste item classification information is provided. In a further embodiment, a control system is configured to compare information obtained from the handheld waste item identification device to information contained in the database. In another embodiment, the control system is further configured to assign the item to at least one waste category. In yet another embodiment, the control system is further configured to identify at least one of the containers based on the waste category.

In some embodiments, the handheld waste item identification device comprises a barcode scanner. In some embodiments, the handheld waste item identification device is wireless. The wireless handheld waste item identification device, in some embodiments, communicates wirelessly using infrared technology, Bluetooth technology, and/or radiofrequency. In a preferred embodiment, the handheld waste item identification device displays information regarding the waste item being discarded. In one embodiment, the information displayed on the handheld device comprises information regarding the particular waste container in which the waste item should be placed. In some embodiments, the handheld device may be capable of determining the user's location so that the nearest waste container in which the waste item should be placed may be identified.

In one embodiment, the system comprises a handheld device that is used to scan the waste item. The system then determines in which remote container the waste item should be disposed. The handheld can provide text instructions to the user as to the proper container. For example, the handheld can instruct the user (via text or otherwise) to deposit the waste item into a certain container. The handheld can also identify the proper container for waste disposal in certain embodiments. Alternatively, the system can automatically open the proper container for disposal. After the waste item is disposed, the container can be manually or automatically shut.

In some embodiments, the waste comprises medical or pharmaceutical waste. In some embodiments, the waste item classification information comprises classification information based on local, state, or national environmental laws or regulations. In other embodiments, the waste item classification information comprises classification information based on local, state, or national drug enforcement laws or regulations. In other embodiments, the waste item classification information comprises classification information based on a user's customized requirements. In yet other embodiments, the waste item classification information comprises classification information based on one or more different bases, including environmental laws or regulations, drug enforcement laws or regulations and/or a customized system. In one embodiment, at least one container comprises at least one lid that is operable to be manually closed by the user. In some embodiments, one or more containers comprise a machine-readable identification key enabling said container to be hot-swapped.

BRIEF DESCRIPTION OF DRAWINGS

FIG. 3 is a perspective illustration of an embodiment of a wall-mounted sorting and disposal station;

FIG. 4 is a perspective illustration of one embodiment of a floor-standing sorting and disposal station;

FIG. 22A is an electronic schematic of one embodiment of an array of light detectors, illustrated further in FIGS. $22A_1$-$A_5$;

FIG. 26 is a diagram of one embodiment of machine-readable patterns for containers;

FIG. 27 is a table of examples of a 2-button action file;

FIG. 29 is a table of examples of a 4-button action file;

FIG. 48I is a cross-sectional view of the drive mechanism illustrated in FIG. 48B

DETAILED DESCRIPTION

Waste Sorting and Disposal System

Figure 1:
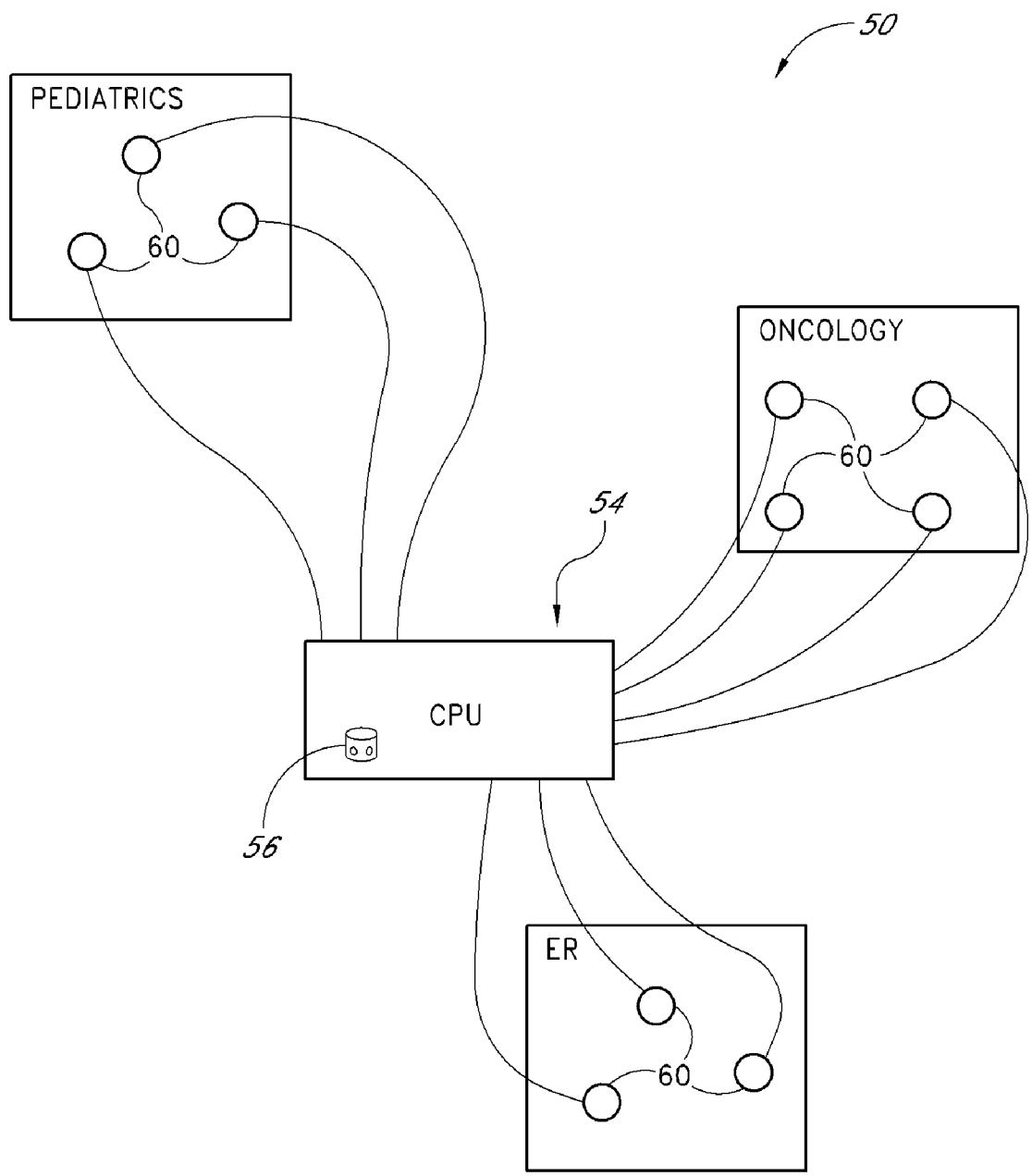
FIG. 1 is a schematic illustration of one embodiment of medical waste sorting and disposal system including a plurality of interconnected sorting and disposal stations in a centralized network.

Several embodiments of devices and methods for sorting a plurality of medical wastes will now be described with reference to the attached figures. In several embodiments, the waste sorting and disposal system is automated. In some embodiments, a medical waste sorting system comprising a plurality of individual sorting and disposal stations connected to one another via a centralized or de-centralized network is provided. Alternatively, a medical waste sorting system can comprise one or more stand-alone sorting and disposal stations configured to operate independently of any other device. Although some of the following embodiments are described in the context of individual stand-alone stations, it should be recognized that such individual stations can be connected in a networked system to provide additional functionality or to improve efficiency. Conversely, some embodiments are described below in the context of networked systems, certain features and advantages of which can be readily applied to individual stand-alone systems as will be clear to the skilled artisan. The term "sorting" is a broad term and shall be given its ordinary meaning and generally refers to the distribution of one or more waste items into one or more appropriate waste receptacles. The term "disposing" is also a broad term and shall be given its ordinary meaning and shall, in some embodiments, generally refer to the discarding, "throwing out" or otherwise placing of one or more items of waste into an appropriate receptacle, container or liner. The terms sorting and disposing may be used interchangeably. As used herein, the terms receptacle and container are broad terms that can be used interchangeably.

In one embodiment, a waste sorting and disposal station comprises a sorting station or machine, which includes a series of container positions or compartments, each compartment being configured to receive a removable container for collecting waste belonging to a particular category or classification. Some embodiments of a sorting station comprise a waste-identifying device, a processor configured to carry out a waste-sorting algorithm, and a waste-sorting mechanism. As used herein, the term "removable" shall be given its ordinary meaning, and shall include disposable or reusable containers.

In some embodiments, a sorting machine comprises one or more sensors for determining the presence of a container, a type of container, and/or a volume or weight of a container. In another embodiment, the sorting machine includes one or more sensors (e.g., an optical sensor) to determine which container the item was deposited into and/or a time at which an item is deposited. Additionally, a sorting machine/station can include any of a variety of computer peripherals, such as user input devices (e.g., touch screens, keyboards, pointer devices, etc.), display devices, sound-producing devices (e.g., speakers or buzzers), or any other peripheral device.

In many embodiments, several container types are provided, each type being associated with one or more particular categories or classifications of pharmaceutical waste. In one embodiment, a single container is associated with a single waste category. In another embodiment, a single container is associated with multiple waste categories.

In some embodiments, container types can include sharps containers, chemotherapy agent containers, infectious waste containers, ignitable waste containers, hazardous P-list waste containers, hazardous U-list waste containers, toxic pharmaceutical waste containers, non-toxic pharmaceutical waste containers, chemotherapy sharps containers, corrosive waste containers, or reactive waste containers. Additional container types can also be used as desired. In one embodiment, the container types are pre-designated by the container provider. In other embodiments, the container types are assigned by the hospital so that the hospital can individually customize its waste sorting system. For example, some hospitals may desire to define their own waste categories in order to comply with internal goals, thus user-defined container types can also be provided.

In a preferred embodiment, a waste identifying mechanism is provided. In several embodiments, the waste identifying mechanism is configured to identify a particular item of waste. Identification is preferably accomplished prior to deposit into the appropriate container. Identification of the waste item can be accomplished by scanning a barcode, reading a label (e.g., using an optical scanner and Optical Character Recognition software), reading a Radio Frequency identification (RFID) tag, chemical sensors, spectroscopic analyzers, or by measuring or evaluating any other qualitative parameter of the waste item presented for identification. Alternatively still, an item of waste can be identified by user input of information such as a trade name, a generic name, a chemical name, National Drug Code (NDC), the abbreviated name of the drug (or mnemonic), or other data associated with a particular item of waste. For example, a 325 mg dose of aspirin can be identified by ASPIOT3272. In one embodiment, a user can simply read a waste identifier from an item of medical waste and enter the identifier into the system via a keyboard, touch screen or other user input device.

In one embodiment, once an item of waste is identified, the sorting algorithm determines to which of a plurality of waste categories the item belongs. The station then indicates to the user which container is associated with that category. For example, in some embodiments the station indicates a correct container by opening a door providing access to the container. Alternatively, such an indication can be provided by illuminating a light or displaying a name or number of a container on a display device. In some embodiments, a waste sorting mechanism can carry out or instruct a user in delivery of the waste item to the appropriate container.

In some embodiments, the waste sorting mechanism comprises a plurality of openings providing access to the plurality of containers. For example, each of the containers can be configured to interface with an automatically operable door or other means to present the container opening to the user. Some embodiments of such an interface are described in further detail below. Alternatively, the sorting machine can be configured to provide access to an appropriate container in other ways, such as by moving a container relative to the machine in order to present a container opening to a user. In further alternative embodiments, the sorting mechanism can include a series of lights or other indicators configured to inform a user of the correct container for a particular item of waste. Alternatively still, the sorting mechanism can include an apparatus configured to receive an item of waste from a user and physically convey the item to the appropriate container, which may be removable.

In some embodiments, a single waste item may call for disposal in multiple containers. For example, a syringe might contain a quantity of a hazardous or controlled substance, which requires disposal in a first container. However, the syringe itself may require disposal in a second, separate container. In such embodiments, it is desirable for the system to determine an appropriate sequence for the disposal of the separate parts of a single item. In the event that a waste item contains information (such as a barcode or label) sufficient to inform the system of the need for a sequence of disposal steps, the system can determine the optimum sequence, and can then inform the user of the appropriate sequence. The system may inform a user of the appropriate sequence by sequentially opening appropriate doors and/or by displaying instructions on a display screen. In one embodiment, a means can be provided for the user to indicate whether an item of waste is empty or contains residual or bulk hazardous or non-hazardous contents.

Alternatively, it may be desirable for a user to determine the best sequence for disposal, in which case, the user may enter information into the system requesting a particular sequence. Additionally, it may also be desirable for the system to include "shortcut keys" in order to provide quick access to frequently-used containers, such as sharps containers. Such shortcut keys can be configured to quickly open a selected container.

In some embodiments, when a single waste item comprises a composite of elements falling into different waste categories, such as a syringe containing a controlled substance, which might, if disposed separately, be sorted into two different containers, the waste sorting system can indicate disposal of the composite waste item into the correct container. In this manner, when it is inefficient, ineffective or even dangerous to separate the single composite waste item into its individual components, hospitals can still achieve compliance by disposing of such hybrid or composite items into the most conservative hazard container. In some embodiments, if a composite waste item could be deposited in more than one container, the containers within a sorting station can be ranked in order from "less" to "more" desirable in order to facilitate a determination of which container is the "most appropriate" hazard container in a given station. A determination of whether a particular container type (and corresponding waste category or categories) is more or less appropriate can be determined by a variety of suitable methods. In some cases, a selection priority can be determined empirically, while in other embodiments, the choice may be determined by comparing properties, such as amount of residual content, relative chemical toxicity, etc. bioactivity, etc., of elements of a particular waste item.

In some embodiments, when a waste item is unrecognized by the identification means, the sorting system will indicate disposal to the highest hazard waste container. The system will notify the disposer that the waste item was unrecognized. In another embodiment, the sorting system may also notify a database or database personnel that the waste item is unrecognized, thus facilitating a database upgrade to include that waste item for future disposals. In one embodiment, the system may be equipped with a dedicated container that is exclusively used for disposing such unrecognized waste items. The subsequent handling of waste items in such a dedicated container may depend on regulatory requirements, the facility's personal preferences or any other relevant consideration.

In another embodiment, a waste item identification device is configured to receive a waste item identifier from a waste item, and a decision system is configured to assign the waste item to a waste category using the waste identifier and information contained in the classification database. Each of the containers is associated with at least one of the waste categories, and the decision system is further configured to indicate into which of the containers a waste item should be deposited based on the waste category. The decision system is further configured to open an alternate container if the station does not include a container associated with the assigned category. In one embodiment, for example, the alternate container is a container associated with the highest hazardous level will be opened. In another embodiment, the alternate container is a container associated with the "next best" disposal category for the waste item.

In one embodiment, the alternate container is located adjacent to the preferred (or "first choice") container. In another embodiment, the alternate container is located in a different location from the preferred container. For example, the alternate container can be located in a different room or on a different floor. In yet another embodiment, if an alternate container is unavailable, then the item may be rejected. In this situation, the user may be instructed to obtain additional information on disposal.

Each of the containers is associated with at least one of the waste categories, and the decision system is further configured to indicate into which of the containers a waste item should be deposited based on the waste category. The decision system is further configured to open an alternate container if the station does not include a container associated with the assigned category. In one embodiment, for example, the alternate container is a container associated with the highest hazardous level will be opened. In another embodiment, the alternate container is a container associated with the "next best" disposal category for the waste item.

In one embodiment, the alternate container is located adjacent to the preferred (or "first choice") container. In another embodiment, the alternate container is located in a different location from the preferred container. For example, the alternate container can be located in a different room or on a different floor of a hospital or other institution.

In some embodiments, it may be advantageous to determine the quantity of waste that has already been deposited into one or more containers. In some embodiments, one or more sensors are used to quantitatively assess one or more parameters of the container and/or waste. These quantitative sensors include, but are not limited to, sensors that detect the weight, volume, density, and/or fill level of the waste in the container.

In one embodiment, one or more fill sensors are provided. A fill level sensor can be used to monitor a fill level of each of the containers to determine when a particular container is full. Once a container is determined to be full, the sorting system can signal a user to replace the full container with a new empty container. Additionally, once a particular container is full, some embodiments of the system can be configured to determine the weight or volume of waste material within the full container. The system can also be configured to print a label to be affixed to the container. The label can include a variety of information relating to the disposal of the waste items, the quantity, weight or volume of the items contained therein, a waste category name or code, etc. The label may also include a list of items that are in the container based on hazard classification, which, in some embodiments, will facilitate compliance with EPA laws. In other embodiments, the system may be configured to alert a user of other nearby waste containers capable of accepting the waste.

In some embodiments, quantitative sensors are not used. Instead, in one embodiment, the quantity of waste is determined by direct visualization of the waste in a container. Transparent or translucent containers are provided to facilitate visualization in some embodiments. In several embodiments, the containers are opaque, but provide a section or "view-strip" of translucent or transparent material to permit visualization. In one embodiment, one or more sensors are provided in conjunction with means to directly visualize waste quantity. In one embodiment, means for detecting a quantity of waste are not needed because the containers are replaced at regularly scheduled intervals, as determined by a waste transport company, a disposal company or hospital staff and independent of how much waste is in any given container.

In some embodiments, when a new container is placed in a sorting and disposal station, the system can be configured to identify the new container according to the type of waste the container it is permitted to hold. In some embodiments, a waste sorting and disposal station can be configured to recognize containers in a static mode in which each container position within the station/machine is associated with a specific container type. Upon insertion of a new container into the station, the system can recognize the type of container and can determine whether the new container is the correct type for the position in which it was placed. Thus, a system of this type can insure that a consistent arrangement of container types is maintained.

Alternatively, and more preferably, a sorting and disposal station is configured to recognize container types in a dynamic mode in which the machine is able to recognize and adapt to changing container arrangements. Thus, according to this embodiment, each container position/compartment in a station will recognize and accept any new container regardless of the container type, and the software will adapt a sorting routine to account for the new configuration. In some cases, it may be desirable for a single station to have multiple containers of a single type. For example, an oncology department may desire several chemotherapy containers and no hazardous pharmaceutical containers, while an area of the hospital that does not use chemotherapeutic drugs may want several sharps containers and no chemotherapy containers. This allows for substantial flexibility and customizability in system set up. In further embodiments, a sorting and disposal station can exhibit aspects of both static and dynamic systems, such as by allowing any type of container in any container position, while requiring a minimum number of containers of a particular type.

Figure 50:
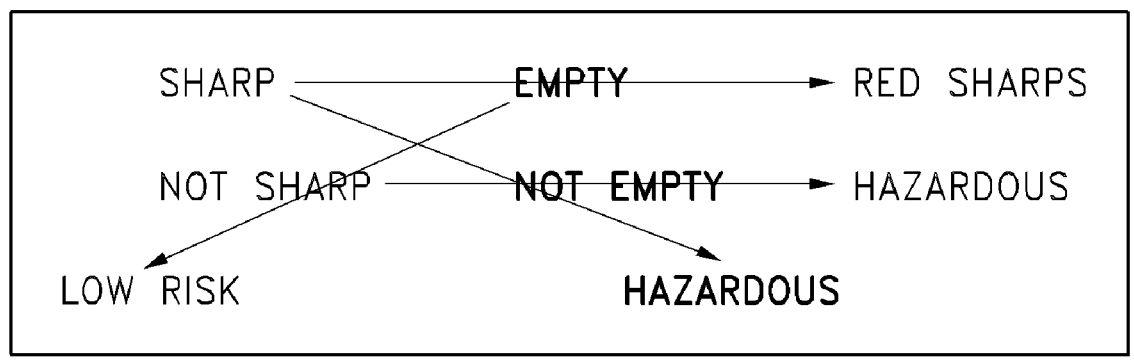
FIG. 50 is a schematic of one embodiment of a prescription drug label that facilitates proper disposal of the item.

In some embodiments, the waste sorting and disposal system can be significantly simplified by appropriately labeling products that will eventually be disposed as waste. For example, in one embodiment, a prescription drug label may provide disposal information at the time the label is generated. For example, the drug vial or other pharmaceutical product label may indicate in what waste category the item should be disposed. As illustrated in FIG. 50, in one embodiment, the label may provide alternative waste categories under which it should be disposed, depending on whether the item is empty or not empty and/or whether the items is or is not a sharps. Such waste categorization information printed on such labels may be obtained from a waste disposal database as discussed herein.

For example, in one embodiment, an institution may print its own specific labels that are based on waste categories. In one embodiment, multiple labels are generated, each with its own simple code (color, numerals, letters, etc) and affixed to a drug vial. At the time of disposal, the scanner (which is configured to read these institution specific codes) is able to associate the waste item with the appropriate waste container. In one embodiment, a scanner is not needed. Rather, the user can read the symbol and dispose of the waste accordingly. A 2-D barcode label may also be beneficial in some embodiments by eliminating the need for an HL7 interface.

In another embodiment, the system comprises a plurality of containers associated with a plurality of waste categories and a waste item identification device that is configured to determine a qualitative parameter of an item of waste. The system may also comprise a manual input system for entering additional information regarding the waste item. In a further embodiment, the system includes a database comprising waste item classification information. In one embodiment, the system may also comprise a control system programmed to compare the qualitative parameter of the item to information contained in the database, and assign the item to a waste category based on the manually entered additional information and the waste item classification information. In yet another embodiment, the control system may be configured to identify at least one of the containers based on the waste category.

In one embodiment, the control system is further configured to notify a user of the assigned waste category. In another embodiment, the control system is configured to notify a user of the assigned waste category by indicating an appropriate container into which the item should be deposited. In one embodiment, the control system may be configured to indicate the appropriate container by opening a door. In other embodiments, the control system may be configured to indicate the appropriate container by illuminating a light. In yet other embodiments, the control system may be configured to indicate the appropriate container by both opening a door and illuminating a light. In one embodiment, the control system may be configured to indicate the appropriate container by indicating the necessary information on a fixed and/or handheld display.

In some embodiments, the manual input system comprises a display and a keyboard having at least one button. In one embodiment, the keyboard comprises two buttons. In another embodiment, the keyboard comprises four buttons. In one embodiment, the keyboard is an alphanumeric keyboard, permitting the user to enter more detailed information.

In one embodiment, the manual input system comprises one or more soft keys on a display. In one embodiment, the display is a low cost display. In another embodiment, the manual input system queries the user for information regarding the waste item. In some embodiments, the system queries the user visually and/or audibly. In some embodiments, at least one button and/or soft key includes a graphical description. In other embodiments, the manually entered additional information is related to the volume of remaining contents in a waste item. In yet other embodiments, the manually entered additional information is whether the waste item is a sharps. In further embodiments, the manually entered additional information is related to both the volume of remaining contents in a waste item and whether the waste item is a sharps. In one embodiment, the system comprises keys, buttons, or other means to input whether or not the waste is sharps or not sharps, empty or not empty. In another embodiment, the system is designed to accept only toxic pharmaceuticals and reject sharps. For example, the system may be designed to inform a user presenting sharps to dispose the sharps elsewhere.

In some embodiments, the waste item identification device is at least partially available or situated on a handheld electronic device. In one embodiment, the additional information is manually entered into a handheld electronic device. In a further embodiment, access to the internal contents of the containers is restricted.

In one embodiment, a system and method for sorting waste using different modes of operation is disclosed. In a preferred embodiment, the system comprises a plurality of container compartments, each container compartment configured to receive a removable container. A plurality of removable containers may also be provided, wherein each removable container comprises an opening and a movable lid. In one embodiment, the removable containers are configured to be placed within the container compartments, wherein each removable container is associated with at least one waste category. In one embodiment, the movable lid is movable to an open position and/or a covered position. The system and method may be further configured to allow a user to select a mode of operation. In one embodiment, a waste item identification device is configured to read a barcode on an item of waste. In a further embodiment, a database comprising waste item classification information derived from rules and regulations affecting the disposal of waste items is provided. In another embodiment, a control system is configured to compare information obtained from the barcode to information contained in the database and to assign the item to a waste category. In another embodiment, the control system is further configured to identify one or more removable containers based on the waste category. In a preferred embodiment, the control system is also configured to allow the movable lid of the identified removable container to move to the open position and to lock the movable lid in the covered position when the control system determines that the container is full.

In another embodiment, the system comprises a plurality of containers associated with a plurality of waste categories, and a waste item identification device configured to determine a qualitative parameter of an item of waste. In one embodiment, a database comprising waste item classification information may be provided. In one embodiment at least one mode of operation may be selected by a user. In another embodiment, a control system is programmed to compare said qualitative parameter of the item to information contained in the database and to assign the item to a waste category according to the selected mode of operation. In a preferred embodiment, the control system is further configured to identify at least one of the containers based on the waste category.

In some embodiments, the mode of operation differentiates between economic and environmental benefits. In some embodiments, the mode of operation depends on the accommodation of available waste haulers. In further embodiments, access to the internal contents of the containers is restricted.

In some embodiments of the invention, a method of sorting waste is disclosed. In one embodiment, the method comprises receiving an identifier associated with waste to be disposed. In one embodiment, the method further comprises retrieving, based on the identifier, information from a database, wherein the information is derived from applicable rules regarding disposal of waste items. In one embodiment, the method also comprises assigning the waste to a disposal category based on the information retrieved from the database. In one embodiment, the method further comprises locating a container associated with the assigned disposal category. In a preferred embodiment, the method comprises providing access to an opening of the container while simultaneously restricting access to the interior contents of that container. In some embodiments, receiving an identifier associated with waste is accomplished using a handheld device.

In one embodiment, a method of sorting waste is disclosed. In some embodiments, the method comprises receiving an identifier associated with waste to be disposed of using a handheld device. In one embodiment, the method further comprises retrieving, based on the identifier, information from a database, wherein the information is derived from applicable rules regarding disposal of waste items. In one embodiment, the method may also comprise assigning the waste to a disposal category based on the information retrieved from the database. In one embodiment, the method may comprise locating a container associated with the assigned disposal category. In a preferred embodiment, the method may comprise facilitating disposal of the waste item into the container associated with the assigned disposal category. In other embodiments, access to the internal contents of the container is restricted. In other embodiments, locating a container associated with the assigned disposal category also takes into consideration a machine-readable identification key located on each container that enables the containers to be hot-swapped.

Network-Implemented System

In some embodiments, a waste sorting and disposal system, alone or combined with a dispensing system, can be configured on a hospital-wide level by providing a plurality of cooperating sorting and disposal stations throughout the hospital. The system can include a plurality of individual sorting and disposal stations in a variety of types, arrangements, sizes, functionalities, etc.

In one embodiment, a system and method for sorting waste using at least one authenticated network connection is disclosed. In one embodiment, the system comprises a plurality of containers associated with a plurality of waste categories. In one embodiment, a waste item identification device is configured to determine a qualitative parameter of an item of waste. In a further embodiment, a database comprising waste item classification information is provided. In other embodiments, a control system is programmed to compare the qualitative parameter of the item to information contained in the database and to assign the waste item to a waste category. In other embodiments, the control system is further configured to identify at least one of the containers based on the waste category. In one embodiment, at least one network connection is provided, permitting the control system to communicate with at least one other component of the system. In a further embodiment, the one or more network connections are authenticated and/or encrypted.

In some embodiments, the one or more network connections comprise a hardwired connection. In one embodiment, the hardwired connection comprises an Ethernet connection. In other embodiments, the one or more network connections comprise a wireless connection. In one embodiment, the one or more network connections may comprise both hardwired and wireless connections. In one embodiment, authentication is accomplished by using the entry of at least one necessary code. In one preferred embodiment, the necessary code or codes are entered using one or more flash drives and/or keyboarded devices. In one embodiment, the keyboarded device is a personal computer. In one embodiment, the one or more necessary codes is entered using one or more Ethernet ports. In some preferred embodiments, the one or more network connections are secured by one or more firewall systems. In other embodiments, access to the waste items after the waste item is placed into said container is restricted to authorized personnel.

FIG. 1 illustrates an exemplary embodiment of a centralized waste sorting and disposal network. As shown, a centralized network 50 can include a main central unit 54 provided in electronic communication with a plurality of smaller "satellite" units 60 throughout a facility. In such a centralized network, the main unit 54 can include a server containing the classification database 56 and any other information to be shared with the satellite units 60. As information is needed by a satellite unit 60, it can query the database via the network in order to obtain that information. Alternatively, or in addition, the main unit 54 can be configured to push updates to the satellite units at regular intervals, or as new information becomes available. In some embodiments, the main unit 54 can also act as a central hub for various communications, tracking, maintenance and other system functions.

Figure 2:
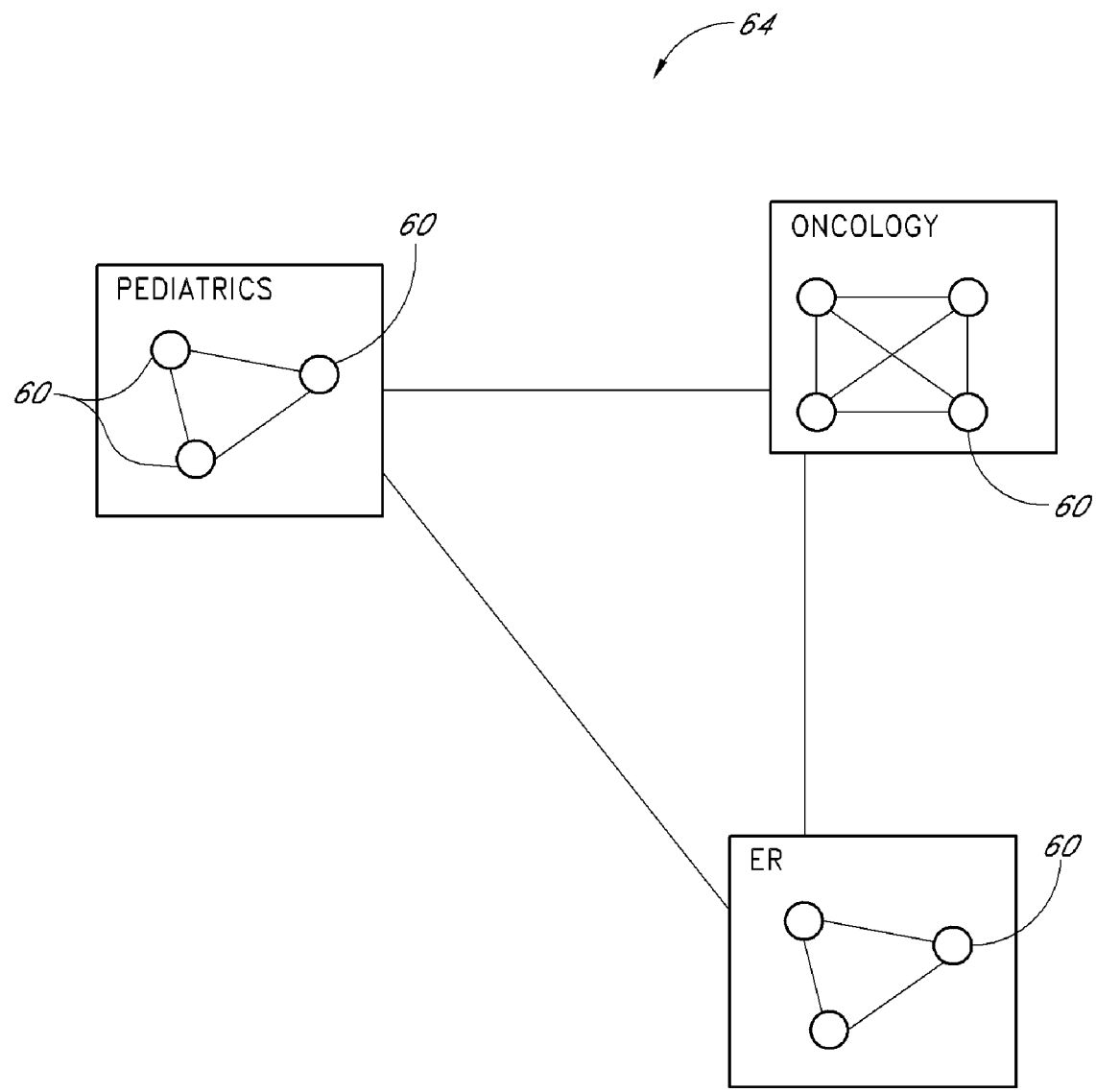
FIG. 2 is a schematic illustration of one embodiment of medical waste sorting and disposal system implemented in a decentralized network.

FIG. 2 illustrates an embodiment of a de-centralized medical waste sorting and disposal system. The network 64 of FIG. 2 is substantially decentralized and comprises a plurality of sorting and disposal stations 60 which can communicate with one another according to any suitable method. For example, in a decentralized network, each of the individual units may locally store a copy of the classification database. In order to keep the classification database updated, the individual units can share information with one another according to any of a variety of peer-to-peer network protocols. The individual stations can also share other information with one another as will be further described below.

In either case (centralized or decentralized network), the network elements can be configured to communicate with one another via any suitable wired and/or wireless network communication protocol. Many hospitals already have existing wired and/or wireless networks connecting computers and communications devices throughout the facility. Thus, in some embodiments, a networked medical waste sorting and disposal system can be configured as an add-on to an existing network. Alternatively, a networked medical waste sorting and disposal system can be configured as an independent network. Additionally, the main unit (if present) and/or the satellite unit(s) can further be connected to external networks (e.g., the internet) via wireless or wired connections as desired, consistent with a hospital protocol.

In some embodiments, it may be desirable for one sorting and disposal station to have access to information about one or all of the other stations in the network. For instance, it may be desirable for any one station to determine an arrangement of containers in one or more nearby stations. For example, if a clinician presents an item of waste to a station which does not presently have a container suitable for disposal of the presented item, that station can direct the clinician to the nearest station that does have an appropriate container installed. In further embodiments, a log of such re-directions can be kept in order to increase efficiency by arranging the sorting and disposal stations to include the most frequently used containers for a given location.

Some embodiments of a waste sorting and disposal system are configured to communicate information directly to a technician, maintenance person, clinician or other person. For example, the system can be configured to alert a maintenance person when a container is full by sending an alert signal to a pager, cell phone, PDA, computer terminal, or any other suitable device. The maintenance person can then remove the full container and replace it with an empty container (of the same or a different type). For example, the system may be set up to detect certain types of waste (e.g., P-listed waste) and start a timer for removal, thereby, in some embodiments, facilitating compliance with EPA laws.

Individual Sorting/Disposal Stations

A medical waste sorting and disposal station can take a variety of forms depending on the specific needs of a given clinic, hospital, department, clinician, etc. For example, some embodiments of sorting and disposal stations 60 are illustrated in FIGS. 3-12. For example, a station can be provided in a wall-mounted unit 60a (e.g., see FIG. 3), in a floor-standing unit 60b (FIG. 4), on a wheeled cart 60c (FIGS. 5 and 6), attached to a patient bed, attached to an IV pole, attached to an existing wheeled medications cart 60d (FIGS. 7-9), or any of a variety of other shapes, forms and mounting locations.

Figure 6:
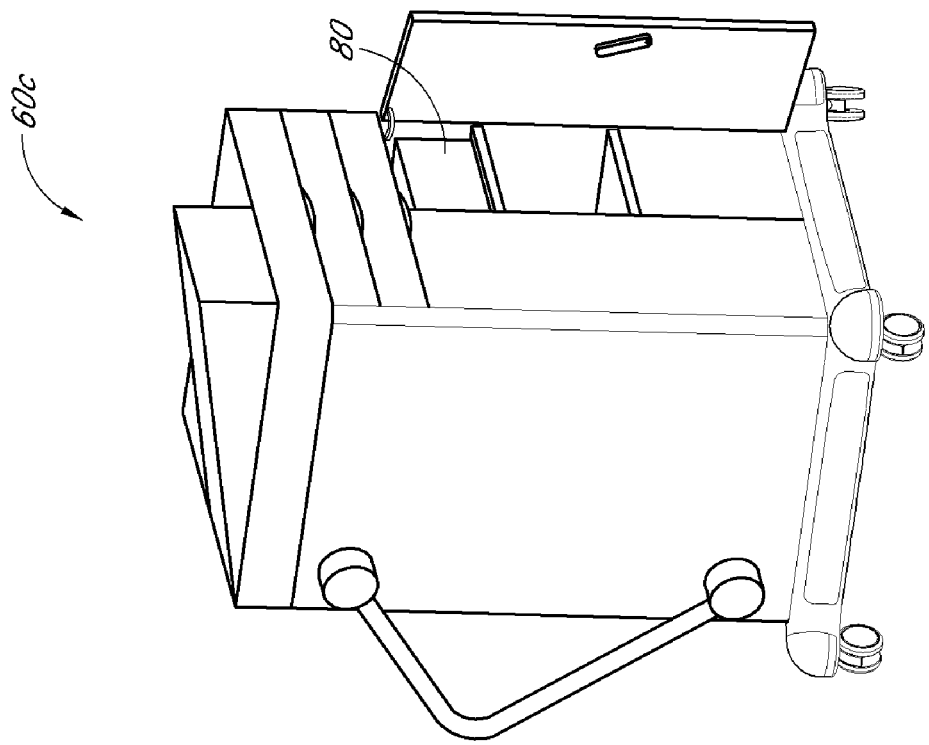
FIG. 6 is a rear perspective view of one embodiment of a rolling cart sorting and disposal station.
Figure 5:
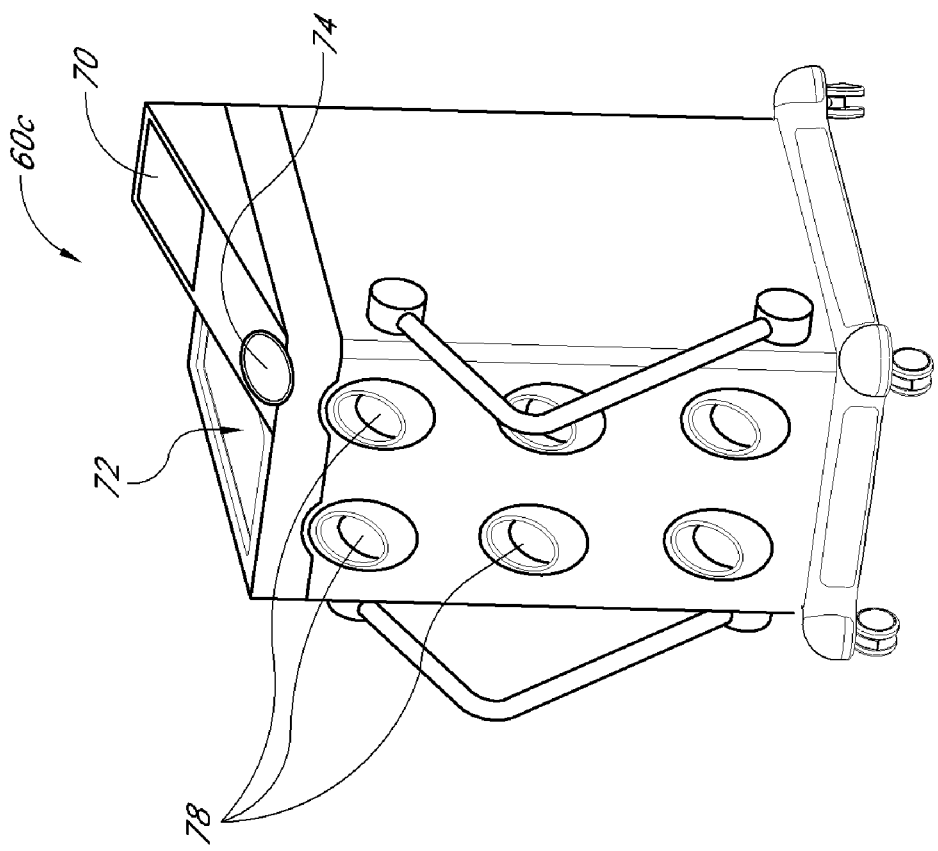
FIG. 5 is a front perspective view of one embodiment of a rolling cart sorting and disposal station.

The embodiment of FIGS. 5 and 6 also includes a display device 70, a weight scale 72, a scanner 74 for identifying waste items and a plurality of apertures 78 configured to reveal openings to respective containers 80. In other embodiments, the apertures are designed to selectively occlude and reveal openings or access ports.

Figure 7:
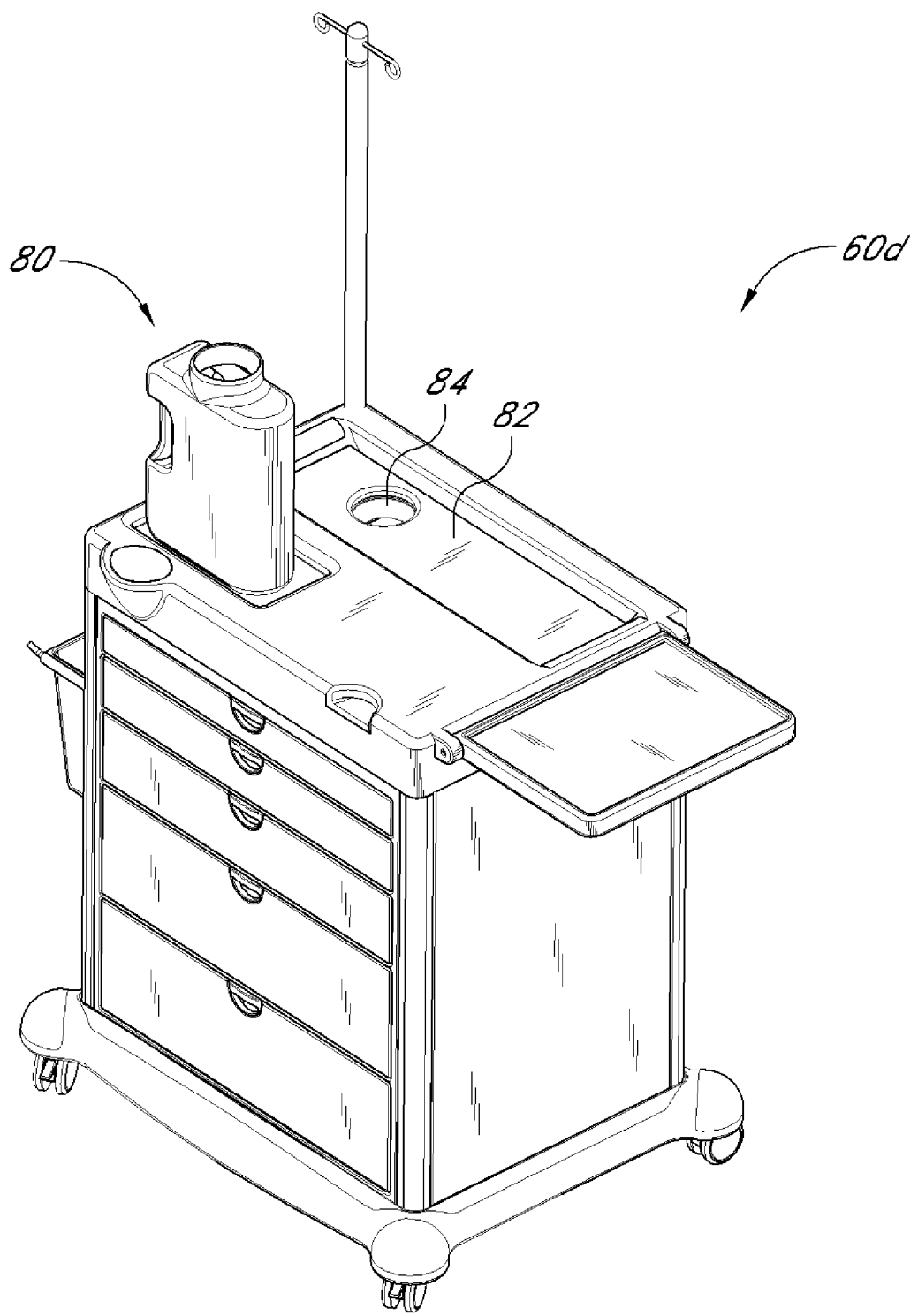
FIG. 7 is a perspective view of one embodiment of a sorting and disposal station incorporated into a rolling medications cart.
Figure 8:
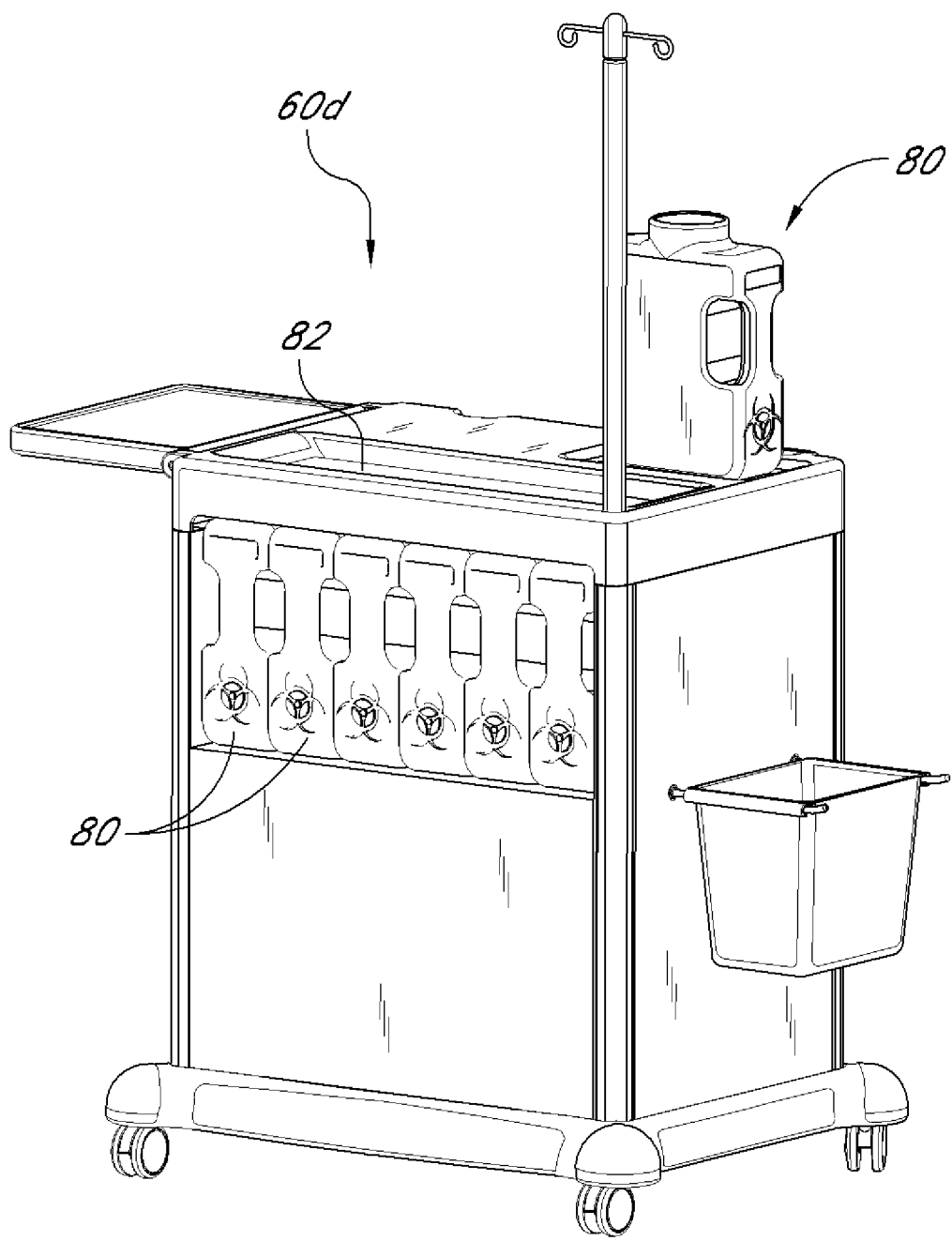
FIG. 8 is a rear perspective view of one embodiment of the cart of FIG. 7.
Figure 9:
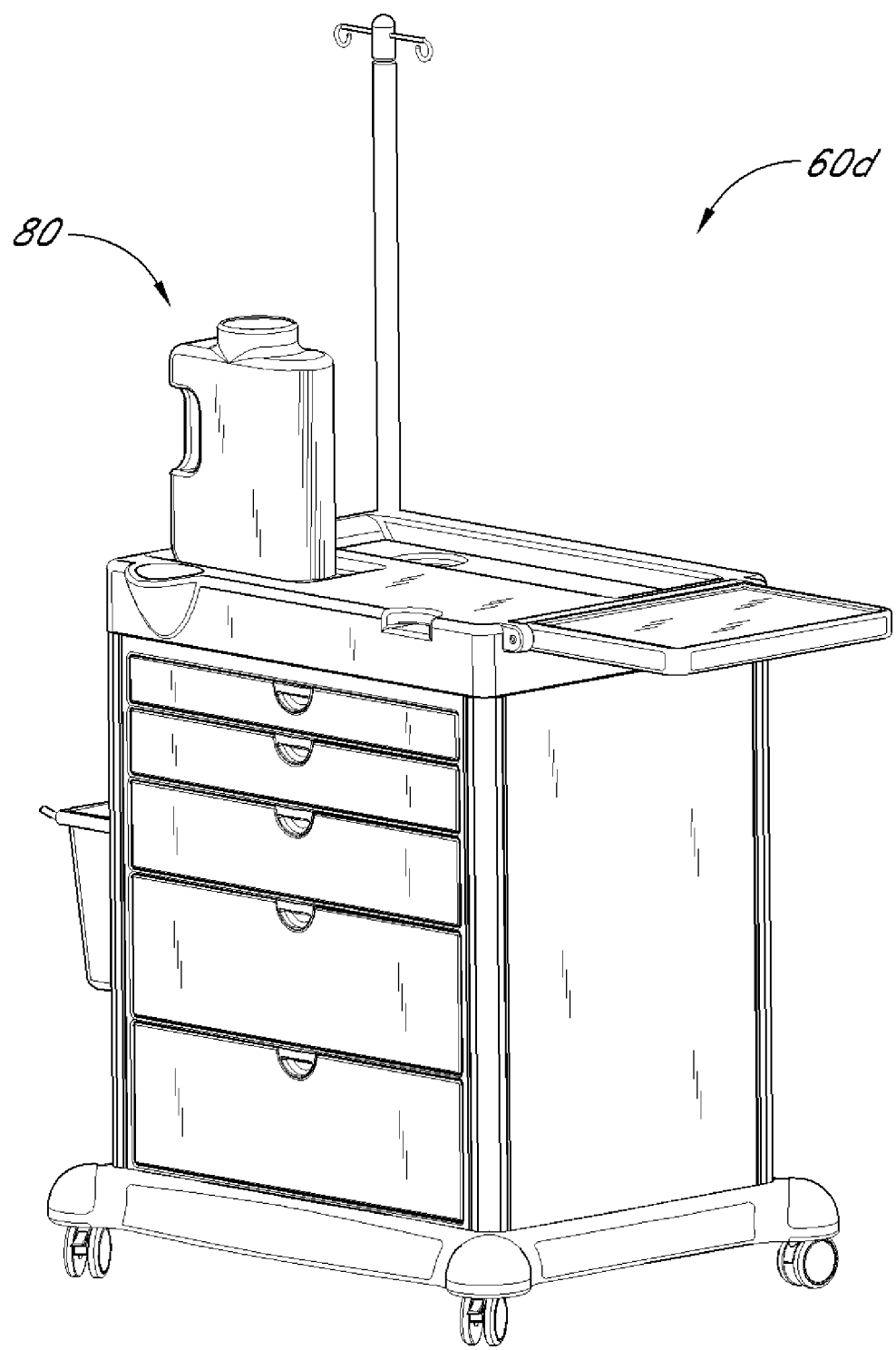
FIG. 9 is an alternative embodiment of the cart of FIG. 7.

With reference to FIGS. 7-9, some embodiments of a station can comprise a movable lid 82 with a single aperture 84. The lid 82 can be substantially flexible such that it can be driven to translate above the containers in order to selectively provide access to any one of the containers below the lid 82.

In some embodiments, the sorting machine can be configured to provide access to an appropriate container in other ways, such as by tilting, raising, lowering, pivoting, translating or otherwise moving a container relative to the machine in order to present the container opening to a user.

Figure 10:
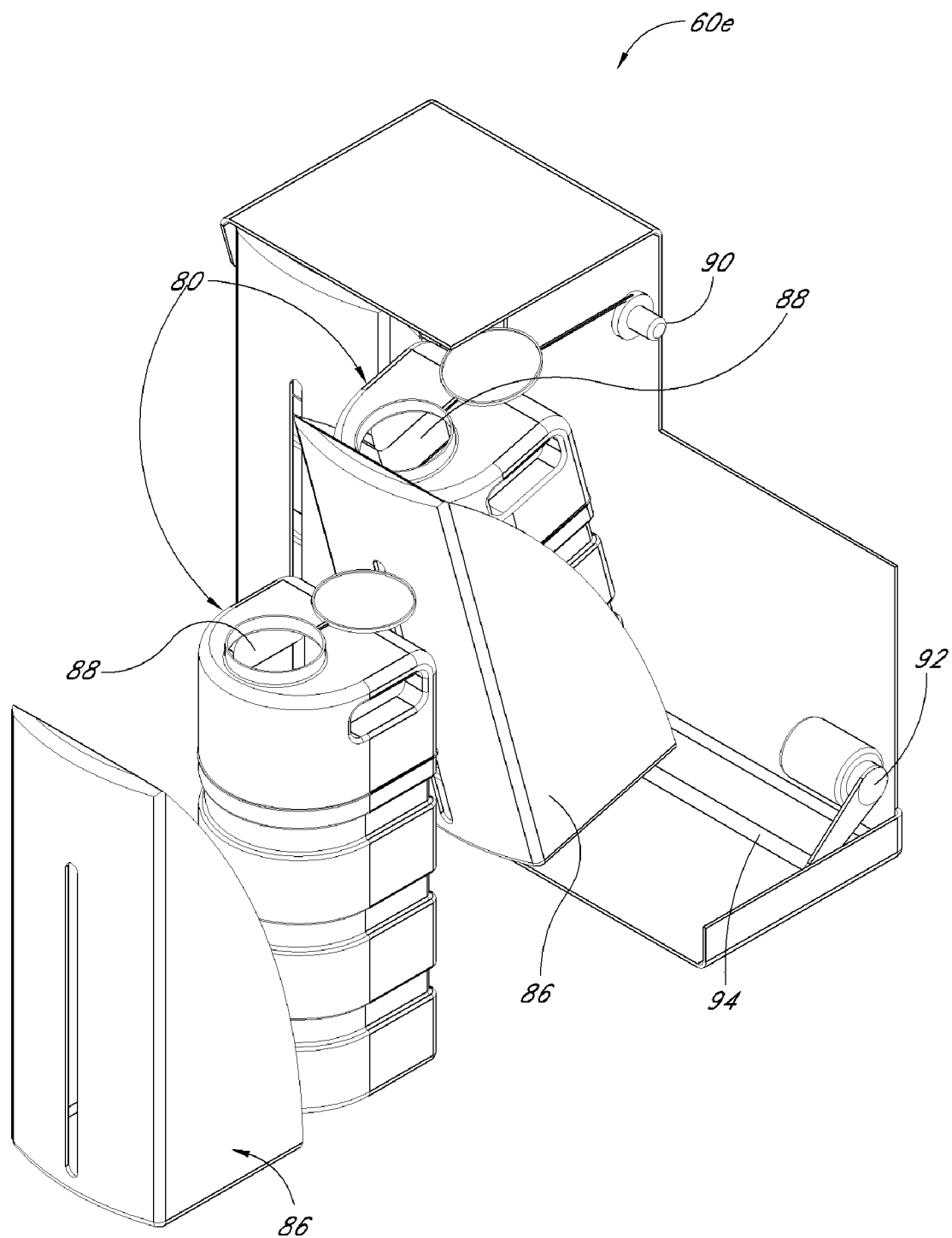
FIG. 10 is a partially exploded perspective view of one embodiment of a sorting and disposal station comprising pivotable containers and sleeves.

FIG. 10 illustrates an embodiment in which a sorting station comprises a series of hinged sleeves 86 configured to pivot relative to a fixed portion of the sorting station. Each sleeve 86 is generally configured to temporarily house a container 80, which may be removable. The station 60e comprises a series of actuators configured to pivot each sleeve 86 and its associated container 80 outwards, thereby exposing the container opening 88. In one embodiment, an actuator 90 can be located adjacent an upper portion of a container 80 and can be configured to push the upper portion of the container outwards from the station. Alternatively the sleeve 86 can be biased outwards by a spring or simply by gravity, and an upper actuator can be configured to release the sleeve/container to allow it to pivot outwards to open. The upper actuator can then pull inwards to return the container/sleeve to a closed position.

Alternatively or in addition, a lower actuator 92 can be provided adjacent a bottom portion of the container/sleeve combination. In one embodiment, a lower actuator 92 can comprise a drive axle 94 rigidly mounted to the sleeve 86. The axle 94 can be driven by a motor or other mechanism in order to pivot the sleeve 86 inwards and outwards. A container 80 can be inserted into the sleeve 86 and pivoted back so that a fixed portion of the station 60e covers the container opening 88. During use, the actuator 90 or 92 causes the sleeve 86 to pivot outward from the station 60e, thereby exposing the container opening for use. The container 80 can be removed by sliding it out of the sleeve 86. In an alternative embodiment, the above system can be provided without a sleeve 86 by incorporating an actuator and a pivot point into the container itself. In further alternative embodiments, other actuators, drive mechanisms, etc can be used in order to selectively provide access to a container opening.

In another embodiment, the station can be configured to house each of the containers in a sliding drawer. The drawers can include actuators configured to move the drawer outwards until an opening is exposed. The containers can then be easily removed once they are full.

Figure 12:
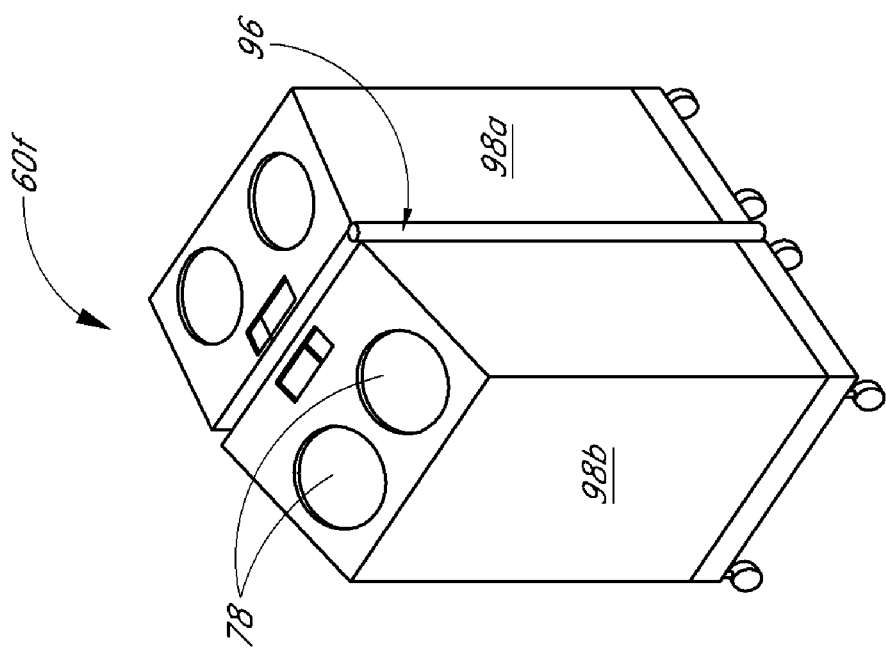
FIG. 12 is a perspective view of one embodiment of the convertible rolling cart in a second configuration.
Figure 11:
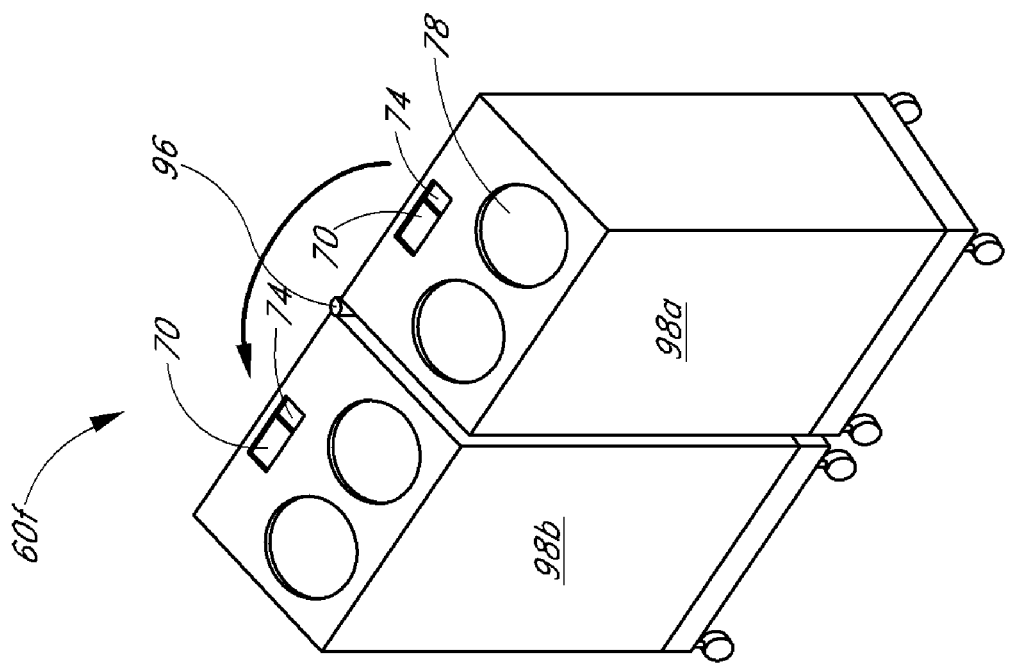
FIG. 11 is a perspective view of one embodiment of a sorting and disposal station in the form of a convertible rolling cart in a first configuration.

FIGS. 11 and 12 illustrate another embodiment of a waste sorting and disposal station 60f in the form of a convertible rolling cart. In a first orientation, illustrated in FIG. 11, the station 60f is a two-sided rolling cart. The station 60f of this embodiment can be provided with a hinge 96 configured to allow the two sides 98a, 98b of the cart 60f to unfold into a one-sided arrangement. FIG. 11 shows the cart in an unfolded form, so that it may be placed or mounted against a wall. FIG. 12 shows the cart in a folded form, and thus suitable for use as a cart.

In some embodiments, a sorting and disposal station 60 can include a scale configured to determine a weight of a full container. Thus, a scale 72 can be provided on an upper or other accessible portion of the station. Alternatively, the station can include a scale (e.g., a load cell) to continuously or repeatedly weigh each container within the station. Such information can be useful in creating a manifest for the containers before transportation of the containers to an appropriate disposal facility. Additionally, or alternatively, a station can include a fill level sensor for continuously or intermittently determining a fill level of a container. Embodiments of a fill-level sensor are described in further detail below.

Figure 32:
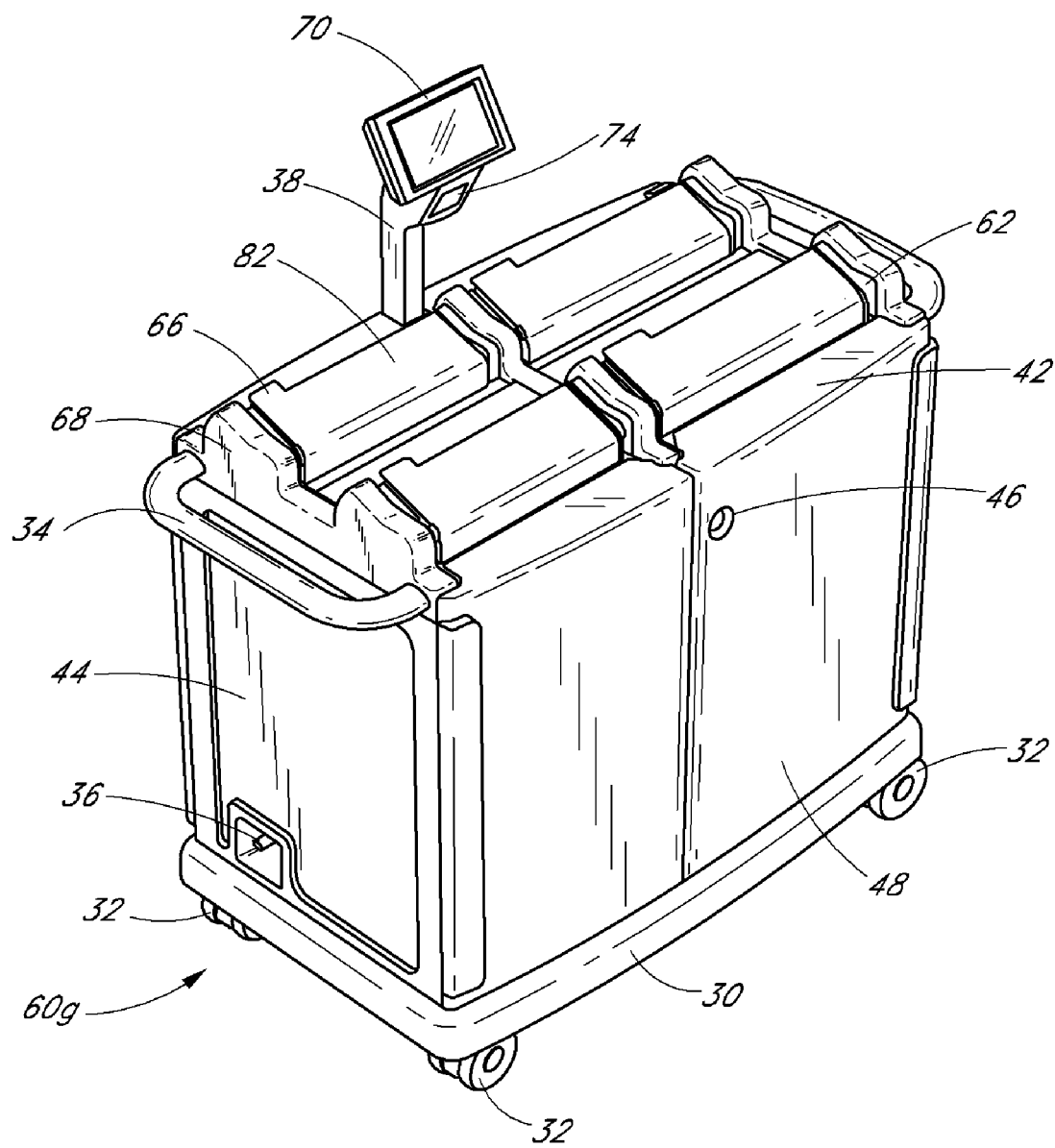
FIG. 32 is an isometric view of one embodiment of the invention, showing a cart version of a pharmaceutical waste collection and sorting device.

FIG. 32 shows another embodiment of the invention comprising a wheeled cart 60g, a display 70 (which in some embodiments may be a touch-screen display), and a barcode scanner 74. The display 70 and barcode scanner 74 are supported by a post 38 of suitable size and shape to orient the display 70 and scanner 74 for convenient access by a user.

According to one embodiment, a user holds a pharmaceutical waste item to be discarded near the scanner 74 and responds to one or more questions presented on the display 70. Using a database lookup and a specialized computer algorithm, a CPU then determines the proper container to receive the waste item. In other embodiments, the user simply scans the item to be discarded without answering any questions or inputting any information into the system.

The cart 60g is equipped with a plurality of lids 82. As shown in FIG. 32, each lid 82 is latched in a closed position by a release mechanism 62. When a particular lid 82 is directed to open, electronics, a solenoid, and a spring (not shown) cause the lid 82 to rotate to an open position revealing a container (not shown) for receiving the pharmaceutical waste item. Following manual deposit of the item into the appropriate container, the user closes the lid 82 by applying hand pressure to a lever 66, which, in one embodiment, is an extension of the lid 82. The release mechanisms 62 can be protected by covers 68 to prevent tampering with the release mechanisms 62 contained therein.

The cart 60g is further provided with a deck 42, side skins 44, and doors 48 to prevent damage resulting from spills and unauthorized access of the mechanisms 62, internal components, and the containers. The doors 48 are provided with a key lock 46 so that only authorized service personnel may change out the containers when full.

A power entry module 36 provides an electrical cord for connection to a wall outlet for powering the cart and/or charging an internal battery (not shown). One of ordinary skill in the art will recognize that other means for supplying power may also be used.

The cart 60g is also equipped with a base 30, wheels 32, and one or more handles 34 to enable pushing the cart 60g from one location to another.

Figure 33:
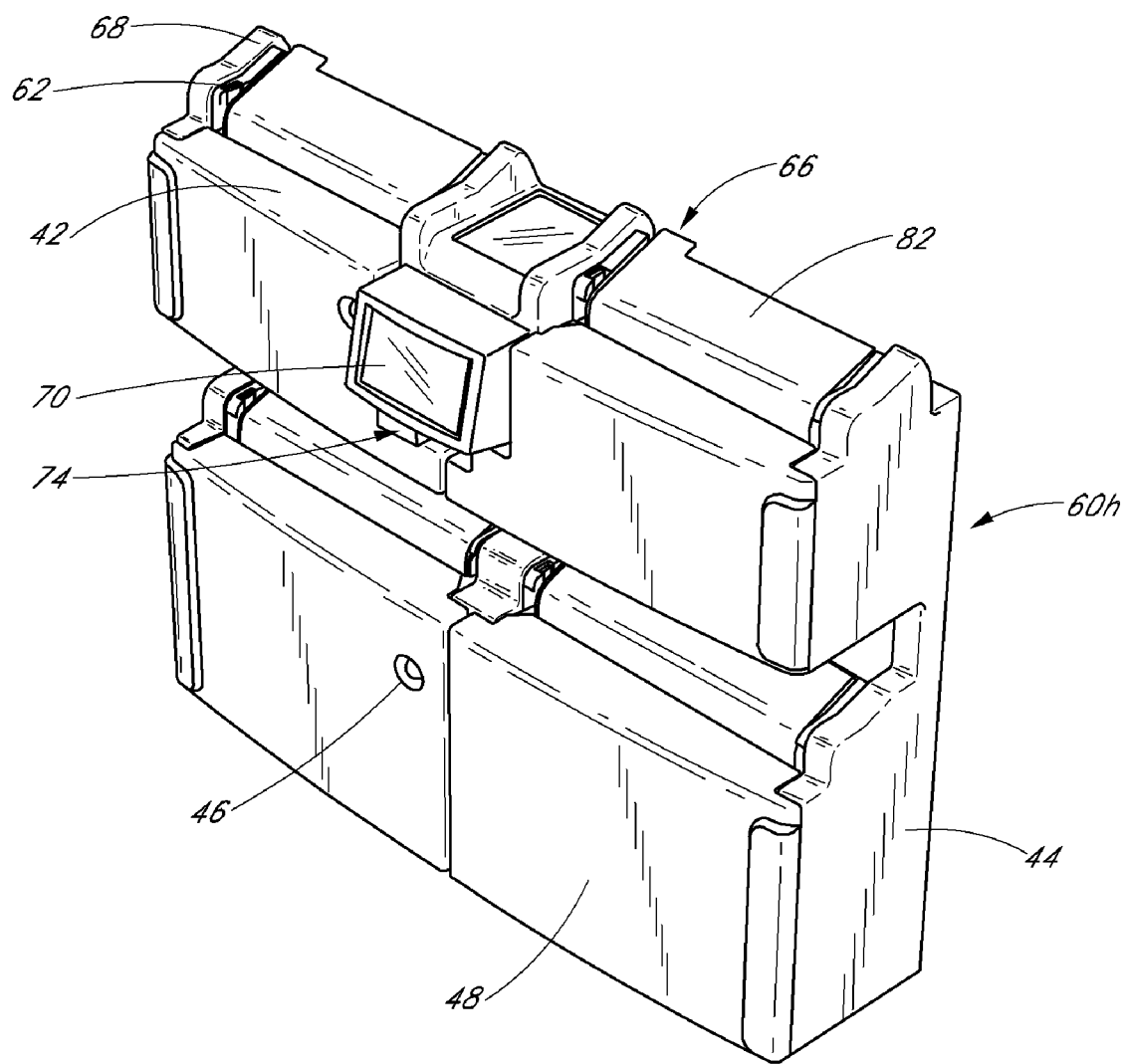
FIG. 33 is a perspective view of one embodiment of the invention, showing a wall unit version of a pharmaceutical waste collection and sorting device.

In some embodiments, the invention is provided as a wall unit. FIG. 33 shows one embodiment comprising a wall unit 60h, a display 70 (which in some embodiments may be a touch-screen display), and a barcode scanner 74. The display 70 and barcode scanner 74 are oriented for convenient access by a user.

In one embodiment, a user holds a pharmaceutical waste item to be discarded near the scanner 74 and responds to some questions presented on the display 70. Using a database lookup and a specialized computer algorithm, a CPU then determines the proper container to receive the waste item. In other embodiments, the user simply scans the item to be discarded, without answering any questions or imputing any information into the system.

The wall unit 60h is equipped with a plurality of lids 82 arranged in an array. As shown in FIG. 33, each lid is latched in a closed position by a release mechanism 62. When a particular lid 82 is directed to open, electronics, a solenoid, and a spring (not shown) cause the lid 82 to rotate to an open position revealing a container (not shown) for receiving the pharmaceutical waste item. Following manual deposit of the item into the appropriate container, the user closes the lid 82 by applying hand pressure to a lever 66, which in one embodiment is an extension of the lid 82. The release mechanisms 62 can be protected by covers 68 to prevent tampering with the release mechanisms 62 contained therein.

The wall unit 60h is further provided with a deck 42 (one at each level in the array), side skins 44, and doors 48 to prevent damage resulting from spills and unauthorized access of the mechanisms 62, internal components, and the containers. The doors 48 are provided with a key lock 46 so that only authorized service personnel may change out the containers when full.

The wall unit 60h, in one embodiment, can include an electrical connection or other means (not shown) for powering the unit and mounting brackets (not shown) for anchoring the unit 60h to a wall.

Figure 34A:
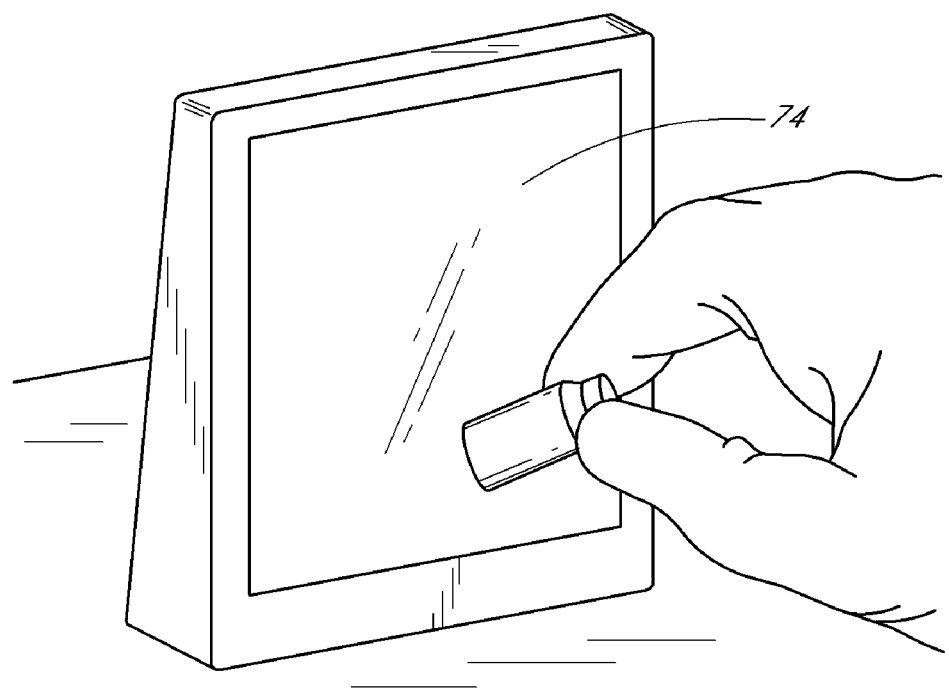
FIG. 34A is a perspective view of one embodiment of a sorting and disposal system, shown presenting a waste item near the scanner.
Figure 34B:
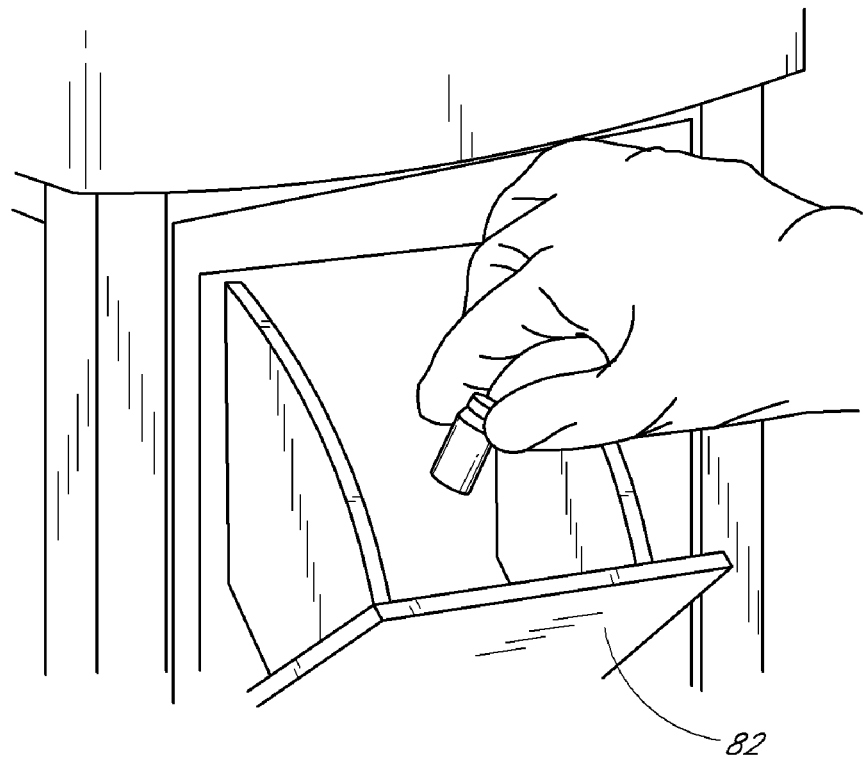
FIG. 34B is a perspective view of one embodiment of a sorting and disposal system, shown dropping a waste item into a container.
Figure 34C:
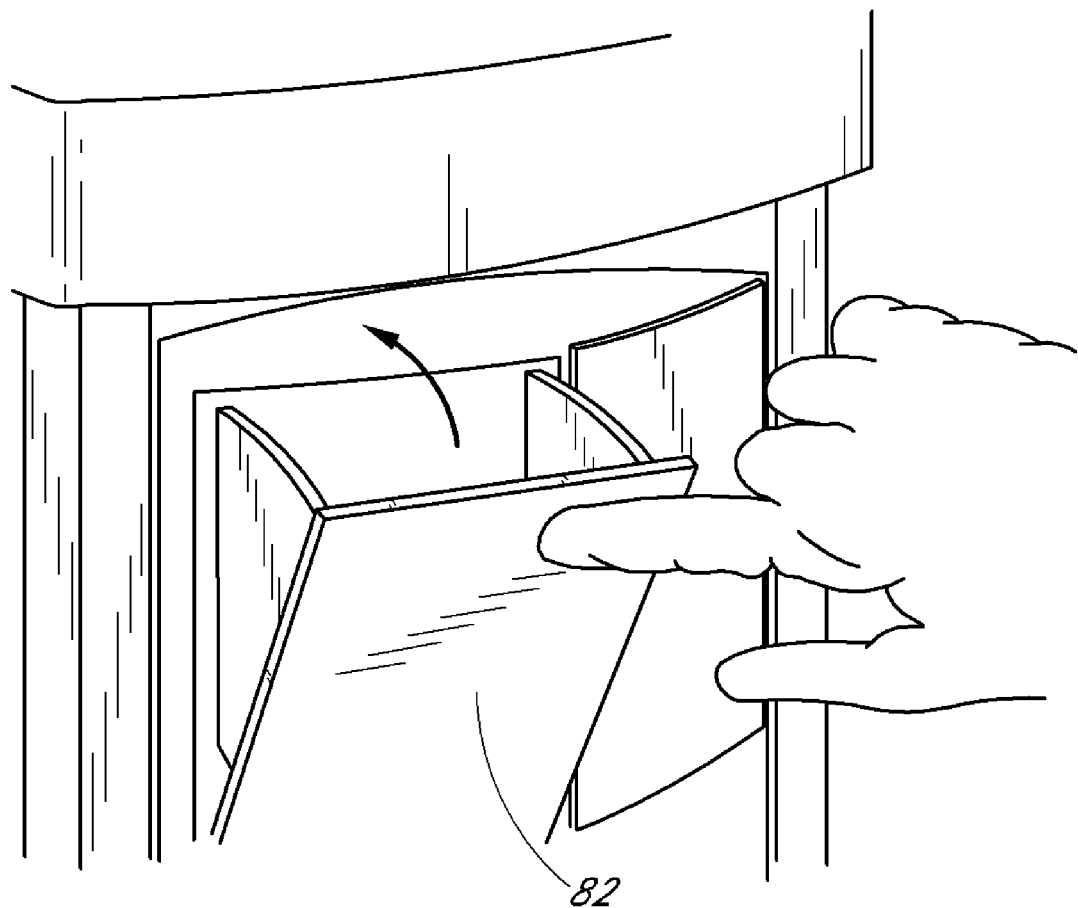
FIG. 34C is a perspective view of one embodiment of a sorting and disposal system, shown closing the container.

FIGS. 34A, 34B and 34C show an embodiment, which may be provided in cart form or as a wall unit. In one embodiment, a user holds a waste item to be discarded near a barcode scanner 74. In one embodiment, using a database lookup and a specialized computer algorithm, a CPU determines the proper container to receive the waste item. The waste item can be discarded into the appropriate container after the corresponding lid 82 has been opened. Once the waste item has been discarded, the user may push the lid 82 to its default, closed position.

Figure 35A:
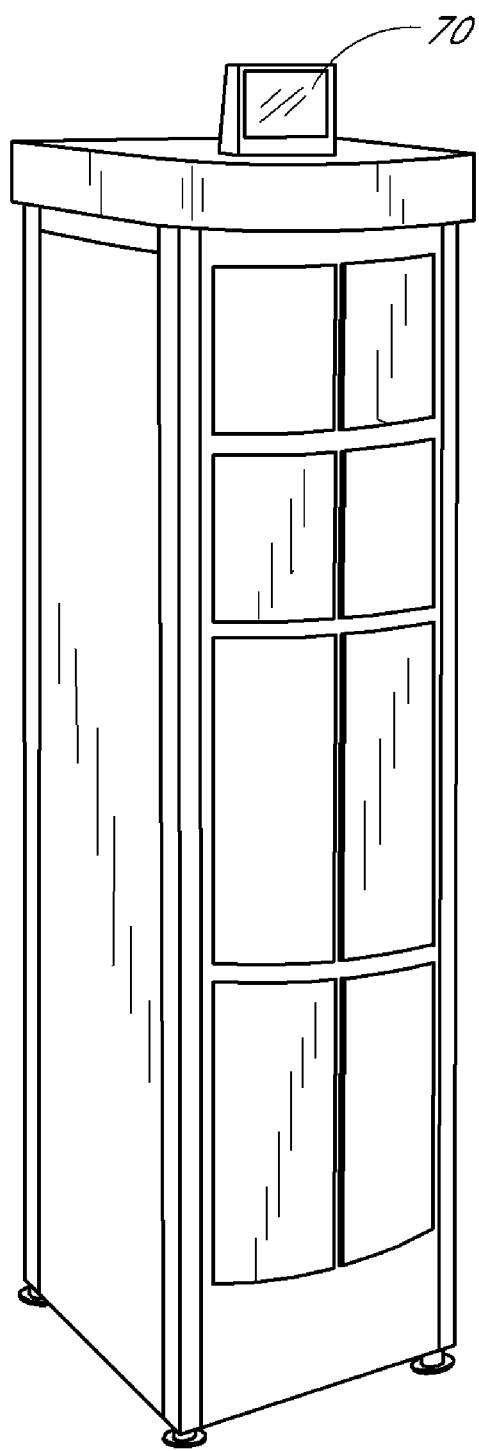
FIG. 35*a* is a perspective view of one embodiment of a substantially vertically-oriented sorting and disposal system.
Figure 35B:
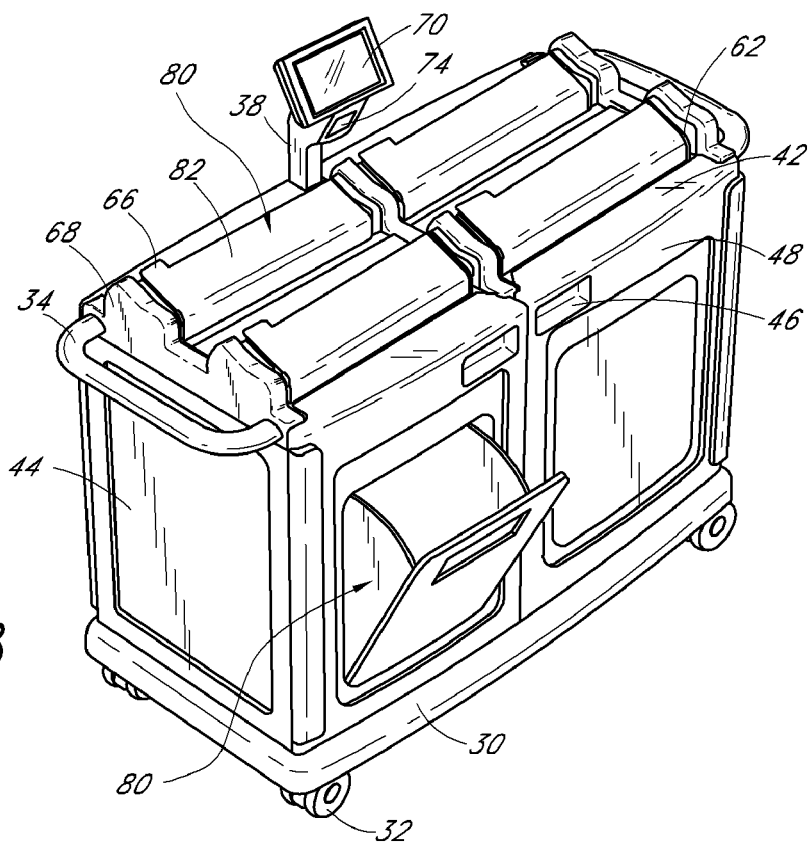
FIG. 35*b* is a perspective view of one embodiment of a sorting and disposal system.
Figure 35C:
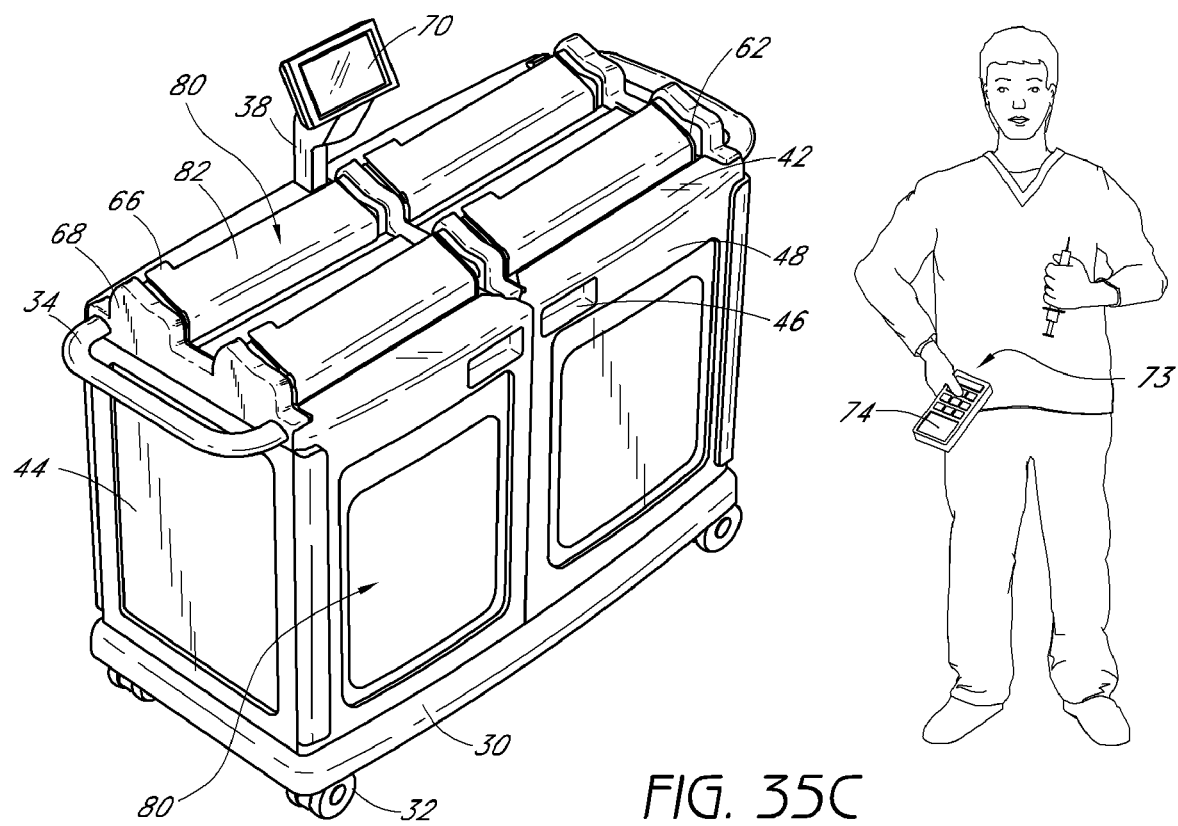
FIG. 35*c* is a perspective view of one embodiment of a sorting and disposal system, showing a handheld waste identification device.

FIGS. 35a, 35b, and 35c show alternative embodiments of the waste collection system. FIG. 35a shows a sorting device that is oriented in a substantially vertical position. FIG. 35b shows a sorting device that has a plurality of top and side access regions. As in other embodiments, using a database lookup and a specialized computer algorithm, a CPU determines the proper container to receive the waste item. The waste item can be discarded into the appropriate container after the corresponding lid has been opened. This embodiment is advantageous in healthcare facilities where available space is limited. In some embodiments, the sorting device is further provided with a deck 42, side skins 44 and doors 48 to prevent damage resulting from spills and unauthorized access of the mechanisms, internal components and the containers. In one embodiment, the doors 48 are provided with a key lock 46 so that only authorized service personnel may change out the containers 80 when full. In some embodiments, the sorting device may also be equipped with a base 30, wheels 32 and/or one or more handles 34 to enable pushing the cart from one location to another. FIG. 35c shows alternative embodiments (for example, alternatives of FIGS. 32 through 35b) in which the waste identification device (such as barcode scanner 74) is provided as or on a handheld 73 or other portable device. The display 70 may be provided as or on the handheld 73 or other portable device. Handheld embodiments may be used instead of or in addition to waste identification devices that are attached or fixed to a sorting station or other location.

In some embodiments, the container lid or other mechanism that provides access to the interior of the container, may be configured to open and close automatically. In other embodiments, for safety purposes, the container lid or other mechanism that provides access to the interior of the container, may not be capable of closing automatically. In such embodiments, the user is required to manually close the lid or other mechanism.

In a preferred embodiment, as illustrated in FIGS. 34a, 34b and 34c, the sorting system may be configured to automatically open a container lid following a barcode scan of the waste item. The user can then manually close the lid after discarding the waste item in the container. In one embodiment, the container automatically opens and closes. In another embodiment, the container automatically opens and can be closed manually. In yet another embodiment, the container is operable to be manually opened and closed. In a further embodiment, the container is opened manually, and closes automatically. Automatic closure of the container can be based on a pre-determined time interval. Alternatively, once a waste item is disposed within the container, the container may use one or more sensors to determine that the waste has been appropriately discarded, and automatically closes upon this sensor determination. In yet another embodiment, the user can communicate to the system (e.g., by pressing a button) to close the container automatically.

Containers

In some embodiments, the containers are generally designed to be low cost, yet include features that provide a functional interface with mechanisms in a sorting station to perform several desired functions. For example, in some embodiments, each container includes a door or lid which can be opened and closed automatically in order to allow or prevent access to a particular container at a particular time. Additionally, the containers can be configured to interface with sensors for determining a quantity of contents within the container, and/or sensors for determining a type of container.

In some embodiments, the containers 80 are blow molded (or otherwise formed) from polypropylene, high molecular weight polyethylene, polyvinylchloride or any other suitable plastic or other material as desired. In some embodiments, the containers 80 have substantially frosted or translucent side walls. The containers will typically be sized to have an internal volume of anywhere from 1 to 20 gallons, however greater or smaller volumes can also be used as desired. For example, in some particular embodiments, containers can be provided in 1-gallon, 2-gallon, 3-gallon, 5-gallon, 8-gallon, 10-gallon, and 13-gallon sizes. Other sizes can also be used.

The shape of the containers can vary widely. In some preferred embodiments, the containers include a lifting handle, a primary opening which can be automatically and/or manually closed or sealed, and a bottom surface configured to allow the container to stand upright. Additionally, the containers can also include features such as an automatically-openable door or lid, a manually closeable lid, features for accurately locating the container in a container compartment of a station, a viewing window for visually verifying fill level, and/or identification information for informing a user of a container's contents (or intended contents).

The containers can be provided with an opening 88 having a variety of shapes and/or features. For example, in one embodiment, the opening 88 is substantially circular and has a minimum internal diameter of at least about three inches (~76 mm). In other embodiments, the opening 88 can be substantially elliptical, rectangular, polygonal or otherwise shaped, and can be any suitable size, including sizes smaller than three inches in diameter. The particular type or types of waste to be deposited in a particular container can be a significant factor that can be used in determining a suitable size and/or shape of a container opening. In general, the container opening should be sized to easily accept the largest waste item that is expected to be deposited in the container. For example, some containers might receive full or partially full liter-sized IV bags, gallon-sized biohazard bags or other large items. It is generally desirable that the container opening be configured to accept these large items easily and without tearing the bags or otherwise damaging or causing spillage of a waste item. The skilled artisan will recognize that other factors may also affect a choice of container opening size or shape.

In some embodiments, containers are provided in a plurality of types, each type corresponding to a respective waste category or waste classification. In order to allow clinicians, maintenance people, and any other persons who may handle the containers to quickly and easily differentiate containers of various types, the containers can be color-coded to correspond with a particular type or category of waste. In some embodiments, a color-coding scheme can be selected to match industry standards for various types of medical waste. Red, for example, typically signifies infectious waste, while yellow typically signifies chemotherapeutic waste. Color-coded containers can advantageously simplify the tasks associated with manual transportation and processing of the containers, and can aid in ensuring that such tasks will be handled correctly for each waste stream.

Alternatively, such visual verification of a container's type can be provided by any other suitable method. For example, the various container types can be indicated by labels bearing numeric, alphanumeric, graphical or symbolic information. Such labels can include printed stick-on labels or various features molded or formed directly into portions of the containers themselves. If desired, such type-identification features can be provided in addition to color-coding of the containers in order to further simplify identification of a container's type. Providing simple visual verification of a given container's type advantageously simplifies and facilitates handling of medical waste materials throughout many aspects of collection and disposal.

In some embodiments, the containers can be configured in such a way that a sorting and disposal station can automatically identify a type of container. Such automation allows a station/machine to detect the mix and arrangement of container types in the station at any given time. In some embodiments, each container includes an identification key that can be read by corresponding structures in a sorting station. The key generally allows the sorting station to automatically identify the type of each container occupying a compartment or container position within the station. As discussed above, the station can be configured to identify container types in either a static or dynamic mode depending on a desired degree of flexibility for a given station.

Figure 13:
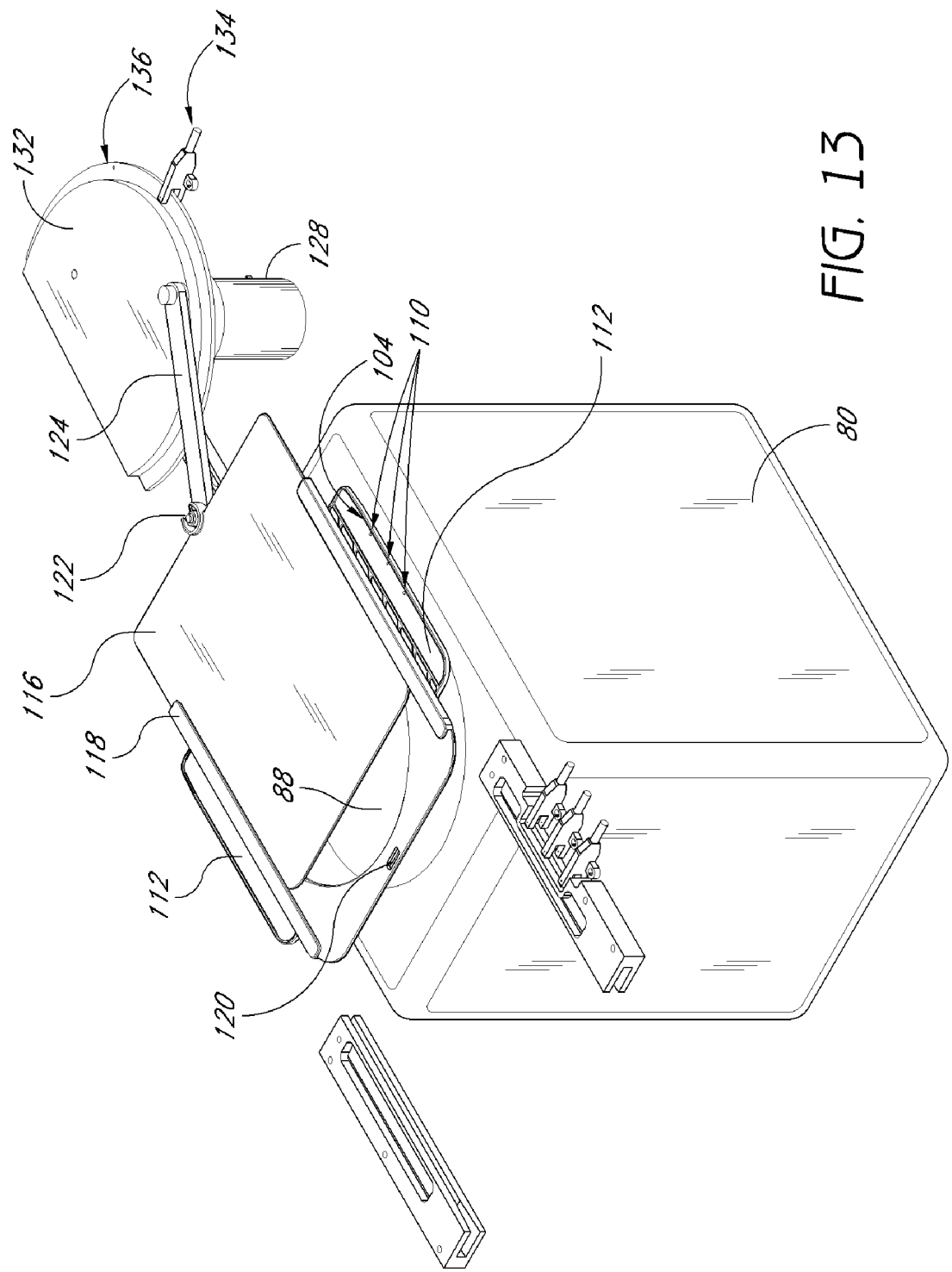
FIG. 13 is a perspective view of one embodiment of a container and portions of an interface with a sorting and disposal station.
Figure 14:
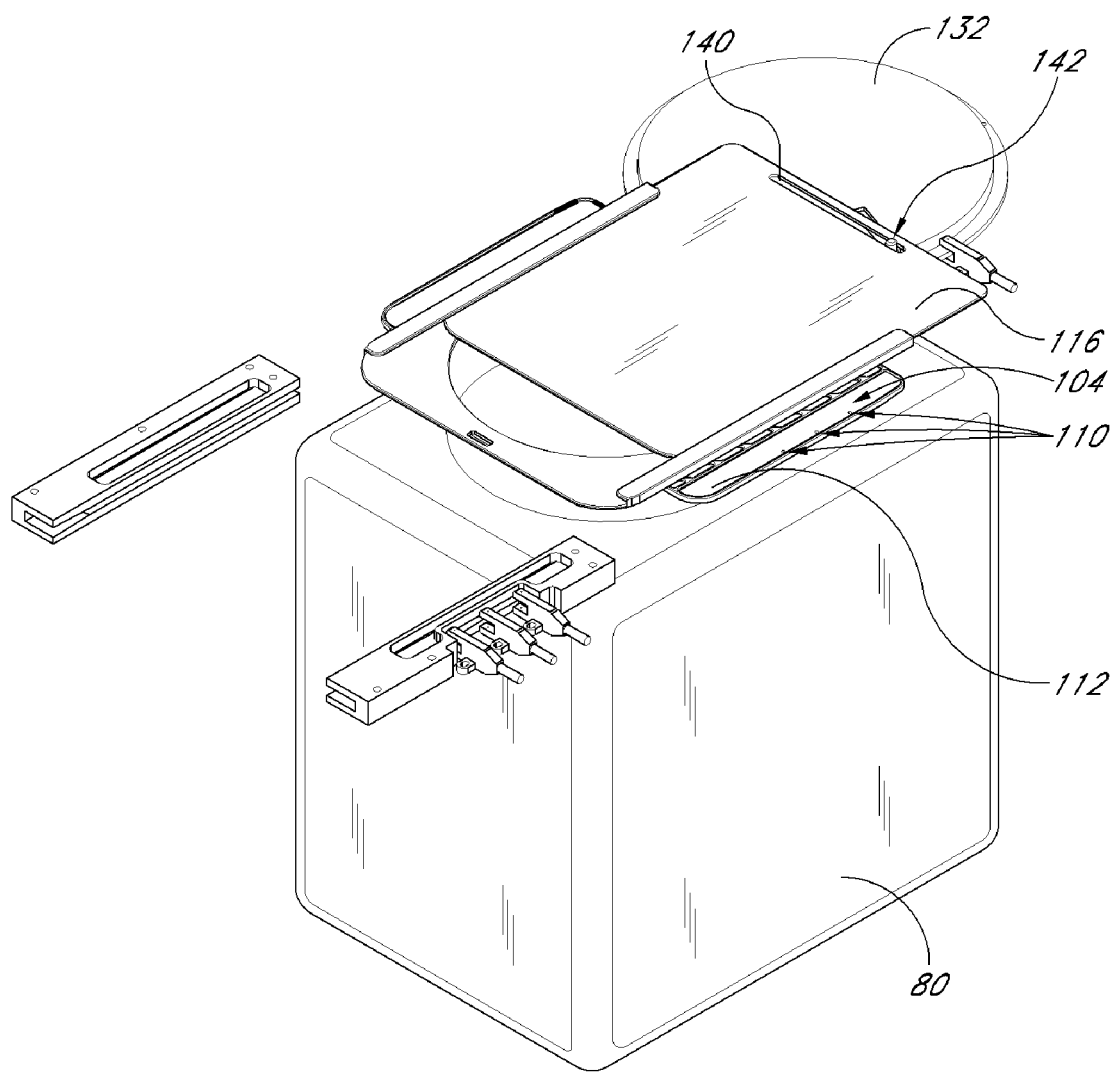
FIG. 14 is a perspective view of an alternative embodiment of a container and portions of an interface with a sorting and disposal station.

Identification keys may be physical features such as fingers molded into or attached to each container. Alternatively, identification keys can be holes, notches, or grooves molded or cut into a portion of each container. In some embodiments, identification keys include optically-readable features such as holes, dark or light colored dots, text, symbols, graphics, etc. A physical key may be configured to be read by mechanical or optical switches associated with each compartment or container position within the station. For example, FIG. 13 illustrates an embodiment of a container 80 with an identification key 104 made up of a series of holes 110 in a flange 112 extending from an upper portion of the container 80. The holes 110 of FIG. 13 can be detected by a plurality of optical switches 138 mounted to a portion of the station adjacent a container position. Thus the various container types can be identified by providing holes (or other features) in varying combinations and positions.

Alternatively, a key may be an optical mark, such as a bar code, that can be interpreted by a sensor such as a bar code reader. Alternatively still, the key may be a radio frequency identification (RFID) tag that can be read by a transponder associated with each compartment. In still further embodiments, container identification keys can comprise microchips, magnetic strips, or other electronic media that can be read by a waste sorting and disposal station into which the container is placed. In one alternative embodiment, a polychromatic sensitive optical sensor can be provided to directly determine a color of a container or a colored label affixed to the container.

As discussed above, some embodiments of a container are provided with automatically operable doors. In such embodiments, a container can be closed by default to prevent insertion of items into an incorrect container. Then, once an item is scanned or otherwise identified, the station can open the appropriate container or otherwise signify the single correct container to receive that particular waste item.

FIGS. 14-17 illustrate embodiments of containers comprising integrally-formed automatically operable doors and corresponding structures in a sorting station. The illustrated structures are generally configured to provide an automated interface between a container 80 and portions of a sorting and disposal station in order to allow the station to automatically recognize and operate a container. According to these illustrated embodiments, each compartment includes an actuator mechanism configured to automatically and selectively open and close the corresponding container 80. The selective opening and closing of each container may be accomplished via interaction of structures on both the container and the station, and can ultimately be controlled by a computer system within the sorting and disposal station.

In some embodiments, a container may include a movable lid molded or otherwise joined to the container opening. The lid can generally be configured to pivot, slide, hinge or rotate relative to a container in order to reveal or cover the container opening. In some embodiments, the lid is configured to mate with a mechanical actuator in the station upon installation of the container in a given container compartment. The actuator can be configured to allow the lid to open and close by translating, rotating or pivoting the lid. The actuator and lid can be further configured to separate from one another when the container is removed from the station.

FIG. 13 illustrates one embodiment of an interface between a container 80 and portions of a sorting station. In the illustrated embodiment, the container 80 comprises a gate 116 covering an opening 88 and configured to slide in tracks 118 between an open position and a closed position. The gate 116 can include a latch 120 configured to lock (e.g., automatically lock) the container opening when the gate 116 is completely closed. When a new container 80 is inserted into a station, a drive pin 122 on the gate control arm 124 is engaged by the gate 116 of container. The control arm 124 is configured to open and close the gate 116. The gate control arm 124 can be coupled to a drive motor 128 via a transmission element such as a disc 132 or a similarly functioning arm. If desired, a position switch 134 can also be provided on the disc 132, control arm 124, gate 116 or other component in order to detect a position of the gate 116. In the illustrated embodiment, the position switch 134 is an optical switch configured to detect one or more holes 136 in the disc 132. Additionally, the sorting station can include a plurality of optical switches 138 for detecting the presence of a container and/or the type of container 80 inserted into the sorting station. The embodiment of FIG. 14 replaces the gate control arm 124 of FIG. 13 with a slot 140 in the gate 116 in order to convert the rotational motion of the pin 142 extending from the disc 132 into linear motion of the gate 116.

Figure 15:
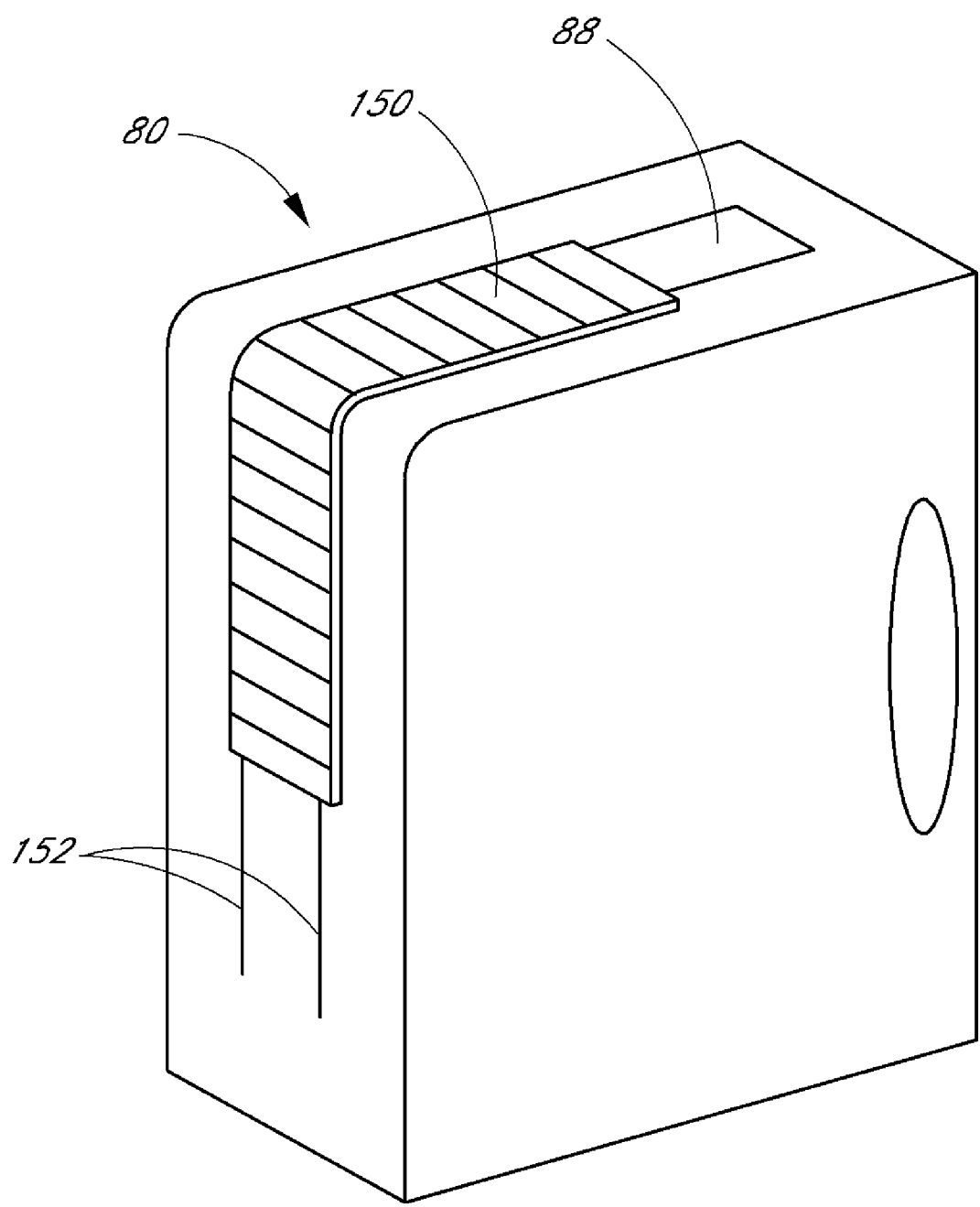
FIG. 15 is a perspective view of an alternative embodiment of a container.
Figure 16:
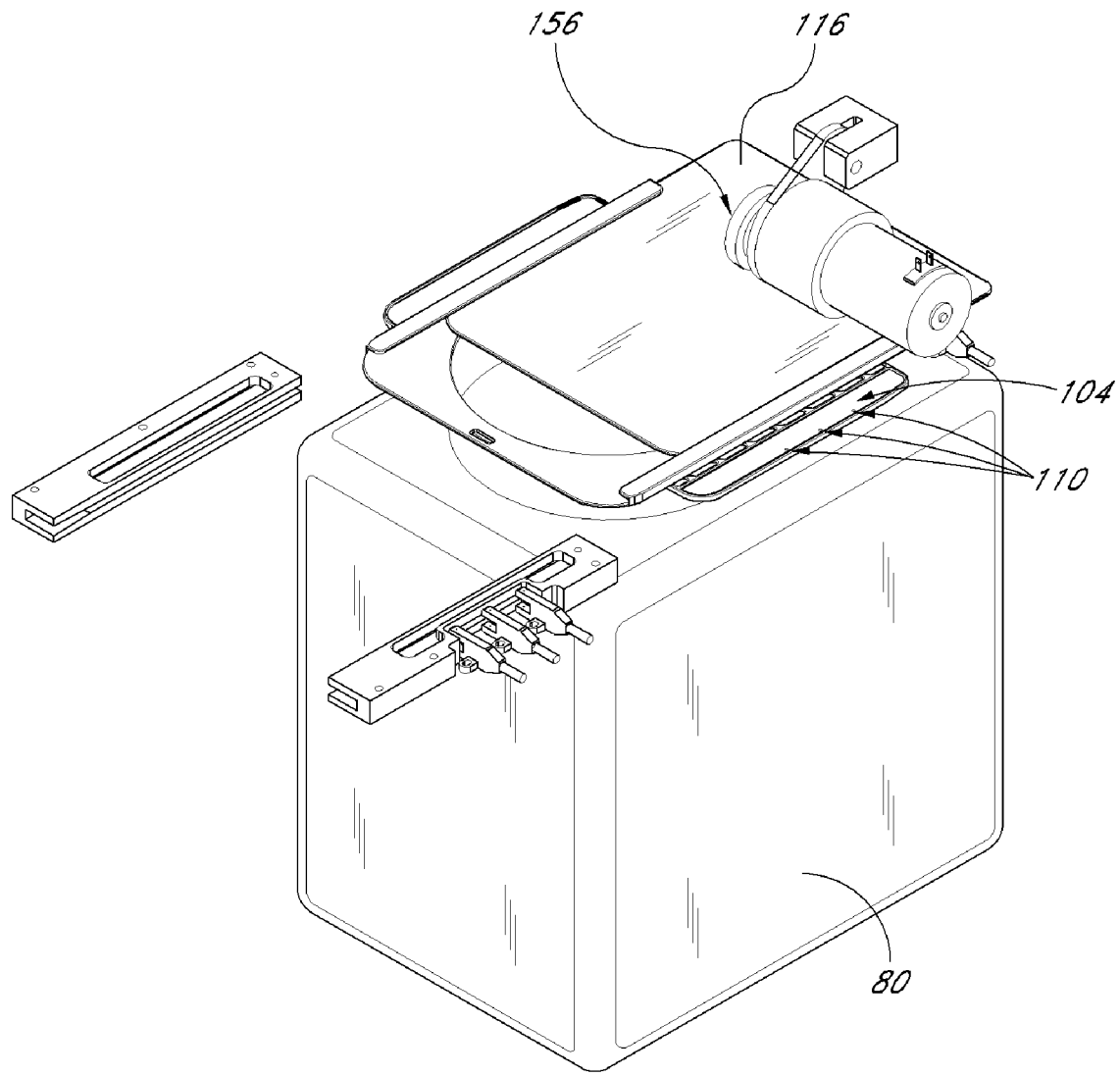
FIG. 16 is a perspective view of an embodiment of a container and an alternative embodiment of portions of an interface with a sorting and disposal station.
Figure 17:
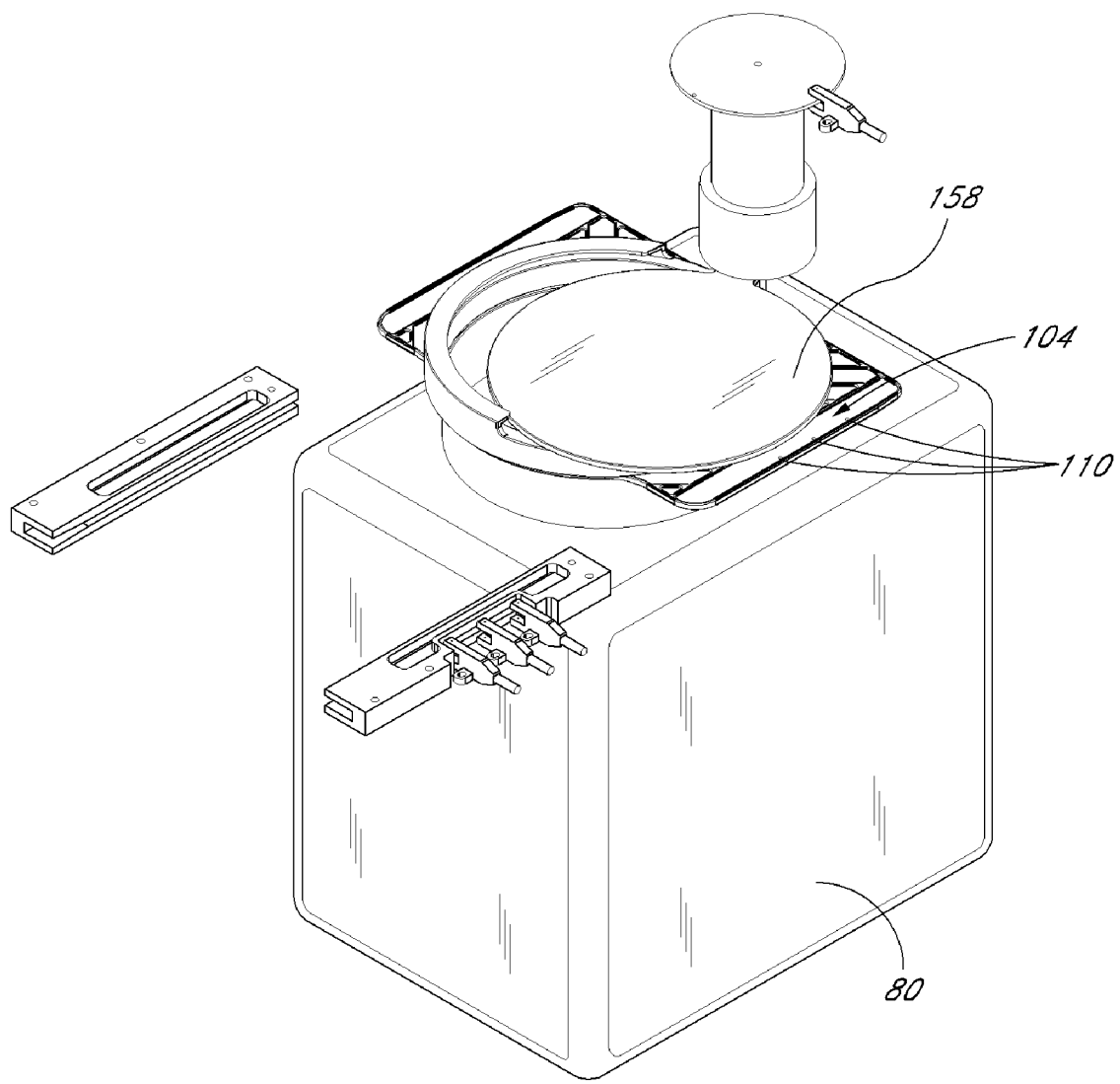
FIG. 17 is a perspective view of an embodiment of a container and an alternative embodiment of portions of an interface with a sorting and disposal station.

In alternative embodiments, other configurations of automatically openable doors/gates can be provided. For example, FIG. 15 illustrates an alternative embodiment of a container comprising a sectioned door 150 configured to slide along tracks 152 extending from the exterior surface of the container 80. The slidable lids of the above embodiments can be provided with a latch (such as that shown in FIGS. 13 and 14) which can be automatically engaged in order to lock the container once a sorting station determines the container is full. The embodiment illustrated in FIG. 16 can include a slidable door 116 driven by a rack and pinion drive mechanism 156. Alternatively, the drive mechanism 156 of FIG. 16 can comprise a driven friction wheel configured to engage a portion of the slidable lid 116. A similar pinion or friction wheel drive system can be used to automatically operate the sectioned door 150 of the embodiment shown in FIG. 15. FIG. 17 illustrates an embodiment of a container 80 with a lid 158 configured to open by pivoting relative to the container 80. In further alternative embodiments, a door can be opened or closed by any of a variety of other mechanisms. For example, worm screws, pneumatic pistons, hydraulic pistons, solenoids, or any other motion-transferring mechanism can be used to selectively open and close a container door.

In some embodiments it may also be desirable to provide an outer lid configured to seal a container opening once the container is full. The outer lid is preferably configured to attach to the container sufficiently securely to prevent spillage or tampering. An outer seal also shields users from contaminants that may have come in contact with the container top area during use. For example, in some embodiments a flexible lid can be configured to seal over a top of the automatically actuated door by frictionally engaging a lip, groove, or other structure in a manner similar to many flexible lids used in food storage containers. In alternative embodiments, outer seals can be provided in the form of a bag or shrink-wrap material that surrounds a substantial portion of a container's exterior.

In some embodiments, it may be desirable to provide a container configured to render waste items non-recoverable by providing a substance within an "empty" container that can react chemically with waste items. In another embodiment, a solidifying agent can be provided within a container in order to solidify non-hazardous pharmaceuticals allowing for their disposal in a landfill. In some embodiments, such solidifying agents can include materials capable of absorbing a quantity of a liquid non-hazardous pharmaceutical material. For example, such absorbent materials can include ceramic materials, sponge materials or other porous materials. Alternatively, such solidification may involve a chemical reaction between the waste material and a substance provided within the container.

Fill-Level Detection System

In several embodiments, a system for determining the level of contents within a container is disclosed. The internal contents can include waste items or alternatively, can include drugs or other medical devices that are to be dispensed.

In one embodiment, the system comprises a plurality of containers, with each container associated with at least one waste category. In one embodiment, waste is placed in the containers based on a determination by a database that comprises waste classification information. In one embodiment, the system comprises a bar passing through each container at approximately the fill level of the container. The system may also comprise one or more detectors positioned to detect movement of the bar. In one embodiment, the system further comprises one or more position indicators attached to the bar. In one embodiment, movement of the bar is detected by having the one or more detectors detect movement of one or more position indicators. In some embodiments, the detector may be an optical detector, a non-optical detector, a photodetector, a photo-interruptor, a mechanical sensor, an electrical sensor or an acoustical sensor.

In some embodiments, each container further comprises a lid which works in conjunction with the bar of the corresponding container. In a further embodiment, when it is determined that the container is not capable of accepting any additional waste items, the lid operates to exclude further access to that container. In some embodiments, the position indicator may be situated on the outside of the container. In other embodiments, the position indicator may be situated on the inside of the container. In some embodiments, the detector may be situated on the outside of the container. In other embodiments, the detector may be situated on the inside of the container. In a preferred embodiment, the bar is released at intervals to sweep across the container to determine the level in the container. In one embodiment, the bar is released every time the lid is opened. In some embodiments, access to the internal contents of the containers is restricted.

In some embodiments, it is desirable to measure a fill level of waste within a container throughout the sorting and filling process. In some embodiments, such fill level sensing can be performed by measuring a weight of a container, such as by using a load cell, balance, or other weight measurement device. In further embodiments, float systems can be adapted for use in determining a level of a waste material in a waste sorting system. In some cases, it is also desirable to perform such fill level measurements without the sensor physically contacting the container or the container contents.

Level sensors are commonly used in many fields to determine a quantity of a solid or liquid within a container. Three popular level sensors include floats, sight glasses and ultrasonic systems.

In a float system, a buoyant device or "float" is placed in the container, where it remains partially submerged in the liquid retained within the container. The float is used to detect a level of a fluid in the container by activating a switch located at a pre-determined point. Alternatively, the float detects the container's fluid level by activating a potentiometer, which reports the fluid level over a calibrated range.

Sight glass type level sensors evolved from manual systems in which an operator observed the level in a container through a transparent window. Sight glass type sensors which today are implemented using light sensors, generally require a window through which to project and receive light.

Ultrasonic fill level sensors direct a beam of ultrasonic energy toward an object and detect the time delay associated with that beam of energy reflecting off the object and returning to the sensor. Thus, the time delay correlates to a particular height of the contents in the container.

The assignee of the present application also owns technology related to the optical detection of the level of material in a translucent plastic waste container. See, e.g., application Ser. Nos. 10/945,223; 10/946,252; 10/946,161; 10/945,773; 10/946,164; 10/946,207; 10/946,208; and 10/946,054, herein incorporated by reference. As described below, in some embodiments, measurements are made by illuminating one side of the container and collecting the light received by an array of photo detectors located on the opposite side of the container. In one embodiment, a microprocessor interprets the light received at the array of receptors, compensates for ambient light and the relative transmissivity of individual containers, and determines whether the container is full.

In some embodiments, a piezo transducer can be used to determine a volume of air remaining in a container by conducting a frequency sweep of the transducer to determine the resonance of the air in the container. Once the volume of air in the container is known, the air volume can be subtracted from the known total container volume to obtain the volume occupied by the container contents. In another alternative embodiment, a distance-measuring sensor (such as SONAR, RADAR or optical distance-measuring sensors) can be located above and directed through the opening of the container in order to determine a "height" of the container contents. In another embodiment, a sensor can be provided for determining whether a container includes any waste at all. Such a "waste presence" sensor can be used in combination with a timer to determine a replacement schedule for a particular container based on a maximum acceptable dwell time for a particular waste item in a container. Still other embodiments may use optical sensors to measure a fill level of a container.

Figure 18:
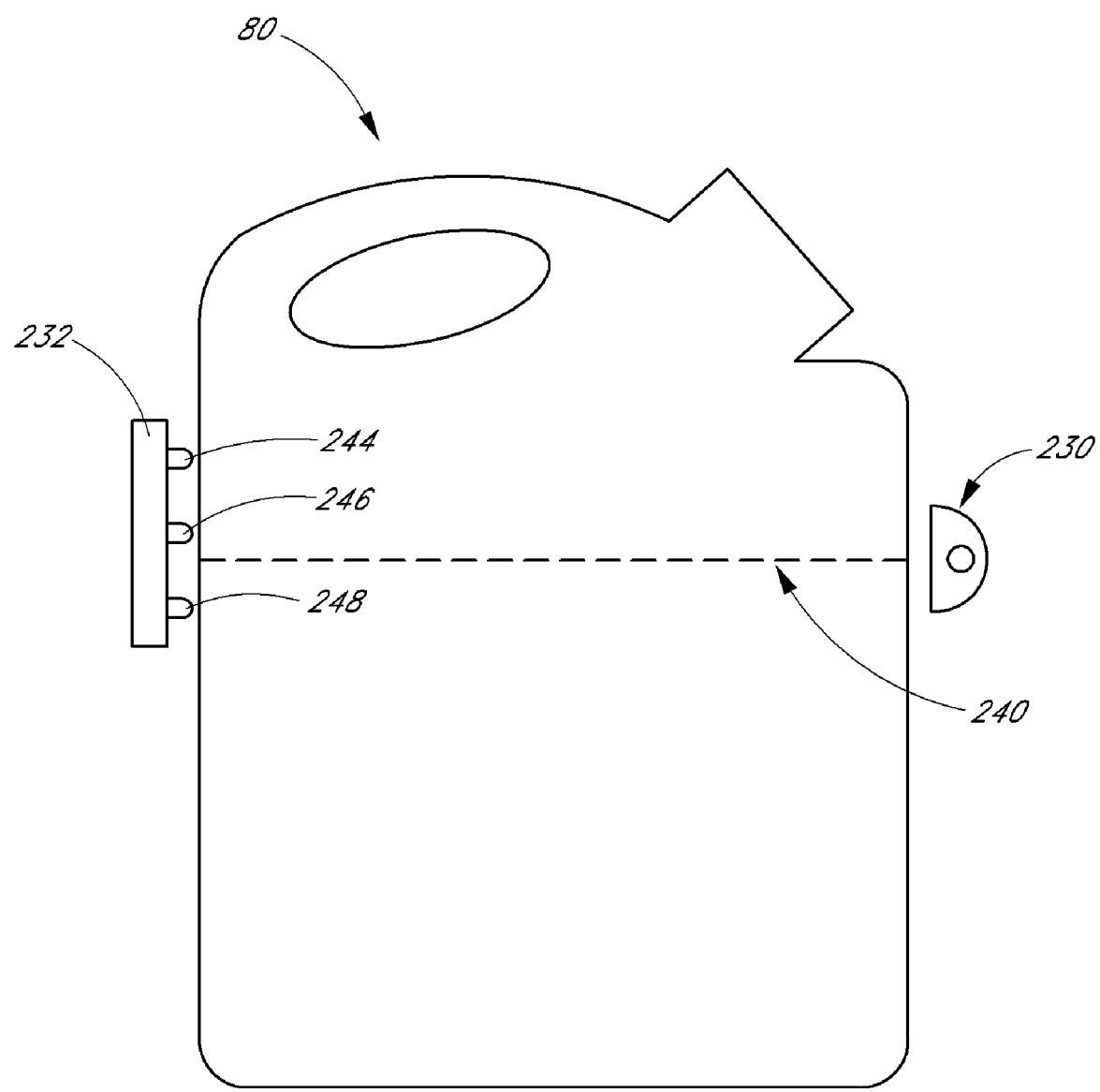
FIG. 18 is a schematic side elevation view of an embodiment of a fill level sensor.
Figure 19:
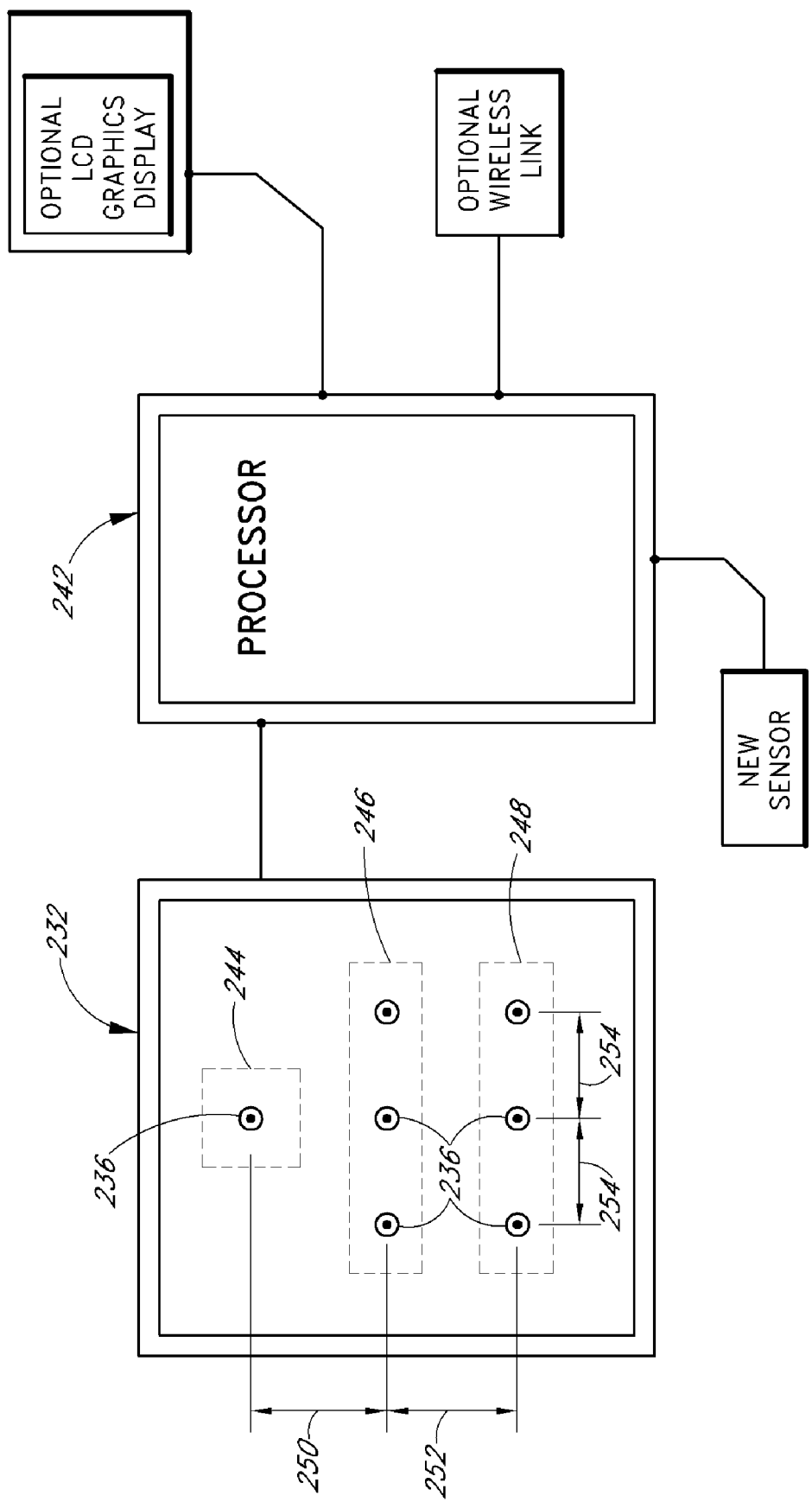
FIG. 19 is a block diagram of one embodiment of a fill-level detection system.

FIGS. 18-19 illustrate one embodiment of a level sensor which can be used to automatically determine a fill level of a container using an optical method. As shown in the schematic illustration of FIG. 18, one embodiment of a fill level sensing system comprises a light source 230 and a light detector 232 positioned on opposite sides of a container 80. In alternative embodiments, the light detector 232 need not be located immediately opposite the light source, for example, in some embodiments the detector can be located on a wall adjacent to the source 230. The sensor system of FIGS. 18 and 19 generally operates on the principle that an "empty" container will permit more light to pass from the source, through the container, and to the sensor than will a "full" container. This is simply due to the fact that the contents of the container 80 will absorb and/or reflect a substantial portion of the light which enters the container from a light source.

As used herein, the terms "empty" and "full" shall be given their ordinary meaning and shall be used to define relative amounts of debris, or other matter, in a container. For example, in certain embodiments, the sensor may indicate that the container is ready to be emptied or discarded, not because it is completely saturated, but because it has reached the desired point of fill or saturation. In some situations, it may be desirous to empty or remove a container when anywhere from about 1% to about 100%, often from about 25% to about 100% of that container contains waste material. In other situations, it may be desirable to remove a container when about 50% to about 95% of its volume is occupied by waste material.

In some other embodiments, a parameter other than weight or filled volume may be used to determine when a container is "full." For example, in one embodiment, a sensor to detect radioactivity is used to determine the amount of radioisotope in a container or receptacle. The radioactivity sensor may be used in connection with a fill sensor, or it may be used alone. Thus, in some embodiments, a container may be emptied, discarded, or replaced based on a certain amount of radioactivity, rather than (or in addition to) the surface area, volume, weight, density and/or another parameter of the material in that container.

In yet another embodiment, a sorting and disposal system can be provided without any automatic level detection apparatus. For example, in such an embodiment, the containers can be configured to allow a clinician, maintenance person, or other user to visually verify a fill level of the container. In such embodiments, the containers can be made of a substantially transparent or translucent material. Alternatively, the containers may be substantially opaque but can include a transparent viewing window to allow visual verification of a fill level. Such viewing windows could extend substantially an entire height of the container, or could extend only a height of a desired portion of the container.

In some embodiments, the source 230 and detector 232 are located along a "fill line" which generally defines a "fill plane." The fill plane 240 is generally the level within the container 80 which a processor 242 defines as "full." In some embodiments, the actual free surface of contents within a container may not necessarily be planar. In such embodiments, the "fill plane" used by the processor and fill level sensing system is simply an average height of the material.

In the embodiment illustrated in FIG. 18, a light source 230 is located at a "front" of the container and a detector 232 is located at a "rear" of the container. In alternative embodiments, the positions of the light source 230 and detector 232 can be reversed, or positioned at any other position around the container 80. In still further embodiments, multiple sources and/or detectors can also be used as desired.

As discussed above, the containers 80 are typically made of a translucent material which allows at least some amount of light to pass through its walls. The embodiments of a fill level sensor illustrated in FIGS. 18 and 19 are particularly advantageous when used to measure a fill level of a container with translucent sidewalls. However, the skilled artisan will recognize that certain advantages of the embodiments described herein may be advantageously applied to systems using containers having transparent sidewalls or containers with transparent windows in otherwise relatively opaque sidewalls. As used herein, the term "translucent" is used in its ordinary sense and refers without limitation to a material which allows the diffuse transmission of light when illuminated, while remaining substantially non-transparent when not illuminated.

The light source can comprise any suitable source of light such as incandescent bulbs, white or colored LED's, or other sources. In some embodiments, the light source 230 is located such that it is vertically centered on a desired "fill line" 240 of the container. The light source can be laterally centered relative to the container, or can comprise a width that is about as wide as the container 80. In still further embodiments, a plurality of light sources can be used to illuminate a container from multiple points.

As illustrated in FIG. 19, the light detector 232 can comprise an array of photo detectors 236 such as cadmium sulfide photo detectors or photodiodes. In the illustrated embodiment, the array of photo detectors 236 comprises three rows 244, 246 and 248 of detectors 236. The upper row 244 contains a single detector 236 while the middle 246 and lower 248 rows contain a plurality of detectors 236 (three in the illustrated embodiment). In alternative embodiments, the upper row 244 can be provided with additional detectors which equal or exceed the number of detectors in the other rows. Similarly, the middle 246 and lower 248 rows can include fewer or more than three detectors as desired. The number of detectors in each row will typically be determined by the algorithm used to determine the fill level of the container and/or the degree of accuracy desired. In some embodiments, it may also be desirable to provide more than three rows of detectors. For example, in some embodiments, a fill level detection system can be provided with four, five or more rows of detectors.

In some embodiments, the middle row of detectors is positioned to lie just above the fill line 240 of the container 80, and the lower row 248 of detectors 236 is positioned just below the fill line 240. The upper row 244 of detectors 236 can be located substantially above the fill line, and can be used to calibrate the detectors middle 246 and lower 248 rows as will be described in further detail below.

In some embodiments, the upper and middle rows can be spaced by a distance 250 of between about ½" and about 2 inches, in other embodiments the upper and middle rows can be spaced by a distance 250 of between about 1 inch and about 1½ inches, and in one particular embodiment, the upper and middle rows are spaced by a distance 250 of about 1¼ inches. Similarly, the middle and lower rows can be spaced by a distance 252 of between about ½" and about 2 inches, in other embodiments, the middle and lower rows can be spaced by a distance 252 of between about 1 inch and about 1½ inches, and in one particular embodiment, the middle and lower rows are spaced by a distance 252 of about 1¼ inches. In some embodiments, the detectors 236 of the middle 246 and lower 248 rows are spaced horizontally by a distance 254 of between about ½ inch and about 3 inches, in other embodiments, the detectors 236 of the middle 246 and lower 248 rows are spaced horizontally by a distance 254 of between about 1 inch and about 2 inches, and in one particular embodiment by a horizontal distance 254 of about 1½ inches. In some embodiments, the sensors are evenly spaced, while in other embodiments, the sensors of the middle row are horizontally spaced differently than the sensors of the lower row. In further alternative embodiments, the spacing of the detectors 236 can be determined by factors such as the size of the container or the material to be placed within the container.

In operation, the individual photo detectors 236 pick up light transmitted through the container and output corresponding signals to a processor 242. On one hand, the light intensity arriving at the detectors 236 depends on the fill level of the container 80. In addition, a number of secondary factors also affect the light intensity reaching the detectors 236. These include the strength of the light source 230, the color and opacity of the container 80, the amount of ambient light, and other factors such as dust in the air. The light intensity at the top detector row 244 is almost completely governed by these secondary factors, since it is located well above the fill line 240. By contrast, the light intensity arriving at the middle 246 and lower 248 detector rows will be affected more by the fill level of the container contents as the container 80 becomes more full (e.g., as the fill level approaches the fill line).

When the container 80 is empty and the overall light intensity is greatest, a baseline reading is recorded and calibration coefficients are generated for each of the detectors 236 and detector rows 244, 246, 248. As the container fills, the received light reaching the detectors decreases slightly as material in the container blocks a portion of the diffused light transmitted through the container 80. During this phase, the top detector reading is used to compensate the readings of the middle and lower detector rows accordingly. When the container contents reach the fill line, the bottom row of detectors will be blocked by the container contents, while the middle 246 and upper 248 detector rows remain unobstructed. This results in a substantial drop in the light intensity reaching the bottom row 248 of detectors, and correspondingly, a substantial difference in signal strength between the middle 246 and lower 248 detector rows. When this signal difference reaches a pre-determined threshold level, the processor determines that the container is "full."

In some embodiments, the items being deposited into a container may be stacked unevenly or oddly oriented within a container so that the contents of a container vary from a neat horizontal fill level. For example, some large items, such as syringes or other contaminated medical devices, may stack oddly within a container, thereby creating voids of unfilled space in a central portion of a container, above which waste items may be stacked. Such variations in filling can lead to measurement errors. Thus, in some embodiments, a level sensing system can be provided with error processing capabilities to account for variations in orientation and/or uneven loading of a container.

For example, in some embodiments, the signals from the plurality of detectors in each row are averaged to provide a consensus value for the respective detector row. This advantageously allows the processor to determine an average fill level in the event of an uneven fill surface. For example, in an idealized case, a container filled with a plurality of spherical particles through a hole in the top center of a regularly-shaped container will typically have a free surface in a shape of a cone with a peak at the center, and dropping off evenly in each direction. In such a case, the center detector of the lower row 248 will typically receive a lower light intensity than the detectors on either side. Thus, by using the data from all of the detectors in a horizontal row, a processor can calculate an approximate average fill level in order to prevent over-filling of the container.

These or other error-processing techniques can also be used to compensate for manufacturing defects in a container that might result in erroneous results. For example, if a plastic container wall comprises an air bubble or a dark spot in a region adjacent one or more of the detectors, these abnormalities could cause erroneous readings by those detectors. To compensate for this, a system may give less weight (or no weight at all) to signals from detectors that are out of a statistically expected range of variation from the remaining detectors. By taking an average signal across all detectors in various combinations and/or by assigning varying weights to individual detectors, a control algorithm can teach itself to recognize and adapt to such error-causing situations in order to obtain consistent readings.

In some embodiments, the functionality of a fill level sensing system employing a light source and a plurality of optical detectors can advantageously be enhanced by containers with "frosted" or translucent walls. Another advantage of certain embodiments of a level sensing system as described herein is that such systems can be polychromatic sensitive (e.g., configured to sense light of various colors with consistent accuracy). Thus, in addition to measuring a fill level of a container, the above-described sensors can be configured to determine a color of a container (each container color being associated with a particular container type as discussed above). In some embodiments, these and other advantages are achieved through the use of cadmium sulfide photosensitive cells. In alternative embodiments, optical level sensors can be constructed using other optical detectors, including other photoconductive cells, photo diodes, or other sensors capable of detecting light in the visible or infrared spectrum.

In some embodiments, each one of a plurality of fill-level sensors is controlled by a single processor in a waste sorting system. In one embodiment, a plurality of photo detector arrays can be connected to a single multi-channel bus, and a plurality of light sources can be controlled by a processor. In this embodiment, the processor can illuminate a single container at a time. Thus, the detectors behind each of the "dark" containers would be at high impedance, and would therefore be out of the circuit, In some embodiments, a fill level sensing system employing optical sources and detectors can include an additional photo detector that is generally configured to measure changes in "ambient" light within the system in order to appropriately adjust the readings from the detector arrays measuring fill level. An ambient light detector can comprise a single optical detector, or a plurality of detectors in a circuit. In one such embodiment, an additional ambient light detector is provided within a waste sorting system in a location selected to measure any light entering the system from the exterior of the sorting system. For example, the ambient light detector can be located adjacent a container-replacement door or any other portion of the system that is open to external light.

In one embodiment, optical detectors may be located on opposite sides of a container, or on the same side of the container.

FIG. 22A illustrates one embodiment of a circuit schematic which can be used in building an optical fill level sensor such as that illustrated in FIGS. 18 and 19. The skilled artisan will recognize that this is merely one exemplary schematic, and that alternative embodiments of the system of FIGS. 18 and 19 can be built using any appropriate components.

Figure 20:
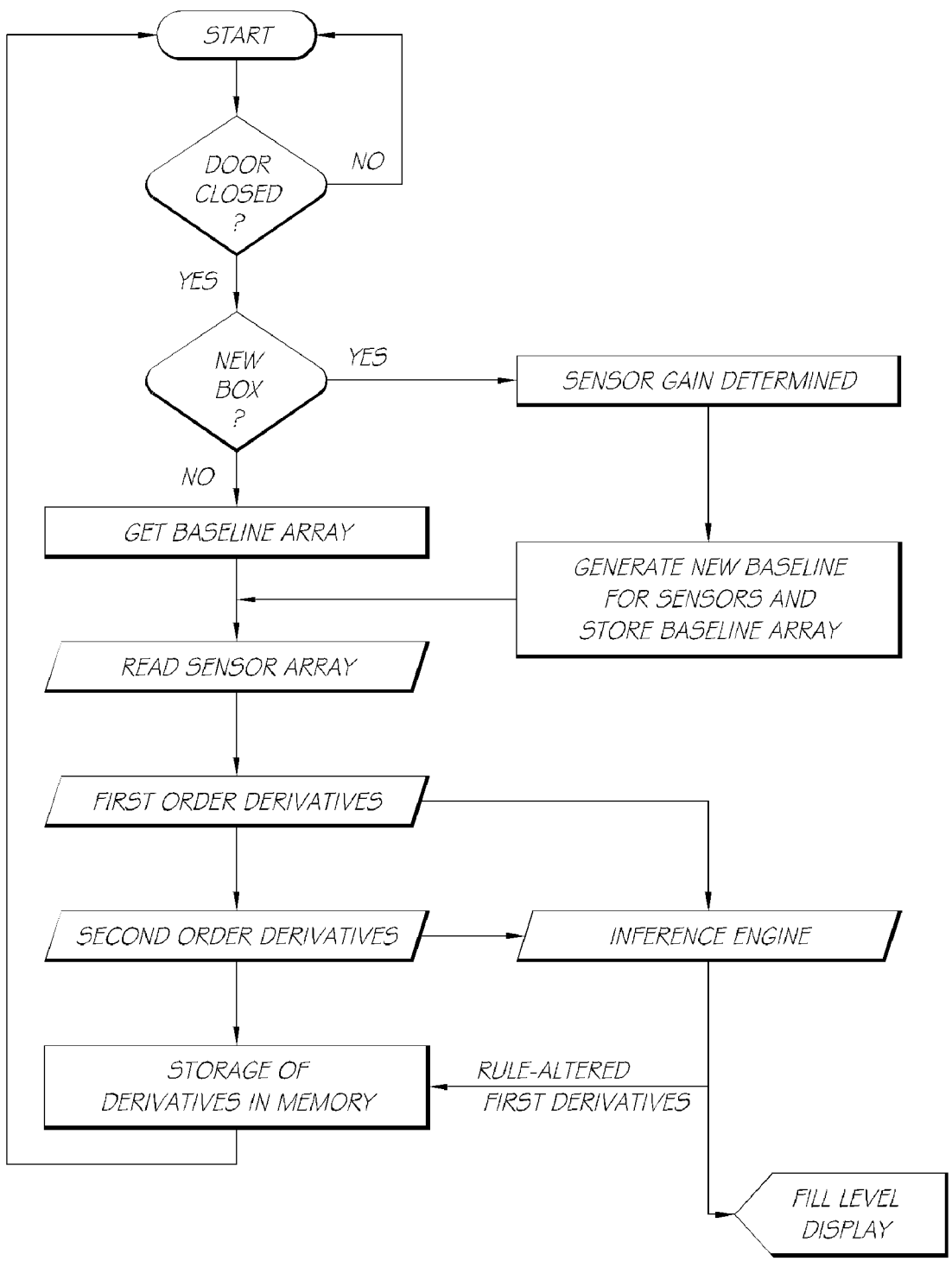
FIG. 20 is a an overview flow chart of one embodiment of a software algorithm for measuring a fill level of a container.
Figure 21:
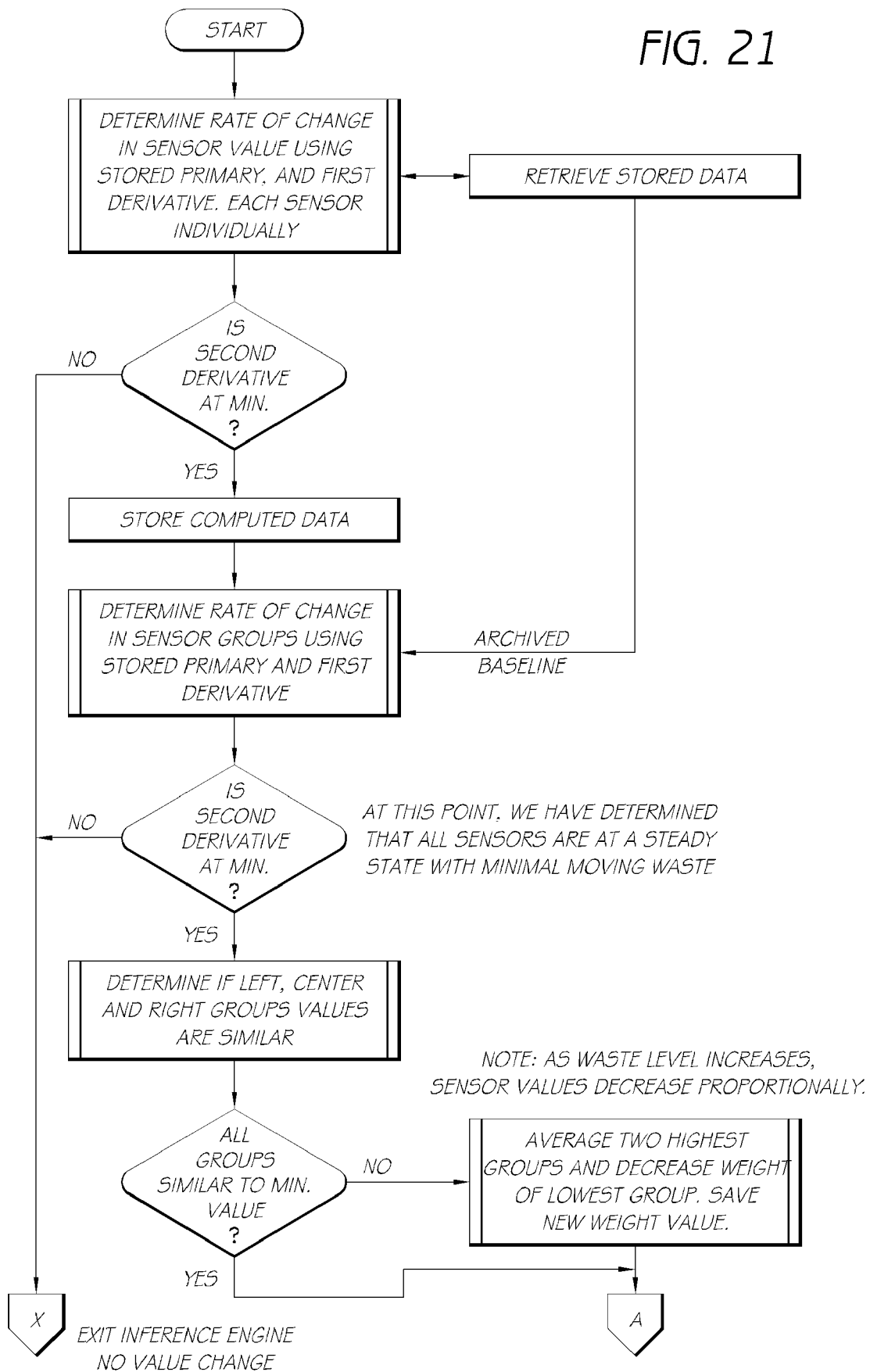
FIG. 21 is a detailed flow chart of one embodiment of a method of measuring a fill level of a container
Figure 22:
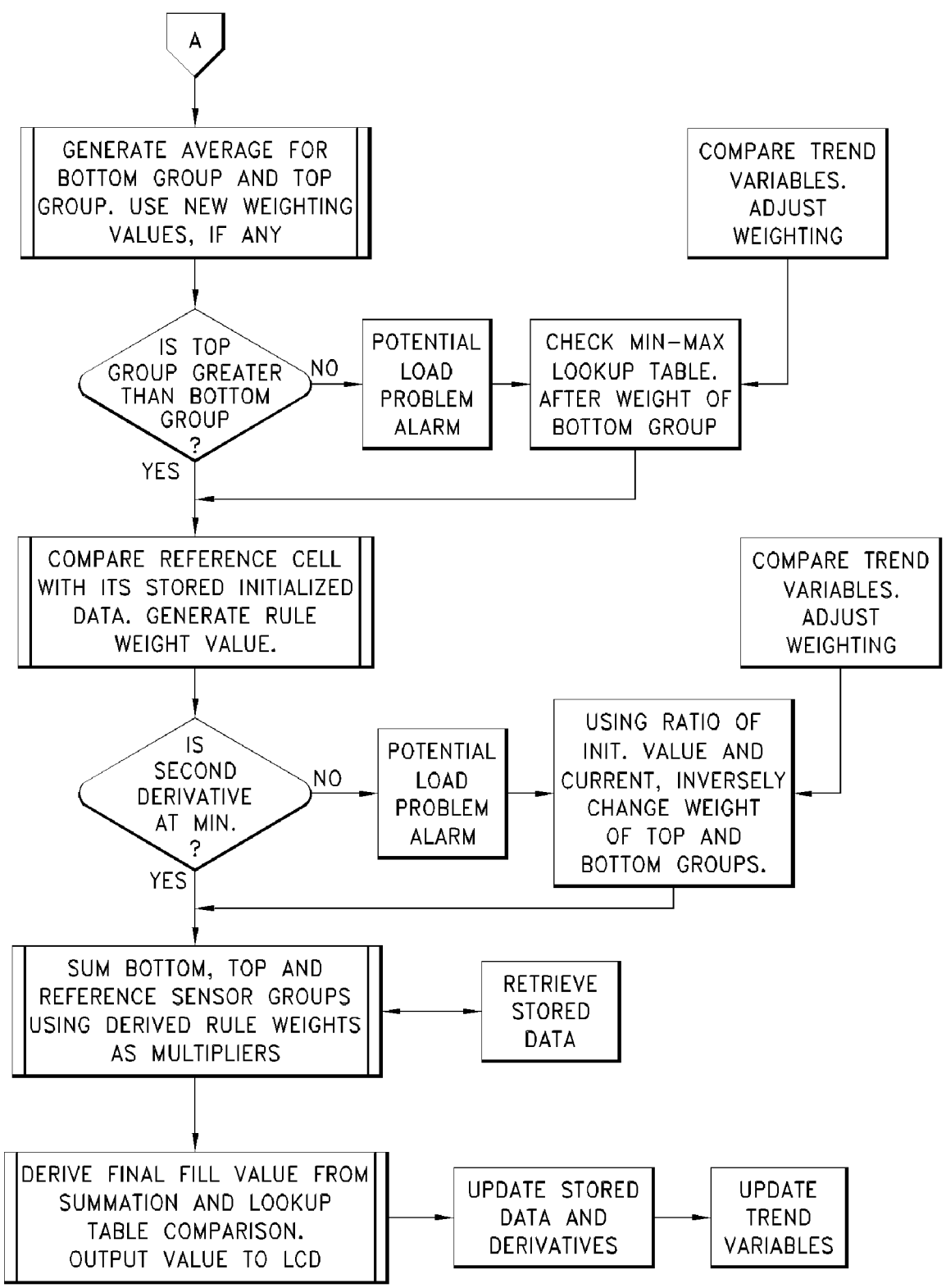
FIG. 22 is a continuation of the flow chart of FIG. 21.

FIGS. 20-22 are flow charts illustrating embodiments of software algorithms used by a level detector for use in a sorting system. FIG. 20 is a flow chart illustrating an overview of a level testing algorithm. When the system determines that a new container has been inserted, the level sensor establishes new baseline values for the detectors in order to define the "empty" state. The level sensing system then reads values of the detectors 236 and inputs the detector values to an inference engine (FIGS. 21 and 22).

The inference engine can use a "fuzzy logic" method similar to the Sugeno method. In one embodiment, the inference engine uses a table of empirically-determined data to establish rule weights. The inference engine can also use multiple grouping of detectors in addition to individual detector levels to calculate a final fill level of the container. In some embodiments, the empirically-determined lookup table can be developed by performing various calibration experiments using an optical level sensing system to measure containers at known fill levels. In addition to any controlled experiments, the lookup table can be supplemented by analysis of information it receives during use in measuring fill levels of new containers. For example, as optical anomalies are detected and accounted for, the software can adapt to correct for them.

FIGS. 21 and 22 are flow charts illustrating one embodiment of an inference engine. In order to avoid misleading readings during filling, the system can be configured to determine when the detectors are at a steady state (e.g., when the movement of waste within the container drops below a threshold level). This is particularly helpful in embodiments in which a waste material is a liquid, and thus may continue moving for a period of time.

Once steady state is reached, the inference engine compares the values of the detector readings and ultimately derives a final fill value which can be stored and/or output to a user-readable device such as a liquid crystal display. In alternative embodiments, an output of the system can include other visible, audible or tactile alerts, such as LEDs, buzzers, bells, vibrators, etc. In some embodiments, an output signal is used to notify the user that a particular container is ready to be emptied, discarded, replaced etc. In an alternative embodiment, an output signal is provided substantially continuously or at various intervals, so that the user can determine or monitor the amount of material in a given container at any given time. For example, in some embodiments, the fill-level of a container can be measured at regular intervals, such as every ten minutes, every hour, every two hours, every six hours, every 12 hours, or every 24 hours. In still further embodiments, the system can comprise a sensor (such as an optical sensor) to determine when an item is deposited into a container. Then a fill-level of the container can be measured after each item is deposited in the container.

Figure 23:
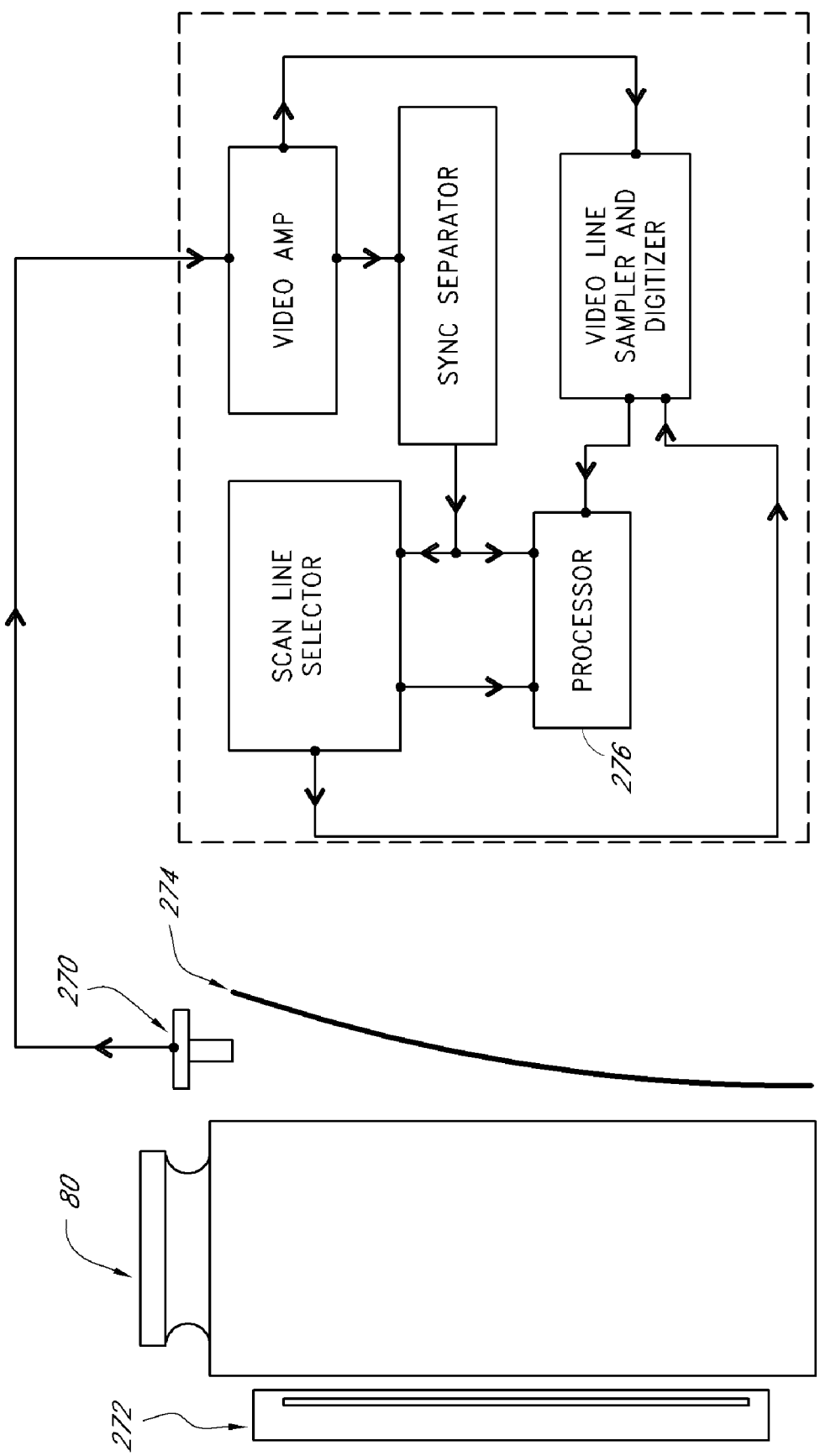
FIG. 23 is a block diagram of an alternative embodiment of a level sensor system employing a video camera.

FIG. 23 illustrates an alternative embodiment of a video fill level sensing system. The embodiment of FIG. 23 employs a camera 270 to continuously detect an intensity of light exiting the container from the source. In the illustrated embodiment, a light source 272 is positioned to illuminate the container 80, and a curved mirror 274 and pinhole video camera are located adjacent another side of the container 80. The system can also include a software-based processor 276 and other electronic hardware. In the illustrated embodiment, the light source 270 is located adjacent one vertical side of the container 80 and the camera and mirror are positioned on the opposite side of the container. In alternative embodiments, the light source 270 and camera/mirror assembly can be located on adjacent sides of the container 80. Alternatively still, the light source 270 can be located above the container such that light is directed downward into the container, thereby allowing the waste to absorb as well as reflectively diffuse the light source onto the walls of the container 80.

In some embodiments, the camera 270 is directed at the mirror 274 to detect light emitted from the container 80 and gathered by the mirror 274. The curved mirror 274 provides a linearization of scanline width by distorting the optics of the camera. In one embodiment, the camera 270 is a pinhole camera, which is selected due to the depth of field this type of lens provides. In one embodiment, the curved mirror 274 has a shape substantially similar to a shoehorn, e.g., it is curved about two perpendicular axes (e.g., longitudinal and transverse axes). Alternative mirror configurations can also be used as desired. The particular curvature of the mirror 274 is determined empirically depending on the width of scanline needed and the height of the measured area (e.g., the height of the container wall). Variation in the curvature of the mirror along its length allows the scanline to be optimized in order to emphasize areas of higher interest and to de-emphasize lower interest areas. The mirror can be convexly curved at the height of higher interest areas, and concavely curved to de-emphasize lower interest areas.

In some alternative embodiments, the light source can include bands of varying color or intensity along the height of the container in order to provide emphasis to portions of the container, or to provide "watermark" levels that can be measured against. In some embodiments, the software can be configured to interpret information received from the camera to learn about points of interest in order to further optimize a measurement algorithm. For example, rather than programming an algorithm to anticipate areas of higher or lower interest, the algorithm can be configured to recognize variations in light intensity during calibration in order to detect such areas of higher or lower interest.

Figure 23A:
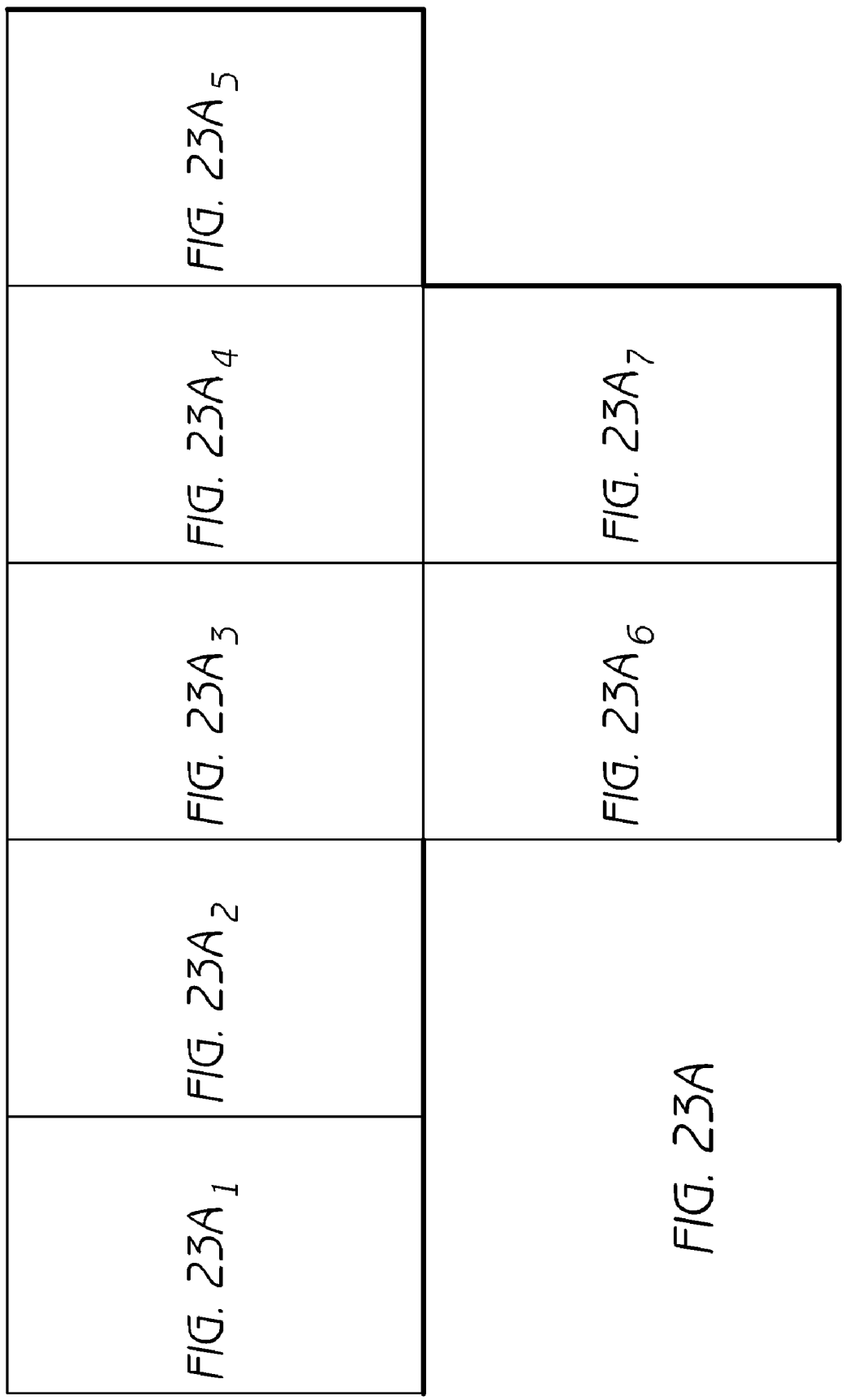
FIG. 23A is an electronic schematic of one embodiment of an alternative embodiment employing a video system, illustrated further in FIGS. 23A$_1$-A$_7$.

The processor and its support hardware provide the sampling of multiple luminance intensities along the wall of the container 80 adjacent the mirror 274. The analog video signal is amplified and ground-referenced by the video amplifier. This amplified signal is scanned for a selected scanline to digitize for quantifying its luminance value. The amplified video is also applied to the Sync Separator module, which produces timing pulses for the scanline selector module. The processor receives the scanline data from the scanline selector, digitizer and sync separator. The video level sensor can determine a current fill level of the waste in the container 80 using a similar software method to that described above with reference to FIGS. 18 and 19. FIG. 23A illustrates one embodiment of a circuit schematic which can be used in building a video fill level sensor such as that illustrated in FIG. 23. The skilled artisan will recognize, however, that this is merely one exemplary embodiment. In alternative embodiments, the system of FIG. 23 can be built using any appropriate components.

Many of the above embodiments of fill level sensors were described with reference to a single container. In some alternative embodiments, it may be desirable to provide a single fill level detection system configured to selectively measure a fill level of any one of a plurality of containers. For example, in one embodiment, a light source may be provided on a first side of a plurality of containers, and a light detector can be movable into a position opposite the light source of the containers. In one embodiment, this may take the form of a circular arrangement of containers in which a light detector is located at a center of a circular arrangement of containers. One or more light sources can be positioned on an outer portion of the circular arrangement such that the light source and/or the light detector is capable of measuring a fill level of each one of the plurality of containers around the circle.

In some embodiments, the sorting system can also include a weight scale (such as a load cell, pressure transducer, mechanical scale or other device) configured to weigh either a single spent drug, container or individual segregated spent drugs. In one embodiment, the information from the scale can be sent to a printer providing a means for printing a manifest for the container. Additionally, such information could be combined with other information available to a clinician in order to determine a quantity of a drug or substance that has been used or consumed. Many hospitals are automating the dispensing of drugs. The automation is usually embodied in a piece of equipment that a doctor or nurse accesses with a patient and clinician code and the correct amount of drug is dispensed. The automation provides pharmacists, nurses, doctors and administrators with information from a database on what drugs are dispensed and to which patient. These systems can typically indicate how much of a drug was administered, but entering this information typically requires a clinician to return to the dispenser (which may be inconvenient, and thus not done regularly). This information can be quite useful because it will demonstrate any inefficiencies or mistakes in administrating the drugs as well as point out any theft of drugs. In some embodiments, a sorting and disposal system can be configured to track dispensing information because at the point of throwing the spent drug away, they are automatically providing information to a central database.

In another embodiment, the invention comprises one or more level sensors, wherein the level sensor comprises a bar, wherein the bar is periodically adapted to pass through a container at approximately the fill level. In one embodiment, a position indicator (or other visual indicator) coupled to the bar is also provided, wherein movement of the bar causes movement of the position indicator. In some embodiments, the position indicator may be comprised of a physical flag. In one embodiment, a detector adapted to detect movement of the position indicator is also provided. Thus, in one embodiment, the invention detects movement of the bar, thereby sensing the level of waste in a container. The position indicator can be fixed, tied, attached, connected, or otherwise coupled to the bar. Physical contact between the position indicator and bar is not needed.

In one embodiment, the container comprises a level sensor that comprises a bar, wherein the bar is adapted to pass through the container. In one embodiment, a photo-detector adapted to detect movement of the bar is also provided, thereby sensing the level of waste in a container. A position indicator, or other mechanism, may also be coupled to the bar for detection by the photo-detector. The photo-detector can be adapted to either detect transmission of light or to detect the absence of transmission. Thus, in some embodiments, the photo-detector can be a photo-interruptor. One of skill in the art will understand that several optical sensors can be used in accordance with some embodiments of the present invention. One of skill in the art will also understand that non-optical sensors (such as mechanical sensors, electrical sensors, and acoustic sensors) may also be used in accordance with some embodiments of the invention. For example, mechanical sensors, electrical sensors, and/or acoustic sensors may be used to detect the movement of the bar, and thus detect the level of waste in a container.

In yet another embodiment, a method of detecting the level of material in a hazardous waste container is provided. In one embodiment, the method comprises passing a bar through the container at the approximate fill level, wherein the bar is coupled to a position indicator (or other mechanism), wherein the position indicator (or other mechanism) activates a photo-interruptor to determine whether the container is full. The method further comprises detecting whether the bar is free to move or is blocked by the contents, thereby detecting the level of material in a hazardous waste container.

In a further embodiment, a method of detecting the level of material in a hazardous waste container (opaque or translucent) by passing a bar through the container is provided. In one embodiment, the bar is passed at the approximate fill level and a detector is used to determine whether the bar is free to move or is blocked by the contents. A position indicator fixed (or otherwise coupled) to the bar activates a photo-interruptor, to detect the end position and determine whether the container is full. The bar operates in conjunction with a lid, that excludes access to the contents of the container. The lid may also have a position indicator and photo-interruptor for determining its position.

Some embodiments of the present invention can also be used for receptacles containing materials other than medical or pharmaceutical waste. Thus, in some embodiments, the level sensor can be used with non-medical, non-pharmaceutical containers, holders, or vessels.

The level sensor apparatus, in one embodiment, comprises a bar, a position indicator tied to the bar, a photo detector, and processing electronics. The level sensor apparatus, in one embodiment, is used to determine when a container is full, thereby necessitating the need for action, such as emptying or replacing the container. The level sensor apparatus, in one embodiment, is directed at the problem of level detection in hazardous waste containers. In one embodiment, the level sensor comprises a bar, induced under spring force (or other force) to pass through a container approximately at the fill level. The bar is activated periodically, such as when the container lid is operated. Since the bar may come into contact with hazardous waste, it may become soiled in use or otherwise contaminated. In a preferred embodiment, the bar is part of the container, so that it may be disposed, or cleaned for reuse, along with the container.

In another embodiment, a position indicator (or similar feature), is coupled to the bar, so that movement of the bar causes movement of the position indicator. In a preferred embodiment, the position indicator resides outside the container, so that the associated detecting means are not in contact with the hazardous waste. However, one of skill in the art will understand that the position indicator may also be located within the container. The position indicator can be fixed, tied, attached, connected, or otherwise coupled to the bar. However, physical contact between the position indicator and bar is not needed. Moreover, one of skill in the art will understand that a position indicator is simply provided in one exemplar embodiment, and therefore, other indicators can also be used.

In one embodiment, a photo-interruptor, or other detecting means, is utilized to detect movement of the position indicator. In a preferred embodiment, the detector is situated on the outside the container, so that it is not in contact with the hazardous waste. However, one of skill in the art will understand that the detector may also be located within the container.

In one embodiment, the bar is released at intervals to sweep across the container. In a preferred embodiment, the bar operates each time the lid is opened. The bar can operate in a horizontal, circular, or other motion. In a preferred embodiment, the lid and bar are both rotary, and share a common axis. Thus, both the lid and bar describe a circular motion as they rotate from the closed to the open position.

In one embodiment, the opening forces may be applied by compression, extension, or torsion springs, or by other motive forces, such as a torque motor. In a preferred embodiment, the spring forces are provided by torsion springs.

In one embodiment, the lid may be closed manually, by a motor, or by other means. In a preferred embodiment, the lid is closed manually. In one embodiment, in the closed position, the lid and bar are restrained by one or more latches, which control the opening of the lid by opposing the opening spring force. In a preferred embodiment, the lid is latched, and the bar is in turn restrained by the lid by an interfering stop. Thus, the latch reacts to the sum of the two spring forces. In one embodiment, when the door opens, the latch releases the lid, and both the lid and bar open simultaneously under independent spring forces. In one embodiment, as the lid is rotated closed, the bar remains in contact with the lid and is pushed along ahead of it the lid until the latch clicks into the closed position. As the lid rotates open, the bar follows the rotation of the lid.

In yet another embodiment, if the container is not full, the lid and bar both complete their full excursion and arrive at the open position. If the container is full, the lid rotates open, but the motion of the bar is impeded by the container contents, and cannot reach the open position. Thus, according to one embodiment, the bar photo-interruptor remains unactivated, and the circuit detects a full container.

Other embodiments that incorporate one or more level sensors are described below, in conjunction with restricted access containers.

Sorting Algorithm

Embodiments of a pharmaceutical waste sorting and disposal system will generally employ a waste sorting algorithm to assign each item of waste to a particular waste category and correspondingly to a particular waste container. A waste sorting algorithm can take a variety of forms, and can include a range of functionalities.

In some embodiments, as discussed above, determination of the waste categories themselves can depend on a number of factors, including RCRA hazardous waste definitions, state and federal EPA regulations, OSHA regulations, and any institution-specific regulations. For example, RCRA definitions generally include a P list, a U list and four characteristics of hazardous waste: ignitability, corrosivity, toxicity and reactivity. Materials exhibiting each of these characteristics typically call for different handling, treatment and/or disposal. Thus, in some cases waste categories can be defined based on groups of materials that require the same or similar handling, treatment, or disposal. However, in some cases, two materials that may be handled and/or treated in a similar manner might react adversely if they are combined with one another. Thus, in further embodiments, determination of the waste categories can also depend on the combinability of materials exhibiting one or more of the above characteristics.

Once a series of unique waste categories is established, lists of known pharmaceuticals, chemicals, materials and waste items can be selectively assigned to at least one of the waste categories. In some embodiments, as discussed above, when a waste item is presented to a sorting station, the item is identified according to a waste item identifier. Such identifiers can include a trade name, a generic name, a National Drug Code (NDC), one or more components or ingredients of the item, or any other sufficiently unique or relevant waste-identifying datum. Thus, a category database can be developed which correlates a number of known waste identifiers with respective waste categories according to existing federal, state, local, institution-specific or other rules and regulations.

In some embodiments, it may also be desirable to provide a database which lists ingredients of a plurality of known pharmaceuticals or other chemicals that have not yet been correlated to a waste category by the category database. Such an ingredient database can be used by the sorting algorithm in an intermediate step between identifying an item and assigning the item to a category on the basis of one or more ingredients. In some embodiments, an ingredient database may reside within the waste sorting and disposal system. In alternative embodiments, an ingredient database can reside at a remote location, such as on a server operated by a manufacturer of a particular item, or another remote location. The waste sorting and disposal system can be configured to access such remote databases via any available network, including the internet. In some embodiments, the remote or local databases may receive updates to maintain the sorting process current. In some embodiments, the updating occurs periodically based on a predetermined time interval (e.g., once every 24 hrs, week, month, etc.). In another embodiment, the updating occurs when a user prompts the system for an update. In yet another embodiment, the updating occurs when the system encounters a waste item for which no appropriate waste classification can be found.

In some embodiments, on a first level, assignment of waste items to waste categories can be performed simply by sorting the items according to known characteristics. In some embodiments, a waste sorting algorithm simply involves locating a waste item identifier in a look-up table or database which lists known identifiers correlated to respective waste categories, such as the category database described above. Thus, to the extent that an item can be assigned to a waste category based solely on one or more waste item identifiers, the sorting algorithm can comprise a simple look-up routine. If needed, the sorting algorithm may also seek additional information such as from the ingredient database described above, or any other available source of additional information.

Cases may arise where a single waste item possesses two or more waste identifiers (such as ingredients) belonging to two or more different waste categories. Thus, in the event that a particular waste item can reasonably be assigned to two or more waste categories, yet is only physically capable of being placed in a single container, the waste sorting algorithm can be configured to assign the item to a single category by reviewing a number of secondary variables. Such secondary variables may include a dosage or quantity of specific ingredients; a dilution or concentration level of one or more ingredients; a relative hazardousness level of one or more specific ingredients; a relative reactiveness of one or more ingredients; a shape, size, type or other feature of a waste item container (e.g., a pill bottle, syringe, etc); a physical property of the item (e.g., liquid, solid or gas), or any other datum that may be available to a user, but that might not be automatically determinable by the sorting station. If such a piece of additional information is needed in order to complete an assignment of an item to a container, the sorting station can prompt a user to input further information. Such additional information can be input by selecting from multiple answer choices or by typing.

Figure 24:
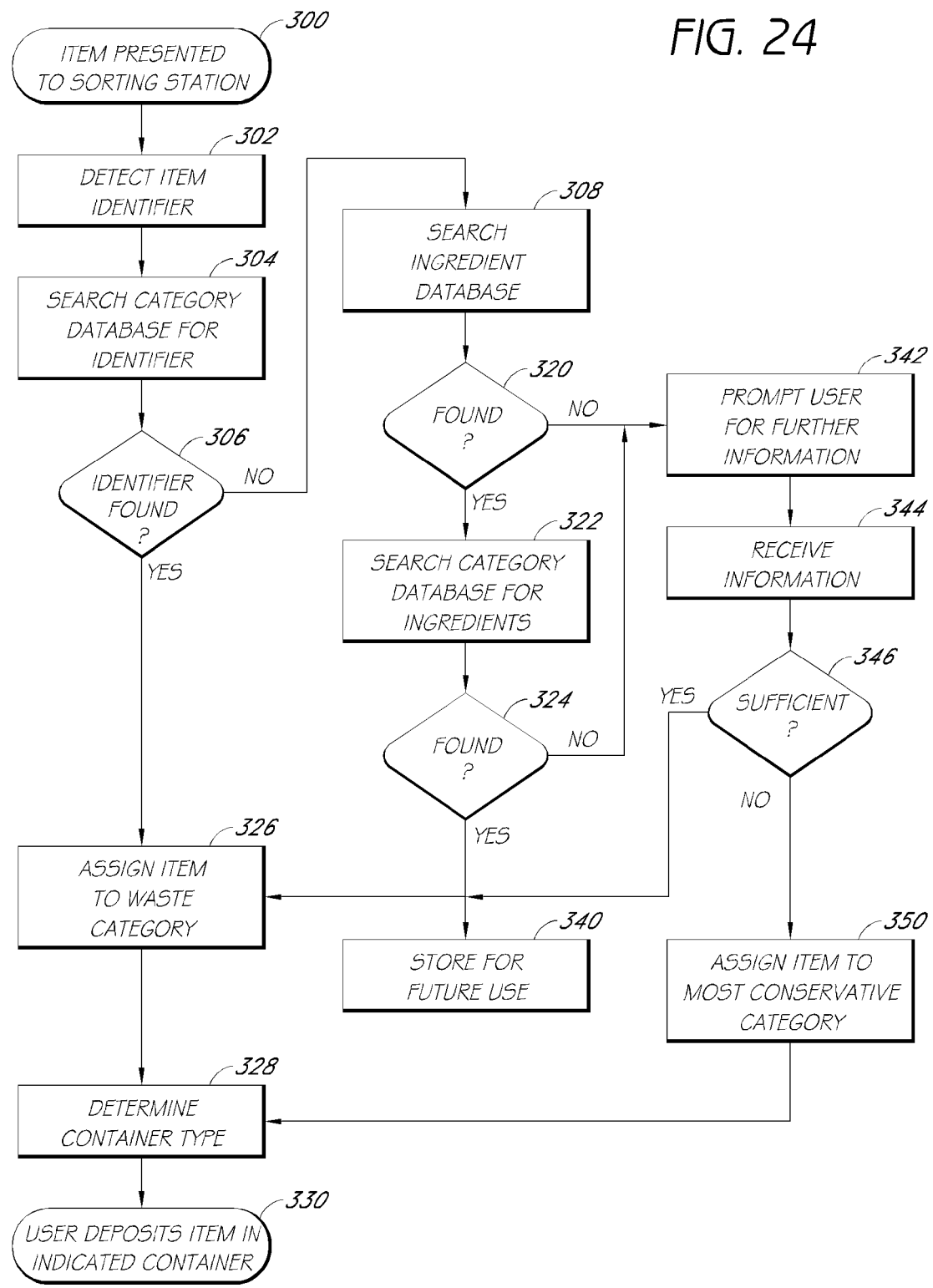
FIG. 24 is a flowchart illustrating one embodiment of a sorting algorithm for use by embodiments of a medical waste sorting and disposal system.

FIG. 24 is a flow chart illustrating one embodiment of a sorting algorithm. In the illustrated embodiment, a user initiates the process by presenting 300 a waste item to be identified by the sorting station. The sorting station then detects 302 a waste item identifier in any manner discussed above, such as scanning a barcode, reading an RFID tag, or scanning a textual or graphic label. The system then searches 304 the category database using any information or identifier determined from the item in an attempt to discover whether the determined identifier has previously been correlated to a waste category. If the identifier is found 306 to have been correlated to a waste category, the system continues by assigning the item to the appropriate waste category, and facilitating disposal of the item in the appropriate container.

On the other hand, if the identifier is not found in the category database (e.g., if the system discovers that the determined waste item identifier is insufficient to determine an appropriate waste category), the system may search an ingredient database 308 for additional information or further details about the item. If additional information is found 320 in an ingredient database, the additional information, along with the originally-detected waste item identifier can be used to again search the category database 322. If this information is found to be sufficient 324 to assign the item to a waste category, then the system assigns the item 326 to that category, determines an appropriate container 328 and facilitates disposal 330 of the item in a container associated with the assigned category. The system can also store 340 the identifier/category assignment combination in the category database for use in accelerating the sorting of future waste items with the same identifier.

However, if the search of the ingredient database yields insufficient information to assign the item to a waste category, the system may seek additional information by prompting a user 342 to input additional information. Such a prompt may request specific information, such as a choice between known alternatives, or may be more general in nature. The information received 344 from the user can then be combined with previously-obtained information about the item, and the category database can again be searched in an attempt to assign the item to a category. If this information, in combination with the previously-obtained information, is sufficient to assign the item to a waste category 346, then the system assigns the item 326 and facilitates disposal 330 of the item in the appropriate container. As above, the system can also store 340 the identifier/category assignment combination in the category database for use in accelerating the sorting of future waste items with the same identifier.

If the information received 344 from the user is insufficient 346 for the system to make a category assignment, the system can either prompt the user for still more information 342, or the system can simply assign 350 the item to the most conservative waste category for disposal of the item as hazardous waste.

Figure 25:
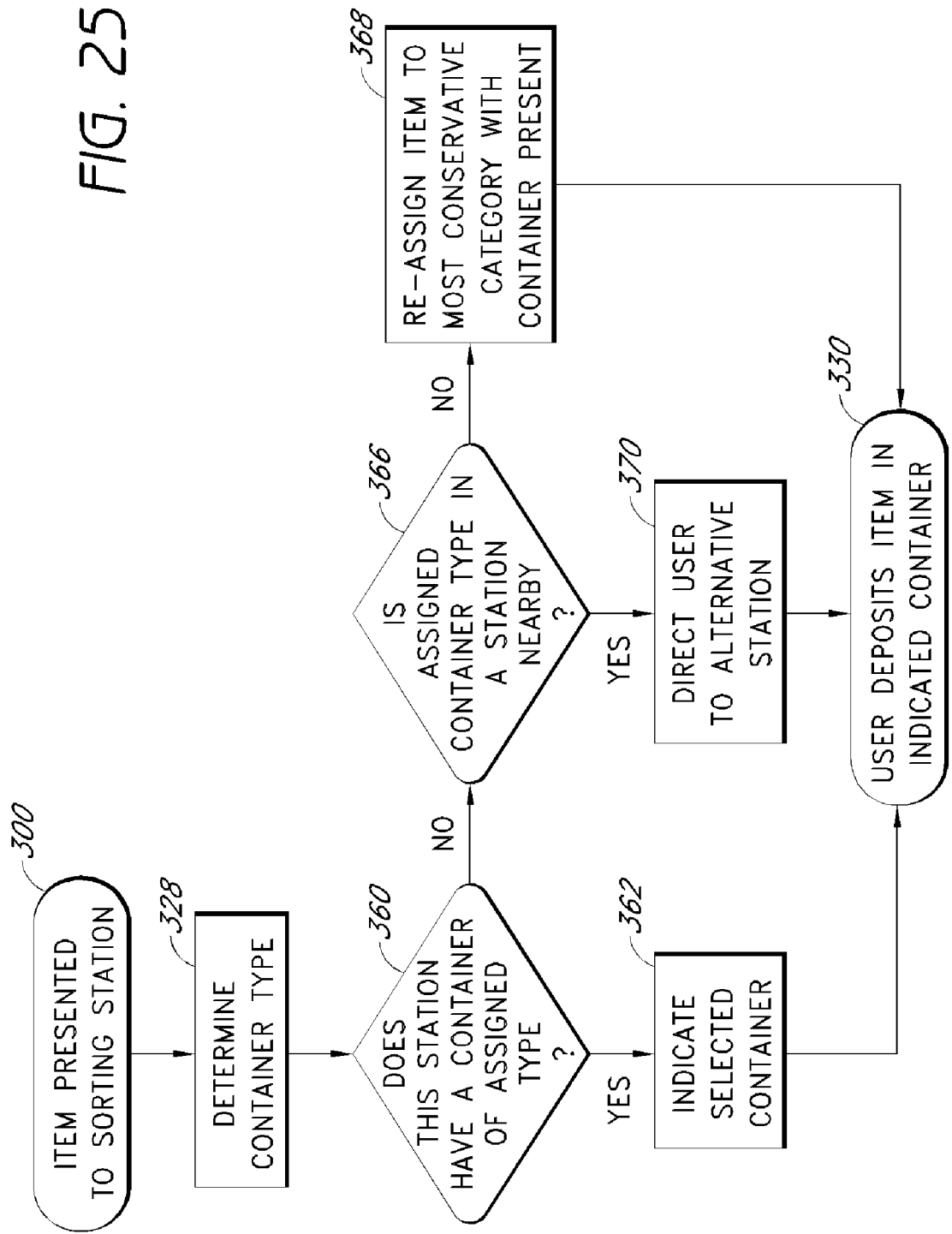
FIG. 25 is a flowchart illustrating a container-checking subroutine for use by embodiments of a medical waste sorting and disposal system.

FIG. 25 illustrates one embodiment of a portion of a sorting algorithm which can be used in determining the best container for a particular item. Once the sorting algorithm has assigned an item to a waste category, the system determines 328 the container type associated with the assigned waste category. In the illustrated embodiment, the station searches the stock of the containers currently loaded into that station to determine whether the assigned container type is present in that particular sorting station 360. If the container type is present, the station proceeds to indicate 362 the appropriate container to the user, and the user may then deposit 330 the item into the selected container. However, in some embodiments, if the selected container type is not present, the station can assess 366 whether another sorting station nearby contains a container of the assigned type. If a station with the selected container is nearby, the system can direct the user 370 to the nearby station to deposit the item. If a station with the selected container type is not nearby, the system can re-assign 368 the waste item to the most conservative (e.g., the highest level hazardous waste) category for which a container is loaded into the station.

In an alternative embodiment, a station may indicate that the selected container is full and thus cannot accept any further waste items. In such a case, the station can instruct the user to replace the container with an empty one of the same type. Alternatively, the station can instruct the user to use a container in a nearby station. In some embodiments, the station may offer the user a choice between replacing a container and using a nearby station.

The term "nearby" is a relative term, and can include any actual distance deemed appropriate by a particular user or system administrator. For example, in some embodiments, a station located on another floor of the hospital may be considered nearby, while in other embodiments, a sorting station across the hallway may not be considered nearby for the purposes of re-directing disposal of the waste item.

In some embodiments it may be inappropriate or undesirable to re-assign an item to a higher level container in the event that an appropriate waste category cannot be determined (e.g., as in step 350 of FIG. 24), or that an appropriate container cannot be located within an acceptable proximity (e.g., in step 368 of FIG. 25). In such embodiments, it may be desirable to provide a temporary holding space for items that cannot be placed in any currently present container to the extent allowed by regulations governing satellite storage of hazardous waste. Such items can then be analyzed at a later time by a hazardous waste analyst in order to determine the most appropriate disposal of the item. Once such an analysis is performed, the analyst preferably enters such information into the category database in order to facilitate future sorting of items having similar characteristics.

In some embodiments, the waste sorting software can be configured to maintain a log file of all identified waste items and the categories/container to which each item was assigned. Such information can be used by hospital administrators, regulatory auditors, pharmacists, or other entities to determine what items were disposed of and how. This information can be used to further optimize the sorting algorithm, to audit compliance with regulations, to audit usage or disposal of specific items, to alter a container arrangement in a station to increase sorting efficiency, or any of a variety of other purposes.

By enlisting the use of one or more embodiments of the present system, hospitals can demonstrate to their communities and their staff that they are participating in the improvement of the environment. It has been demonstrated by the US Geological Survey that the groundwater in the United States is contaminated with drugs. Although in trace amounts, the cumulative effect of these contaminants have been shown to be endocrine system disrupters contributing to the rise in cancers, birth defects and other ailments. By properly sorting the spent drugs into appropriate containers, the waste can be properly processed in order to leave only an inert residue that cannot contaminate the ground water.

Thus, embodiments of a medical waste sorting and disposal system advantageously provide a convenient means for clinicians to automatically sort pharmaceutical waste streams in order to comply with RCRA without the need to manually classify and sort each item individually. Additionally, the system advantageously provides hospitals with a means for participating in the improvement of the environment while avoiding fines for non-compliant waste disposal methods.

Additionally, as described above, some embodiments of the system can be configured to create a manifest to provide administrators suitable tracking information on the amount of a drug that has been actually used. Many hospitals are now moving toward implementing drug dispensing automation. The automation provides the hospital pharmacist and administrator information on what drugs are dispensed but not a convenient way of generating information on how much of a drug is used.

Medical Waste Treatment System

In one embodiment, a medical waste treatment system is provided. The medical waste treatment system is a product that renders infectious waste non-infectious, compacts it to a fraction of the original volume and uniquely maintains the treated material in a compact form. The cost of present embodiments of a medical waste treatment system is much less than competing technologies, because the footprint of the equipment is, in one embodiment, about one fourth the size. Competing technologies have cycle times that are long (usually about one hour) which necessitate large vessels for acceptable throughput versus the medical waste treatment system which has a cycle time of less than five minutes.

In one embodiment, the operating cost goal (about $0.09/lb) will be equal or better than most common technology, autoclave sterilization. Other competing technologies may have lower operating costs but they have many drawbacks. Incinerators may be one option, but it is possible that the EPA may tighten regulations and force many of the remaining incinerators to shut down. Many states do not allow incinerators to operate within their boundaries. For example, much of California's infectious waste is trucked to a Kansas City incinerator. The transportation costs add to the actual operating costs. Plasma technologies have equipment costs that are very high ($1-$3 million) and are, therefore, only suitable for central processing plants.

In one embodiment, a medical waste treatment system as a truck mounted service to hospitals is provided. The medical waste treatment system has significant advantages over truck mounted chemical processors. The medical waste treatment system unlike the chemical processors has a residue that is substantially innocuous such as common sand. It has been demonstrated that if there are any concentrations of organic matter, such as blood, the chemicals tend to be consumed by the organics leaving some of the remaining waste in a load untreated or partially treated. In one embodiment, the medical waste treatment system uses a unique heat technology that quickly and uniformly decontaminates the waste regardless of the amount of organics present. In several embodiments, the heat technology comprises use of sand or wax (including, but not limited to, paraffin) or a combination thereof. In one embodiment, the sand and/or wax is heated to a temperature of about 150° C. to about 250° C., preferably between about 165° C. to about 225° C. In one embodiment, the sand and/or wax is heated for less than about five minutes. One particular advantage of this method is the ability to produce highly stiff and/or compacted medical waste. In some embodiments, the volume and/or surface area of the treated medical waste is reduced to about 1/10 of its original size.

In addition to truck mounted systems, stand alone versions of the system or a central off-site processing unit can be made available for hospital purchase. In this way, infectious waste can be treated efficiently.

Up to about 50% of infectious medical waste can be plastic, of which about 25% can include disposable PVC waste. Utilizing sand or wax to treat such plastic waste may not be any more cost effective than an autoclave or other processing approach for these materials. It also may cause a number of problems such as the PVC outgassing chlorine because the temperature may be greater than 320° F. (the effective melting temperature of PVC).

Thus, in one embodiment, a potential processing system for such plastic waste includes a rough grinder to grind the heterogeneous infectious medical waste into 2" by 5" strips. A second grinder grinds the waste into small pellets that are less than 0.25" in diameter. The waste pellets are mixed with a whitening agent and moisture that in the presence of UVC and/or UVA will cause an oxidative reaction which in turn will denature protein or organics, thereby inactivating some if not all of the microorganisms or spores present in the pelletized waste. This will set up the microorganisms and spores for a shorter sterilization procedure.

In some embodiments, the moisture can be removed by a dryer and then conveyed to a hopper of a plastic extruder. The extruder can be set to temperature less than 320 degrees F. but hot enough to melt the PVC. Plasticizers and other additives may be introduced to get the heterogeneous pelletized mix of waste to flow homogeneously and not clump or dissociate. This process is also the final sterilization procedure. Many of the states have adopted a document called the STAAT II (and soon STAAT III) sterilization guideline that spells out the amount of reduction of spores and microorganisms required for sterilization.

In some embodiments, the effluent from this plastic-treating process could then be used as a filler for a product that is extruded into useful products rather than being placed in a landfill. Reducing disposal of solid waste is desirable because of the disposal cost (0.02 to 0.05 cents per pound). In one embodiment, the effluent can be used in the manufacture of fence posts and building materials. For example, the effluent may be used for a security fence that is composed of a hollow extrusion that forms posts and walls. Extruded hospital waste may provide such hollow extrusions with more weight and structural integrity than wood. In another embodiment, multiple compressed Mylar sheets may be applied to the exterior of the fence to provide additional benefits (e.g., rendering the wall bullet resistant or proof).

Other embodiments are possible, for example freeway dividers, caskets, asphalt filler for roads or any proprietary design that incorporates previously extruded hollow profiles that are filled with the extruded sterilized infectious medical waste can be used.

Medical Waste-Water Monitoring System

In one embodiment, a medical waste water management system is provided. In one embodiment this system is a water quality sampling service that is supplied to hospitals, clinics and labs. The product would be installed at the P trap of a sink. The medical waste-water monitoring system would sense water draining and a sample of water would be directed to a cuvette on a carousel. The samples could be taken randomly or in some predetermined sequence at a number of different sinks throughout a facility. The carousel of cuvettes would be removed, and then sent to an inside or outside lab for analysis. The analysis would pinpoint the location of any water pollution. Training classes to reinforce the proper disposal of pharmaceuticals are provided according to one embodiment of the invention. The service would continue on a less frequent basis once clinician habits had improved.

Despite a plethora of federal, state and local regulations, many clinicians continue to inappropriately dispose of pharmaceuticals in the sink. This is especially true of pharmaceutical spiked IV fluids. Verification of this practice has been established in a recent market research effort with 150 hospitals in which 60% of the respondents admitted to inappropriate disposal of drugs down the drain.

One advantage of several embodiments of this system is that it can pinpoint the source of the infraction. By combining this service along with the other products and services owned by the assignee of the present application will provide valuable improvement and advantages.

Air Quality Monitoring System

The air quality monitoring system is a service that utilizes a device to sample the air quality, primarily in the pharmacy, oncology and operating room areas. It is intended to detect hazardous drugs including chemotherapeutics and anesthetics that become volatilized. The service is intended to provide clinicians with drug specific air quality information. The service will also suggest ways of eliminating the contaminants with both devices and a change in protocol. One advantage of some embodiments of this approach is that drug specific information that can be obtained.

Hospital Hazard Prevention

According to the Bureau of Labor Statistics, hospitals and nursing facilities are among the most hazardous work environments. Each year, an average of seven occupational injuries or illnesses out of 100 employees occurs. About half result in lost work time. Working with or exposure to toxic chemicals is the single largest contributing risk factor associated with occupational injury and illness in healthcare Although nanoemulsion disinfectants and microfiber materials for cleaning and disinfection have worked successfully to reduce toxicity, much opportunity remains to improve the hospital environment, making it safer for the healthcare worker. Reducing hospital hazards will also result in savings to the hospital.

In one embodiment, a system for a service to analyze and implement reductions in hospital hazards is provided. Implementing the solutions with hospital personnel will be a process similar to making cost reductions in organizations with significant numbers of administrative procedures.

Handheld Devices

In one embodiment, the waste sorting device comprises a computer, barcode scanner, memory, and wireless communication connected or coupled to an array of containers with automated opening means. In order to address anticipated cost concerns, less expensive means of sorting medical waste have been considered. One embodiment of a low-cost medical waste sorting system and method comprises the use a wireless handheld computer or similar wireless device having a barcode scanner. Such a wireless device can be used to scan waste items and determine the waste classification of the item being discarded. In one embodiment, the scanner communicates with an array of collection containers (either directly, via the system's control unit or via some other system component) using an infrared (IR) light beam (similar to that used by television or stereo remotes). The IR beam causes the correct container to open. This approach has the potential of redistributing hardware costs in a more favorable way. Thus, in one embodiment, the cost of the container array is reduced by implementing the IR receiver and container controls in dedicated electronics. Of course those of skill in the art will recognize that the handheld computer or device may communicate with the other components of the sorting system in various other hardwired and wireless ways, including, but not limited to, Ethernet, cable, radio frequency identification (RFID), Bluetooth, Wi-Fi, etc. Likewise, in another embodiment, hardware costs may be reduced as the necessary portable devices are issued to personnel rather than being dedicated to particular room locations. For example, the handheld computer count can average 1 per nurse rather than 1 per room. Since there are generally many more rooms than nurses in a particular healthcare facility, significant cost savings (e.g., 3 to 5 fold per one embodiment of the invention) are envisioned for the computing, wireless communication and bar code scanning hardware.

In another embodiment, costs are further reduced by displaying the waste item information on the screen of the handheld computer. The user can then place the item in the appropriate conventional waste container. Under such embodiments, where each nurse or other individual responsible for discarding waste must be equipped with his or her own handheld computer, the cost of the automated container array are avoided. Some embodiments also allow leveraging existing handheld computer hardware, if used, by placing Eco-Rex™ or other drug information software on a multi-purpose handheld computer, such as those used for barcode medication administration. A handheld device is particularly advantageous in certain embodiments because it permits the use of waste containers situated within, coupled to, or in communication with a wall unit. Wall units used in conjunction with handhelds may be more economical and cost-effective for certain healthcare institutions.

In some embodiments, handheld devices may facilitate disposal of waste items by indicating to the user, via a display, the closest disposal location for that particular waste item. For example, in one embodiment, a user may use his or her handheld device to scan a medical waste item while in a patient's room. In one embodiment, the handheld device and the facility may be equipped with the appropriate wireless technology to enable the system to determine the current location of the user. Thus, the display on the handheld device may be configured to locate the closest suitable waste container capable of handling the particular waste item. In other embodiments, the system may use level sensing and/or container sensing means to direct the user to the appropriate waste container. The handheld system may be well-suited to track multiple features of drug administration and/or personnel. For example, if handheld units are associated with a specific individual, the institution may be able to monitor drug administration and disposal on an individual basis. Whether handheld or not, some embodiments of the present invention may be particularly useful for monitoring the percentage of hospital drugs that are properly disposed.

Container Sensing

One feature of some embodiments of the invention is the ability to automatically detect containers. Knowledge of whether or not a container is present allows the device to disable a bay that is not populated with a container. In another embodiment, each container is also provided with a machine-readable pattern that is applied to the container surface by a label or the like. One embodiment of different machine-readable patterns for containers is shown in FIG. 26.

In one embodiment, when a bay is empty, the machine will know not to direct waste to that bay. However, when a bay is occupied, the device, using the information provided by the machine-readable pattern, will correctly identify the container and direct the waste accordingly.

In another embodiment, containers can be "hot-swapped," (e.g., changed from one bay to another during use, and the device will register the order or position of the containers and/or container positions. In one embodiment, the system instantly registers the container mix and/or container positions.

In one embodiment in which the device is capable of identifying containers, usage information can be collected and used to implement a use-fee based payment schedule.

In another embodiment, the usage information can be used to detect improper or unauthorized disposal of waste into the containers by comparing the accumulated machine usage data to corresponding data retained by the particular facility (e.g., sales figures). Another advantage of some embodiments involves the ability to track container change out, storage time, and usage information.

In one embodiment, the containers are manufactured using common tooling techniques known in the art and injection moldings that are made with a single color (e.g., white). Container types may be distinguished for human recognition using color coded labels. In other embodiments, specialized tooling is used. In yet another embodiment, containers are manufactured with one or more special distinguishing characteristics, including color, size, shape, material, codes, etc.

In one embodiment, labels are used in conjunction with the containers. Optionally, the labels may also contain the above mentioned machine-readable patterns to allow machine recognition.

In one embodiment, the container labels (e.g., adhesive labels) may also include optional serialization that would permit tracking of the waste items placed into a specific container. Consequently, a container can later be identified by its serial number and tracked on a computer. Further, this information can optionally be used to print a manifest describing the contents of a given container. This is especially helpful since regulatory authorities often require a manifest to be placed on waste containers. Presently, these requirements are sometimes met by "over manifesting" (e.g., listing all possible types of waste that may be discarded in the container). However, as regulation of such waste becomes more stringent, this practice may be disallowed in the future. In addition, some embodiments of the invention use serialized containers that provide an elegant method of detailed container manifesting.

In yet another embodiment, the number of times a particular reusable container has been used will be tracked. One advantage of such a tracking system is to aid users in determining when a reusable container is approaching the end of its life cycle. This is particularly useful for containers that may be reused for only a predetermined number of times.

Manual Input System for Additional Waste Characteristics (e.g., Not Empty/Empty, Sharp/Not-Sharp)

In some embodiments of the invention, the system determines one or more characteristics of the item that is to be sorted or disposed. In one embodiment, the system incorporates a manual input system that prompts the user to indicate information regarding certain waste item characteristics that may not be automatically detectable by the system. For example, in some embodiments, the system may query a user as to whether the waste item is empty or not-empty. This distinction can be important as waste items that are not empty (e.g., those that still contain a volume of bulk chemistry) pose a greater risk of groundwater contamination if landfilled. For example, drugs on the EPA P-list must be triple-rinsed before they are allowed into a public solid waste disposal facility. The user prompt may occur either prior to or following the scanning of the waste item for a determination of the National Drug Code (NDC) number. Further, the user may be prompted to provide this information in one of several ways. For example, the user may be queried using either a visual instruction or a voice command.

In a further embodiment of the invention, the system interacts with the user to determine whether the item to be disposed contains a needle, and therefore, should be handled as bio-hazardous waste. For example, the system prompts the user, by one of several means, to indicate whether a sharps item is being disposed. In some embodiments, a visual instruction or voice command is used to prompt the user to indicate such information. In most hospitals, because a needle is assumed to have been in contact with the bodily fluids of a patient, it is treated as infectious. Such items are referred to as "bio-hazardous" by lab personnel and as "regulated medical waste" by waste haulers. Thus, a preliminary determination as to whether a particular waste item qualifies as a sharps determines whether the item needs to be handled as infectious. In one embodiment, if the waste item is an empty sharp, it would normally be directed to the "red sharps" waste stream. If the waste item is a non-empty sharp, then it must be handled according to the chemical risk, possibly ending up in a container with mixed medical and hazardous waste. Thus, disposal costs of the waste may be influenced by such preliminary qualifications. Proper handling may result in lowering of disposal costs, added safety for personnel, and an increased sensitivity for the environment.

Waste Sorting Decision Matrix

In one embodiment of the invention, the system for sorting waste comprises a computer equipped with one or more software applications and a database system that control the handling of each identified NDC. In one embodiment, the system could be enabled to identify the specific prompts and actions for each of the approximately 135,000 drugs in the NDC database. In an alternative embodiment, the actions are grouped into approximately two-dozen different handling procedures. In this embodiment, the database only needs to associate the NDC with a code representing the corresponding procedure. A separate database can then be used to define the details for prompts and actions associated with each waste group. This classification simplifies processing and database maintenance. One of skill in the art will understand that the number of handling procedure classes may vary in order to facilitate processing.

In one embodiment, the sorting system comprises a computer that is programmed to operate as a state machine. A state machine is a concept originated by Turing and is sometimes called Finite State Automata or a Turing machine. A state machine remains in a known condition or state until a specific set of inputs causes a transition to a new state. For each state, a finite library of subsequent states is possible based on a finite library of input sets. In one embodiment, the computer has a state for each class of waste. Subsequent state transitions are invoked for various flags, as described below.

2-Button Action File

In some embodiments, the sorting system uses a manual input system in conjunction with a waste item identification device to further enhance the disposal of waste. For example, in one embodiment, the sorting system uses a 2-button action file to determine prompts and action steps for each type of item scanned. Questions are prompted sequentially, and thus, require the sustained attention of the user on the display and/or keypad to provide the necessary answers or to follow the necessary instructions. Under this approach, the system uses only two buttons, which may be incorporated into a low-cost textual display, such as an alphanumeric LCD having as few as one line of text. In addition, questions to the user can be worded for a yes/no answer. In a more elaborate embodiment, a graphical display may be used. The graphical display may even be color, such as a small computer monitor.

Figure 28A:
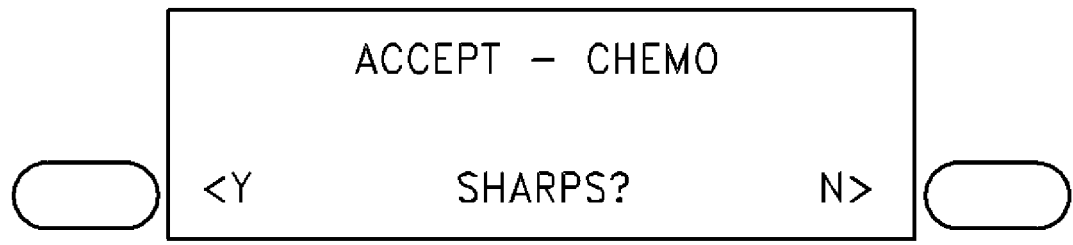
FIG. 28A is a schematic of one embodiment of a 2-button keyboard and display indicating a first prompt.
Figure 28B:
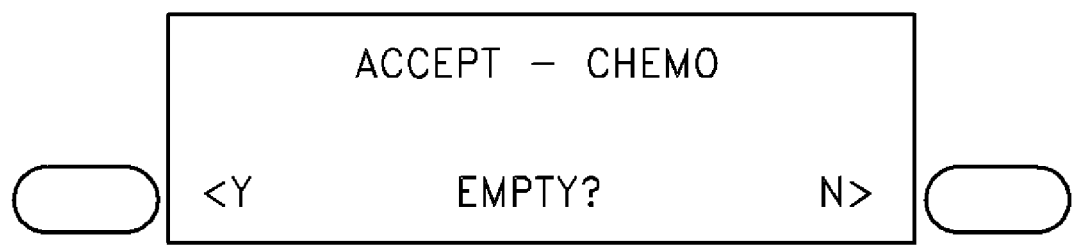
FIG. 28B is a schematic of one embodiment of a 2-button keyboard and display indicating a second prompt.

In one embodiment, the keys can be 2 dedicated buttons or may be soft keys on a low cost text display. FIG. 27 provides examples of a 2-button action file. FIG. 28a provides an example of a 2-button keyboard and display indicating a first prompt requiring a yes/no response. FIG. 28b provides an example of a 2-button keyboard and display indicating a second prompt requiring a yes/no response.

4-Button Concept

In one embodiment, the 2-button prompt concept is modified to simultaneously obtain information regarding more than one inquiry, thus avoiding "menu layering," e.g., sequentially presenting menus. Various embodiments of the 4-button concept are feasible. For example, pairs of buttons serve to distinguish between "sharps" and "non-sharps" and "empty" and "not empty" in respective quadrants. Questions can be textual or graphical and can be color coded to enhance the user interface. In one embodiment, the buttons can be physical switch keys with permanent nomenclature (e.g., silk-screened). However, the buttons may also be represented by electrically activated annunciators or as touch screen zones of a high resolution display.

In one embodiment, once familiar with using a particular machine, a user can go to the keypad as the item is being scanned and select from the four available selections without waiting for the prompt, thereby saving time.

First 4-Button Graphics

Figure 30A:
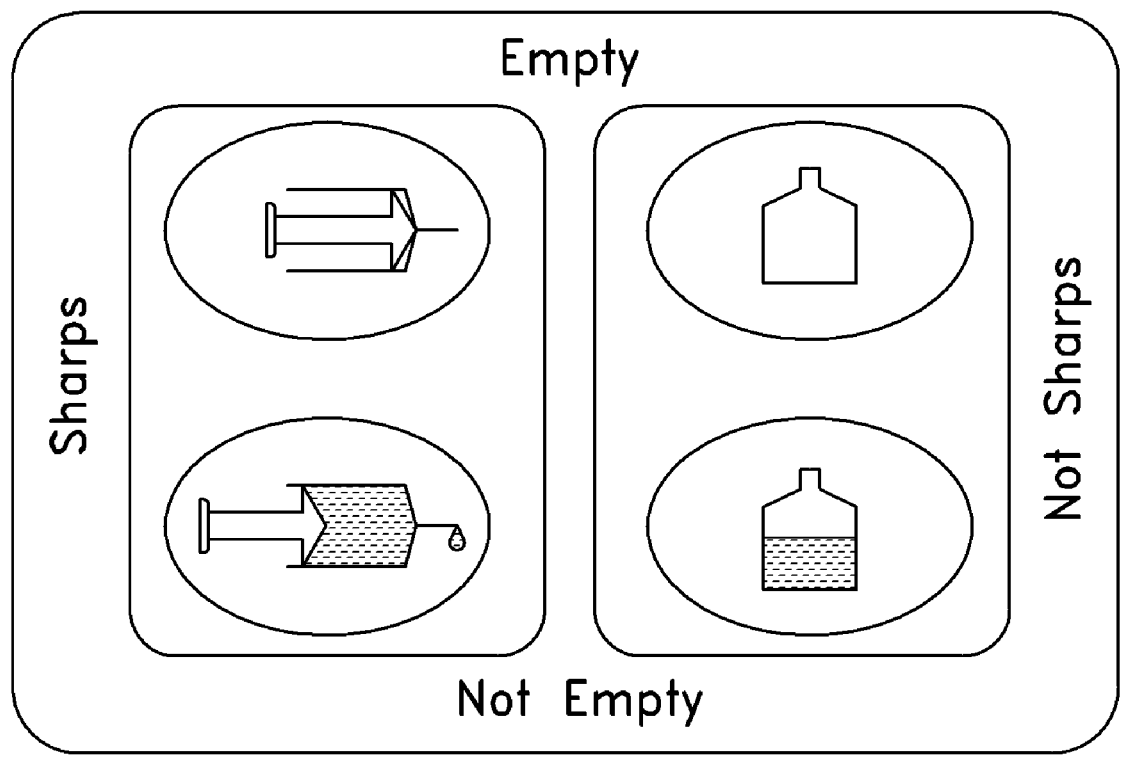
FIG. 30A is a schematic of one embodiment of a switch arrangement utilizing graphic images.

FIG. 30a illustrates one embodiment of a switch arrangement that utilizes four graphic images. Such a design can be used to simultaneously obtain key information from the user. In FIG. 30a, the two left buttons are for sharps, while the two right buttons are for non-sharps. In addition, the two top buttons are for empty waste items, while the two bottom buttons are for non-empty waste items. Therefore, if the waste item is a sharps and is empty, the user should select the top, left button.

4-Button Action File

In one embodiment, a 4-button action file is used to determine prompts and action steps for each type of item scanned. Questions to the user are prompted simultaneously, and thus making it easier for the user to respond. The keys can be fixed or represented on a monochrome or a color graphics display. Moreover, keys can be implemented using 4 dedicated buttons or with 4 soft keys (e.g., on a low cost text display). Examples of a 4-button action file are provided in FIG. 29.

Second 4-Button Graphics

Figure 30B:
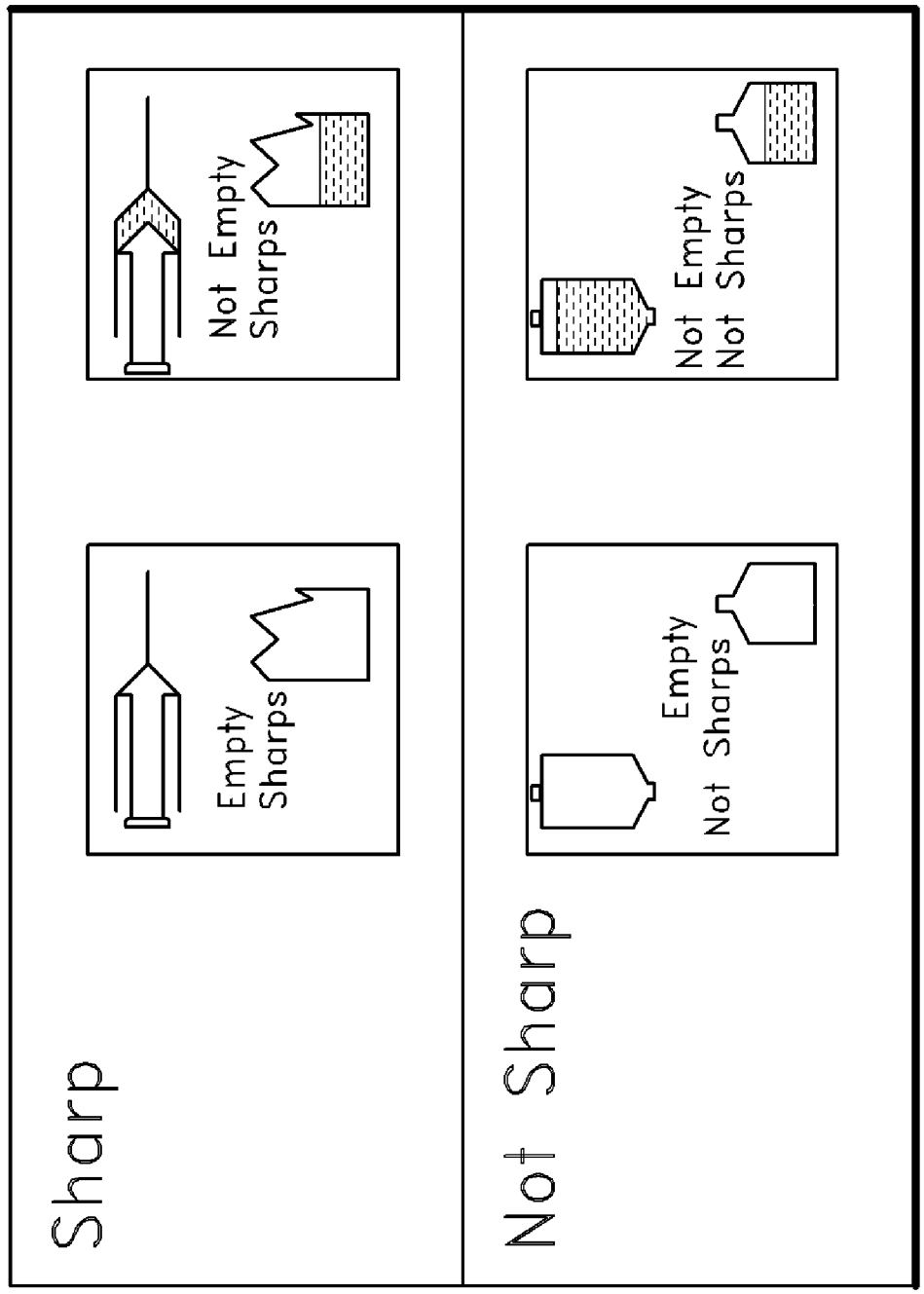
FIG. 30B is a schematic of one embodiment of a switch arrangement utilizing graphic images.

One of skill in the art will understand that several graphic designs can be used in accordance with several of the embodiments disclosed herein. For example, FIG. 30b shows a second design for a switch arrangement using four graphic images specifically designed to obtain information related to whether a waste item is or is not a sharps and whether a waste item is or is not empty.

Software Flags (Modes of Operation)

In some embodiments, the user (or another entity) can define configuration settings or "flags" for the device which change the entry point into the Action File and, in one embodiment, can increase the number of items in the Action File. Effectively, this permits a user to alter the system's mode of operation. For instance, if an embodiment includes the use of a cost/eco flag, there may be two lines in the Action File (e.g., one to handle waste as the most cost effective route and another to handle waste in the most ecologically conscious route). However, if the method of disposal were to be the same regardless of the setting of the flag, there may be only one item in the Action file. In an alternate embodiment, the Action File can have two items that are identical. Examples of several flags (or modes of operation) are described below.

COST-ECO Flag

In one embodiment, a "COST-ECO" flag is used. Implementing a COST-ECO flag may permit a hospital to specify a level of concern for waste disposal. If the hospital specifies the COST setting, the device operates in a manner that satisfies all regulatory and other legal requirements at the lowest cost. In practice, this can mean landfilling items with multiple toxic ingredients because they do not qualify as hazardous under Resource Conservation and Recovery Act (RCRA). Under RCRA regulations, medical waste is considered hazardous only if it contains an active ingredient on one of the EPA lists (e.g., P-list, U-list, or D-list).

Alternatively, the ECO flag emphasizes greater concern for the environment and shows a willingness by the facility to spend more money for the potential environmental benefit. When the ECO flag is set, the device assigns multi-ingredient waste items, endocrine disrupters, estrogen mimics, and other high risk waste items into recommended waste streams that exceed the minimum regulatory and legal requirements.

Waste Hauler Flag

Certain waste haulers are licensed to handle bio-hazardous (regulated medical waste or RMW) waste, while others are licensed to handle toxic (hazardous) waste. In one embodiment, a flag may be used that allows sorting into different containers to accommodate the available waste haulers requirements. Thus, it may possible to prevent filling a container with a particular type of waste if the waste hauler cannot handle such waste.

POTW (Publicly Owned Treatment Works) Flag

Publicly Owned Treatment Works (POTW) facilities may or may not be set up to handle and/or treat certain wastewater contaminants. Thus, in one embodiment, a POTW flag may be used. By adding a POTW flag to each item in the database, it is possible to identify whether a waste item can be directly discharged into a particular sewer system.

Jump Drive and Barcode for Configuration

Figure 49:
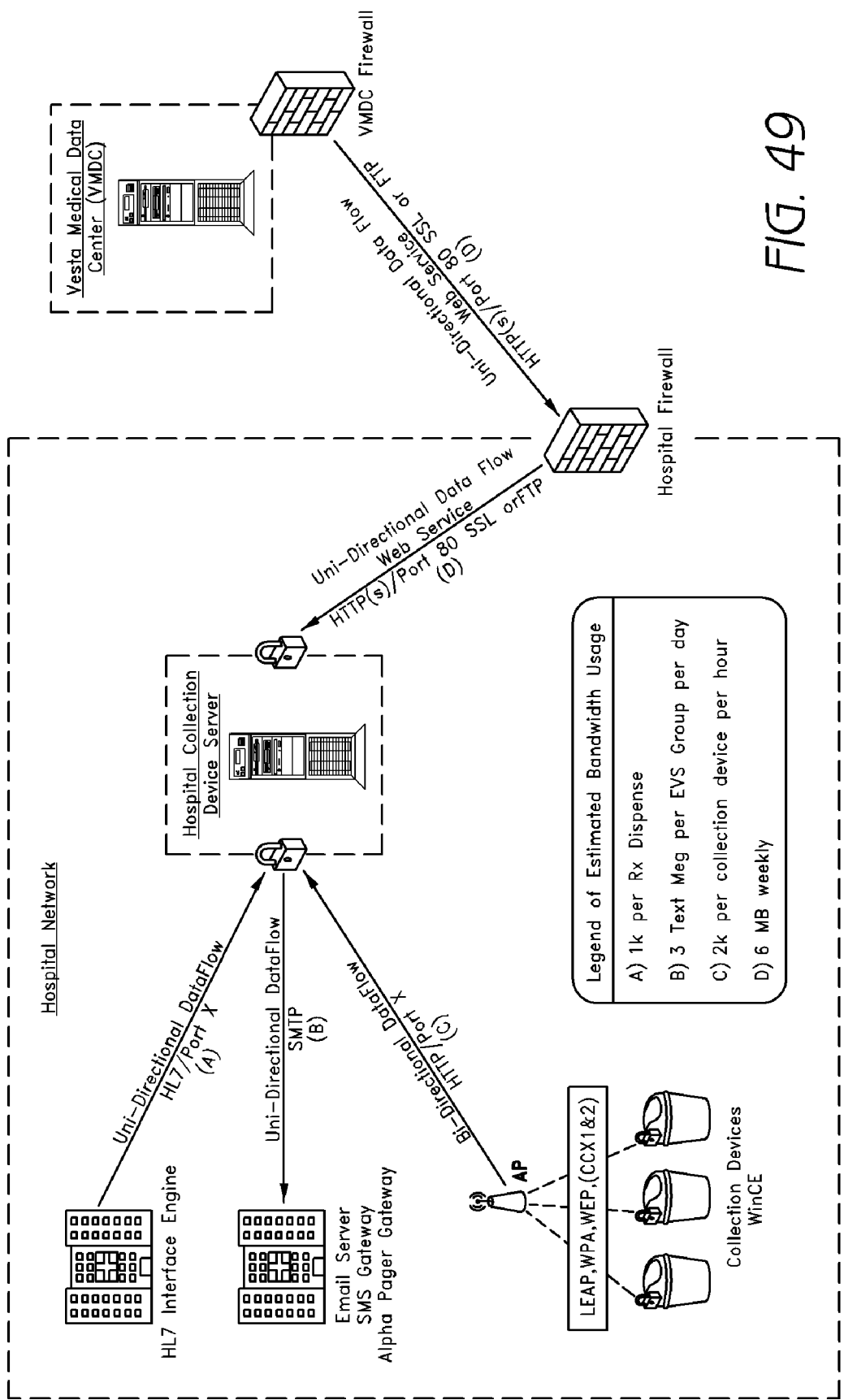
FIG. 49 is a schematic of one embodiment of a firewall system used for data network protection.

In one embodiment, the sorting system will receive updates to the database to account for new drugs, repackaged drugs, admixtures, and the like. In one embodiment, the carts are not hardwired to an Ethernet connection port (CAT-5) and, thus, instead rely on a wireless communication to connect with the hospital's or facility's network (e.g., intranet). Since data security is a foremost concern in hospitals and other healthcare facilities, in one embodiment, new devices may be precluded from accessing the network until properly authenticated. In one embodiment, as shown in FIG. 49, one or more firewall systems are used to enhance a facility's data security networks. Typically, hospital devices conform to the Lightweight Extensible Authentication Protocol (LEAP) standard. In order for a device to become LEAP authenticated, it typically needs to present certain keys. On a general-purpose computer, it is possible for the system administrator of a particular network to manually enter these keys (e.g., via keyboard and monitor). For those embodiments of the invention that are particularly cost-effective, less expensive, special-purpose, "headless" (no display or keyboard) devices can be used. Thus, alternative methods of supplying the necessary authentication codes are used.

For example, in one embodiment, the authentication codes are inserted during the manufacturing process. However, this may not be possible if the customer is not known at the time of manufacture. Another method involves the temporary connection to a keyboard and display device in order to enter the codes. A third method uses a laptop computer connection for assigning codes. A fourth method is to temporarily dock the collection device to an Ethernet port and load the codes from another computer. These approaches, although usable in accordance with several embodiments of the invention, may require knowledge that is unavailable at a particular point in time, or may require unreasonable hardware intervention. A preferred method of loading the LEAP authentication codes is to insert a flash or thumb drive into a Universal Serial Bus (USB) port to download the codes. The USB drive could also be used for other computer setup tasks.

In one of the several embodiments that use a barcode reader, the system employs authentication codes to a series of barcodes that may be presented to the scanner sequentially. Thus the device will read one or more barcodes and use the information to set up LEAP authentication. For those embodiments that do not use a bar code reader, other alternatives may be used (e.g., RFID, magnetic card, etc.).

With respect to updated information for the waste item or for the medical item that is to be dispensed, a database configured to receive updates to the information is provided. In one embodiment, a control system is programmed to compare the qualitative parameter of the item to information contained in the database and assign the item to a waste category. The control system may be further configured to identify at least one of the containers based on the waste category.

In another embodiment in which a combination disposal and dispensing system is used, updates to patient information, user information, and/or drug information, including the availability of generic drugs, may be provided.

In one embodiment, the updates are received in real-time. In one embodiment, the updates are received from one or more networks. In a further embodiment, the updates are received at least once during a pre-determined time period. In some embodiments, the one or more networks are secured by one or more firewall systems. In other embodiments, access to the internal contents of the containers is restricted.

Repackaged Drugs and Admixture Sorting

Several embodiments of the invention are adapted to receive waste from multiple sources. In one scenario, three main classes of pharmaceutical items are expected to reach the collection devices that are located in a point of care patient area. These can be described as (i) pass-through drugs; (ii) repackaged drugs; and (iii) admixtures.

Pass-through drugs are drugs that reach the point of use in the original package as provided by the manufacturer. Examples include I.V. bags, syringes, inhalants, patches, and all single use items such as pills, liquids, creams, or others. According to one embodiment, once the item is used and presented to the sorting system, a barcode on the waste item can be easily read and decoded since the system's database should contain information on all of the roughly 135,000 known FDA registered drugs. Ideally, the barcode for these pass-through drugs will be (or may contain) the FDA registered NDC number.

Repackaged drugs are those that are received from the manufacturer in a first package, and are transferred to a second package for distribution to the point of care patient area. The repackaging may take place in a pharmacy, another location within the hospital, or an off-site commercial repackaging house. Examples of commonly repackaged drugs include bulk packaged pills, powders, or liquids that usually must be repackaged into smaller portions or "unit dose" packages for distribution. Repackaging facilitates handling, billing, and verifying correct medication administration.

The package for repackaged drugs can be bar-coded to be recognized by embodiments of the invention. Typically, it is the hospital's responsibility to design the barcode that accompanies repackaged goods. For example, the selected barcode may be the NDC number of the larger package. Although this "borrowed" barcode correctly identifies the drug's chemistry, it is not entirely correct, because it does not provide package code information as does a full NDC code. By changing the package and keeping the barcode, a portion of the barcode becomes technically incorrect. However, it is still usable by some embodiments of the sorting system and is one of the preferred barcodes for the second package of a repackaged drug.

The hospital may also generate a site-unique barcode for the second package. In one embodiment, the site-unique barcode typically starts with an "L" or "99" to distinguish it from manufacturer NDC codes. In order for embodiments of the sorting system to dispose an item with a site-unique barcode, communication between the collection device and the pharmacy is preferred. In one embodiment, the pharmacy provides the collection device with an NDC code with which to associate the barcode appearing on the repackaged item. In one embodiment, the communication may occur in real-time, when the item is presented for disposal. However, real-time communication may slow the operation of the collection device, as the pharmacy computer may be busy or unacceptably slow due to authentication and encryption requirements or communication traffic. In one preferred embodiment, the necessary communication between the collection device and the pharmacy occurs before the item is discarded (e.g., by a broadcast message from the pharmacy at the time the order is filled and sent to the floor).

Communications of this sort often take the form of a Health Level 7 (HL7) message. HL7 is an industry standard communication scheme for information transfer among diverse hospital systems such as billing, admissions, patient records, medication administration and the like. The HL7 formatted message will associate the NDC of the waste item contents with the barcode on the package. In one preferred embodiment, the HL7 message directed to the sorting system will safeguard patient-specific information in compliance with all privacy requirements, such as HIPAA (Health Insurance Portability and Accountability Act).

Figure 31:
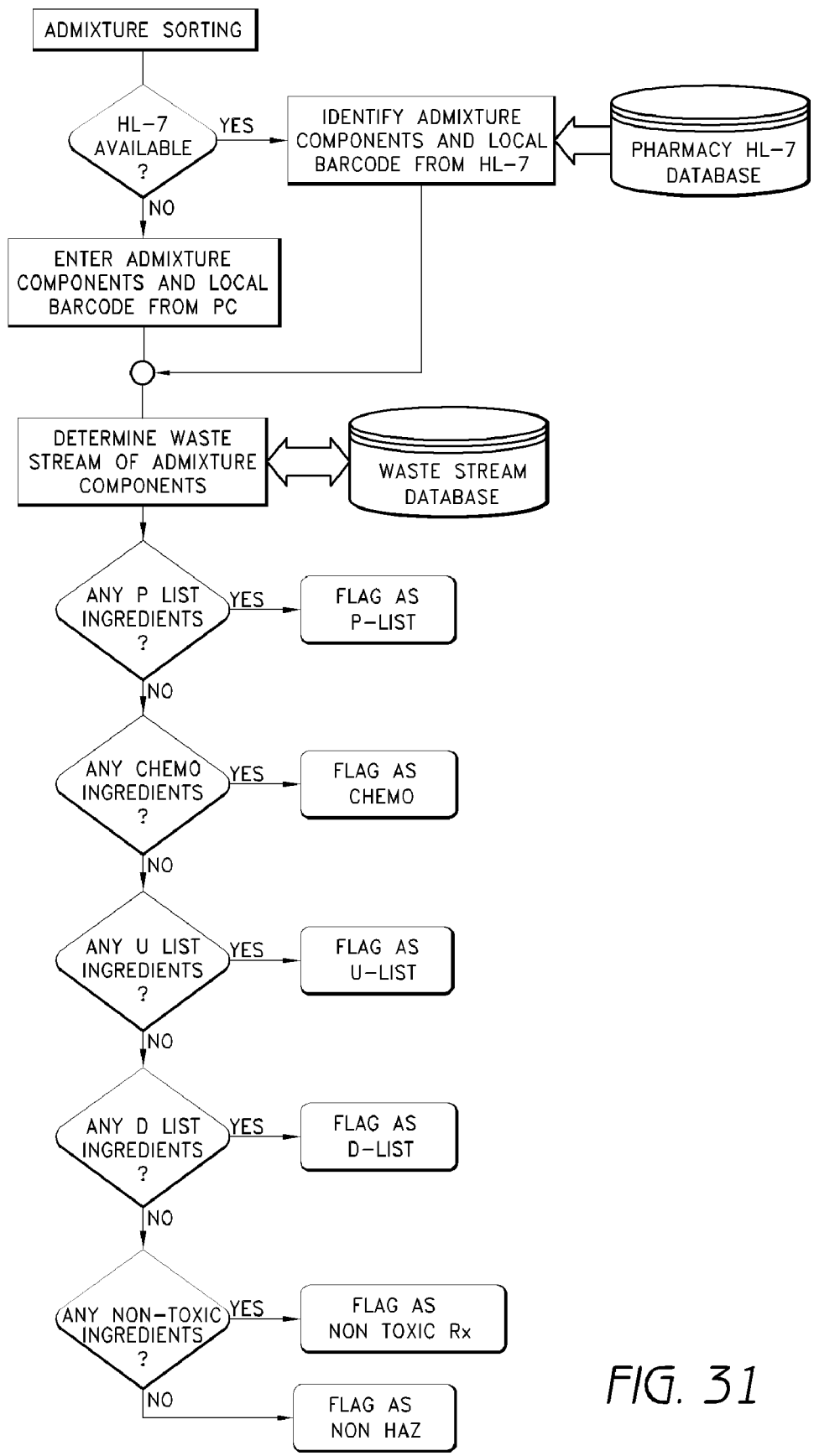
FIG. 31 is a flowchart illustrating a decision logic for identifying and categorizing a particular waste item.

In addition to pass-through and repackaged drugs, pharmacies often create custom recipes containing multiple pharmaceutical ingredients. These "admixtures" are generally labeled with a site-specific barcode rather than the NDC code of their ingredients. In one embodiment, the site-unique barcode is decoded. In one preferred embodiment, the sorting system is instructed to sort the admixture waste via an HL7 message or the like. Unlike a single repackaged item, an admixture message will associate the barcode with multiple NDC numbers contained in the admixture being discarded. In one embodiment, once the sorting system is in possession of the list of NDC numbers, it can quickly identify the container in which the waste item should be placed, Such a determination is based on individual waste stream codes for the various constituent ingredients in the waste item. FIG. 31 illustrates a flowchart of one embodiment of the decision logic related to the identification and classification of the waste items.

One of skill in the art will appreciate that the flowchart in FIG. 31 shows one example of how the waste sorting system can handle admixture waste in real-time.

On Screen Waste Stream Display

In one embodiment, a display is provided to indicate selected information, including, but is not limited to, the NDC decoded from the barcode on the package, the chemistry formulation derived from the database lookup (which would match that listed on the package), the waste composition and categorization determined by the machine (which should match the open door), and/or the reasons for the particular waste decision.

Restricted Access Containers

In one embodiment of the invention, the present invention comprises waste receptacles that are adapted to restrict access to medical or pharmaceutical waste, once that waste has been deposited in the receptacle.

Figure 36:
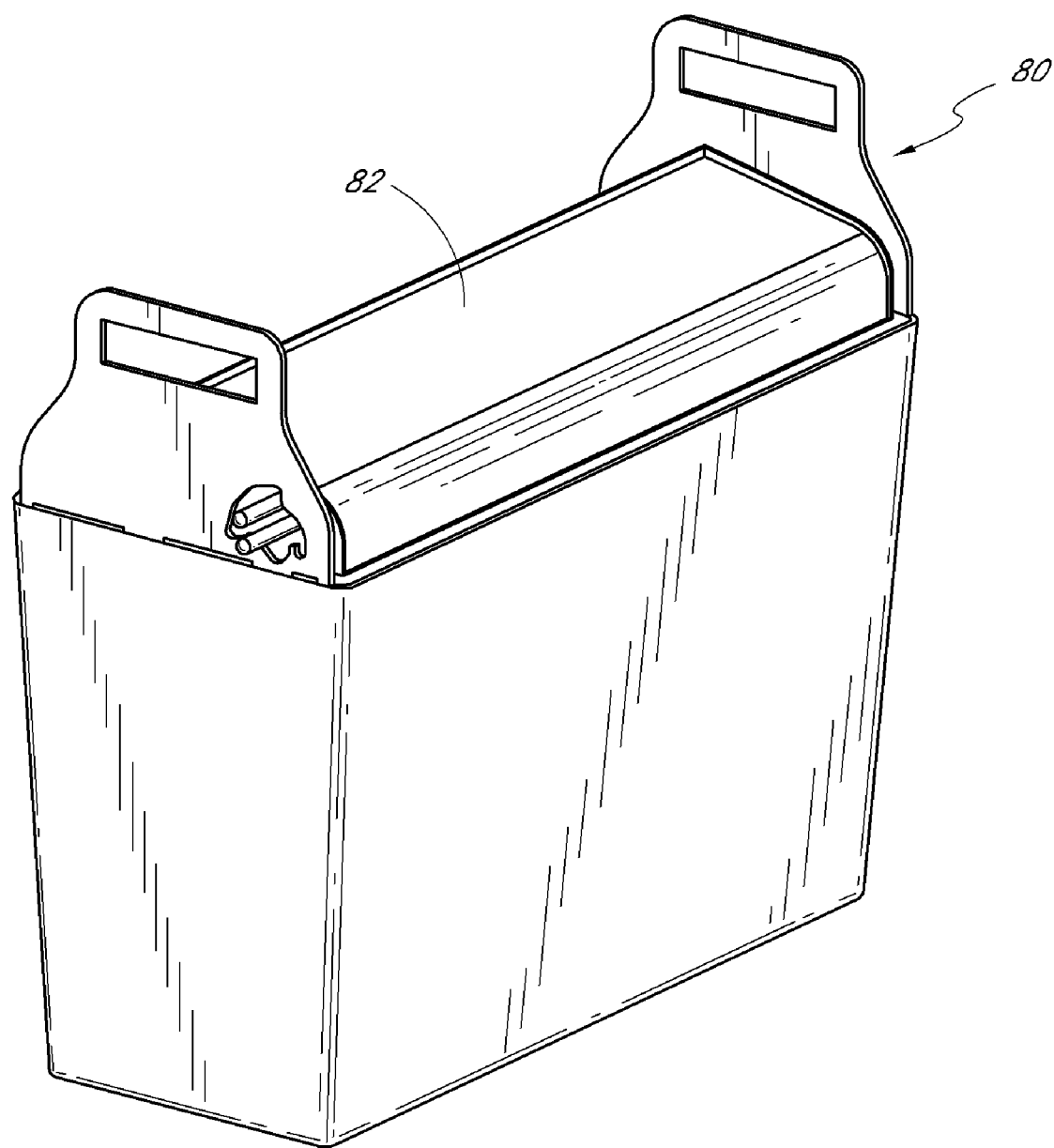
FIG. 36 is a perspective view of a container with a lid and a bar.
Figure 37:
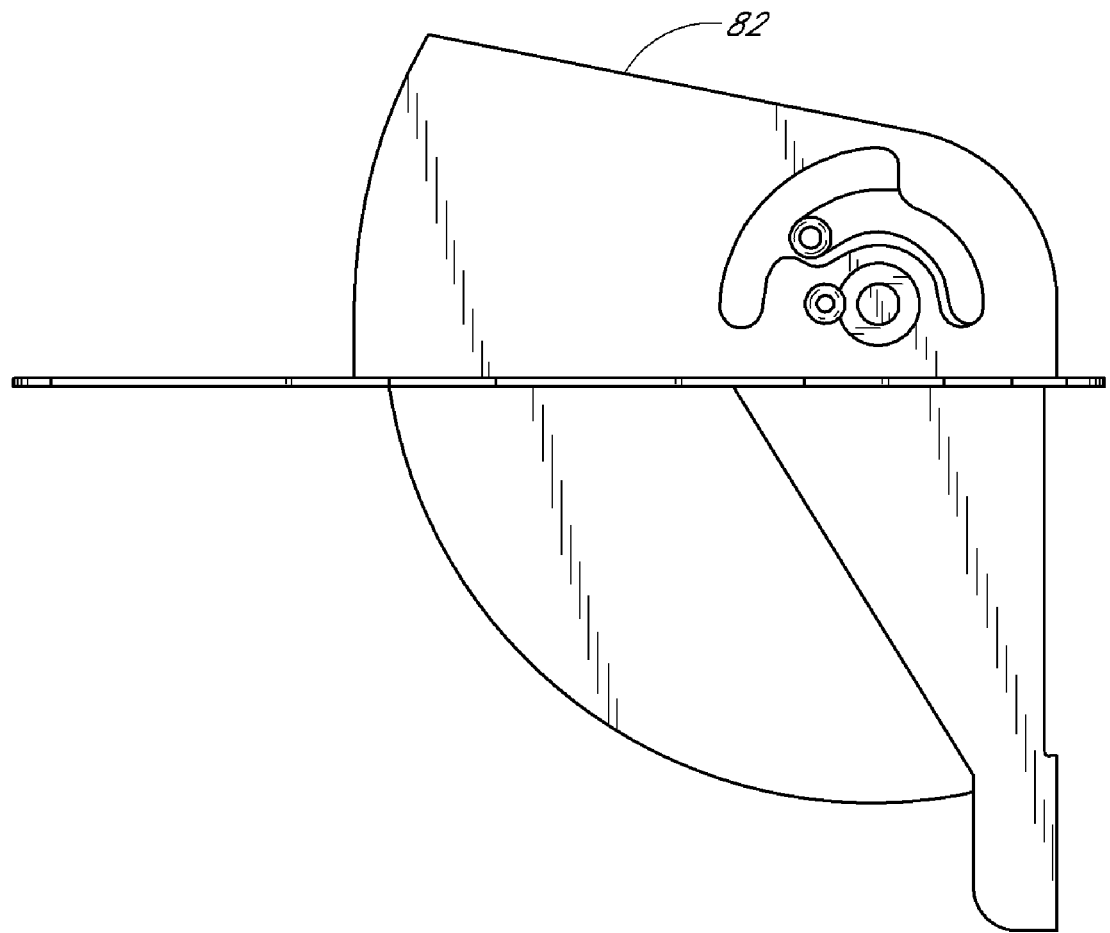
FIG. 37 is side elevation view of a lid and a bar in the closed position.
Figure 38:
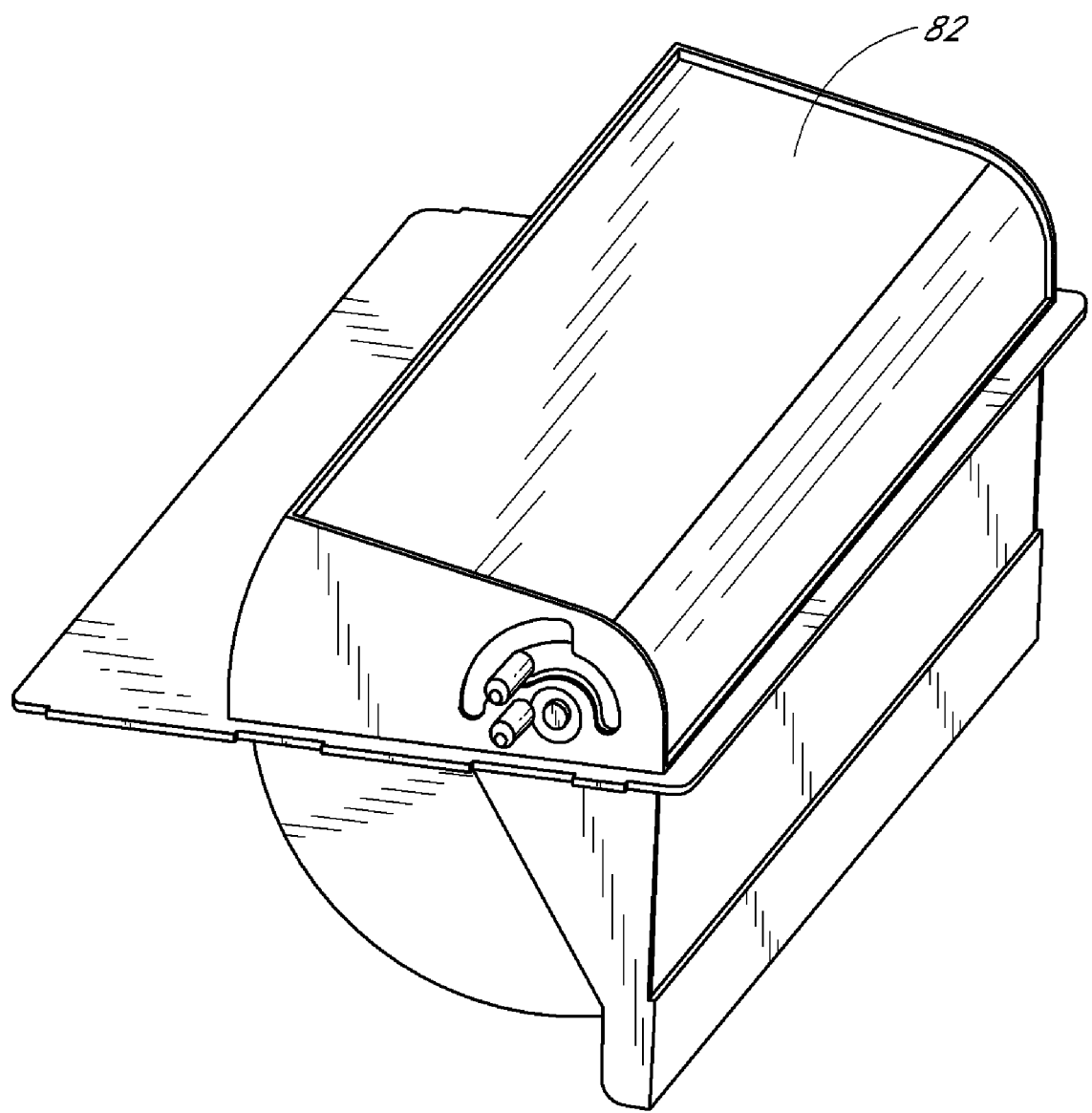
FIG. 38 is a perspective view of a lid and a bar in the closed position.
Figure 39:
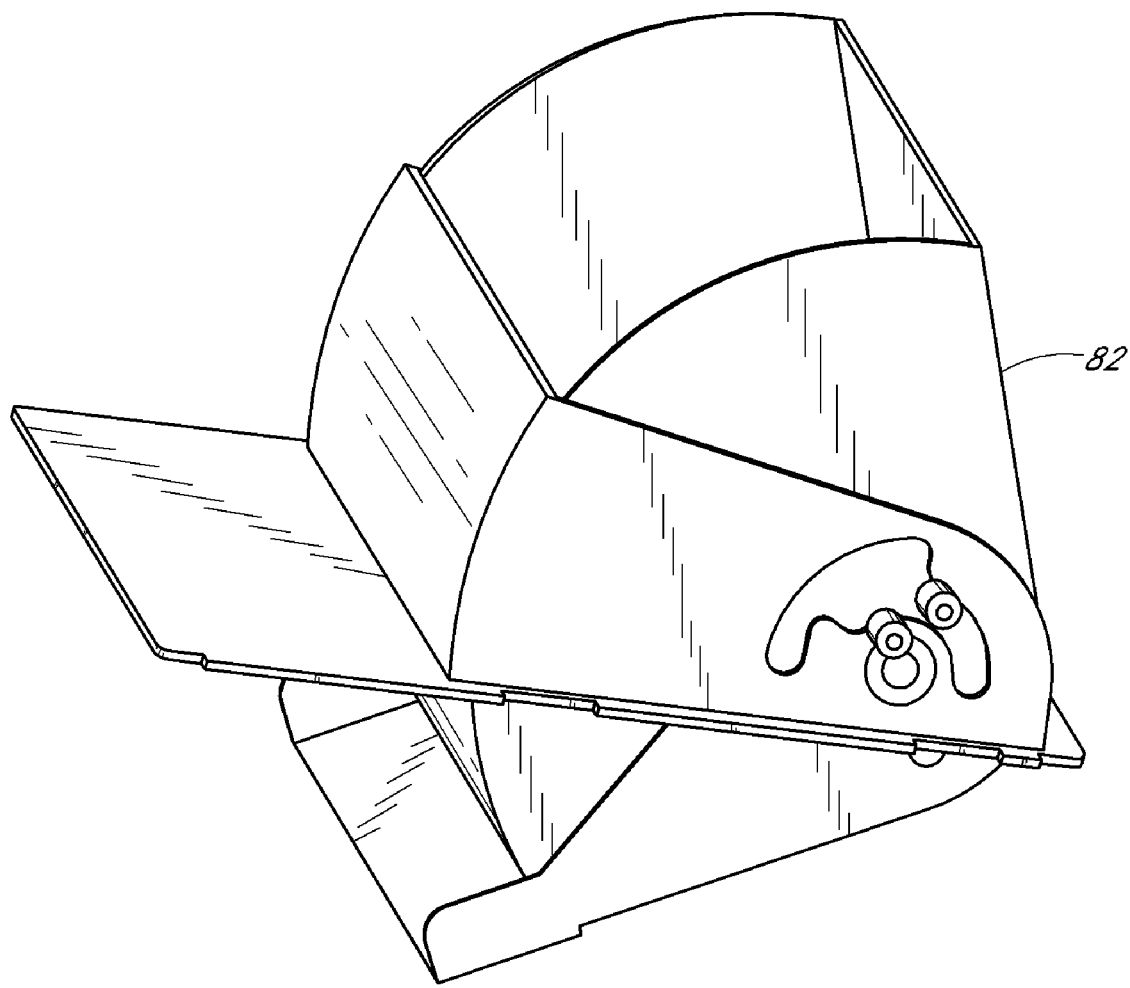
FIG. 39 is a perspective view of a lid and a bar in the partially open position.
Figure 40:
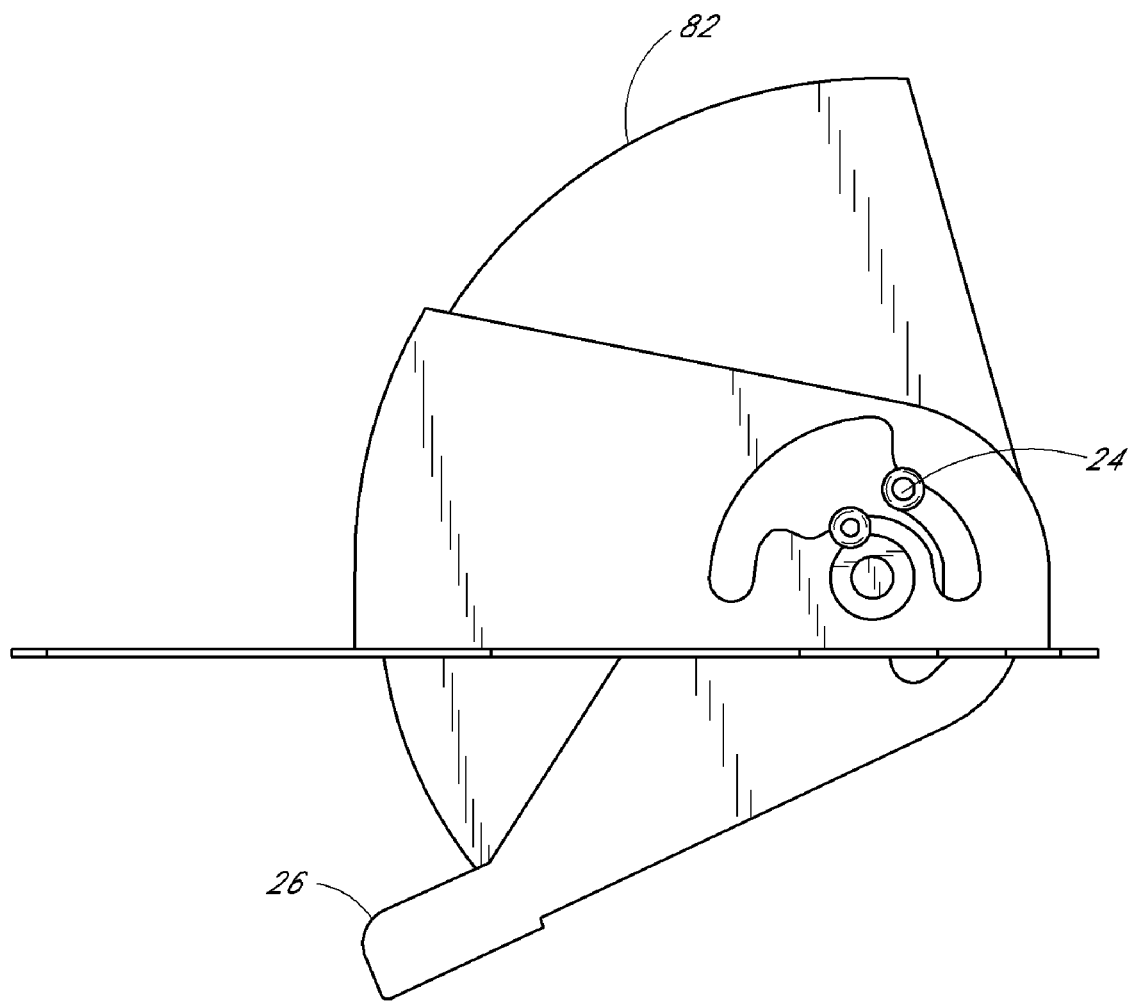
FIG. 40 is a side elevation view of a lid and a bar in the partially open position.
Figure 41:
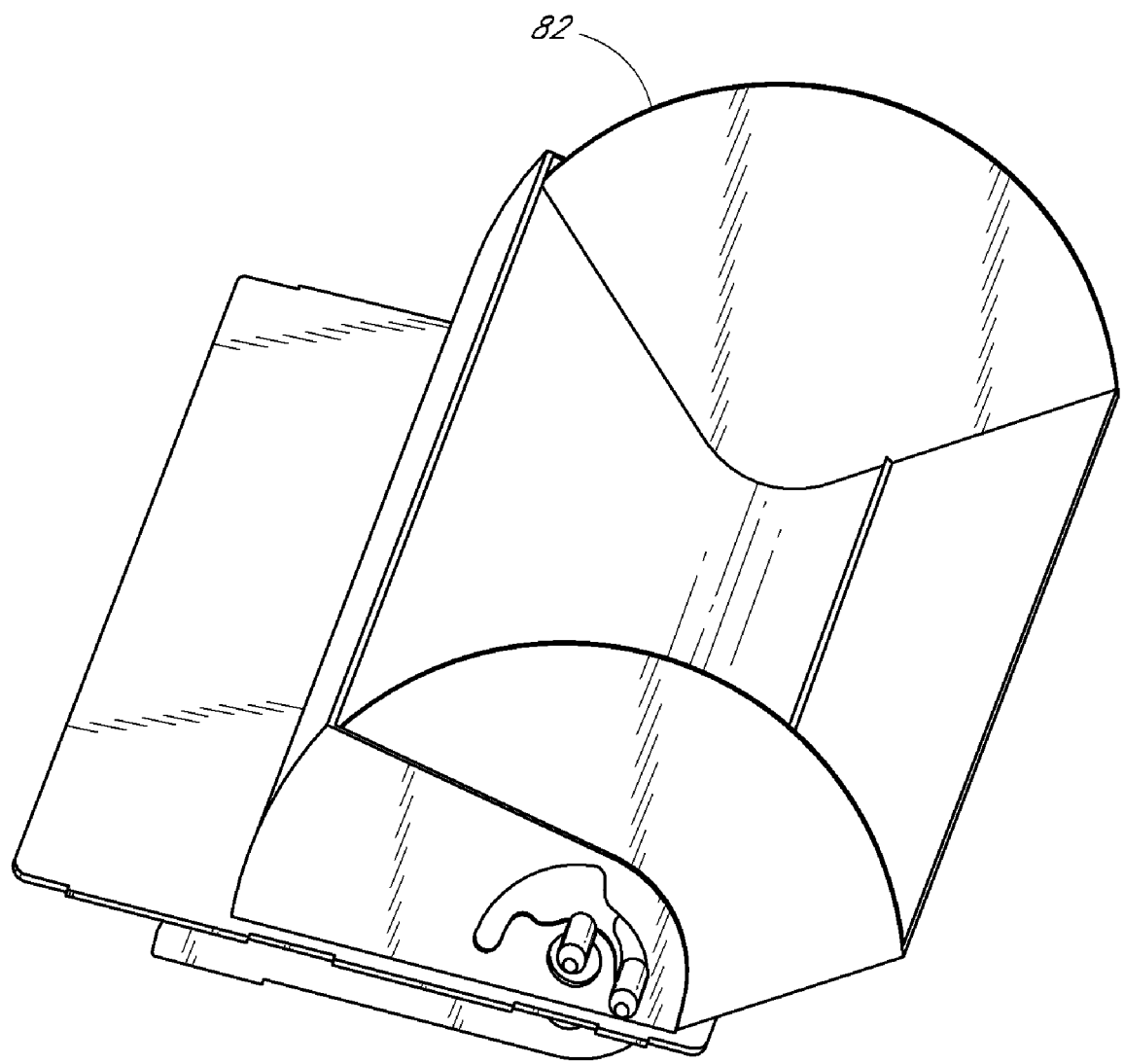
FIG. 41 is a perspective view of a lid and a bar in the open position.
Figure 42:
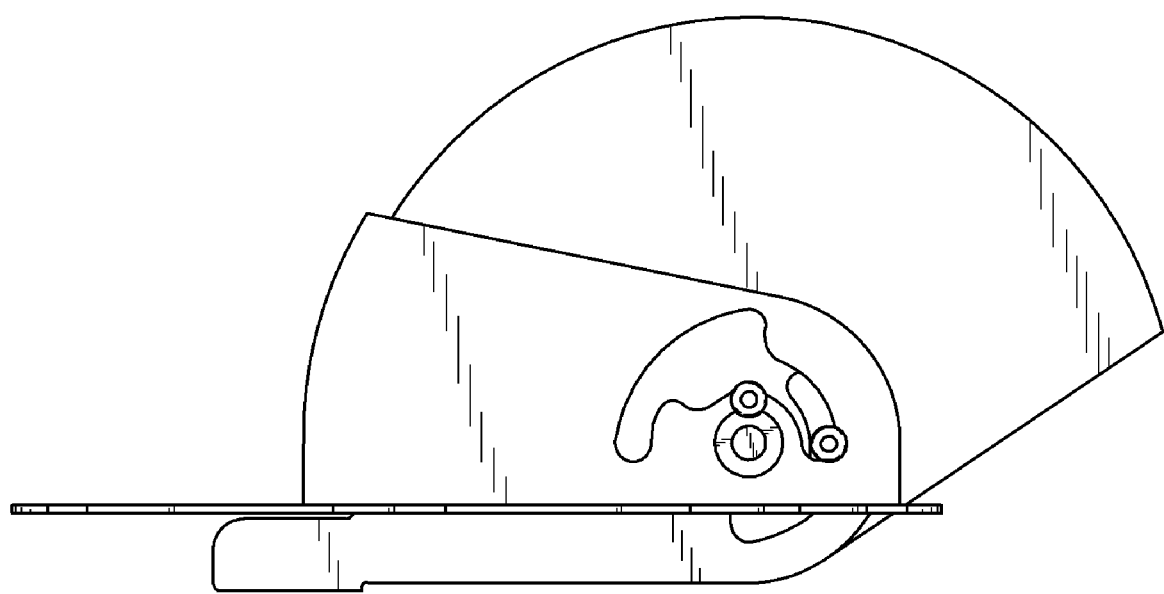
FIG. 42 is a side elevation view of a lid and a bar in the open position.
Figure 43:
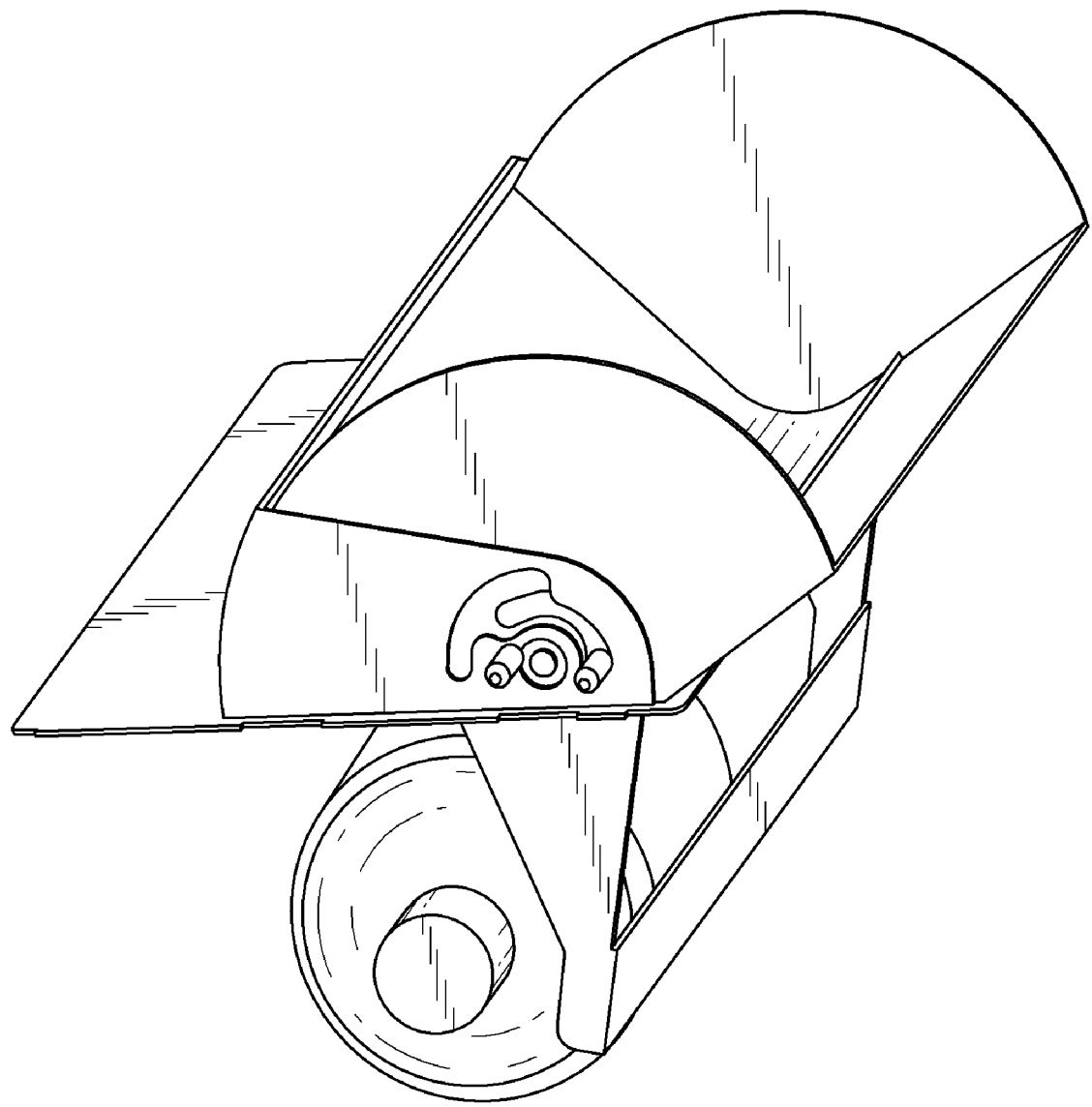
FIG. 43 is a perspective view of a bar blocked by the container contents.
Figure 44:
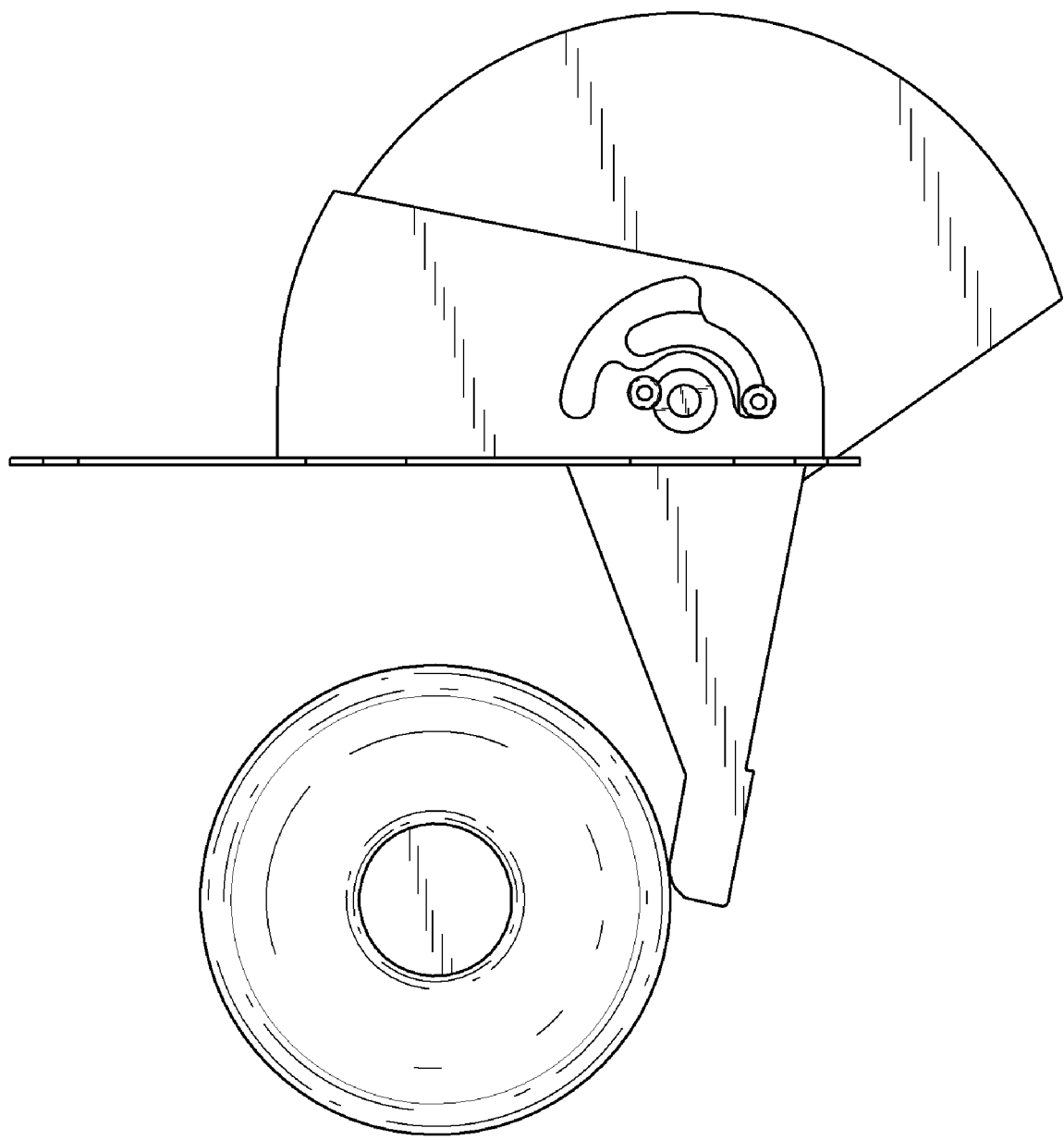
FIG. 44 is a side elevation view of a bar blocked by the container contents.
Figure 45:
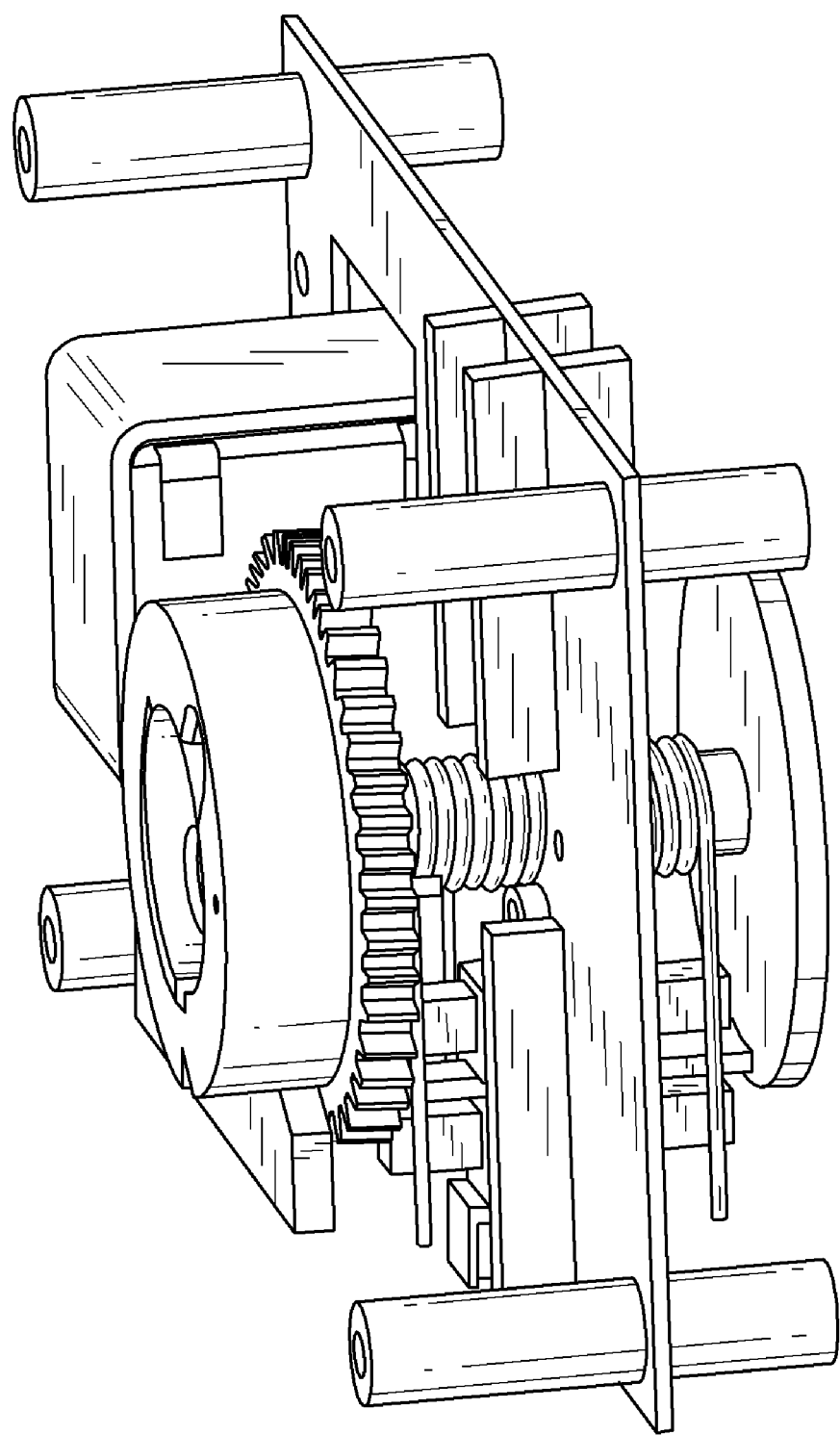
FIG. 45 is a perspective view of a latch assembly.
Figure 46:
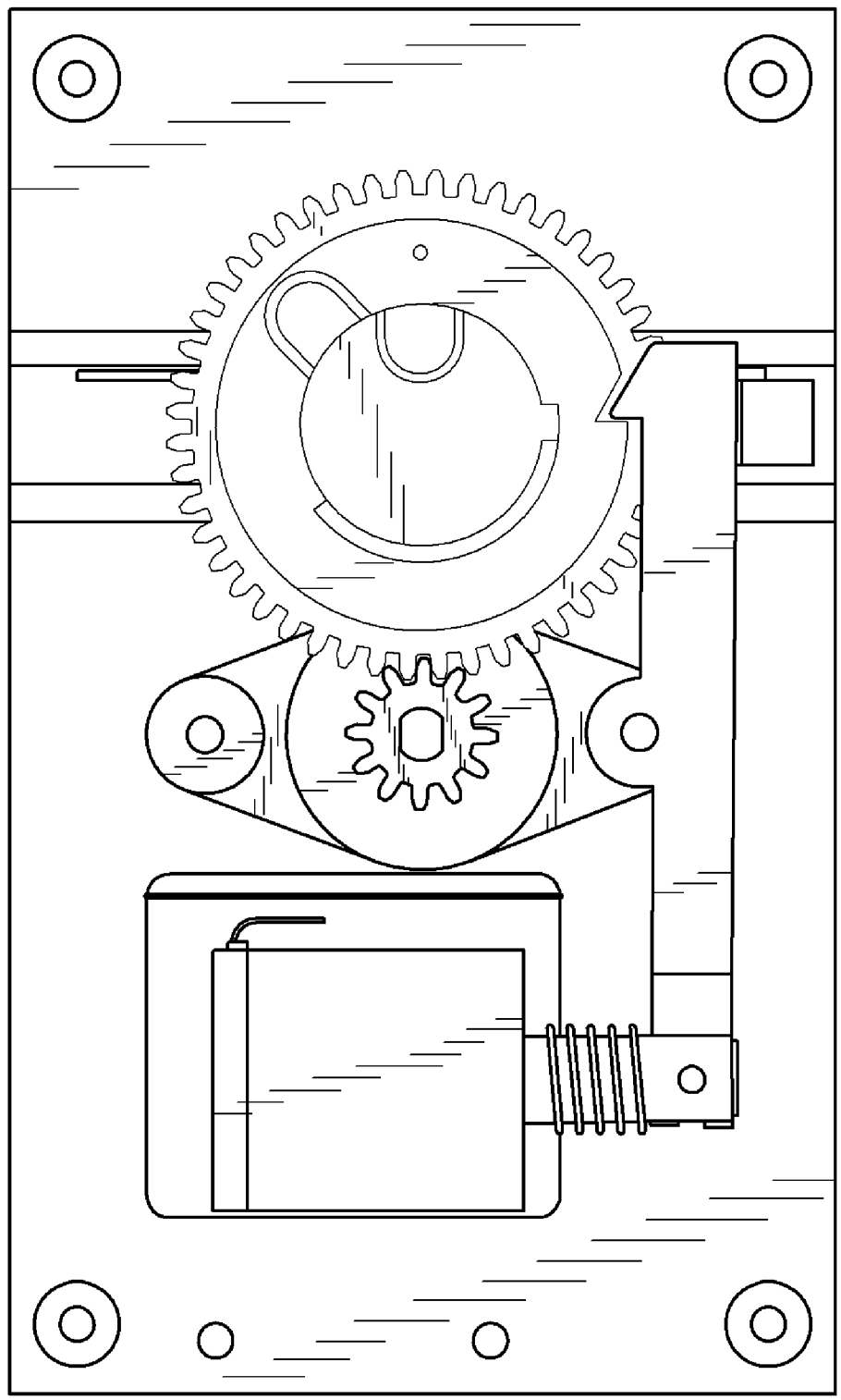
FIG. 46 is an elevation view of a latch assembly.
Figure 47:
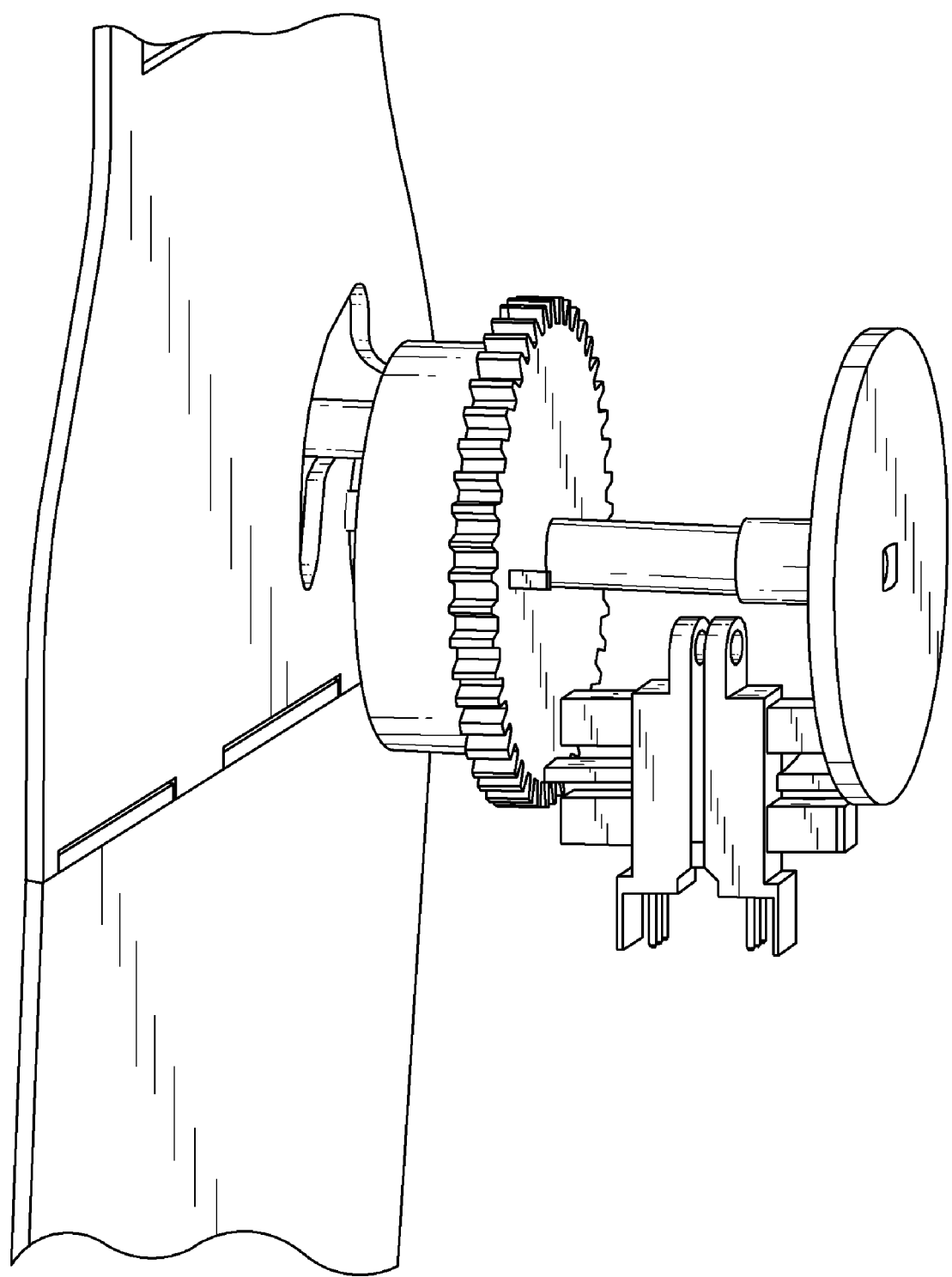
FIG. 47 is a perspective view of a lid and a bar position detectors.

In one embodiment, a receptacle for medical or pharmaceutical waste is provided. In one embodiment, the container is adapted to restrict access to disposed waste. FIGS. 36 and 44 illustrate some of the features of some of the embodiments discussed below. In one embodiment, the container comprises a lid 82 formed in a V-shaped cross section, with circular outer edges. In a further embodiment, a shield 26 having a circular cross section, wherein the shield is positioned at the perimeter of the arc formed by said lid 82 is also provided. In yet another embodiment, a latch assembly 24 is provided. In one embodiment, the container comprises a V-shaped lid, one or more shields, and one or more latch assemblies.

In another embodiment, a restricted access container for medical or pharmaceutical waste is provided wherein the container comprises a lid having substantially circular outer edges, wherein the lid is rotatably operated so that the circular outer edges remain at a constant radius from the axis in all positions, a blocking means adapted to block access to waste contents in all lid positions, and a latch assembly.

In one embodiment, the lid is adapted to restrict, exclude, reduce, or minimize access to deposited waste when in the closed position. In a preferred embodiment, the lid is further adapted to restrict, exclude, reduce, or minimize access to deposited waste during the opening cycle. Thus, in a preferred embodiment, the waste receptacle has a safety feature that restricts (or minimizes) access to disposed medical or pharmaceutical waste while the receptacle is being opened. Thus, in one embodiment the container permits disposal of additional waste while simultaneously restricting access to waste that has been previously disposed.

Some embodiments of the present invention can also be used for receptacles containing materials other than medical or pharmaceutical waste. Thus, in some embodiments, the restricted access lid can be used with non-medical, non-pharmaceutical containers, holders, or vessels.

In one embodiment, a rotary level sensor operates in conjunction with a rotary lid. One function of the lid, according to several embodiments of the invention, is to open upon command from the electronics, allowing an item of hazardous waste to be deposited.

A second function of the lid, according to several embodiments of the invention, is that the open lid is easily recognizable by the user, from among an array of other container lids, intuitively directing their attention to the open container, thus avoiding the need for lights or other indicating means.

A third function of the lid, according to several embodiments of the invention, is to exclude access to the container contents by the user or other personnel, at all times. The lid, according to some embodiments, may be adapted to accomplish none, one, two, or all three of these functions.

In one embodiment, the restricted access safety feature comprises a lid formed in a V-shaped cross section, with circular outer edges. The lid is rotatably operated so that the circular outer edges remain at a constant radius from the axis in all positions, including open, closed, and in between open and closed. The V-shaped lid forms an approximately 135 degrees angle, and its diameter is such that the resulting opening is large enough to accept the largest anticipated waste item. In one embodiment, the lid motion is also limited to approximately 135 degrees. One of skill in the art will understand that lids of other shapes and other angles can also be used in accordance with several embodiments of the present invention.

A lid according to any of the embodiments described herein may comprise a V-shaped cross-section and circular outer edges. A "V-shaped cross-section" as used herein shall be given its ordinary meaning and shall also include substantially V-shaped configurations. In one embodiment, the V-shaped lid comprises an angle of about 135 degrees. Shapes other than "V" may also be used. In some embodiments, the angle is greater than 0 degrees and less than 180 degrees. In one embodiment, the V-shaped lid (or similar shaped lid, such as a U-shape or L-shape, or T-shape) has an angle that is about 120, 125, 130, 135, 140, 145, or 150 degrees.

In one embodiment, a shielding means, or shield, is also provided. For example, in one embodiment, a shield that is circular in cross section is placed at the perimeter of the arc described by the lid during a portion of its motion. In one embodiment, the lid, in combination with the shield, blocks access to the contents during some or most operating positions. In a preferred embodiment, the lid, in combination with the shield, blocks access to the contents during all operating positions. In one embodiment, the shield acts in concert with the lid to physically restrict access to the inside of the container. In one embodiment, the shield cooperatively moves with the lid. In one embodiment, the shield is positioned at one end of the lid. The shield may be positioned at the end of the lid, at the center of the lid, or positioned somewhere in between. The shield may be independent from the lid and located at another location, e.g., coupled to the container or elsewhere on the system.

In one embodiment, as illustrated in FIGS. 36-48H, a latch assembly is provided. In one embodiment, the latch assembly is coupled to the container and/or the lid. The latch assembly can cause the lid to open and/or close. In one embodiment, a latch assembly is part of the equipment and mates to a container during use. In a preferred embodiment, the container is formed with control rods extending outward from one end to mate with openings in the latch assembly. One control rod is tied to the lid, and the other is tied to the bar. Rotational position information of the lid and bar is transferred to concentric inner and outer rings, which track the rotational motion of the lid and bar. The inner and outer ring are each supplied with a position indicator and opto-interruptor for detecting a predetermined position. In a preferred embodiment, the lid detector is set to indicate when the lid is closed, and the bar detector is set to detect when the bar is fully open. In one embodiment, each ring is supplied with a torsion spring to provide opening force.

Figure 48:
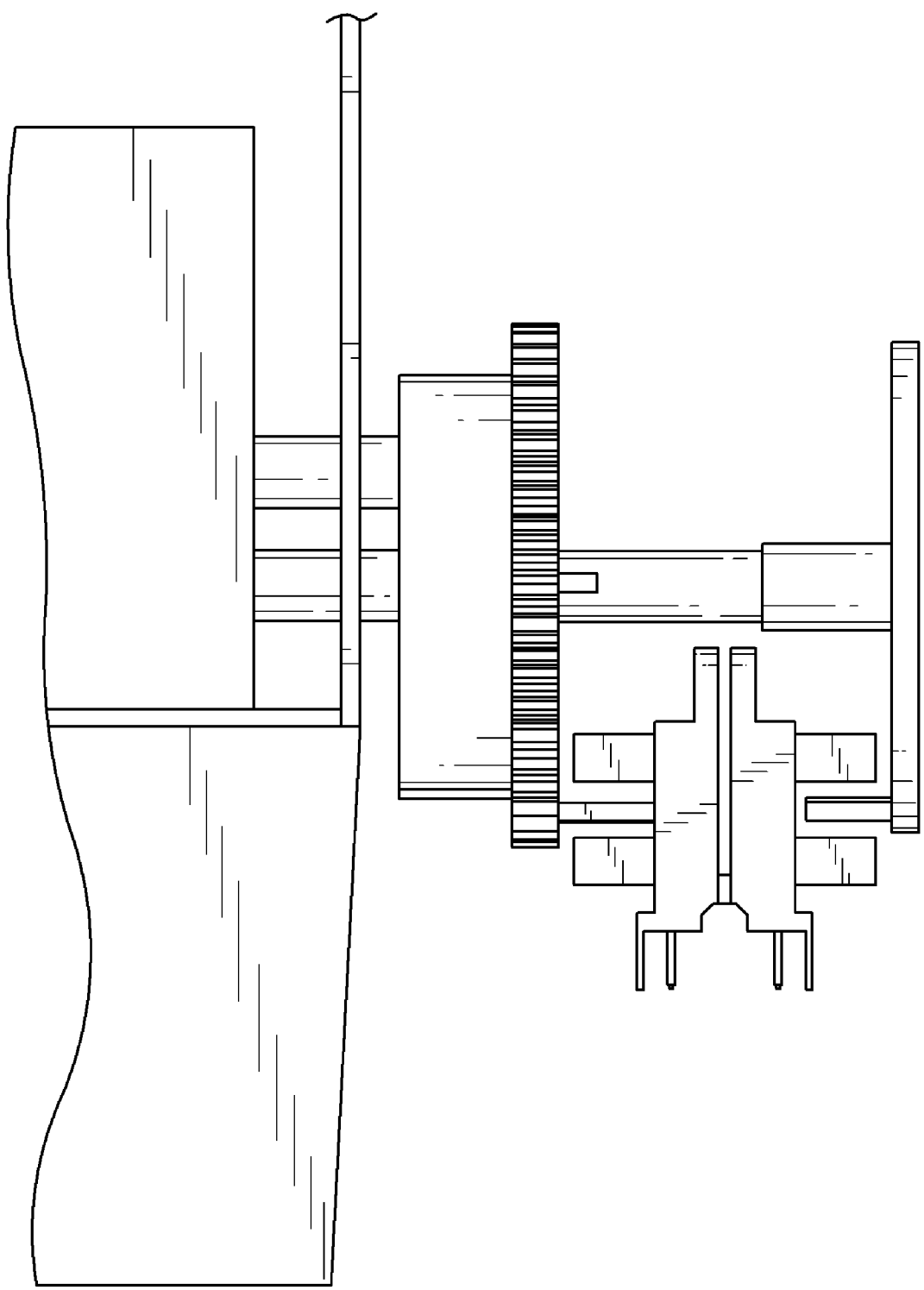
FIG. 48 is an elevation view of a lid and a bar position detectors.
Figure 48A:
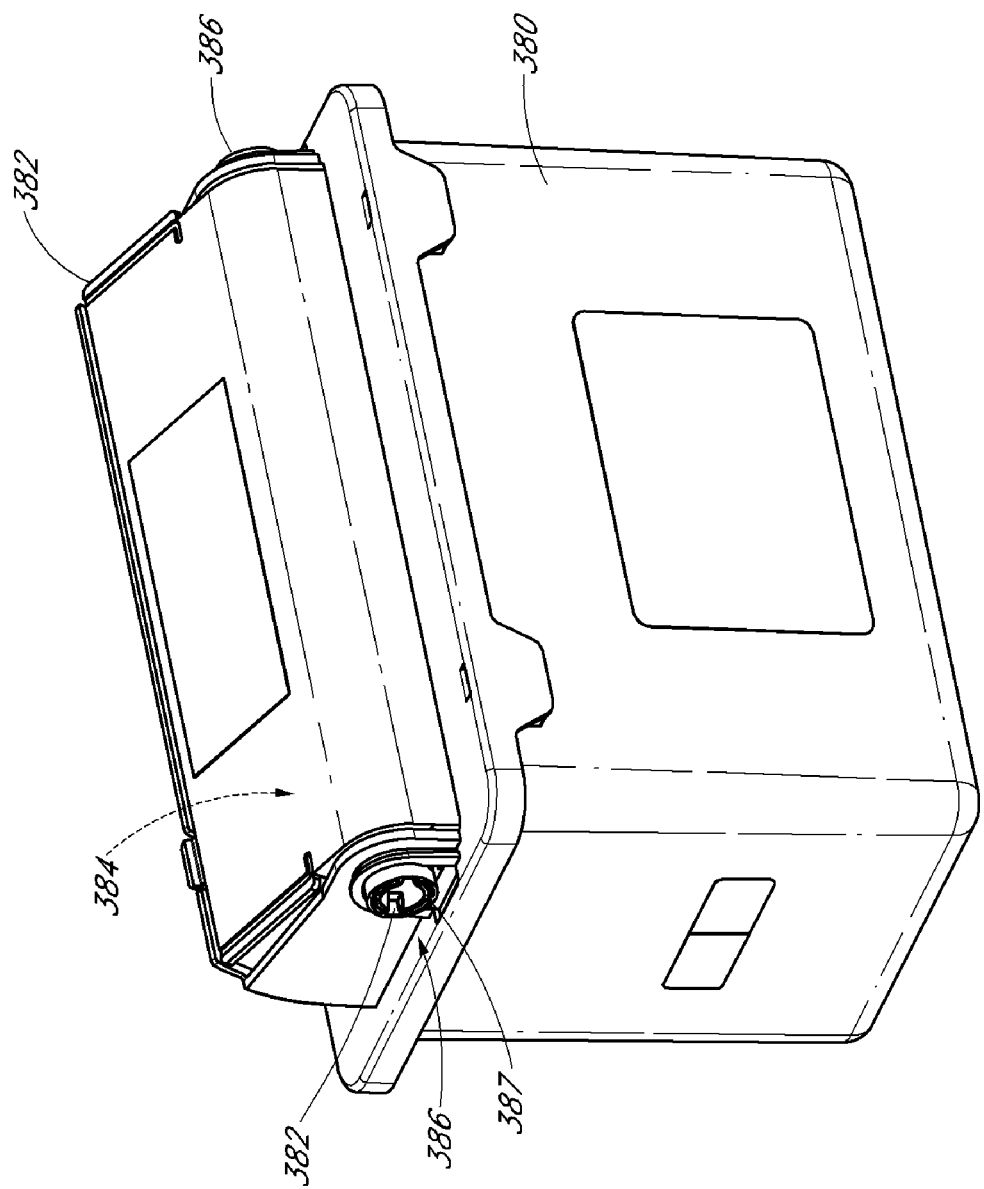
FIG. 48A is a perspective view of a container with a lid assembly according to one embodiment.

FIG. 48A illustrates one embodiment of a container 380 configured to receive waste items as disclosed herein. As shown, a lid assembly 382 can be positioned along the upper, open end of the container 380 to selectively allow access to an interior portion of the container 380. According to some embodiments, one or more portions of the lid assembly 382 are configured to open or otherwise move so as to selectively provide access to the interior of the container 380. For example, the lid assembly 382 can include a flipper member 384 that helps rotate or otherwise move one or more portions of the assembly 382.

Figure 48B:
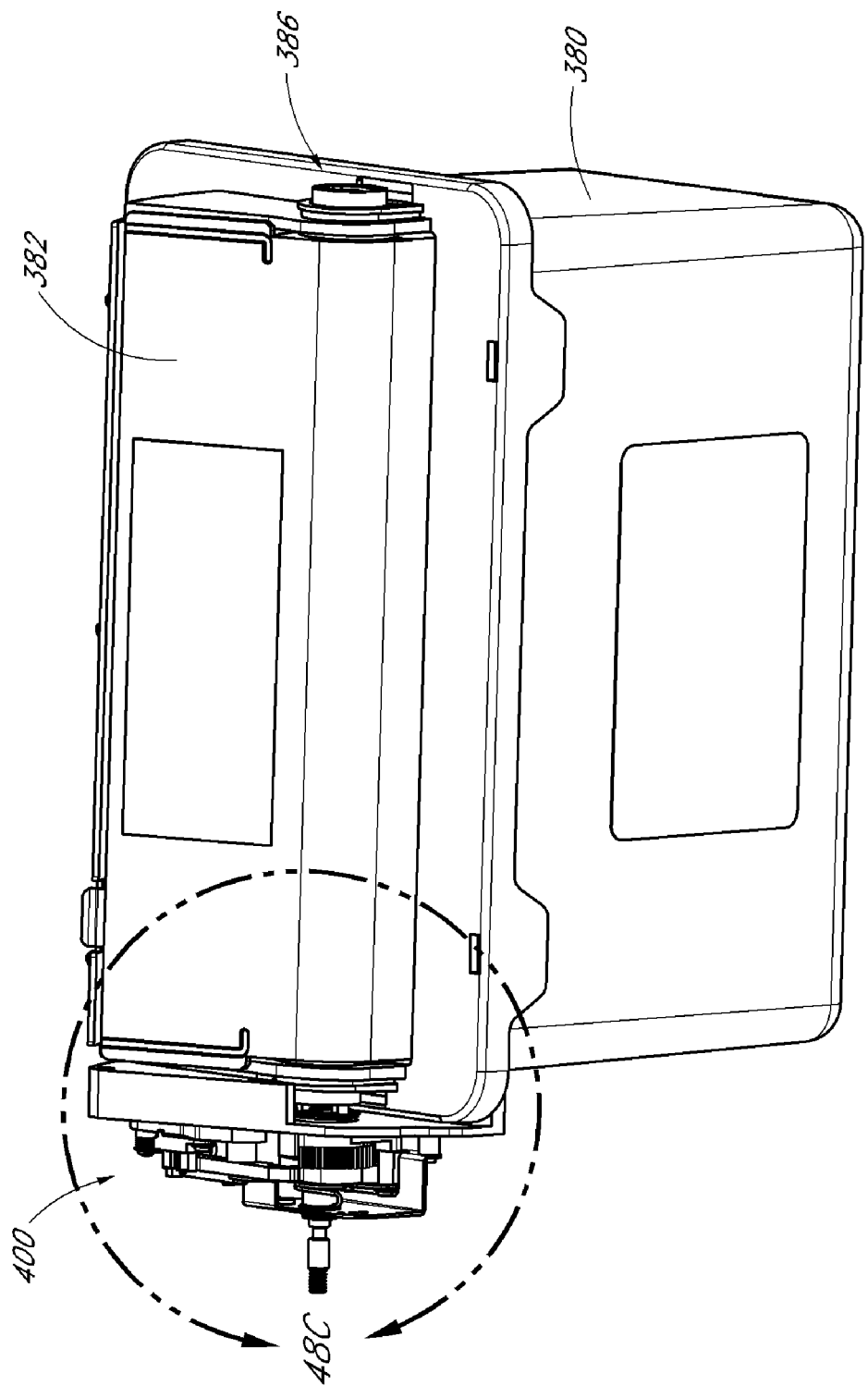
FIG. 48B is a perspective view of one embodiment of a drive mechanism attached to the container and lid assembly of FIG. 48A.

With continued reference to FIG. 48A, the flipper member 384 can extend to one or more ends of the lid assembly 382. In the illustrated embodiment, the flipper member 384 or other portion of the lid assembly 382 includes a coupling 386 on each of its ends. As discussed in greater detail herein, such couplings 386 can be sized, shaped and otherwise configured to engage a drive mechanism or other device that mechanically controls the movement of the flipper member 384 or other portion of the lid assembly 382. For example, the lid assembly 382 can include a boss coupling 386 or any other type of female or male coupling 386. In the depicted embodiment, the coupling 386 includes one or more alignment slots 387 with which a corresponding portion of a drive mechanism can be engaged (FIG. 48B). According to some arrangements, rotating the coupling 386 moves the lid assembly 382 between "OPEN" and "CLOSED" positions (or one or more intermediate positions between fully open and fully closed positions).

Figure 48C:
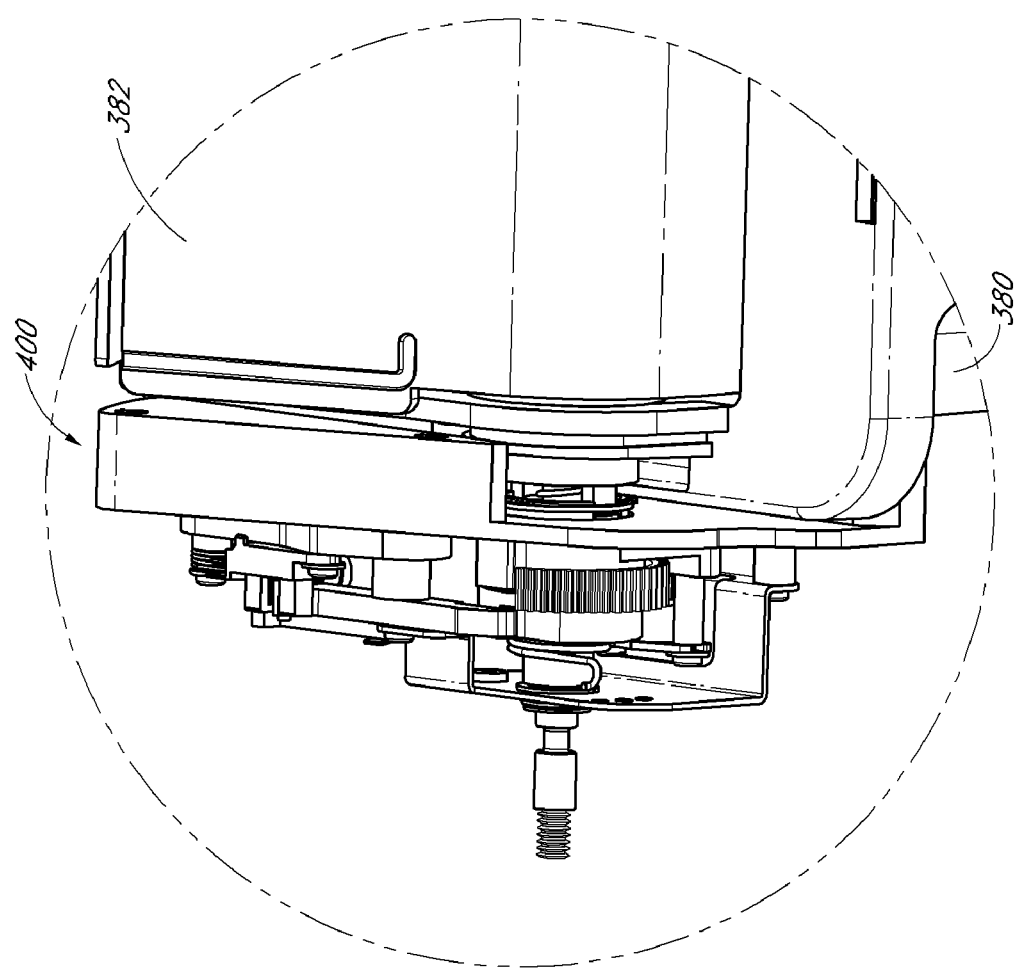
FIG. 48C is detailed perspective view of the drive mechanism illustrated in FIG. 48B.

FIGS. 48B and 48C illustrate perspective views of a drive mechanism 400 mounted to a coupling 386 of a flipper member along one or more sides of the lid assembly 382. The drive mechanism 400 can be attached to the container 380 and/or lid assembly 382 at one or more locations. For example, in one embodiment, the drive mechanism 400 engages only the boss or other coupling 386 of the flipper member 384 or some other portion of the lid assembly 382. However, in other arrangements, the drive mechanism 400 may also be secured to the lid assembly 382 and/or the container 380.

Figure 48D:
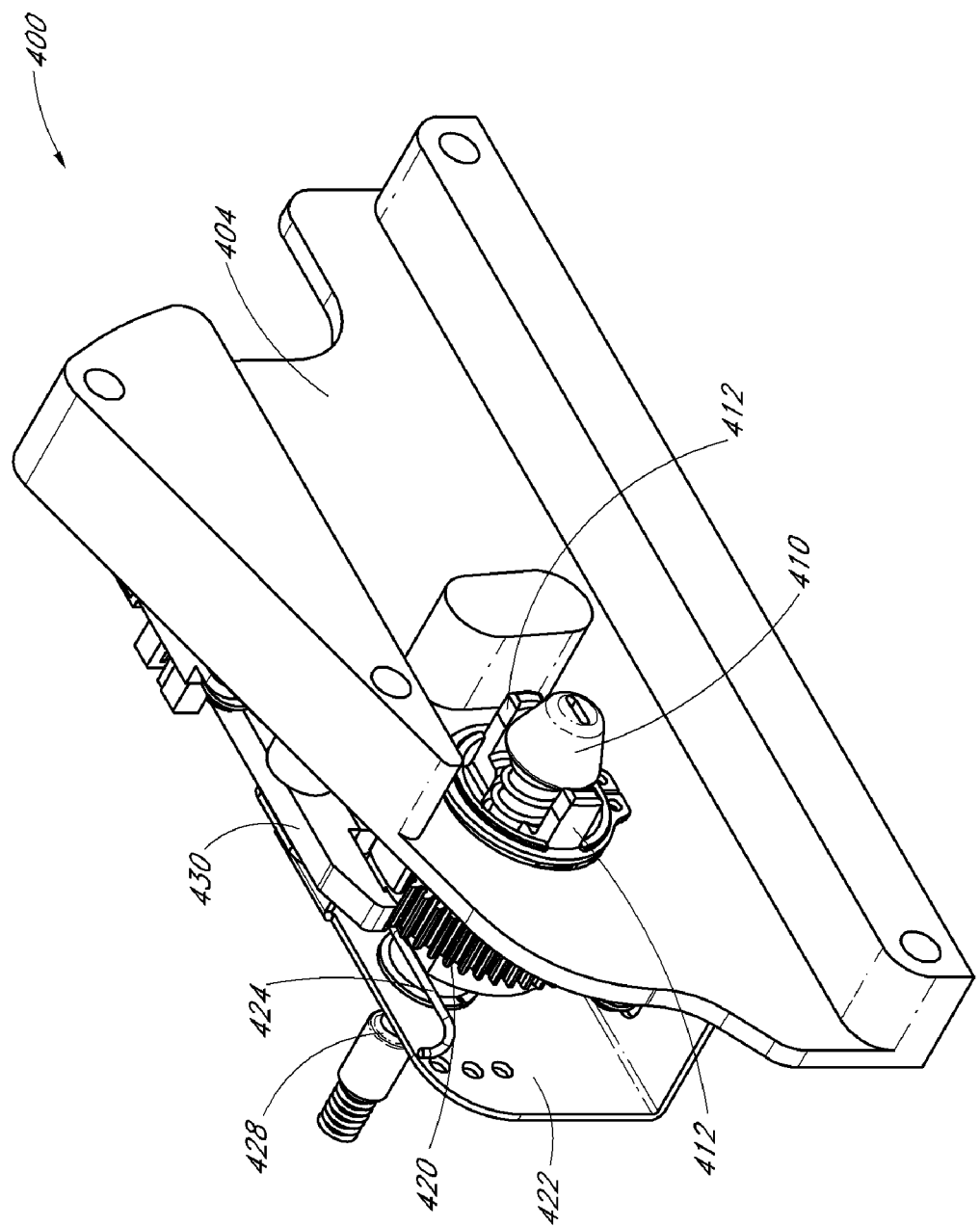
FIG. 48D is a perspective view of the interior of the drive mechanism illustrated in FIGS. 48B and 48C.

Different views of one embodiment of a drive mechanism 400 configured to engage and selectively move a lid assembly 382 are illustrated in FIGS. 48D-48I. As shown in FIGS. 48D and 48I, the drive mechanism 400 can include a shaft 408 or other elongated member that extends at least partially through the mechanism body. The protruding end 410 of the shaft 408 can be shaped, sized and otherwise adapted to engage with and secure into a coupling 386 of the flipper member or other portion of the lid assembly 382. For example, as shown, the protruding end 410 can be generally cone-shaped.

With continued reference to the cross-sectional view of FIG. 48I, a drive coupling 412 can be positioned around the shaft 408 at or near the end that engages the coupling 386 of the flipper member. In some embodiments, the drive coupling 412 comprises one or more alignment members 413 that are positioned adjacent to the protruding end 410 of the shaft 408. Such alignment members 413 can be configured to fit within corresponding slots 387 or other members of the coupling 386 located on the flipper member or other portion of the lid assembly 382. Although in the illustrated embodiment it is depicted as being generally cone-shaped, the protruding end 410 can have any other shape, size or configuration, as desired or required by a particular application.

Figure 48E:
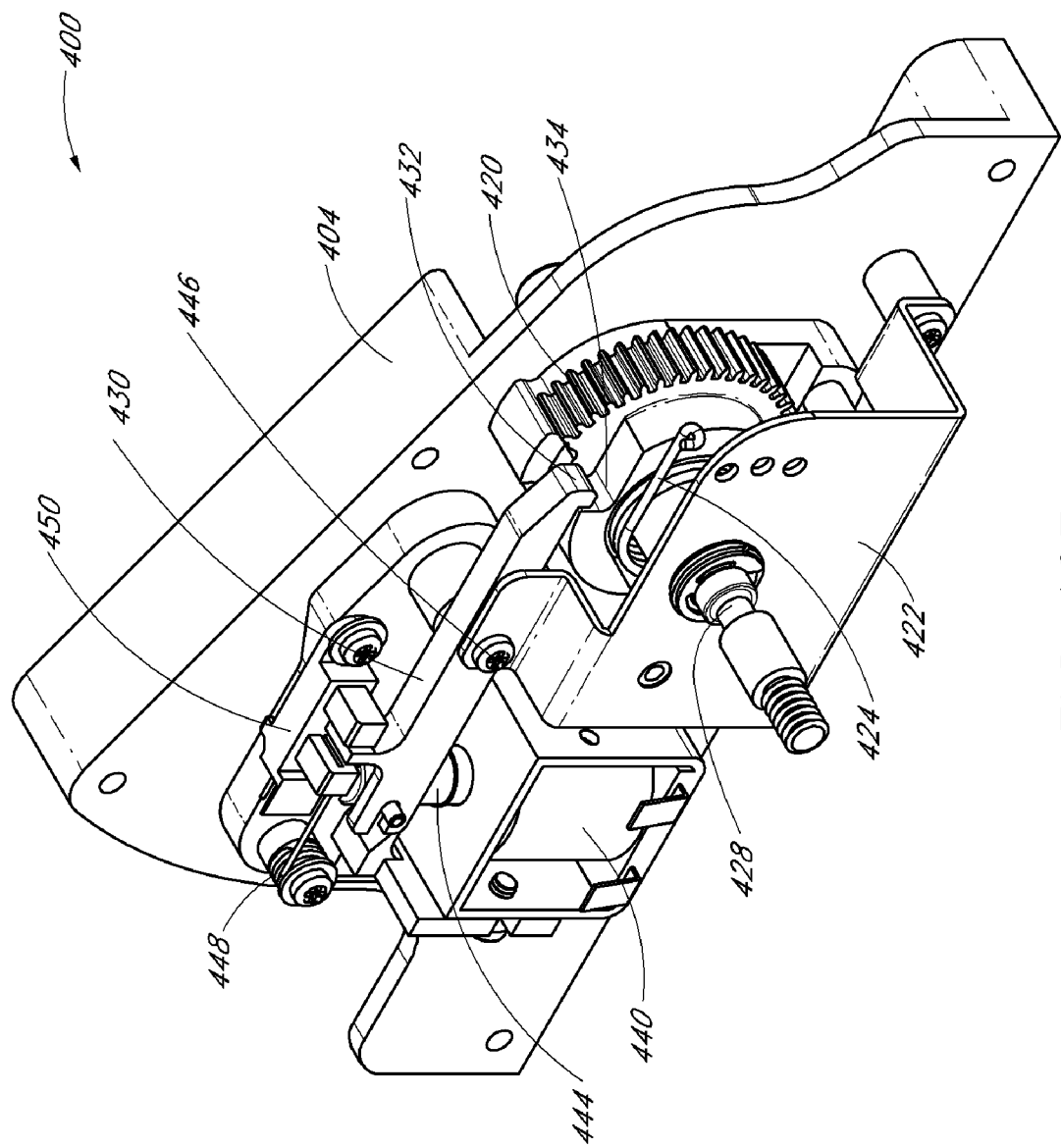
FIG. 48E is a perspective view of the exterior of the drive mechanism illustrated in FIGS. 48B and 48C.
Figure 48G:
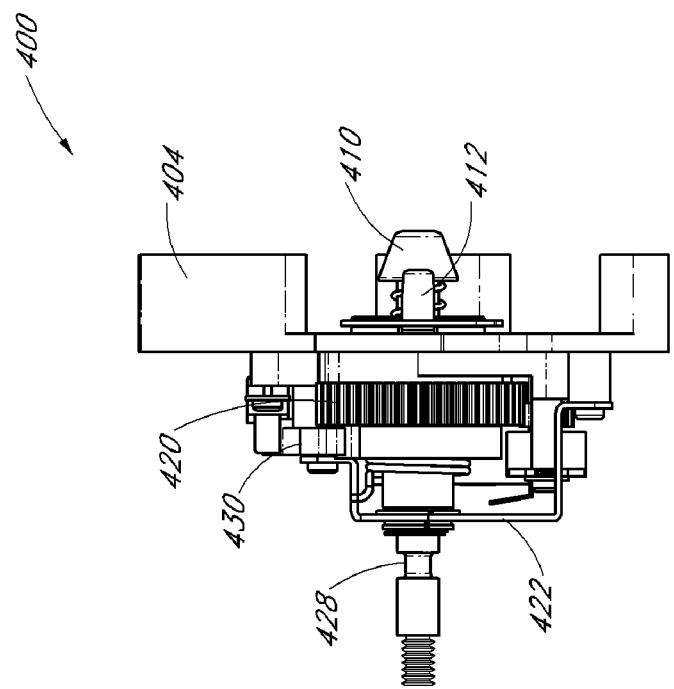
FIGS. 48F and 48G are elevation views of the drive mechanism illustrated in FIGS. 48B through 48E.
Figure 48F:
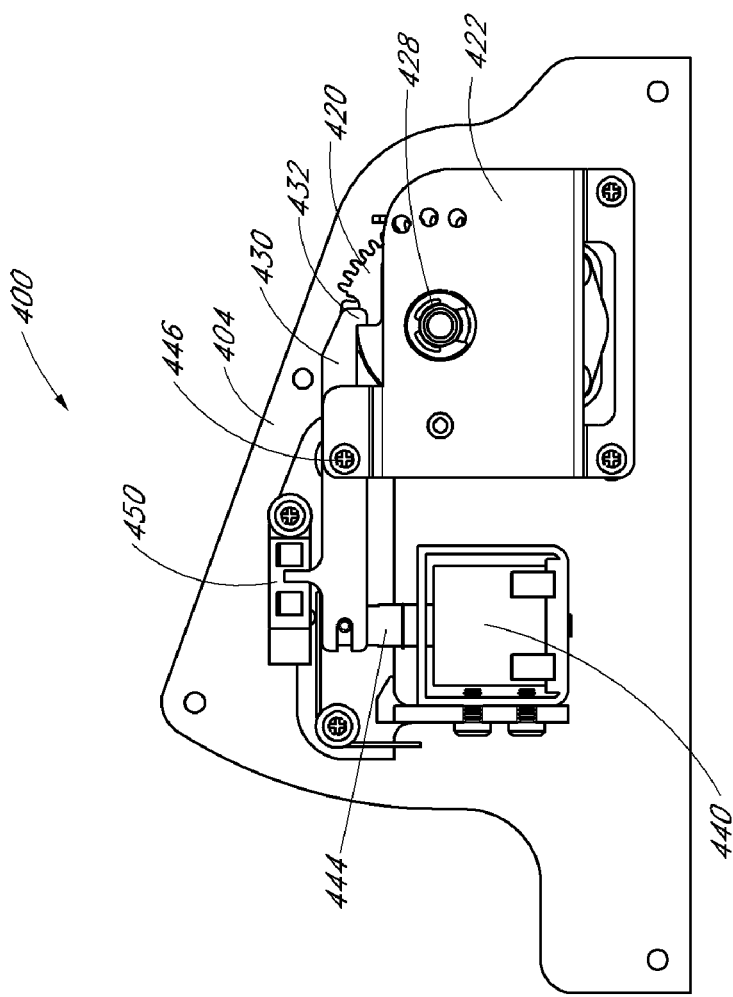
Figure 48H:
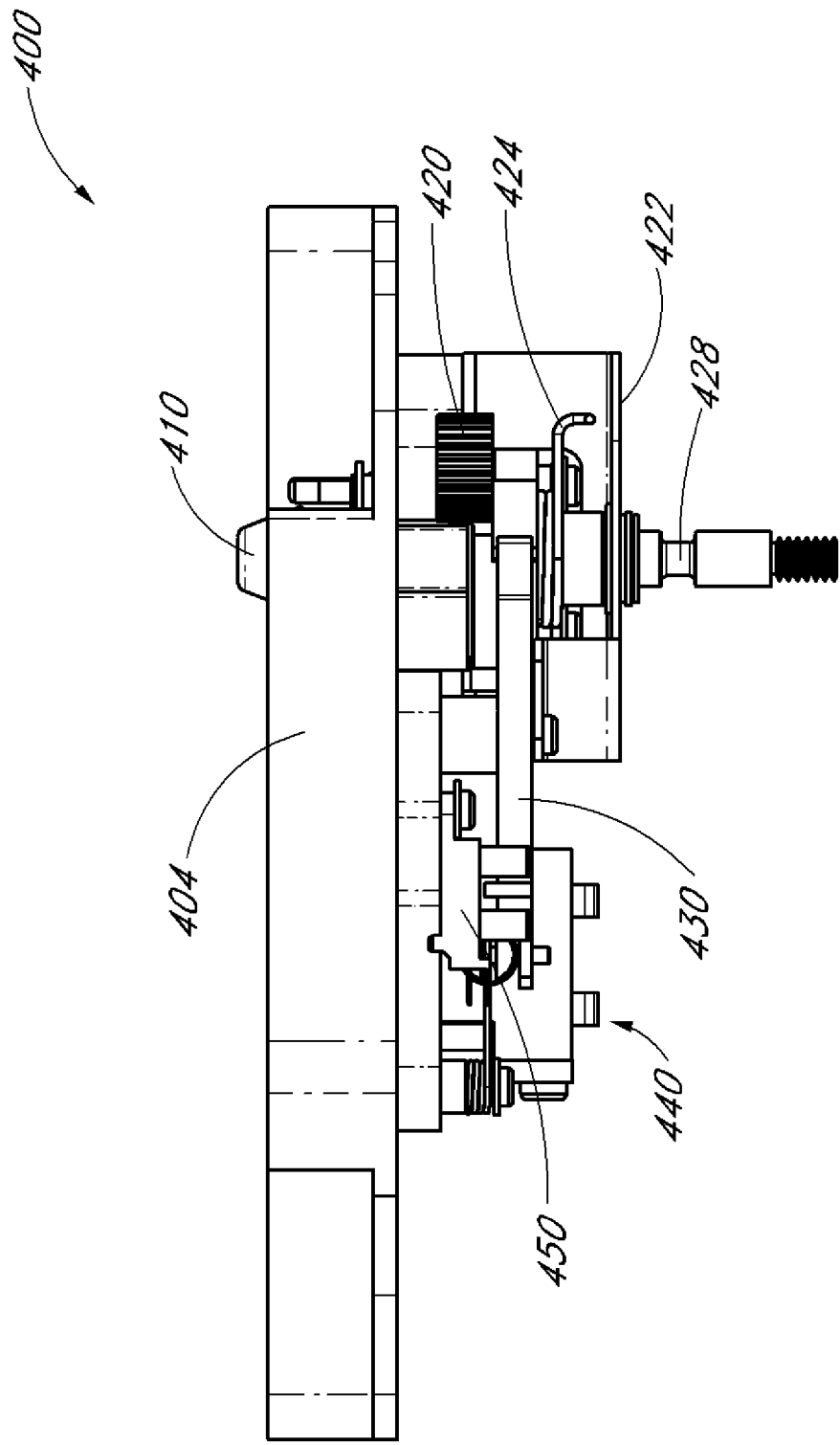
FIG. 48H is a top view of the drive mechanism illustrated in FIGS. 48B through 48E.
Figure 481:
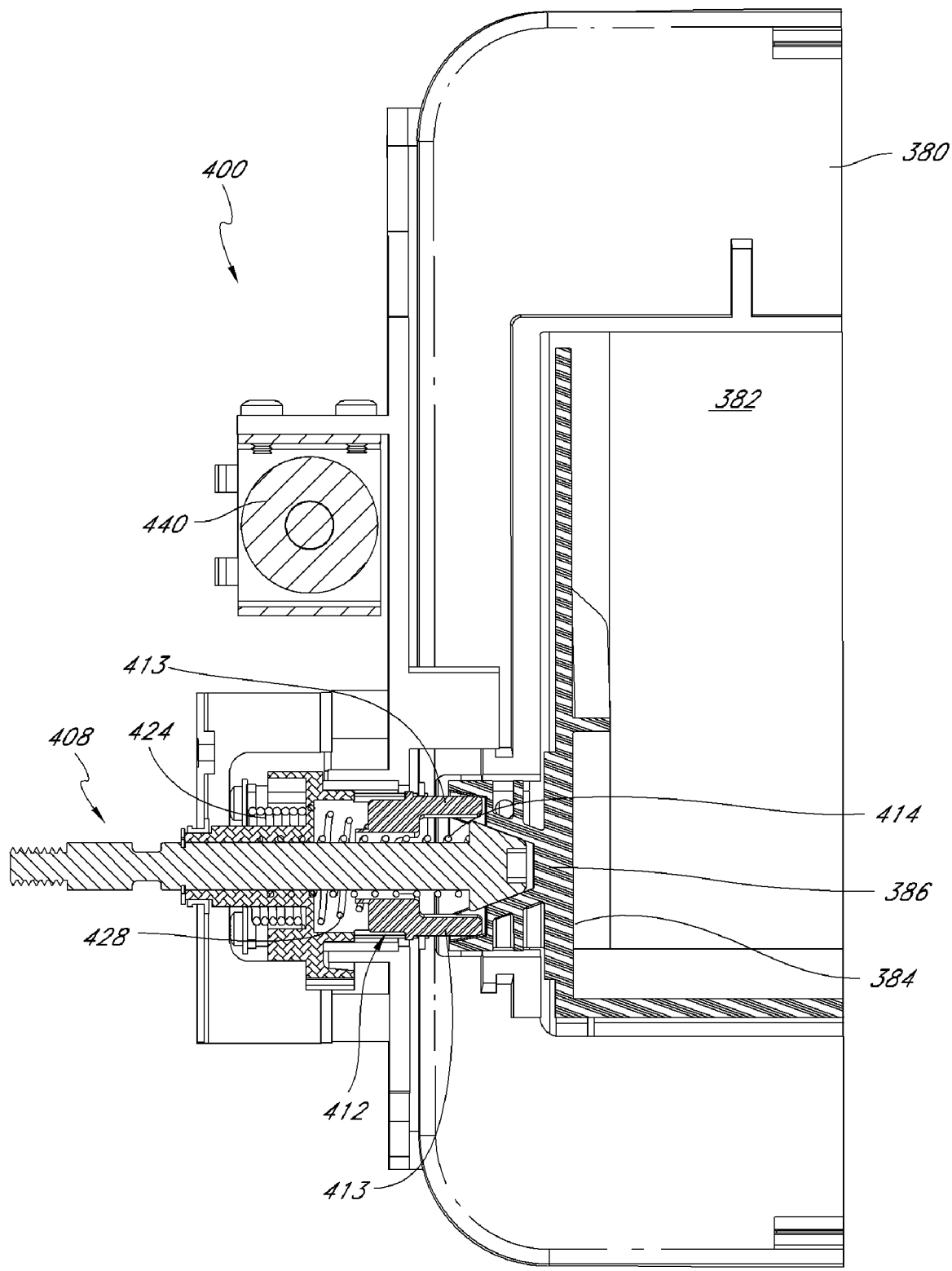

As illustrated in FIGS. 48D, 48G and 48I, a centering spring 414 can be placed around the shaft 408 and within the drive coupling 412. Such a centering spring 414 can help maintain the shaft 408 along a desired orientation (e.g., at or near the centerline of the drive coupling 412), especially when the protruding end 410 is being inserted within or removed from the corresponding coupling 386 of the flipper member 384 or another portion of the lid assembly 382. Further, in some embodiments, the drive mechanism 400 comprises a drive coupling spring 428 or other resilient member configured to urge the drive coupling 412 in the direction of the protruding end 410. Therefore, both the shaft 408 and the drive coupling 412 can be resiliently biased toward a corresponding coupling 328 located on a flipper member or other portion of a lid assembly 382.

With continued reference to FIG. 48E, the shaft 408 can be mechanically coupled to one or more gear assemblies 420. In the embodiment illustrated in FIGS. 48D-48I, the drive mechanism 400 comprises a gear support 422 that is adapted to secure the gear assembly 420 to the frame member 404. As shown, the drive mechanism 400 can also include a torsion spring 424 or another resilient device that is mechanically connected to the gear assembly 420. In some embodiments, using its rotational tension, such a torsion spring 424 can be configured to rotate the adjacent gear assembly 420 to which it is coupled. In one embodiment, the rotational tension force that the torsion spring 424 exerts on the gear assembly 420 is increased when the lid assembly 382 to which the drive mechanism 400 is coupled is closed.

In some embodiments, the position of the gear assembly 420 can be locked or released to selectively permit or restrict rotation of the shaft 408 to which the gear assembly 420 is mechanically connected. For example, in the arrangement illustrated in FIGS. 48D-48I, the drive mechanism 400 includes a gear release member 430. The gear release member 430 can include a lip 432 or other feature that is configured to engage a corresponding structure 434 of the gear assembly 420. Accordingly, when the lip 432 of the gear release member 430 is positioned against the corresponding structure 434 or other surface of the gear assembly 420, the gear assembly 420 is not permitted to rotate. Consequently, the shaft 408 and the drive coupling 412 are not permitted to rotate within the lid assembly coupling 386 to which they are engaged.

Alternatively, when the lip 432 of the gear release member 430 is moved away (e.g., lifted) from the gear assembly 420, the gear assembly 420 is free to move. Thus, the shaft 408 of the drive mechanism can be permitted to rotate (as a result of the rotational tension force applied to it by the adjacent torsion spring 424) in order to selectively open or otherwise change the position of the lid assembly. In the illustrated embodiment, the opposite end of the gear release member 430 is attached to a movable stem 444. The drive mechanism 400 can include a solenoid 440 or other position control device adapted to selectively move the stem 444 generally along a vertical axis. This can cause the end of the gear release member 430 to also move up or down. If the gear release member 430 is connected to the frame member 404 at a center pivot point 446, an upward movement of the stem 444 can cause the lip 432 of the gear release member 430 to move in an opposite direction (e.g., downwardly), and vice versa. Thus, the solenoid 440 can be used to control whether the gear release member 430 is engaged to the gear assembly 420. In some embodiments, a spring 448 or other resilient member is used to urge the gear release member 430 into contact with the gear assembly 420 when the solenoid 440 is not activated. This helps ensure that the gear assembly 420 and the protruding end 410 are not permitted to rotate when electrical power is lost (e.g., fail safe protection).

In addition, the drive mechanism 400 can comprise an optical switch 450 or other position detection device or feature. An optical switch 450 can help determine the orientation of the gear release member 430 at a particular moment in time. Such information can be used to control the operation of the drive mechanism 400 and/or the lid assembly 382 to which the drive mechanism 400 is attached.

In some embodiments, when a user manually (e.g., by pressing a button) or automatically (e.g., by scanning a waste item) causes the lid assembly 382 to open, the solenoid can be energized to move the lip 432 of the gear release member 430 away from the corresponding structure 434 of the gear assembly 420. Accordingly, the torsion spring 424 is free to exert a rotational force on the gear assembly 420, causing the gear assembly 420 and the shaft 408 to rotate. If the protruding end 410 of the shaft 408 is engaged within a corresponding coupling 386 of the flipper member or other portion of the lid assembly 382, the lid assembly 382 can open to permit the user to discard one or more waste items within the container 380. After the waste items have been deposited within the container 380, the user can manually close the lid assembly 382. As discussed, in some embodiments, this causes the shaft 408 and the gear assembly 420 to rotate. In turn, this causes the torsional force within the torsional spring 424 to increase, as the spring 424 is rotated into a further coiled position. In other embodiments, one or more external motors or other devices are used to rotate the shaft 408 in one or both directions. For example, a motor or other actuator mechanically coupled to the shaft 408 can be used to rotate the shaft 408 when the lid assembly 382 is automatically closed.

Combination Disposal/Sorting and Dispensing Apparatus

A system that combines both dispensing and disposing of medical items (such as drugs), is disclosed in several embodiments. In certain embodiments, a combined system is particularly advantageous because it minimizes the foot print or the floor space used. Hospitals are often built to maximize the number of patient rooms. Until recently, less emphasis was placed on logistical and material control issues, such as dispensing and disposal of medications. Hospitals give very little consideration to space for the equipment that supports dispensing of medications.

In several embodiments of the invention, the system is designed to maximize the number of medications that can be stored. Thus, the hospital in-patient pharmacy may be able to reduce the frequency of restocking.

The feeding of commercially available automated dispensing cabinets is typically accomplished back in the central inpatient pharmacy. Unit dose packaging machines take bulk pharmaceuticals (pills) and create blister packs or baggie packs. Massive robot systems are employed to store these unit doses on to pegs. Carousels that reach up several stories are also used to store pharmaceuticals. The technology used in almost every case is outmoded and borrowed from the electronic and aerospace industries with little thought to hospital and pharmacy needs. When automated dispensing cabinets need to be restocked, a pharmacy technician may need to either hand pick the inventory or semi-automatically access the inventory from these systems. This extra step is avoided in several embodiments of the present invention.

It is estimated that hospitals must a dispense a quantity of 20 to 100 each of 350 to 370 pharmacy line items in the medication room. Pharmacy line items come in a variety of different forms, including but not limited to: unit doses (e.g., a pill such as an aspirin) that is in a baggie or in a blister pack; prefilled syringes (e.g., certain narcotics); expensive medications that require refrigeration; bulk medications (e.g., antacids); custom prepared IV solution bags with one or more medication additives; vials; ampoules; and inhalers. The shelf lives and doses may vary. Several embodiments of the present invention will accommodate the large number of pharmacy line items that hospitals dispense.

Most hospitals have regulations that only allow for one patient's medications to be withdrawn at a time and administered to the patient before returning to the ADC for the next patient's medication. This regulation is in place to prevent comingling of medications so that medication errors are minimized. Nurses are under great time pressures and often circumvent this process by gathering more than one patients medications at a time. When they circumvent the regulations, comingling can occur often resulting in patient administration medication errors. Further, controlled substances (e.g., narcotics such as morphine) can represent as much as 25% of the medications that are dispensed. As much as 10% of the narcotics are diverted in hospitals. Some are diverted for personal use, others for curiosity or sale on the street.

Several embodiments of the present invention reduce the risk of circumvention. In several embodiments, the invention reduces the risk of pilferage, diversion and inventory losses because a clinician will not have access to more than one (or the correct unit) of the same medication when filling a patient specific order. Certain embodiments will also reduce comingling of medications, so that medication errors are minimized.

In some embodiments, a waste sorting/disposal system and a medical item dispensing system can be incorporated into a single apparatus or system. This can enable physicians, nurses and other medical personnel to appropriately dispose of sharps, pharmaceutical products and/or other waste items in or near the same apparatus from which such items may be dispensed. As discussed, such combination systems and devices can be particularly advantageous to hospitals and other facilities with relatively limited floor space. One or more different types of items can be dispensed by such an apparatus, such as, for example, tablets, capsules, other pills, vials, syringes, IV bags, other medication bags, bottles, ampoules, inhalers in small metal containers with a delivery nozzle, ointments in tubes, medical supplies and/or any other items.

In some embodiments, a combined apparatus can be configured so that controlled substances, sharps and/or other regulated materials are deposited in a separate container or apparatus. Such a separate container or apparatus may be bolted or otherwise attached to an adjacent wall, situated on a shelf, positioned on another piece of equipment or placed in any other desired location.

For example, a portion of such a combination apparatus can be configured to dispense medications or other items, while another portion of the apparatus can be configured to receive and sort waste items. In one embodiment, an upper portion of such an apparatus can be configured to dispense waste items and a lower portion can be configured to receive waste items, including but not limited to, spent controlled substances. In other embodiments, the disposal and dispensing portions can be reversed or differently oriented (e.g., side-by-side). The exact location and relative orientation of the disposal and dispensing portions can be varied.

The combination dispensing and disposal/sorting apparatus can be floor-mounted, wall-mounted or otherwise positioned within a room. In addition, the apparatus can be mobile or stationary, as desired or needed. For example, the combination apparatus can include wheel assemblies to facilitate its movement from one location to another. The size of the dispensing and disposal portions of the apparatus can be customized according to a particular application. For example, the size of each portion can depend on the anticipated quantity or size of the goods to be dispensed and/or the anticipated types and approximate volume of waste to be discarded. In one embodiment, the system has a minimum foot print in order to utilize most or all of the room's height In one embodiment, the dispensing portion uses a robotic function such as a "pick and place mechanism" (such as an xy or xyz mechanism), that selects and acquires a packaged medication in a magazine after receiving a dispensing instruction. In one embodiment, a dispensing control system is configured to process the dispensing instruction. The dispensing instruction may be manually input or obtained from scanning or otherwise acquiring information from a barcode or other label. The dispensing instruction may be also be obtained via an electronic or telecommunications signal.

In one embodiment, the magazine includes like medications. In one embodiment, each magazine would have several units of the identical drug in the identical dose. For example, a single magazine would contain 5, 10, 15, 20, 25, 50, etc. vials, syringes, packages of a single dose of a single drug. In other embodiments, a single magazine would contain the same drug, but in different doses, which, preferably, would be clearly marked. In an alternative embodiment, a single magazine would contain different drugs. In one embodiment, a single magazine would contain both the branded and generic drug.

In one further embodiment, the picked medications that are specific to a particular patient are automatically deposited into a portable container by the pick and place mechanism or manually to the user who engages the dispenser.

In some embodiments, the dispenser portion of the combined system can extend into the headspace between the hospital or healthcare facility floors. The compartments of medications may be reached by using a dumb waiter approach for medications (or other items) that are above or near the ceiling. The pick and place and mechanism would also accomplish the same in some embodiments.

As discussed in greater detail herein, the disposal portion of the apparatus can include two or more containers for sorting discarded items into different waste types (e.g., hazardous, radioactive, sharps, etc.). The combination apparatus can include a scanner or other identification device to help identify the waste item being disposed. In addition to or in lieu of a scanner or other identification device, the combination apparatus can comprise a keypad or other data entry device that permits users to enter information regarding the waste items being discarded. For example, as discussed herein, a user can use a keypad to indicate whether the waste item is a sharps or a non-sharps, or whether the waste item is empty or not empty. In one embodiment, the system accepts only non-sharp waste items and would direct the user to use existing sharps containers in the healthcare facility for any sharps.

The different waste containers of the combination apparatus can be configured to directly receive waste items. For example, once the container into which a waste item should be placed has been determined, a lid or other closure member of a corresponding container can open. Alternatively, a container may be configured to tilt or otherwise move or orient itself in order to provide access to its interior. In other embodiments, the combination disposal/dispensing device can include only a single disposal opening for the deposit of waste items. In such arrangements, information obtained through the scanning of waste items, using a touchpad and/or by some other method can be used to determine into which container a waste item should be placed. Thus, the apparatus can be configured to internally route a waste item to the appropriate container after the waste item has been deposited in the common disposal opening. For example, the apparatus can include one or more routing members that direct the waste item to the appropriate containers.

Alternatively, an opening of the appropriate waste container can be configured to move, thereby exposing an opening thereto for accepting a waste item. It will be appreciated that other methods of directing waste items into the desired container can also be used.

The dispensing portion of the combination apparatus can include one or more modules or compartments which can house various supplies. For example, the modules can be configured to store and selectively dispense medications (e.g., pills, tablets, capsules, vials, liquid medications, other solutions, lotions, creams, sprays, etc.), medical devices and supplies (e.g., syringes, needles, gauze, etc.) and other medical items. The combination apparatus can be configured so that the modules include one or more items.

The dispensable medical items housed within the modules or other compartments of the apparatus can be accessed using one or more different methods. For example, a module lid, door or other closure member can open to permit a user to remove one or more dispensable items. Alternatively, the apparatus can include one or more trays that are configured to slide, rotate or otherwise move to provide access to items stored thereon. In some embodiments, the trays can be further partitioned into different submodules or subcompartments.

Figure 54A:
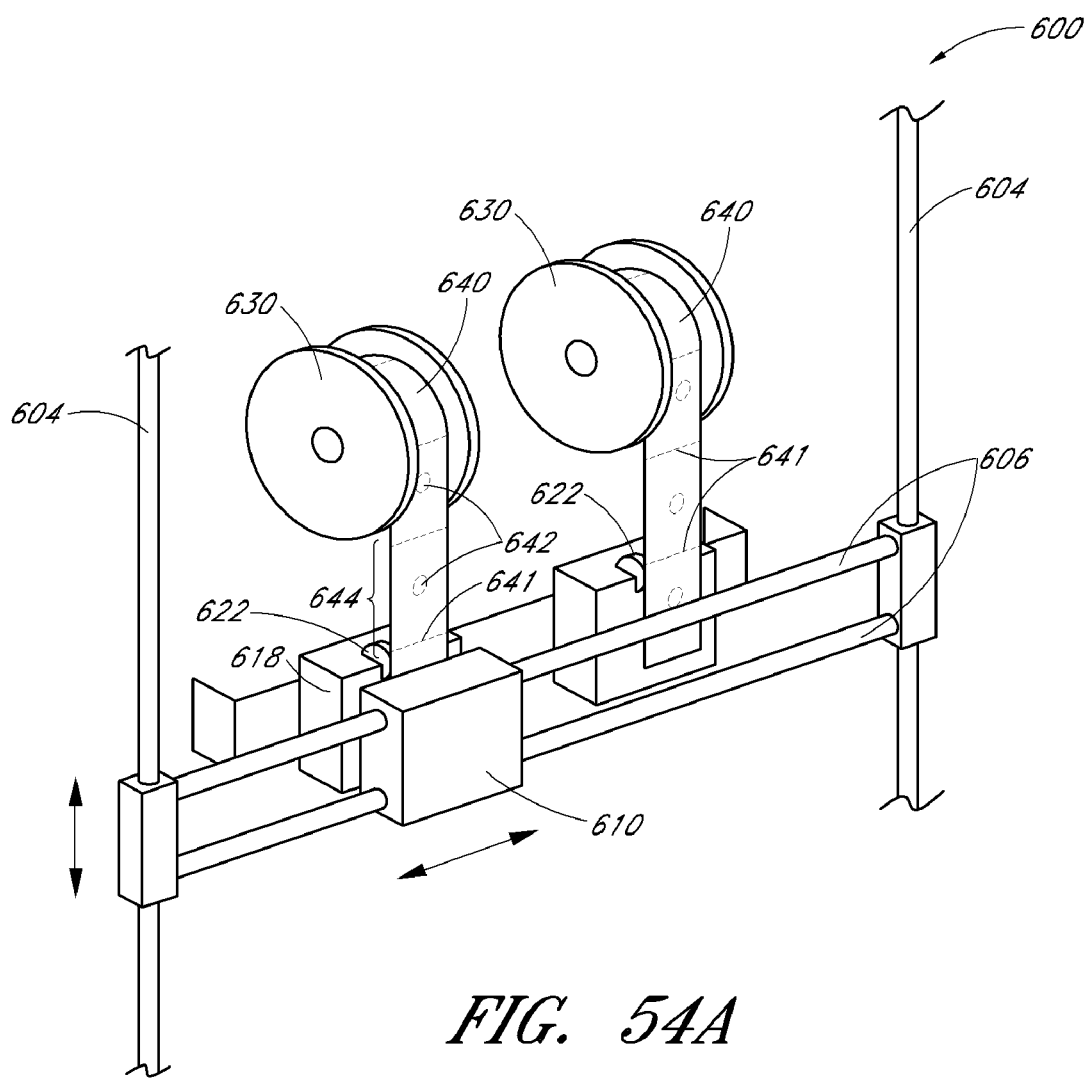
FIG. 54A is a perspective view of a retrieval system for a combination disposal and dispensing apparatus according to one embodiment.
Figure 54B:
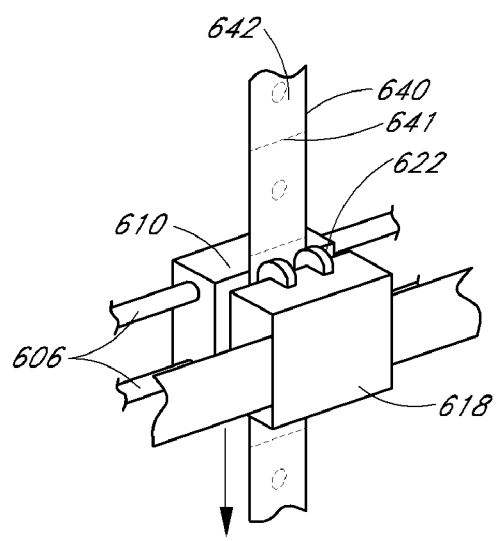
FIG. 54B is another perspective view of the retrieval system of FIG. 54A.
Figure 55:
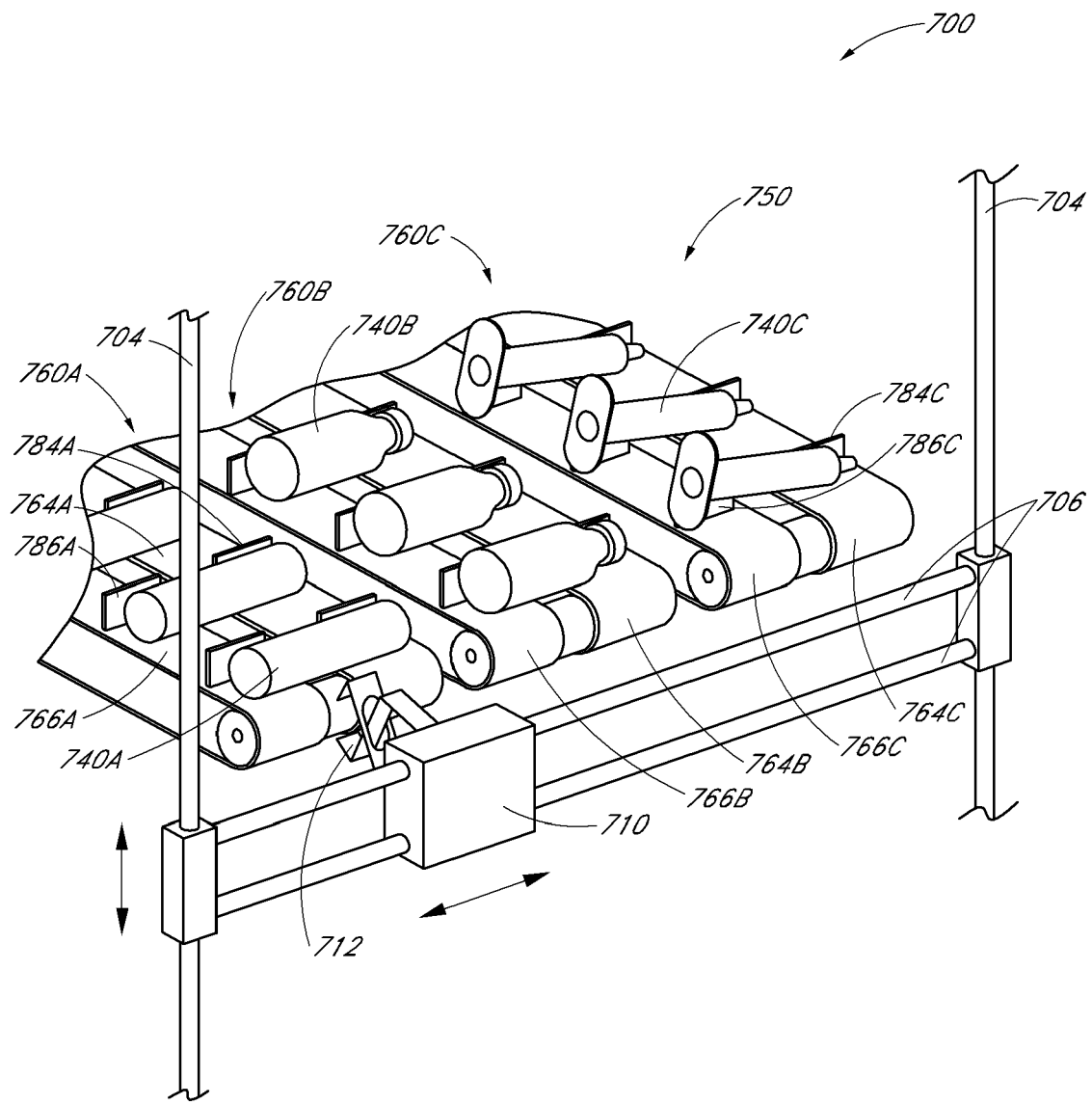
FIG. 55 is a perspective view of a retrieval system for a combination disposal and dispensing apparatus according to another embodiment.

In several embodiments, by using modules or magazines, the medications can be picked up or otherwise acquired for floor use with a simple robot such as a "pick and place mechanism" often referred to as an xy or xyz mechanism. Medications would be conveniently stored in a portable apparatus with an opening (such as a bag or other container). Each bag or container could be designed with an injection molded top with a minimum of one detents to facilitate consistent capture from the magazine storage to a patient specific container or to be retrieved manually for each patient by the user. The top with detent could also include a "living hinge" coined into the top so that the container can be opened and remain open with the end of the bag pressed allowing for easy access to the medication in the container. Embodiments of such an apparatus or system are illustrated in FIGS. 54 and 55.

In one embodiment, drugs (or other medical devices) are grasped using graspers. In other embodiments, air systems or vacuums are used to select and/or position the drug. Means to grasp the drug are particularly advantageous because they permit enhanced control of the drug during the process of picking and placing.

Figure 51:
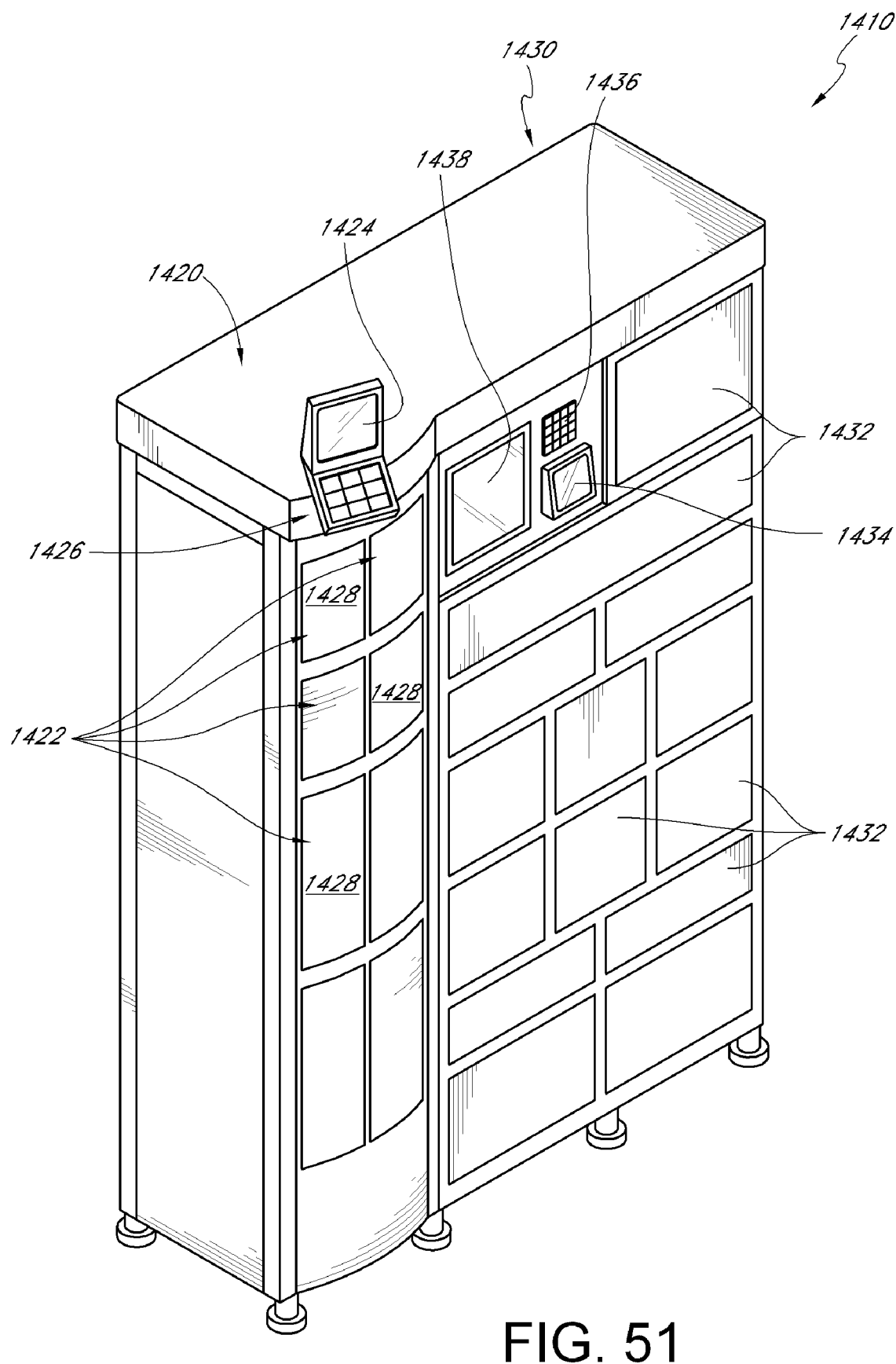
FIG. 51 is a perspective view of a combination disposal and dispensing apparatus according to one embodiment.

FIG. 51 illustrates one embodiment of a combination apparatus 1410 comprising a disposal portion 1420 and a dispensing portion 1430. As shown, the disposal portion 1420 and the dispensing portion 1430 are positioned in a side-by-side orientation. However, the portions 1420, 1430 can be differently arranged (e.g., top-bottom, opposite sides, etc.). In addition, the relative size of the disposal portion 1420 and the dispensing portion 1430 may be varied depending on one or more factors. The disposal portion 1420 and the dispensing portion 1430 can be separate units that are held together using one or more connection methods. For example, the portions 1420, 1430 can be joined by fasteners, clips, pins, hinges, adhesives and/or the like. Alternatively, the apparatus 1410 can be constructed as a unitary unit.

With continued reference to FIG. 51, an outer surface of the disposal portion 1420 can include a plurality of containers 1422. An interior volume of the waste containers 1422 can be accessed by moving an exterior lid 1428 or other cover member. As discussed, after a waste item has been passed near a scanner 1424 or other identification device, and/or information regarding the waste item has been manually entered into a data entry device 1426 (e.g., keyboard, touchpad, etc.), the apparatus 1410 can be configured to automatically determine into which container 1422 the waste item should be deposited. The corresponding lid 1428 can then open so that a user can properly dispose of the waste item therein. Alternatively, a user may be directed to manually open the corresponding lid 1428. For instance, the apparatus 1410 can indicate the appropriate container by illuminating a light (not shown), displaying a container identifier (e.g., number, letter, etc.) or the like. In other embodiments, a container 1422 can be configured to tilt, rotate or otherwise move in order to expose an interior portion for receiving a waste item. After the waste item has been discarded, access to the interior of the container 1422 can be blocked. For example, the lid 1428 can be closed, either automatically or manually, or the container can move to its original (e.g., untilted) position.

As illustrated in FIG. 51, the dispensing portion 1430 of the apparatus 1410 can include a plurality of compartments 1432. The compartments 1432 can have any size, shape and/or configuration. For example, some or all of the compartments 1432 can be similarly shaped, sized and configured. However, in other arrangements, some or all of the compartments 1432 may be different from one another. In one embodiment, the size, shape and other characteristics of the compartments 1432 can be selected according to the quantity, size, shape, volume, anticipated demand and other characteristics or factors related to the dispensable items they are expected to house. Each compartment may be further subdivided into two or more subcompartments. Each compartment 1432 or subcompartment can be configured to house one or more dispensable items. In another embodiment magazines are used instead of, or in addition to, the compartments illustrated in FIG. 51.

One or more of the compartments 1432 of the dispensing portion 1430 can be configured with a climate control system (e.g., temperature regulation, humidity regulation, etc.). Such features can be helpful if, for example, refrigeration, heating or any other type of climate control is desired or required for particular medications, solutions or other dispensable items. These items are typically expensive and can be pilfered or lost. An RFID tag or other identifier may be affixed to the medications and scanned with a handheld or fixed scanner (such as an RFID scanner) once the item is retrieved from the refrigerator, or other location. Other tracking mechanisms may also be used.

Figure 58:
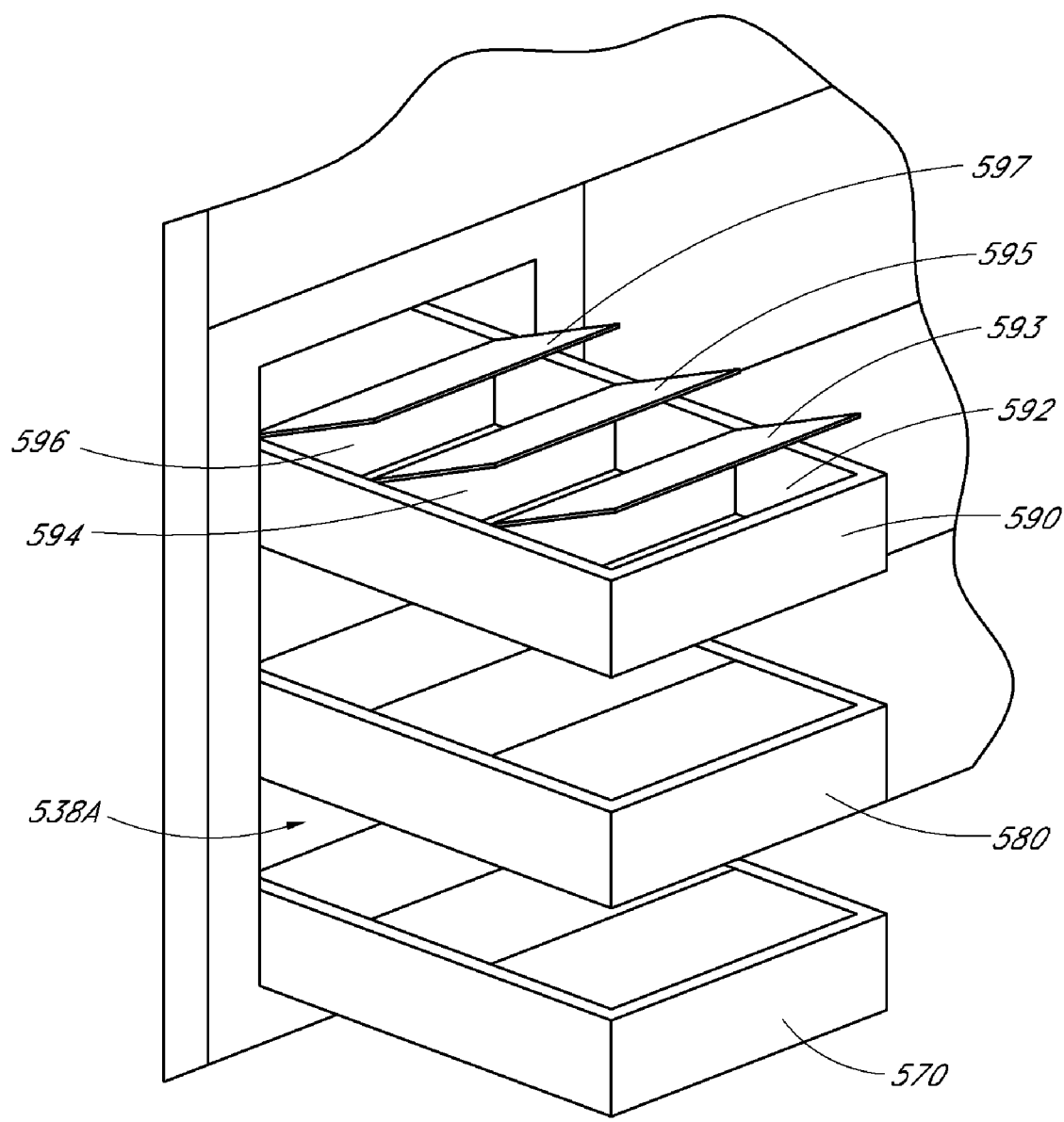
FIG. 58 is a perspective view of a compartment within a combination disposal and dispensing apparatus according to one embodiment.
Figure 59:
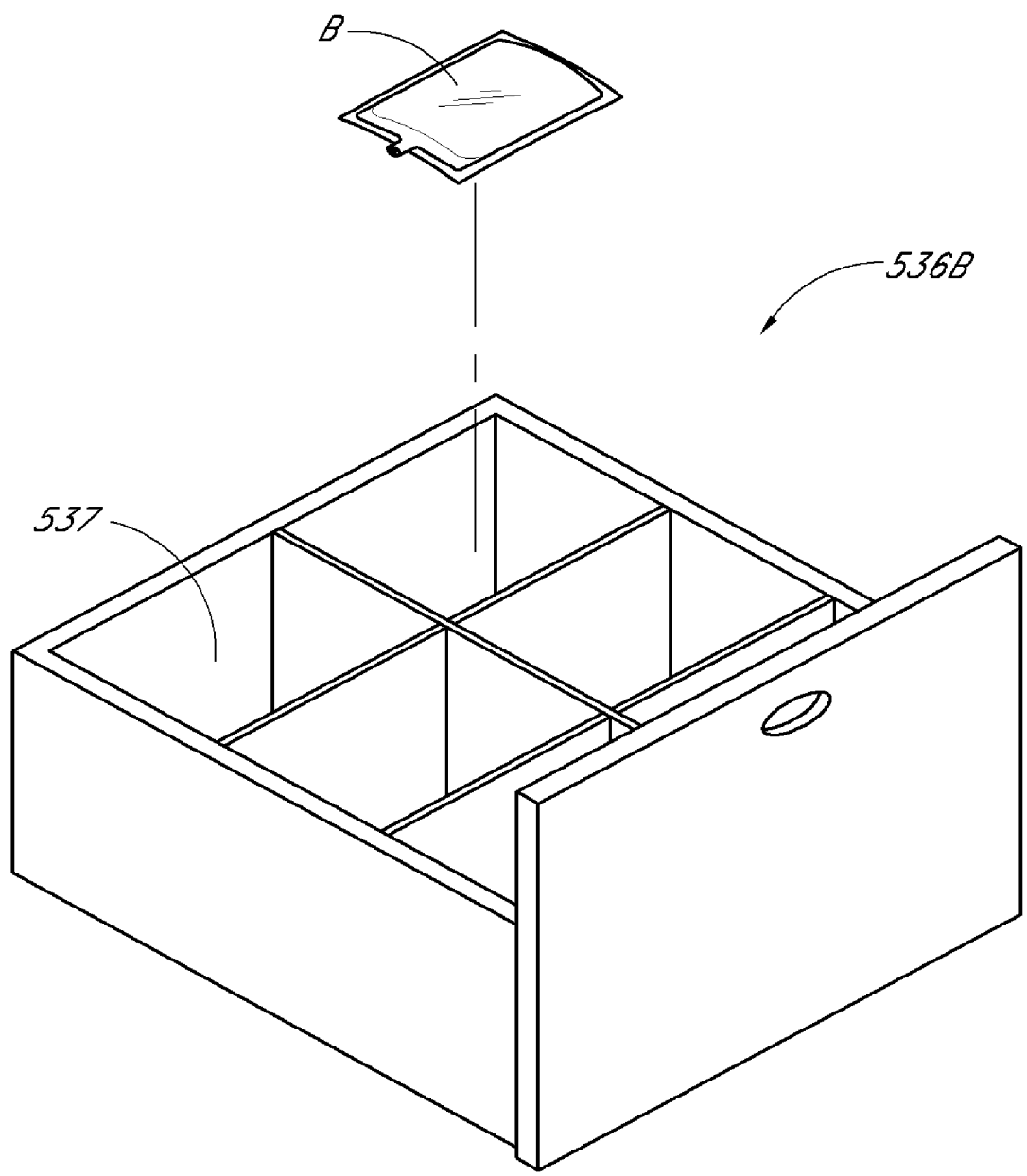
FIG. 59 is a perspective view of a compartment within a combination disposal and dispensing apparatus according to another embodiment.

Items stored within the compartments 1432 of the apparatus's dispensing portion 1430 can be distributed using one or more methods. In one embodiment, as illustrated in FIGS. 58 and 59, items can be situated on a movable tray or shelf configured to extend outwardly toward a user. After a particular item has been removed from the tray, the user can manually return the tray to its original position. The user can physically reposition the tray or manipulate a button, switch or the like that actuates the tray to its original position. In some embodiments, the tray can return to its original position automatically. For example, the tray can be configured to return to its original position after a predetermined time period or after an item has been removed. In order to recognize if and when an item has been removed, the tray can be equipped with one or more sensors. The sensors can be pressure sensors, visual sensors (IR, infrared, etc.) or the like. In another embodiment magazines are used instead of, or in addition to, the trays described herein.

As described and illustrated herein, movable trays can be further subdivided into two or more subcompartments. Access to such subcompartments may be further restricted using lids or other movable closures. Therefore, when a tray extends, rotates or otherwise moves to an open position, one or more of its subcompartments can be configured to open and/or unlock for access to dispensable items stored therein. According to one embodiment, as illustrated in FIGS. 54 and 55, once a magazine or tray is accessed by an xy mechanism, other retrieval system or the like, a packaged unit dose medication or other dispensable item is advanced forward by a tractor mechanism, spring, mechanical actuator, or other advancing mechanism.

In other arrangements, dispensable items can be positioned within fixed compartments 1432 which may include movable doors, hatches, lids or other closure members. In order to permit access to the inside of a compartment 1432, and thus to the dispensable items stored therein, the door or other closure member can be configured to open and/or unlock. For example, the doors can slide, tilt, rotate or otherwise move to an open position. The doors or other closure members can open and/or close automatically. Alternatively, the doors can simply unlock, allowing users to manually open and/or close them.

At least a portion of the doors, hatches, lids or other closure members can be made of a transparent material, such as, for example, glass, clear plastic or other synthetic and/or the like. This may allow people to visually inspect the various dispensable items contained within an apparatus to facilitate accurate dispensing, filling, reordering and/or other tasks. In addition, the compartment doors can be equipped with a handle or other gripping member to assist the manual opening and closing process.

Alternatively, a desired dispensable item can be moved from a storage compartment to a main dispensing location. In such arrangements, the items can be transferred from a storage compartment to a dispensing location using one or more mechanical, pneumatic or other methods and controls. Thus, it may be possible to store dispensable items within compartments that are not visible to a user and/or are not positioned along an exterior portion of the apparatus. In an embodiment similar to a food vending machine, a desired item may be permitted to simply fall towards a common dispensing location. However, recognizing that some dispensable items may be impact-sensitive, the dispensing portion can include one or more compartments with doors, movable trays or the like so that such items can be dispensed without being dropped or otherwise moved in a potentially damaging manner.

Figure 60:
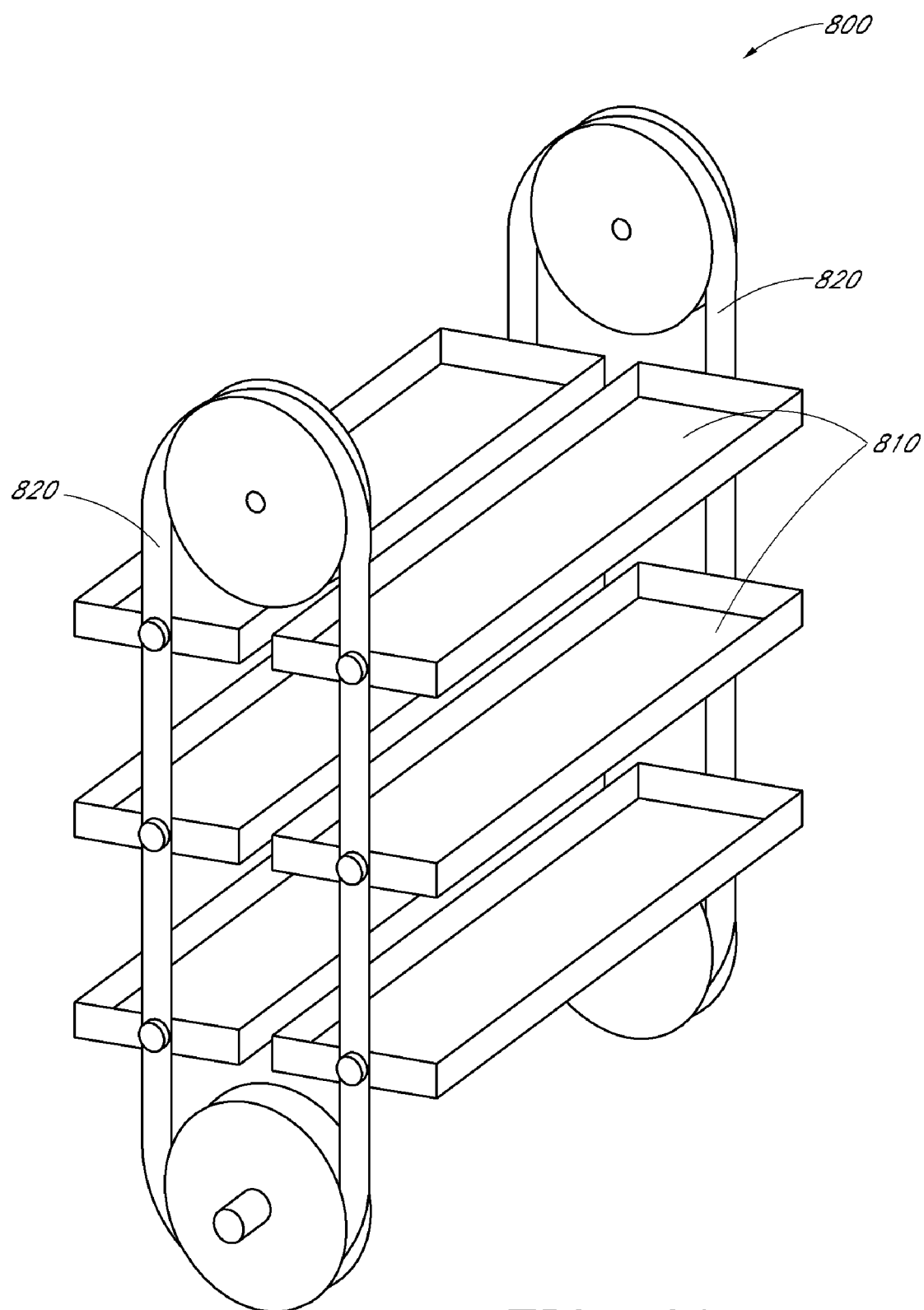
FIG. 60 is a perspective view of one embodiment of a dumb waiter system configured to be used in a combination disposal and dispensing apparatus.

In one embodiment, as illustrated in FIG. 60, a dumb waiter is used to convey medications or other dispensable products. For example, an xy mechanism would convey each medication to a clinician accessible compartment or opening. The medications could drop into a sealable or lockable container (such as a bag or other flexible or inflexible container). Once all patient specific medications are filled and/or order filled, an access door would open to permit access. This would prevent any damage or hangups of the medications. In one embodiment a container with all medications picked would be printed on the container. Thus, in some embodiments, the invention comprises a system and method of automated packaging of patient-specific medical items into a single container. This container, which may be coded with an identifier, such as a bar code or RFID, is then ready for bedside patient administration. In one embodiment, the placement of all drugs needed for a given patient in a single container will reduce medication errors. In other embodiments, the system only permits access to the medical items for a specific patient at a specific time. Thus, a user cannot mistakenly or deliberately take additional or unauthorized medical items.

With continued reference to FIG. 51, the dispensing portion 1430 can include a keypad 1436 or other data entry device. Further, the dispensing portion 1430 can include a scanning device 1434 or other identification member. The keypad 1436 and/or the scanning device 1434 can be used to verify a user's identity and/or to ensure that a particular user is permitted to receive the requested dispensable item. The scanning device 1434 can be configured to detect an optical pattern (e.g., barcode, alphanumeric code, color scheme, graphics, other pattern, etc.); a magnetic, infrared, radio frequency (e.g., RFID) or other transmittable signal; biometrics, retina, fingerprint or other unique anatomical patterns or the like. For example, a user can simply scan his or her identification card in front of the scanning device 1434 or through a card reader slot (not shown). In other arrangements, such as, for example, where a RFID chip is embedded within a user's identification card, the scanning device 1434 can make a reading when a user is within a specific distance of the apparatus 1410.

The keypad 1436 or other similar data entry device can be used to select a desired dispensable item. For example, a user can enter a number or code corresponding with the compartment 1432 in which the desired item is housed. Alternatively, the user can use the keypad 1436 to enter the name of a desired dispensable item. The keypad 1436 can also be used to enter a desired quantity or amount of a requested item.

The dispensing portion 1430 may also include a display 1438 to facilitate the interface with user. Thus, by entering the name, or a portion thereof, of a desired dispensable product, a user can search through a list of available items as shown on the display 1438 or other visual interface. If a particular apparatus 1410 is not stocked with a desired product or if the product has been emptied, the display 1438 can be configured to direct a user to another apparatus that does.

Depending on the items being dispensed, it may desirable to also require a user to enter a personal identification number (PIN) or other security code. This can help prevent unauthorized access to one or more dispensable items, such as, for example, certain medications (e.g., narcotics), other highly regulated substances or items and the like.

Once an item has been dispensed from the apparatus 1410, it may be desirable to pass the dispensed item in front of the scanning device 1434. In addition to or lieu of such scanning, the user can enter information regarding the dispensed item using the keypad 1436 and/or other method. This can help track the items which have been dispensed for security, reordering, restocking, regulatory and/or other purpose.

In some embodiments, it may be desirable to combine certain features of the disposal portion 1420 and the dispensing portion 1430, such as, for example, the display, keypad or other data entry device, scanning device or other identification device and/or the like. This can reduce capital costs, the space occupied by the apparatus, power consumption and the overall complexity of the apparatus's design.

Figure 52:
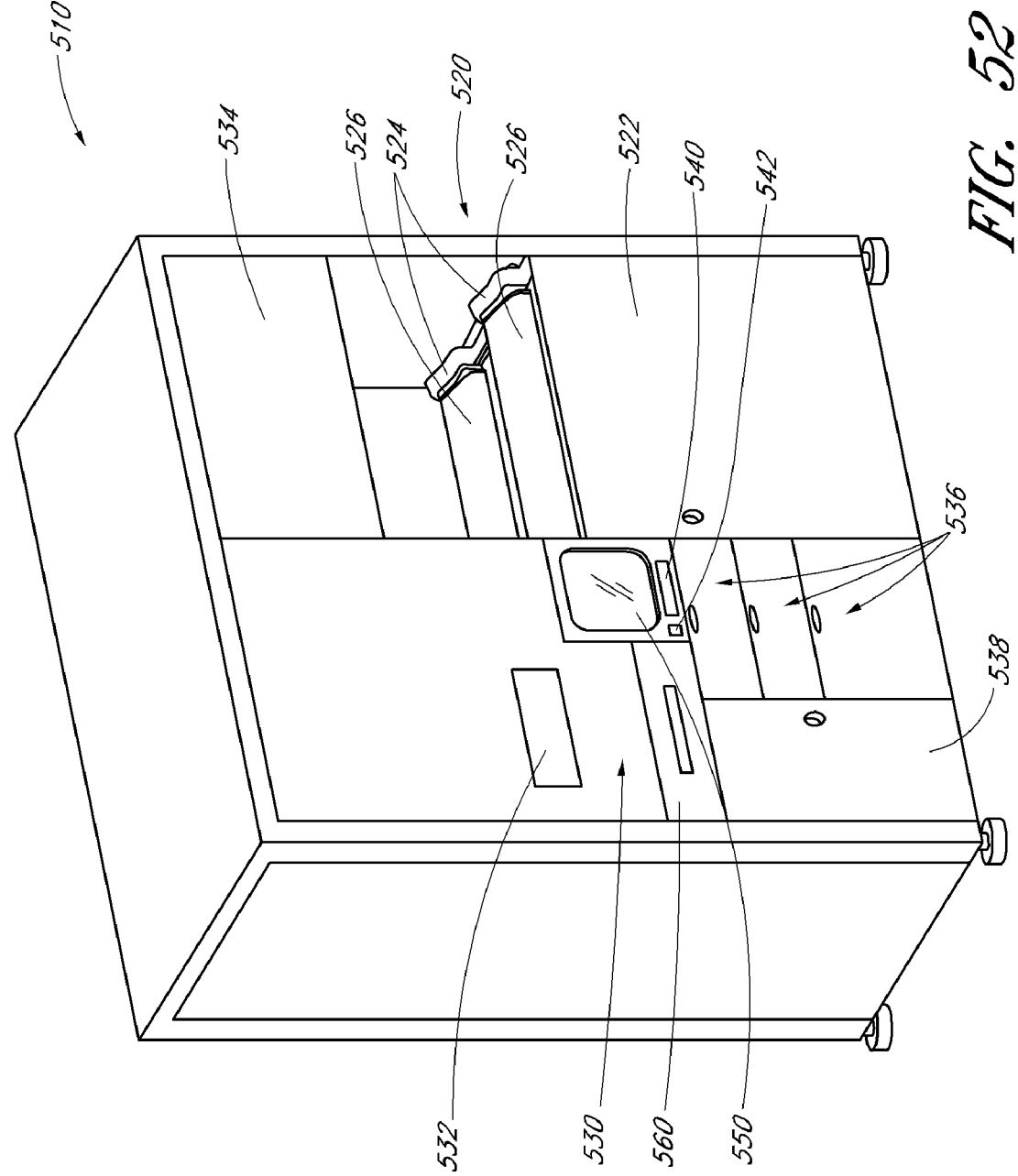
FIG. 52 is a perspective view of a combination disposal and dispensing apparatus according to another embodiment.

Another embodiment of a combination dispensing/waste item disposal apparatus 510 is illustrated in FIG. 52. As discussed, the apparatus 510 can include a disposal portion 520 configured to receive waste items. The disposal portion 520 can include one or more waste containers 524 as discussed herein. In some embodiments, as shown in FIG. 52, a lid assembly 526 or other closure member is used to selectively provide access to the interior of a waste container 524. The containers 524 can be accessed (e.g., removed, replaced, etc.) by opening a cover 522 or other accessway. In some embodiments, entry to such cover 522 is locked or otherwise protected to ensure that waste materials cannot be accessed by unauthorized personnel. As discussed herein, the system can be configured to receive information regarding the particular waste items being discarded so as to direct the user to place such items in the appropriate container 524. Thus, the apparatus 510 can include a scanning device 540, a keypad and/or any other automatic or manual data entry device. In addition, the apparatus can comprise a display 550 adapted to provide information to a user. In one embodiment, the display 550 is a touchscreen display comprising a plurality of softkeys. It will be appreciated that the apparatus 510 can include any other features as discussed or illustrated by other embodiments disclosed herein.

According to some arrangements, the apparatus 510 is configured to receive different types of waste items, such as, for example, spent vials, IV or other medication bags, syringes and/or the like. In other embodiments, certain waste items, such as, for example, sharps, can be discarded in a designated container or compartment which is separate from the apparatus 510. For example, a separate container (not shown) may be positioned on or near the combination apparatus 510 to facilitate disposal of sharps and the like. In such embodiments, the scanning devices 540, other data entry devices, displays 550, processors and/or other portions of the apparatus 510 can be configured to direct a user to discard an item in such a separate container and not within one of the waste containers 524 of the apparatus 510.

As illustrated in FIG. 52, a combination apparatus 510 can include a plurality of drawers, shelves and/or other dispensing compartments or portions 530, 534, 536, 538. The shape, size, method of dispensing, temperature control features and/or other characteristics of such compartments 530, 534, 536, 538 can vary. For example, one compartment of portion 530 of the apparatus 510 can dispense unit doses of pharmaceuticals (e.g., individual tablets, other pills, vials, syringes, medication bags, bottles, ampoules, inhalers in small metal containers with a delivery nozzle, ointments in tubes, medical supplies and/or any other items). As discussed in greater detail herein with reference to FIGS. 52 and 53, such a compartment 530 of the combination apparatus 510 can include a dispensing slot 532 or other opening through which the desired items can be made available to a clinician or another user.

With continued reference to FIG. 52, other compartments 534, 536 can be sized, shaped and otherwise adapted to store large and/or small bulk items, other supplies and/or the like, as desired or required by a particular facility or treatment area. In addition, one or more of the compartments 538 can be refrigerated, heated and/or otherwise climate controlled (e.g., maintained at a desired humidity level) to ensure that pharmaceutical products and other materials contained therein are properly maintained. As discussed, one or more of the compartments 530, 534, 536, 538 adapted to hold dispensable items can be configured to open, either automatically or manually. For example, in some embodiments, compartments comprise doors, drawers or other movable portions that unlock, open or are otherwise made accessible when proper dispensing authorization is received. In other arrangements, the apparatus 510 includes a user identification device 542, such as, for example, a fingerprint scanner, badge identification device reader, biometric data reader and/or the like. Such a user identification device 542 can advantageously permit the apparatus 510 to accurately identify the clinician requesting a particular dispensable item and/or disposing a waste item.

Figure 53:
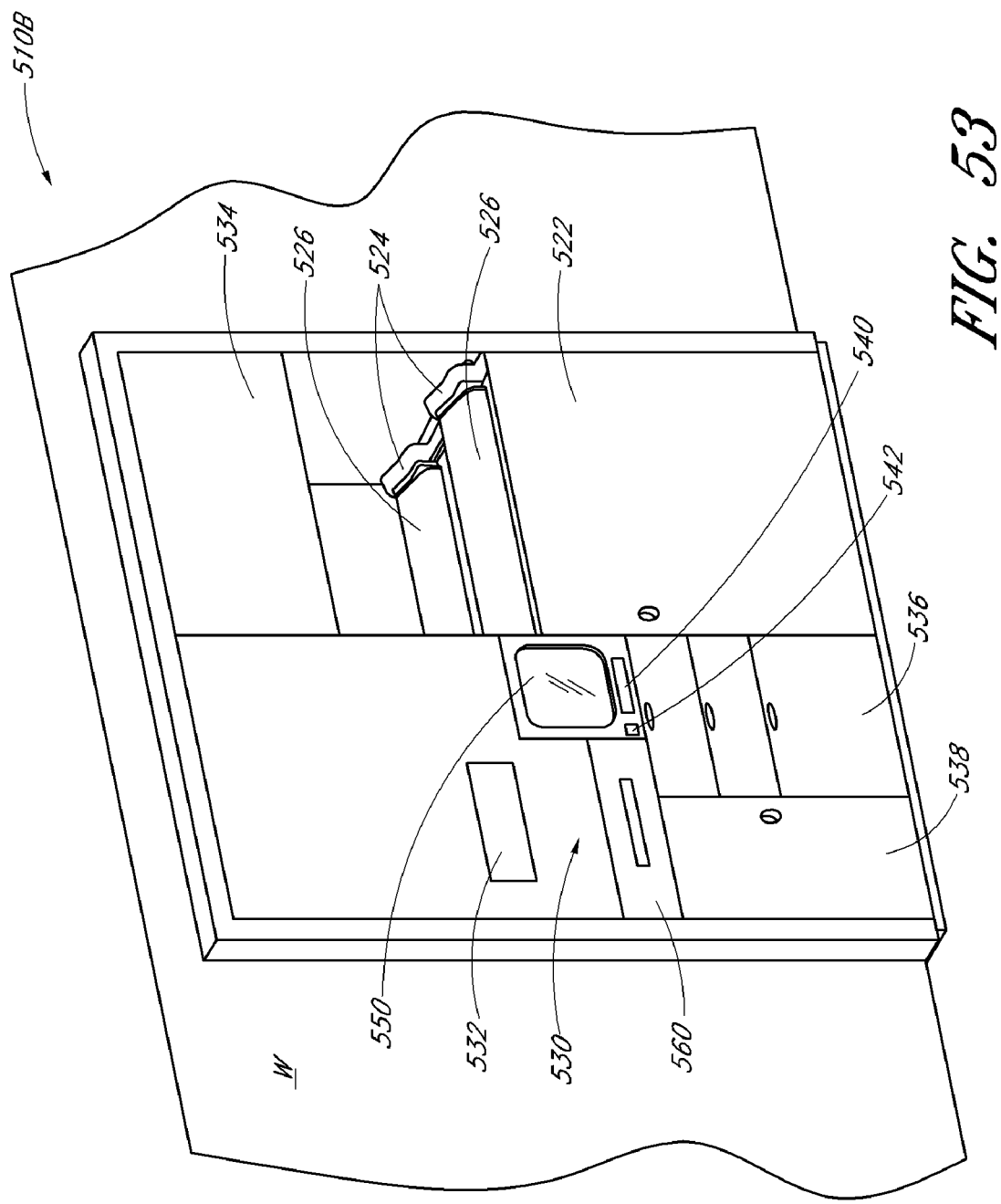
FIG. 53 is a perspective view of a wall-mounted combination disposal and dispensing apparatus according to one embodiment.

The combination dispensing/disposal apparatus 510B illustrated in FIG. 53 is similar to the apparatus 510 of FIG. 52. However, the depicted apparatus 510B is sized, shaped and otherwise configured to be positioned at least partially within a wall W or other stationary portion of a facility. For example, the apparatus 510B can be generally flush with one or more adjacent walls W. Alternatively, a combination apparatus can be configured for placement against or near a wall. In some embodiments, a combination apparatus 510 can include wheels or other features that permit a user to move the apparatus 510 between different rooms or other locations of a facility, as desired or required. It will be appreciated that the shape, size, number and layout of various compartments and other features and/or other details of a combination dispensing/waste disposal apparatus can be different than illustrated and discussed herein.

In some embodiments, medications or other supplies can be picked up or otherwise acquired using an xy or xyz assembly or some other dispensing system. One embodiment of such an assembly 600 is illustrated in FIGS. 54A and 54B. In the depicted arrangement, the assembly 600 comprises a retrieving device 610 that is configured to be selectively moved along one or more directions. In FIG. 54A, the retrieving device 610 is slidably positioned on two lateral rail members 606. However, the assembly 600 can include more or fewer lateral rail members 606 as desired or required. Further, the lateral rail members 606 and the retrieving device 610 are slidably positioned on vertical rail members 604. Thus, the horizontal and/or vertical position of the retrieving device 610 can be adjusted by moving the device 610 relative to the lateral rail members 606 and/or moving the lateral rail members 606 relative to the vertical rail members 604. This can advantageously permit the assembly 600 to be moved to a desired location within a compartment of a dispensing/disposal apparatus 510.

With continued reference to FIGS. 54A and 54B, the dispensing apparatus can be equipped with pharmaceutical products (e.g., tablets, capsules, other pills, small vials or other containers, syringes, medication bags, bottles, ampoules, inhalers in small metal containers with a delivery nozzle, ointments in tubes, medical supplies, etc.), other clinical supplies and/or other dispensable products. In the illustrated arrangement, individual items 642 (e.g., tablets, other pharmaceutical products, etc.) are removably positioned within corresponding pockets or other enclosures 644 of ribbon 640. As shown, the ribbon 640 can be wound around a reel 630 or the like. In some embodiments, the ribbon 640 comprises a plastic material and/or other material that includes one or more perforations 641 between adjacent individual dispensable items 642. As discussed in greater detail herein, such perforations 641 or similar features can advantageously permit the retrieving device 610 to more easily separate and remove a desired number of items 642 from the ribbon 640. Subsequently, such items 642 can be dispensed to a clinician or other user of the combination dispensing/disposal apparatus.

In order to dispense one or more items 642 from the ribbon 640, the retrieving device 610 can be configured to move in an appropriate position relative to the reel 640 from which the desired items 642 will be obtained. Thus, as illustrated in FIG. 54A, the retrieving device 610 can move laterally and/or vertically to a target location. In one embodiment, the retrieving device 610 comprises a gripper member or other portion (not shown) that is adapted to grasp and tear the ribbon 640 along a perforation 641. The retrieving device 610 or some other component of the apparatus can be adapted to perforate or otherwise compromise (e.g., partially tear, weaken, etc.) one or more portions of a ribbon 640 immediately before the desired number of dispensable items 642 are separated from the ribbon 640. In other arrangements, the retrieving device 610 or some other component of the apparatus can remove a desired length or other portion of ribbon 640 using another method or device, such as, for example, blades, other cutting or splicing tools and/or the like.

As discussed, the retrieving device 610 can comprise a gripper member or other portion configured to engage and separate one or more portions of the ribbon 640 from the reel 630. In some embodiments, the gripper member includes a mechanical grasping device, such as, for example, the device 714 illustrated in FIG. 56 and discussed herein. Such gripper members preferably include actuators that selectively permit the grasping and releasing of the ribbon 640 or other material comprising dispensable items.

Regardless of how the targeted portion of the ribbon 640 is engaged by the gripper member or other portion, the retrieving device 610 can be adapted to move the gripper member or portion in such a way so as to separate (e.g., tear) a section of the ribbon 640 from the reel 630. In some embodiments, the gripper member can be configured to rotate, turn, translate (e.g., in one or more directions) or otherwise move in order to separate the desired dispensable items. Alternatively, the retrieving device 610 itself can move (e.g., laterally and/or vertically along the rails 604, 606, rotate, etc.) to help tear and remove the targeted portion of the ribbon 640 along one or more perforations 641.

As illustrated in FIGS. 54A and 54B, each reel 630 or other dispensing device can include an advancing portion 618 located adjacent to the corresponding ribbon 640. As illustrated in FIG. 54B, the advancing portion 618 can comprise one or more sprockets 622 or other members adapted to engage and selectively move the adjacent ribbon 640 downwardly (e.g., away from the reel 640). Therefore, depending on the quantity of dispensable items 642 desired, the advancing portion 618 can be adapted to advance a corresponding section of the ribbon 640 away from the reel 630. As discussed, the gripper portion 614 can then engage and remove the desired section of the ribbon 640 from the remainder of the reel 630. In some embodiments, the advancing portion 618 is permanently or removably attached to the apparatus or some other component. Each reel 630 can include its own advancing portion 618 configured to selectively dispense the desired quantity of the corresponding item.

After a desired quantity of items have been removed from a particular reel 630, the retrieving portion 610 can be moved (e.g., vertically and/or laterally) to one or more other reels 630. Such other reels 630 can include different dispensable items (e.g., different pharmaceuticals, different dosages of the same pharmaceutical, etc.). Accordingly, the retrieving device 610 can collect dispensable items from one, two or more reels 630 positioned within the assembly 600. As discussed in greater detail herein, such dispensable items or combination of items can be collected within a single bag or other container before being made available to the clinician or other user.

Items 642 dispensed from the ribbon 644 can be captured by one or more devices (not shown). Alternatively, such items 642 can be permitted to fall onto a device or surface situated below the assembly 600. In some embodiments, such a receiving structure or surface is cushioned or otherwise adapted to decrease the likelihood that impact-sensitive dispensable items will break or otherwise be damaged during the process. As discussed, in some embodiments, dispensed items 642 are collected in a bag or other container before being made available to the clinician who requested them. For example, various medications released by the assembly 600 can be collected in single bag, sac or other container. In addition, one or more labels, tags or other identification indicators can be automatically or manually placed (e.g., printed, glued, etc.) on such a bag or other container. With reference to FIGS. 52 and 53, the bag or other container can be moved to a dispensing opening 532 of the combination apparatus 510. It will be appreciated that the retrieving assembly 600 can include different mechanisms, components, devices and/or features for advancing, retrieving, collecting and/or dispensing items. For example, the retrieval device 610 can include an escapement or similar device. In other arrangements, one or more other types of devices and/or methods can be used to grasp, release and collect a desired number of dispensable items.

FIG. 55 illustrates another embodiment of a retrieval (e.g., xy or xyz) assembly 700 configured to select, retrieve and collect a desired number of items 742, 744, 746 from an item support structure 750, such as, for example, a shelf, tray, cartridge, cabinet or the like. As with the embodiment disclosed in FIGS. 54A and 54B, the illustrated assembly 700 comprises a retrieving device 710 that can be selectively moved in a vertical, lateral, diagonal and/or any other direction relative to the item support structure 750. In the depicted arrangement, the support structure 750 comprises one or more rows 760A-760C, each of which can include a plurality of various disposable items 740A-740C, such as for example, vials, prefilled syringes, ampoules, bottles, inhalers in small metal containers with a delivery nozzle, ointments in tubes, medical supplies and/or any other items.

With continued reference to FIG. 55, the assembly 700 can include a retrieval device 710. According to some embodiments, the retrieval device 710 can be moved in a lateral and/or vertical direction by the use of slide rails 704, 706. It will be appreciated, however, that one or more other systems and/or methods of changing the position of the retrieval device 710 can be used. In the depicted embodiment, the retrieval device 710 includes a gripper member 712 that is adapted to selectively grasp and secure one or more dispensable items 740A-740C from the support structure 750. In some embodiments, such gripper members 712 are configured to transfer one or more dispensable items 740A-740C from the support structure 750 to a dispensing location, a collection bag and/or the like.

Figure 57:
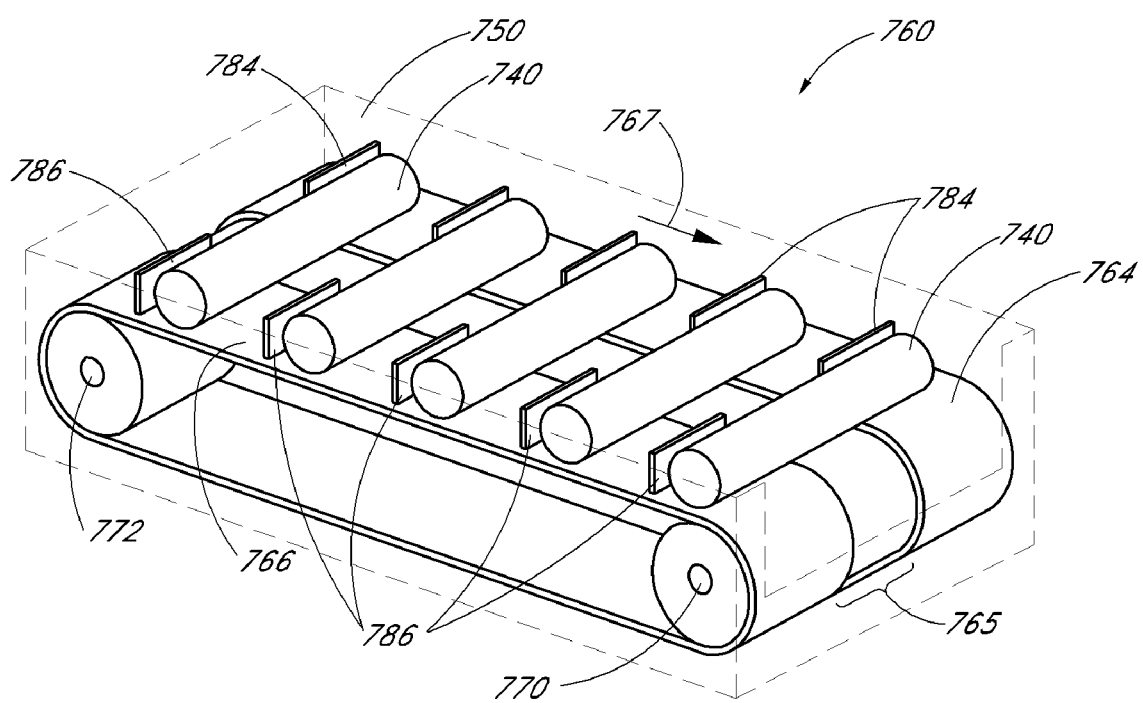
FIG. 57 is a perspective view of items positioned on a conveyor belt of the retrieval system of FIG. 55.

As illustrated in FIGS. 55 and 57, a row 760A-760C of the support structure 750 can include one or more conveyor belts 764, 766 or other advancing members on which a plurality of vials, syringes, ampoules and/or other items 740A-740C can be placed. For example, the advancing members 764, 766 can include belts comprising rubber and/or other flexible materials. In some embodiments, one or more of the rows 760A-760C comprise a tractor feed mechanism or a similar device or system for advancing items 740A-740C toward a retrieving edge of the support structure 750. The conveyor belts 764, 766 can be moved by two or more rollers 770, 772 or other mechanical components. In one embodiment, the belts 764, 766, rollers and/or other components are powered by one or more electrical motors.

Figure 56:
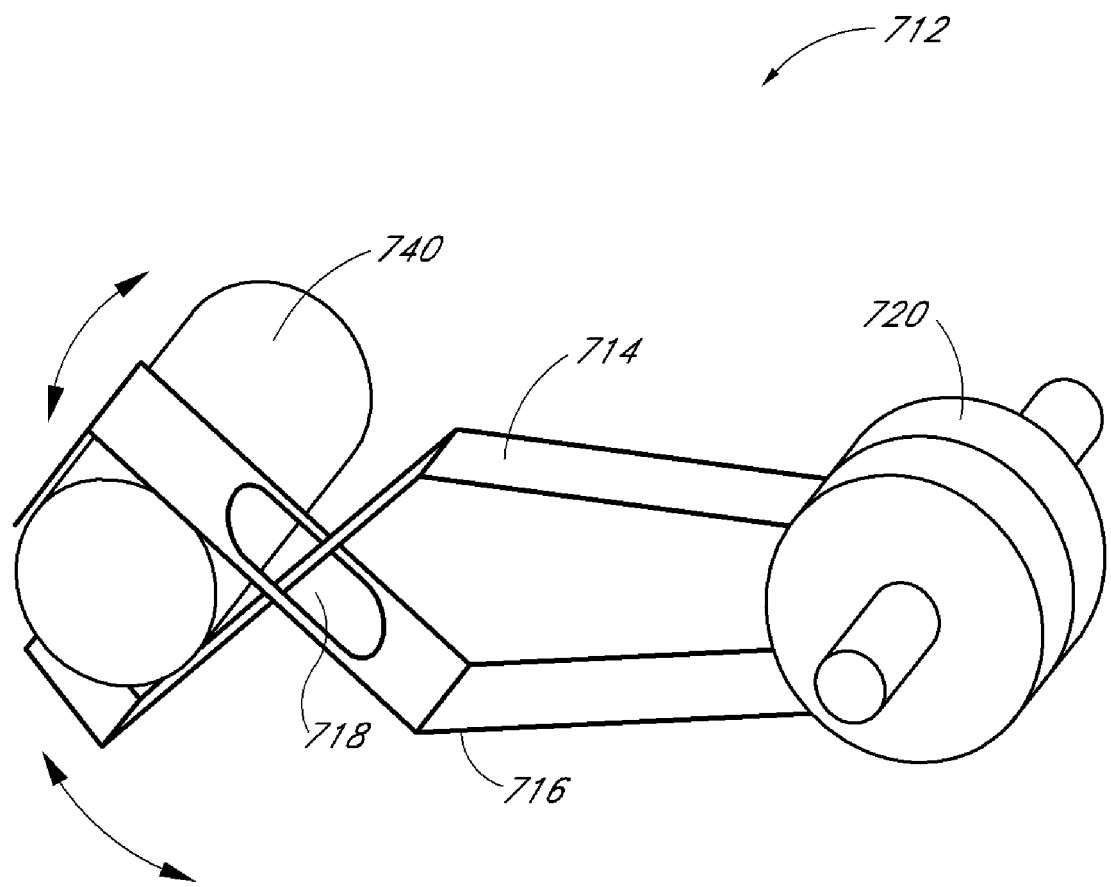
FIG. 56 is a perspective view of one embodiment of a gripper member configured to be used with a retrieval system.

FIG. 57 illustrates one row 760 of a support structure 750, such as the one depicted in FIG. 56. As shown, the belts 764, 766 can be positioned on the same set of rollers 770, 772. Alternatively, each belt 764, 766 can comprise its own set of rollers 770, 772. In one embodiment, the adjacent belts 764, 766 or other advancing members are separated by a gap 765 in order to permit a gripper member 712 (FIGS. 55 and 56) to grasp a vial 740 or other item positioned on the support structure 750. For example, the gap 765 can permit a gripper member 712 to get underneath a portion of the targeted item 740. In other arrangements, however, the gripper member 712 is adapted to grasp items from the top or substantially from the top so that such a gap 765, other recess or feature is not necessary.

With further reference to FIG. 57, the belts 764, 766 can comprise tabs 784, 786, grooves or other protruding (or recessed) members or features that are adapted to advance the items 740 in a desired direction. For example, in the illustrated embodiment, as the conveyor belts 764, 766 are moved, the items 740 are displaced in a direction generally represented by arrow 767. Therefore, the assembly 700 can be advantageously configured so that when a particular item 760A-760C is removed from the support structure 750, the corresponding belts 764A-764C, 766A-766C are advanced in the direction of the retrieving member 710. Accordingly, the retrieval device 710 can grasp and remove the next indexed item 740A-740C when it is instructed to do so by the assembly 700.

FIGS. 55 and 56 illustrate one embodiment of a gripper member 712 adapted to be used on a retrieval device 710. As shown, the gripper member 712 can comprise a device that resembles a test tube clamp. In one embodiment, the gripper member 712 includes oppositely-oriented fingers 714, 716 or other clasping members that are configured to be selectively moved relative to one another. As illustrated in FIG. 56, a first finger 714 is adapted to move relative to a second finger 716, within a slot 718 of the second finger 716. It will be appreciated, however, that a gripper member 712 can include a different design, as desired or required by a particular application. For example, in one embodiment, a gripper member 712 includes additional fingers 714, 716 or other clasping members. Accordingly, the size, shape, configuration and/or other details of the gripping member 712 can vary.

With continued reference to FIG. 56, the gripper member 712 can include a solenoid 720 or other actuator device. In some embodiments, such a solenoid 720 moves the fingers 714, 716 relative to each other, permitting a user to selectively grasp or release an item positioned on the support structure 750. In other arrangements, other methods and/or devices for operating the gripping member 712 can be used. For example, in some embodiments, a more sophisticated gripper member 712 is configured to detect the diameter or other comparable dimension of the item being grasped, so that the appropriate clasping pressure is applied by the fingers 714, 716.

As discussed, the retrieval device 710 and/or the gripper member 712 can be adapted to translate, rotate and/or otherwise move relative to the support structure 750 in order to pick up one or more dispensable items 740A-740C. Once an item 740A-740C has been secured on the retrieval device 710, the retrieval device 710 can move the items 740A-740C to a dispensing location, a collection container (e.g., bag) and/or any other desired designation. As discussed, the retrieval device 710 can be configured so that it automatically picks up and/or drops off desired vials 740A-740C, containers or other items. In one embodiment, the retrieval device 710 is configured to retrieve one or more items based on instructions provided to the assembly 700 by a clinician or other user.

In any of the embodiments of the retrieval systems discussed and/or illustrated herein (e.g., xy or xyz traverse mechanisms, etc.), the retrieval devices, gripping members, conveyor belts and/or any other mechanical devices or components can be powered and/or controlled by a stepper motor, gear driver DC motor, power screw, encoder with a feedback loop and/or the like. In addition, the retrieval devices and/or any other mechanical device can include a plurality of bearings to enhance movement relative to adjacent surfaces.

In addition, the combination disposal/dispensing apparatus can include one or more doors or other accessways that enable a user to easily restock pharmaceuticals and/or other items stored therein. For example, as discussed with reference to FIG. 54A, reels 630 of dispensable products can be used to quickly replenish the supply of a particular item. Further, a combination apparatus can be configured so that reels 630, trays or other structures on which dispensable items are stored are generally close to each other. As discussed, this can help increase the density of the stored items within the apparatus so that the footprint area can be advantageously decreased. In addition, improved access to the interior of the combination apparatus can facilitate with routine maintenance and repair procedures.

FIG. 58 illustrates a perspective view of one embodiment of a dispensing compartment 538A positioned within a combination disposal/dispensing apparatus (FIGS. 52 and 53). As shown, the compartment 538A can include a plurality of drawers 590, shelves or other components that are configured to slide toward a user in order to provide access to items stored therein. As discussed herein, in some arrangements, one or more dispensing compartments 538A are refrigerated or otherwise climate controlled (e.g., heated, cooled, humidity-controlled, etc.). This can help ensure that pharmaceuticals and other temperature-sensitive products are maintained at desired conditions. It will be appreciated that climate control features can be applied to any compartment and/or portion of a combination dispensing/disposal apparatus.

In the embodiment illustrated in FIG. 58, one or more of the drawers 570, 580, 590 comprise a plurality of sub-compartments 592, 594, 596 or smaller storage areas. As shown, one or more of the sub-compartments 592, 594, 596 can include a lid 593, 595, 597 or other cover member. The lids 593, 595, 597 can be configured to unlock and/or open when a desired dispensable item is contained therein.

Another embodiment of a drawer 536B having a plurality of sub-compartments 537 or other smaller storage areas is illustrated in FIG. 59. Such storage areas 537 can be sized, shaped and otherwise configured to receive one or more IV bags B, other medication bags or containers and/or other items. In some arrangements, the storage areas 537 can be climate-controlled (e.g., heated, cooled, etc.) to help preserve fluids or other materials contained therein. It will be appreciated that the size, shape, layout, orientation, general configuration and/or any other details regarding the storage compartments of a combination disposal/dispensing apparatus can vary, as desired or required by a particular application.

FIG. 60 illustrates one embodiment of a dumb waiter storage and retrieval system 800. Such a system 800 can be particularly useful for smaller bulk items. However, the illustrated storage and retrieval system 800 can be used to hold and dispense any other materials, such as, for example, pharmaceuticals, vials, IV bags, custom fluid bags, large or medium sized bulk items, other fluid bags or containers and/or the like. As shown, the system 800 can include a plurality of trays 810 or other containers that are mechanically connected by a series of belts 820 or other driven devices. Such a system 800 can help reduce the overall footprint area and/or size of a combination disposal/dispensing apparatus.

In some embodiments, the system 800 includes a retrieval device (not shown), as described herein, to selectively transfer one or more items stored on the trays 810 to a common collection area, a bag or other container and/or a clinician or other user. Thus, the retrieval device and/or the trays 810 can be configured to advantageously move relative to one another. In one embodiment, the system 800 is sized and designed so that user within a particular height range can comfortably reach items positioned on the lowest tray level 810.

Figure 61:
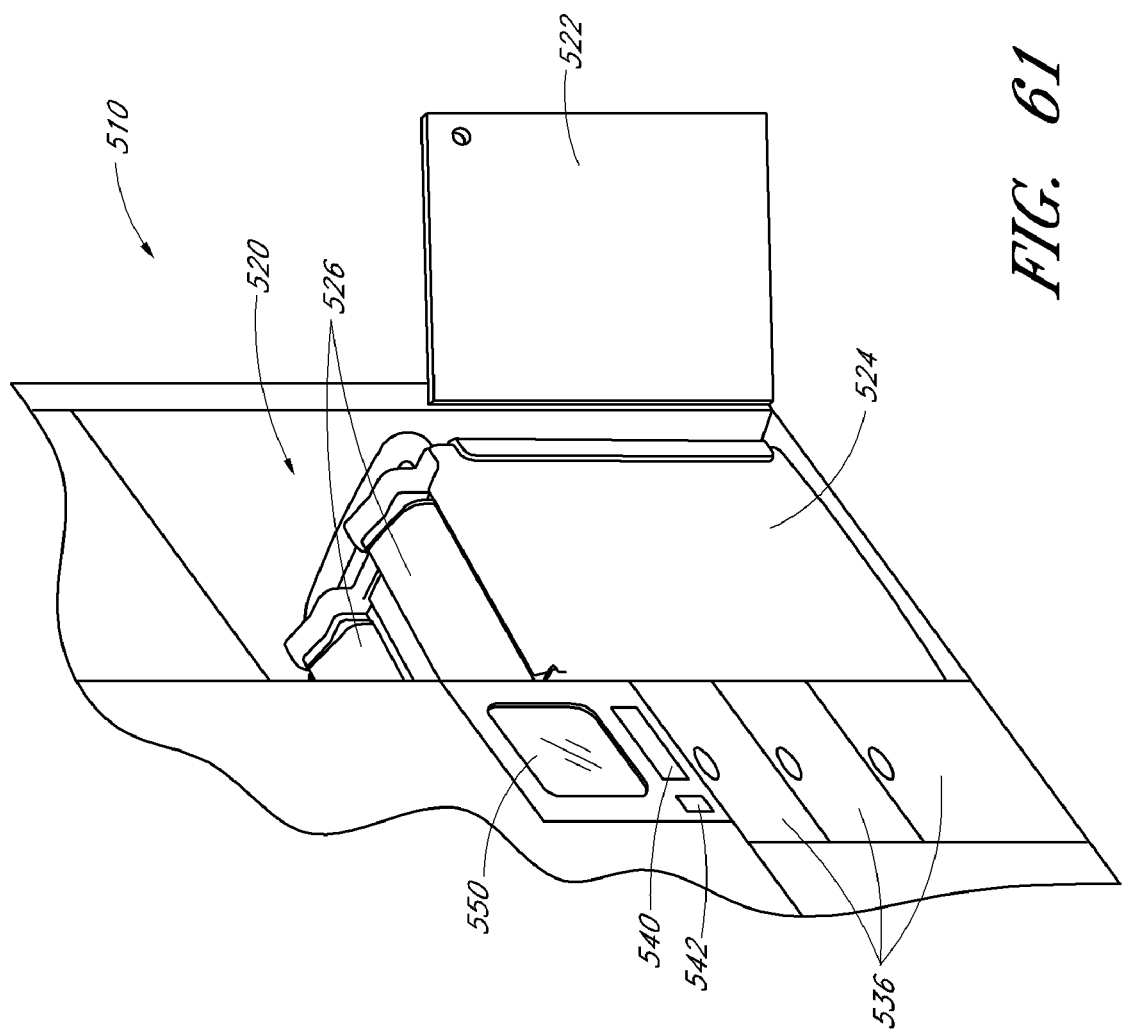
FIG. 61 is a perspective view of a disposal portion of a combination disposal and dispensing apparatus according to one embodiment.

FIG. 61 illustrates one embodiment of a waste disposal portion 520 of a combination disposal/dispensing apparatus 510. In the depicted arrangement, the disposal portion 524 includes two waste containers 524 that are positioned immediately adjacent to each other. As shown, each waste container 524 can include a lid assembly 526 or other cover device or system. The lid assembly 526 can be adapted to selectively provide and/or restrict access into an interior portion of the corresponding waste container 524. In other embodiments, a combination apparatus 510 includes more or fewer waste containers 524, as desired or required by a particular facility. In addition, the orientation, size, shape, location within the apparatus 510 and/or any other details of the waste containers 524 can vary.

As discussed herein, such a disposal portion 520 of a combination apparatus 510 can permit the disposal of hazardous pharmaceutical waste, other high risk materials, low risk materials and/or the like. According to one embodiment, if a waste item comprises sharps and/or certain other types of highly regulated substances, a user can be advantageously directed to deposit such waste items in a container which is not included within the disposal portion 520 of the apparatus 510. For example, the user may be directed by the apparatus to deposit such waste items in a dedicated sharps container located nearby. Further, in FIG. 61, the waste containers 524 are positioned within an enclosure defined by a door 522 or other closure member. In some embodiments, the door 522 can be locked to help ensure that unauthorized personnel cannot access the containers 524.

Figure 62:
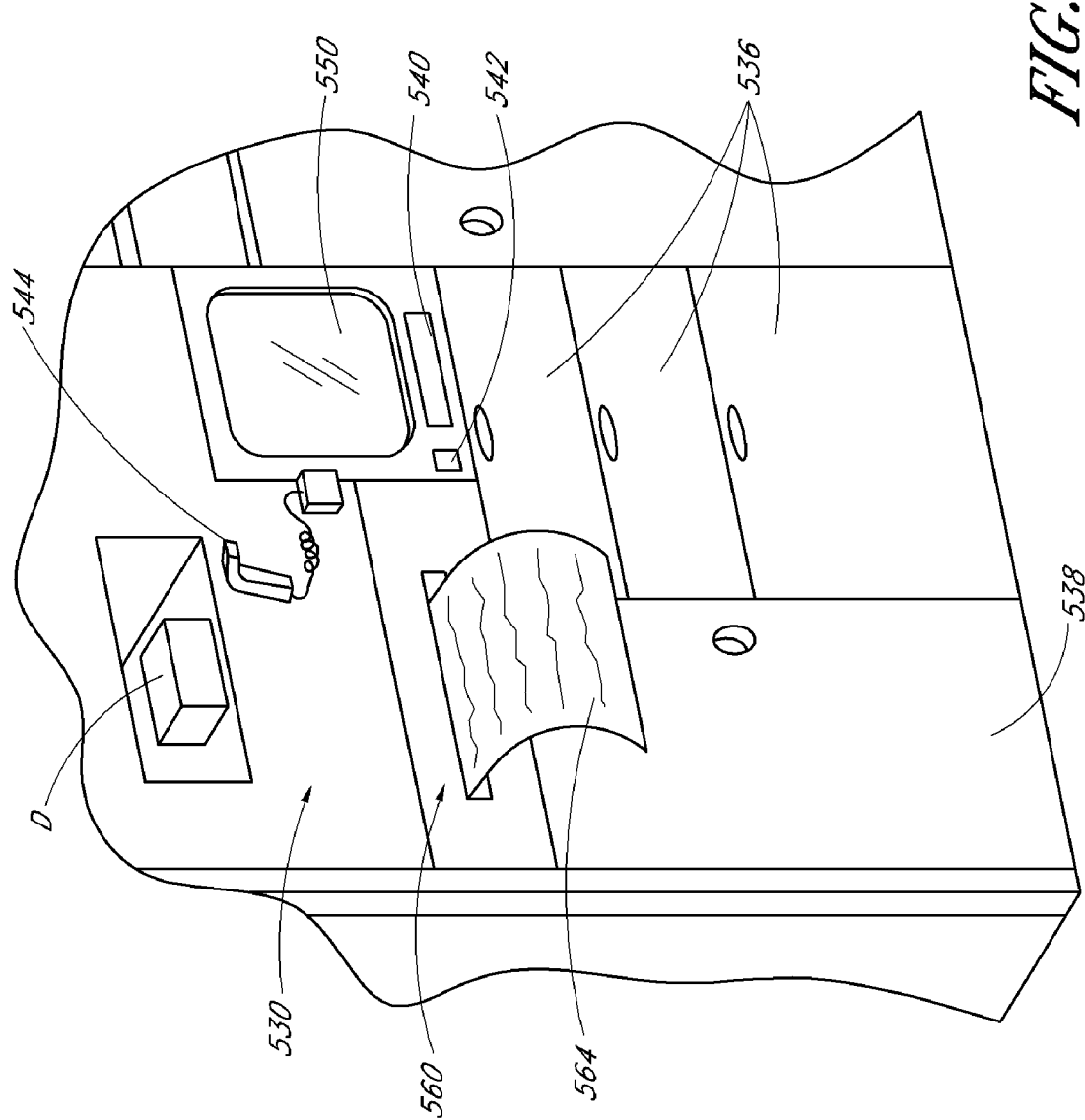
FIG. 62 is a perspective view of a dispensing portion of a combination disposal and dispensing apparatus according to one embodiment.

FIG. 62 illustrates one embodiment of a combination disposal/dispensing apparatus comprising a scanning device 540, a keypad and/or any other automatic or manual data entry device. As discussed, the scanning device 540 can be configured to automatically provide information about the waste item being discarded in the apparatus. In addition, the apparatus can comprise a display 550 adapted to provide information to a user. In one embodiment, the display 550 is a touchscreen display comprising a plurality of softkeys. It will be appreciated that the apparatus can include any other features as discussed or illustrated by other embodiments disclosed herein. In addition, the apparatus can include a user identification device 542, such as, for example, a fingerprint scanner, badge identification device reader, biometric data reader and/or the like. Such a user identification device 542 can advantageously permit the apparatus to accurately identify the clinician or other user who is requesting a particular dispensable item and/or disposing a waste item.

With continued reference to the embodiment illustrated in FIG. 62, the apparatus includes a handheld device 544, which can be configured to communicate with the apparatus and/or any other system of the facility using a hardwired and/or a wireless connection. In one embodiment, the handheld device 544 comprises a RFID scanner, a barcode scanner, a data entry device, a user identification reader and/or the like.

As shown in FIG. 62, the dispensing portion 530 of the apparatus can include a slot or other opening through which pharmaceutical items, supplies or other dispensed items D can be provided to the clinician or user. In some embodiments, the dispensing portion 530 includes a retrieval device, a dumb waiter system and/or one or more other components that facilitate retrieval of the desired items and/or reduce the required footprint area of the apparatus. As discussed, the requested items can be collected in a bag or other container before being delivered to a retrieval opening of the dispensing portion 530.

With further reference to FIG. 62, the apparatus can comprise a printer 560 or other output device. In one embodiment, the printer 560 is configured to print a list of the dispensed items pertaining to a particular patient. Such data can be printed as a separate list and provided to the user and/or other medical personnel. Alternatively, such data can be printed directly onto a collection bag or other container that includes a plurality of dispensed items. According to some embodiments, the printer 560 provides information regarding the patient, the pharmaceuticals and/or other items dispensed by the apparatus, expiration dates for the dispensed products, directions for use, the name of the clinician or other user who requested the dispensed items and/or the like.

Figure 63:
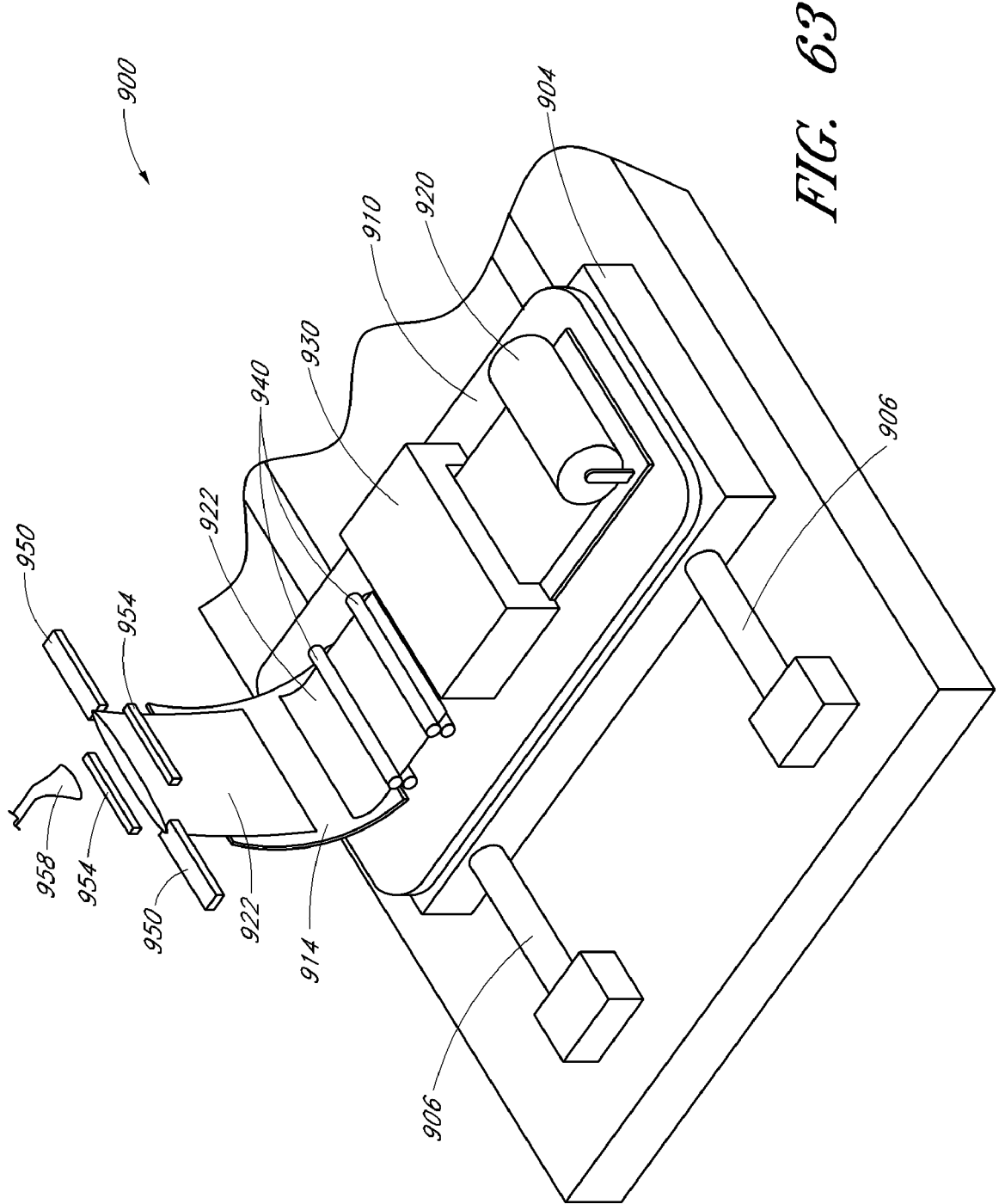
FIG. 63 is a perspective view of a collection system for a combination disposal and dispensing apparatus according to one embodiment.

As discussed herein, medications and other items that are retrieved by a retrieval device can be placed within a bag or other container before they are made available to a clinician or other user. FIG. 63 illustrates one embodiment of a collection system 900 configured to receive one or more desired items. As shown, the collection system 900 can include a shuttle 904 or other movable base member that is slidably positioned on two or more rails 906. Thus, the shuttle 904 can be selectively moved in a plurality of directions as items are collected by one or more retrieving devices (not shown). In some embodiments, the shuttle 904 comprises a turntable 910 or other device that can be selectively indexed or moved relative to the shuttle 904. Thus, the turntable 910 can provide additional flexibility to the collection system 900 in terms of how components situated thereon can be positioned. For example, in one arrangement, the turntable 910 can be rotated or translated relative to the shuttle 904.

With continued reference to FIG. 63, the turntable 910 can include a roll 920 or other stack of collection bags 922. In one embodiment, bags 922 from a roll 920 or other stack can be automatically fed into a printer 930 or other similar device. The printer 930 can include a thermal printer or any other type of printer that is adapted for printing directly on one or more portions of a bag 922. In some embodiments, the bags 922 include a blank space or other designated area (e.g., label) onto which text or images can be printed. As discussed herein, printed material can include patient data, information regarding the dispensed items and/or the like. In some embodiments, the text and/or images printed on a bag can be configured to fade over time and/or with exposure to light. This can be useful because of the enactment of increasingly strict privacy laws (e.g., HIPAA) and other regulations. In addition, one or more other methods of removing certain protected information printed on the bags can be used. For example, text or images can be printed on a removable strip or label, or other portion of a bag 922 that can be easily discarded after use.

In FIG. 63, once a bag 922 has been fed through the printer 930, it can be moved through a series of rollers 940 or other routing or advancing components. The bag 922 can then be advanced along a curved member 914 so that the bag's open end is generally located at the top of the collection system 900. As illustrated herein, two or more opening members 950 located on opposite sides of the bag 922 can be urged toward one another to cause the top end of the bag 922 to open. In some embodiments, the top of the bag 922 can be maintained in an open position during the collection process by selectively directing a volume of air or other fluid into the interior of the bag 922. For example, in FIG. 63, burst of sterile air, nitrogen or other fluid can be injected into the bag 922 using a fluid injection port 958. As an additional safeguard, air or other fluid can be filtered prior to being injected into the bag 922. In one embodiment, a 0.22 micron filter or a similar filtering device can be used to filter the air or other fluid. Accordingly, one or more of the retrieving devices, as disclosed herein, can deposit the desired items into the open end of the bag 922. Once all the desired medications and other dispensable items have been placed in the bag 922, a sealing device 954 can be used to close the open end of the bag 922. In the depicted arrangement, the sealing device 954 comprises a water cooled impulse heat sealer. However, any other type of sealing device 954 can be used.

Preferably, the combination apparatus can be connected to one or more networks in order to communicate data and other information regarding the disposed waste and/or dispensed items. Such information can be used to alert responsible parties of the need to empty waste containers and/or refill dispensing compartments. In addition, the compilation of such data can be used to facilitate the generation of reports and other summaries that may be desired or required for administrative, regulatory or other purposes. For example, the features of the various embodiments of the combination apparatus described herein can permit the tracking of medications and other dispensable items from the time of dispensing until the time of disposal. The collected data can be used to protect against unauthorized distribution or misuse of certain medications and other medical supplies. In addition, such data can be used to better size, position and configure dispensing, disposal/sorting and/or combination apparatuses throughout a hospital or other facility.

As discussed, the incorporation of a dispensing device and a sorting and disposal device into a single apparatus can allow hospitals and other healthcare facilities to save valuable floor space in patient rooms, examination rooms, common areas and/or other locations. Such arrangements can also help reduce the total number of electrical, instrumentation, control, communication and/or other types of connections needed to properly operate such equipment. In addition, the use of combination disposal and dispensing apparatuses can help reduce capital and operation and maintenance costs. Further, such units can be more easily serviced and maintained.

In several embodiments, the disposing portion of the combined dispensing and disposal system is adapted to accept only drugs that have been at least partially used or spent. In one embodiment, the system will not accept drugs that have expired or are unused, as in a reverse distribution system. In other embodiments, the system accepts used or spent drugs, as well as drugs that have expired or are unused, recalled, or otherwise undesired.

In some embodiments, the dispensing device and the sorting/disposal device may be separate units that are strategically configured to attach to one another. Such a modular arrangement allows for combination stations to be easily customized according to the particular dispensing and disposal needs of a particular hospital room or other location. Consequently, existing dispensing or disposal units may be replaced with larger and/or smaller units as the operational practices of a particular station or facility evolve over time.

Alternatively, one or more dispensing and/or sorting/disposal units may be added or deleted from a particular station. Preferably, each dispensing and sorting/disposal unit is configured with one or more connection methods that facilitate attachment and detachment of adjacent units. For example, in one embodiment, the units may be equipped with a slide railing system, latch member or the like. Regardless of their exact configuration, size, design and other characteristics, such combination disposal and dispensing apparatuses can improve the way hospitals and other medical facilities track the fate of pharmaceutical products and other expensive and/or regulated items.

The disposal and sorting portion of the combination apparatus described herein can include one or more other features described in other sections of this specification, such as, for example, the features related to containers (e.g., container sensing, restricted access lids, fill level detection), waste sorting decision matrices, software flags, handheld devices, network implemented systems, waste treatment systems and the like.

In some embodiments, a combined dispensing and disposal system will be particularly advantageous for tracking the movement of a drug from entry into a hospital until it is disposed. Tracking the lifecycle or cradle-to-grave pathway of a drug, which may include tracking data regarding the drug, the patient, and the user (e.g., doctor, pharmacist, nurse, or other user) are incorporated in several embodiments, alone or in combination with waste disposal information. Other drug data such as contraindications, allergy information, and availability of generics may also be included.

For example, cradle-to-grave tracking is accomplished in one embodiment by a system that tracks the number of drugs or medical devices dispensed, and the quantity or amount received by the disposal unit. A user is then notified (e.g., on a periodic basis) when any discrepancies are found between the number dispensed and the empty vials/packages received by the disposal unit.

Although certain embodiments and examples have been described herein, it will be understood by those skilled in the art that many aspects of the methods and devices shown and described in the present disclosure may be differently combined and/or modified to form still further embodiments. Additionally, it will be recognized that the methods described herein may be practiced using any device suitable for performing the recited steps. Moreover, the methods steps need not be practiced in any given order in some embodiments. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined by a fair reading of the claims that follow.

What is claimed is:

1. A method of dispensing and disposing medical items, the method comprising:
   receiving a dispensing instruction associated with a first medical item to be dispensed;
   dispensing said first medical item based on said dispensing instruction;
   receiving an identifier associated with a second medical item to be disposed using a scanner;
   wherein said second medical item comprises the first medical item after it has been at least partially used or emptied;
   retrieving, based on the identifier, information from a database, wherein the information is derived from applicable rules regarding disposal;
   assigning the second medical item to a disposal category based on the information retrieved from the database;
   wherein the disposal category is associated with at least one of a plurality of waste containers of a waste sorting station;
   wherein a control system associated with the database is configured to allow access to one of the waste containers based, at least in part, on the waste category, while preventing access to other waste containers of a waste sorting station to ensure proper disposal;
   tracking the date on which the first medical item was dispensed; and
   tracking the date on which the second medical item was disposed.

2. The method of claim 1, wherein the step of receiving a dispensing instruction comprises receiving information from a barcode scanner.

3. The method of claim 1, wherein the step of receiving a dispensing instruction comprises receiving information via a handheld device.

4. The method of claim 1, wherein the step of receiving a dispensing instruction comprises receiving information that is entered by a user.

5. The method of claim 1, wherein the step of receiving a dispensing instruction comprises activating a button or lever.

6. The method of claim 1, wherein the step of receiving an identifier comprises receiving information that identifies the second medical item from a barcode scanner.

7. The method of claim 1, wherein the step of receiving an identifier comprises receiving information that identifies the second medical item via a handheld device.

8. The method of claim 1, wherein the step of receiving an identifier comprises receiving information inputted by a user that identifies the second medical item.

9. The method of claim 1, wherein the step of receiving an identifier comprises receiving information regarding the trade name, generic name, or chemical name of the second medical item.

10. The method of claim 1, wherein the step of receiving an identifier comprises receiving information regarding the National Drug Code (NDC) of the second medical item.

11. The method of claim 1, wherein the step of receiving an identifier comprises receiving information regarding the abbreviated name or mnemonic of the second medical item.

12. The method of claim 1, wherein the step of receiving a dispensing instruction comprises receiving information from a database, wherein said database correlates the second medical item to a waste category.

13. The method of claim 1, further comprising tracking information regarding a user that requested the first medical item.

14. The method of claim 13, wherein the user is a patient or a practitioner.

15. The method of claim 1, further comprising tracking information regarding a user that disposed the second medical item.

16. The method of claim 1, further comprising tracking information regarding a patient that used the second medical item.

17. The method of claim 1, wherein the step of receiving an identifier comprises receiving information that identifies the second medical item from a RFID tag.

18. A method of dispensing and disposing medical items in a combined system, comprising:
- providing a plurality of dispensing compartments, each of said dispensing compartments configured to hold at least one medical item;
- receiving a dispensing instruction;
- processing said dispensing instruction to select a medical item based on said dispensing instruction, and
- allowing access to said selected medical item; and
- providing a plurality of waste containers,
  - wherein each of said waste containers is associated with at least one of a plurality of waste categories, and
  - wherein each of said waste containers is configured to receive at least one of said selected medical items that is dispensed after said selected medical item is at least partially used or expired;
- receiving identification data for a waste item by positioning a barcode of a waste item near an identification device, wherein said waste item comprises said selected medical item after said selected medical item is at least partially used or expired;
- classifying said waste item into a waste category based at least in part on said identification data;
- allowing access to one of the waste containers based on the waste category, while preventing access to other waste containers to ensure proper disposal.

19. The method of claim 18, wherein the step of allowing access to at least one of the waste containers comprises automatically open a lid on said waste container.

20. The method of claim 18, further comprising automatically locking a lid of a waste container in a closed position after said waste item is deposited into said waste container.

21. The method of claim 18, wherein the step of receiving a dispensing instruction comprises receiving information from a barcode scanner.

22. The method of claim 18, wherein the step of receiving a dispensing instruction comprises receiving information via a handheld device.

23. The method of claim 18, wherein the step of receiving a dispensing instruction additionally comprises receiving information that is manually entered by a user.

24. The method of claim 18, wherein the step of receiving the identification data comprises receiving information that identifies the waste item from a barcode scanner.

25. The method of claim 18, wherein the step of receiving the identification data comprises receiving information that identifies the waste item via a handheld device.

26. The method of claim 18, wherein the step of receiving the identification data additionally comprises receiving information that identifies the waste item from information manually entered by a user.

27. The method of claim 18, wherein the step of receiving identification data comprises receiving information regarding the trade name, generic name, or chemical name of the waste item.

28. The method of claim 18, wherein the step of classifying said waste item into a waste category comprises comparing the identification data with regulations governing pharmaceutical waste disposal contained in a database.

29. The method of claim 18, further comprising a single barcode scanner that both receives the dispensing instruction and the identification data.

30. The method of claim 18, wherein the step of receiving the identification data comprises receiving information that identifies the waste item from a RFID scanner.

\* \* \* \* \*